US012649735B2

(12) # United States Patent
Xia et al.

(10) Patent No.: US 12,649,735 B2
(45) Date of Patent: Jun. 9, 2026

(54) COMPOUND HAVING BRD4 INHIBITORY ACTIVITY, PREPARATION METHOD THEREFOR AND USE THEREOF

(71) Applicant: HAIHE BIOPHARMA CO., LTD., Shanghai (CN)

(72) Inventors: Lin Xia, Shanghai (CN); Leping Li, Shanghai (CN); Haoran Yang, Shanghai (CN)

(73) Assignee: HAIHE BIOPHARMA CO., LTD., Shanghai (CN)

(*) Notice: Subject to any disclaimer, the term of this patent is extended or adjusted under 35 U.S.C. 154(b) by 780 days.

(21) Appl. No.: 17/766,601

(22) PCT Filed: Sep. 24, 2020

(86) PCT No.: PCT/CN2020/117478

§ 371 (c)(1),
(2) Date: Apr. 5, 2022

(87) PCT Pub. No.: WO2021/068755

PCT Pub. Date: Apr. 15, 2021

(65) Prior Publication Data

US 2024/0150343 A1 May 9, 2024

(30) Foreign Application Priority Data

Oct. 8, 2019 (CN) ......................... 201910951369.3

(51) Int. Cl.

*C07D 471/04* (2006.01)
*C07D 491/048* (2006.01)
*C07D 495/04* (2006.01)
*C07D 519/00* (2006.01)

(52) U.S. Cl.

CPC ....... *C07D 471/04* (2013.01); *C07D 491/048* (2013.01); *C07D 495/04* (2013.01); *C07D 519/00* (2013.01)

(58) Field of Classification Search

None
See application file for complete search history.

(56) References Cited

U.S. PATENT DOCUMENTS

| | | | |
|---|---|---|---|
| 7,446,199 | B2 | 11/2008 | Aronov et al. |
| 8,975,417 | B2 | 3/2015 | Bordas et al. |
| 9,085,578 | B2 | 7/2015 | Nagamiya et al. |
| 9,540,368 | B2 | 1/2017 | Combs et al. |
| 9,670,221 | B2 | 6/2017 | Amans et al. |
| 10,017,501 | B2 | 7/2018 | Aktoudianakis et al. |
| 10,131,657 | B2 | 11/2018 | Dai et al. |
| 10,150,767 | B2 | 12/2018 | Albrecht et al. |
| 10,202,378 | B2 | 2/2019 | Adler et al. |
| 11,459,325 | B2 | 10/2022 | Tanaka et al. |
| 11,466,034 | B2 | 10/2022 | Xu et al. |
| 2019/0345153 | A1 | 11/2019 | Fidanze et al. |
| 2022/0017511 | A1 | 1/2022 | Fidanze et al. |

FOREIGN PATENT DOCUMENTS

| | | | |
|---|---|---|---|
| CN | 109071534 | A | 12/2018 |
| JP | 2007-504252 | A | 3/2007 |
| JP | 2016-510783 | A | 4/2016 |
| JP | 2016-520062 | A | 7/2016 |
| JP | 2016-520117 | A | 7/2016 |
| JP | 2016-525503 | A | 8/2016 |
| JP | 2017-513879 | A | 6/2017 |
| JP | 2017-533249 | A | 11/2017 |
| JP | 2018-507191 | A | 3/2018 |
| JP | 2019-511482 | A | 4/2019 |
| WO | 2005-028475 | A2 | 3/2005 |
| WO | 2013-125543 | A1 | 8/2013 |
| WO | 2014-078257 | A1 | 5/2014 |
| WO | 2014-125408 | A2 | 8/2014 |

(Continued)

OTHER PUBLICATIONS

Alzheimers DiseasePrevention, 2025, https://www.alz.org/alzheimers-dementia/research-and-progress/prevention#prevention.*
CardiovascularDisease Prevention, 2025, https://www.mayoclinic.org/diseases-conditions/heart-disease/in-depth/heart-disease-prevention/art-20046502.*
Sun et al., Journal of Advanced Research, 2024, 63, 207-218.*
ViralDisease Prevention, 2025, https://my.clevelandclinic.org/health/diseases/24473-viral-infection.*
RN 2247816-40-4, registry database compound, 2018.*
RN 2247815-64-9, registry database compound, 2018.*

(Continued)

*Primary Examiner* — Sun Jae Yoo

(74) *Attorney, Agent, or Firm* — NKL Law; Bin Lu; Allen Xue

(57) ABSTRACT

Disclosed in the present invention are a compound having a BRD4 inhibitory activity, a preparation method therefor and the use thereof. The structure of the compound having the BRD4 inhibitory activity of the present invention is as shown in formula I, and the definition of each substituent is as described in the description and claims. The compound of the present invention has a high bromodomain protein inhibitory activity, in particular a BRD4-targeting inhibitory activity, and can be used for the treatment and/or prevention of related diseases mediated by bromodomain proteins.

(I)

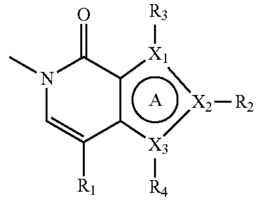

10 Claims, No Drawings

(56) References Cited

FOREIGN PATENT DOCUMENTS

| | | | |
|---|---|---|---|
| WO | 2015-058160 | A1 | 4/2015 |
| WO | 2015/081189 | A1 | 6/2015 |
| WO | 2015/081203 | A1 | 6/2015 |
| WO | 2015/081246 | A1 | 6/2015 |
| WO | 2016/077380 | A1 | 5/2016 |
| WO | 2016-123391 | A1 | 8/2016 |
| WO | 2017-177955 | A1 | 10/2017 |
| WO | 2018-086604 | A1 | 5/2018 |
| WO | 2018-130174 | A1 | 7/2018 |
| WO | 2018/188047 | A1 | 10/2018 |
| WO | 2018-222598 | A1 | 12/2018 |
| WO | 2018-237026 | A1 | 12/2018 |
| WO | 2019-120234 | A2 | 6/2019 |
| WO | 2019-152440 | A1 | 8/2019 |
| WO | 2019-153080 | A1 | 8/2019 |
| WO | 2019-184919 | A1 | 10/2019 |
| WO | 2020-216779 | A1 | 10/2020 |
| WO | 2021003310 | A1 | 1/2021 |

OTHER PUBLICATIONS

Notice of Reasons for Refusal and its English translation mailed Jun. 2, 2023 for JP Patent Application No. 2022-520955, 10 pages.
Beccalli, Egle M. et al., “Pd-catalyzed intramolecular cyclization of pyrrolo-2carboxamides: regiodivergent routes to pyrrolo-pyrazines and pyrrolo-pyridines” Tetrahedron 61, 2005, 1077-1082, 6 pages.
Jones, Raymond C.F. et al. “1,3-Dipolar cycloaddition route to nitrogen heterocyclic triones” Journal of the Chemical Society, Perkin Transactions 1: Organic and Bio-Organic Chemistry, 1999, 765-776, 13 pages.
Gres'ko, S. V. et al., Cyclotransformation of 7-nitro-2-(pyridyl-2')-1,5-dimethylimidazol[4,5-c]pyridine-4-one, Ukrainskii Khimicheskii Zhurnal (Russian Edition), 2003, 69(9-10), 110-112.
Bremer, Von O., Pyridino-3,4-triazole series. II Justus Liebigs Annalen der Chemie, 1937, 529, 288-90.
Kametani, Tetsuji et al., “Studies on the syntheses of heterocyclic compounds. DCLXIII. The reaction of pyridone derivatives with diazoalkane”, Chemical & Pharmaceutical Bulletin, 1976, 24(8), 1870-8.
Gruit, Marina et al., Synthesis of pyrroloazepinones: platinum- and gold-catalyzed cyclization reactions of alkynes, Tetrahedron, 2010, 66(18), 3341-3352.
European Search Report issued in counterpart application No. 20874532.3 mailed Jun. 30, 2023, 23 pages.
RN 2282718-10-7 Registry ED Entered STN: Mar. 11, 2019.
RN 2118352-63-7 Registry ED Entered STN: Aug. 22, 2017.
RN 2117033-82-4 Registry ED Entered STN: Aug. 21, 2017.
RN 2113960-23-7 Registry ED Entered STN: Aug. 15, 2017.
RN 2113067-82-4 Registry ED Entered STN: Aug. 13, 2017.
RN 2112385-70—Registry ED Entered STN: Aug. 11, 2017.
RN 2111854-06-7 Registry ED Entered STN: Aug. 10, 2017.
RN 2111850-03-2 Registry ED Entered STN: Aug. 10, 2017.
RN 2111727-02-5 Registry ED Entered STN: Aug. 10, 2017.
RN 2111513-58-5 Registry ED Entered STN: Aug. 10, 2017.
RN 2111312-37-7 Registry ED Entered STN: Aug. 10, 2017.
RN 2111292-72-7 Registry ED Entered STN: Aug. 10, 2017.
RN 2111091-22-4 Registry ED Entered STN: Aug. 9, 2017.
RN 2111005-64-0 Registry ED Entered STN: Aug. 9, 2017.
RN 2111005-40-2 Registry ED Entered STN: Aug. 9, 2017.
RN 2110897-24-8 Registry ED Entered STN: Aug. 9, 2017.
RN 2110896-82-5 Registry ED Entered STN: Aug. 9, 2017.
RN 2110847-17-9 Registry ED Entered STN: Aug. 9, 2017.
RN 2110743-44-5 Registry ED Entered STN: Aug. 9, 2017.
RN 2110739-06-3 Registry ED Entered STN: Aug. 9, 2017.
RN 2110706-26-6 Registry ED Entered STN: Aug. 9, 2017.
RN 2110284-42-7 Registry ED Entered STN: Aug. 8, 2017.
RN 2110095-67-3 Registry ED Entered STN: Aug. 8, 2017.
RN 2110066-88-9 Registry ED Entered STN: Aug. 8, 2017.
RN 2110055-62-2 Registry ED Entered STN: Aug. 8, 2017.
RN 2109637-79-6 Registry ED Entered STN: Aug. 7, 2017.
RN 2108076-67-9 Registry ED Entered STN: Aug. 3, 2017.
RN 2108072-38-2 Registry ED Entered STN: Aug. 3, 2017.
RN 2107506-79-4 Registry ED Entered STN: Aug. 3, 2017.
RN 2107049-95-4 Registry ED Entered STN: Aug. 2, 2017.
RN 2106982-47-0 Registry ED Entered STN: Aug. 2, 2017.
RN 2106829-25-6 Registry ED Entered STN: Aug. 1, 2017.
RN 2106769-51-9 Registry ED Entered STN: Aug. 1, 2017.
RN 2106706-59-4 Registry ED Entered STN: Aug. 1, 2017.
RN 2105960-09-4 Registry ED Entered STN: Aug. 1, 2017.
RN 2105568-72-5 Registry ED Entered STN: Jul. 31, 2017.
RN 2105567-12-0 Registry ED Entered STN: Jul. 31, 2017.
RN 2105106-74-7 Registry ED Entered STN: Jul. 30, 2017.
RN 2105069-42-7 Registry ED Entered STN: Jul. 30, 2017.
RN 2104991-75-3 Registry ED Entered STN: Jul. 30, 2017.
RN 2104988-83-0 Registry ED Entered STN: Jul. 30, 2017.
RN 2104877-72-5 Registry ED Entered STN: Jul. 30, 2017.
RN 2104470-23-5 Registry ED Entered STN: Jul. 28, 2017.
RN 2104237-66-1 Registry ED Entered STN: Jul. 28, 2017.
2091001-85—Registry ED Entered STN: Apr. 2, 17017CN.
2090917-56-7 Registry ED Entered STN: Apr. 17, 2017.
1783731-07-6 Registry ED Entered STN: Jun. 18, 2015.
1782481-92-8 Registry ED Entered STN: Jun. 17, 2015.
1781350-86-4 Registry ED Entered STN: Jun. 17, 2015.
1556258-87-7 Registry ED Entered STN: Feb. 26, 2014.
1554934-46-1 Registry ED Entered STN: Feb. 25, 2014.
1551554-51-8 Registry ED Entered STN: Feb. 20, 2014.
1547017-97-9 Registry ED Entered STN: Feb. 17, 2014.
1547015-46-2 Registry ED Entered STN: Feb. 17, 2014.
1547014-74-3 Registry ED Entered STN: Feb. 17, 2014.
1547014-30-1 Registry ED Entered STN: Feb. 17, 2014.
1544891-95-3 Registry ED Entered STN: Feb. 16, 2014.
1542050-89-4 Registry ED Entered STN: Feb. 11, 2014.
RN 1539862-98-0 Registry ED Entered STN: Feb. 9, 2014.
RN 1537308-42-1 Registry ED Entered STN: Feb. 5, 2014.
RN 1531204-33-7 Registry ED Entered STN: Jan. 27, 2014.
RN 1510263-69-0 Registry ED Entered STN: Jan. 3, 2014.
RN 1509176-56-0 Registry ED Entered STN: Jan. 2, 2014.
RN 1507569-04-1 Registry ED Entered STN: Dec. 31, 2013.
RN 1506561-40-5 Registry ED Entered STN: Dec. 30, 2013.
RN 1506190-67-5 Registry ED Entered STN: Dec. 29, 2013.
RN 1504424-67-2 Registry ED Entered STN: Dec. 26, 2013.
International Search Report mailed Nov. 25, 2020 corresponding to PCT/CN2020/117478 filed Sep. 24, 2019; 2 pages.

* cited by examiner

COMPOUND HAVING BRD4 INHIBITORY ACTIVITY, PREPARATION METHOD THEREFOR AND USE THEREOF

CROSS-REFERENCE TO RELATED APPLICATIONS

This application is a U.S. National Stage Application under 35 U.S.C. 371 of International Patent Application No.: PCT/CN2020/117478, filed on Sep. 24, 2020, which claims priority to Chinese Patent Application No.: 201910951369.3, filed on Oct. 8, 2019, the content of which is incorporated herein by reference in its entirety.

TECHNICAL FIELD

The present invention belongs to the field of medicinal chemistry. In particular, the present invention relates to a new class of compounds, deuterated compounds, stereoisomers, racemates, geometric isomers, tautomers, prodrugs, hydrates, solvates or pharmaceutically acceptable salts thereof, and a pharmaceutical composition containing them, which are BRD4-targeting inhibitors with novel structures.

BACKGROUND TECHNIQUE

The bromodomain is a protein domain that recognizes acetylated lysine residues, and this recognition is a prerequisite for the binding of some regulatory proteins to histones and the remodeling of chromatin structure. Bromodomain-containing proteins (BCPs) are divided into eight families according to the similarity of structure and sequence. The BET family is currently the most studied family and includes four members: BRD4, BRD3, BRD2 and BRDT. BET bromodomain proteins contain several sets of modular structures: two N-terminal tandem BRDs (BD1 and BD2) associated with acetylation recognition; an additional protein-protein interaction region (ET); BRDT and long mutants of BRD4 (BRD4L), both contain a C-terminal region (CTM) that interacts with the positive transcription elongation factor (P-TEFb); a conserved region and a serine-glutamate-aspartate-rich domain (SEED).

Studies have shown that the dysregulation of BRD4 expression is related to the formation of various cancer diseases such as blood cancer, breast cancer and colon cancer. BRD3 and BRD4 are mis-fused with nuclear protein in testis (NUT), leading to the occurrence of adenocarcinoma in NUT. BRD4 protein can bind to RNA polymerase II (Pol II) and positive transcription elongation factor (P-TEFb) and participate in the transcription of oncogenes MYC, BCL2, BCL6 and the like. A study from Langone Medical Center of New York University in 2014 showed that the BRD4 protein occupies the genetic position of the super-enhancer, which allows cancer cells to maintain a relatively immature stem cell-like state, which drives cancer to some extent. Tumor cell apoptosis can be induced by the targeted inhibition of BRD4, that is, the proliferation of tumor cells can be slowed down, thereby achieving anti-tumor effect. Therefore, as a potential anti-tumor target, BRD4 has received extensive attention and development in recent years.

At present, some literatures have reported research on small molecule BRD4 inhibitors, such as WO2017/177955, WO2018/188047, etc., which disclose some compounds with inhibitory effects on BRD4. The following batches of small molecule BRD4 inhibitors have been entered into clinical studies phase.

Compound Mivebresib (ABBV-075) is a pyridone BRD4 targeting inhibitor developed by Abbvie, which shows good DMPK properties. The compounds have shown good biological activity in various tumor models and are currently in phase I clinical studies for the treatment of solid tumors and hematological cancers.

Compound Apabetalone (RVX-208), derived from a plant polyphenol-resveratrol derivative. This compound is originally developed by Resverlogix and shows stronger inhibitory activity against BRD4 BD2 ($K_d$ for BRD4-BD2: 135 nM; $K_d$ for BRD4-BD1 1142 nM). Apabetalone (RVX-208) can effectively reduce blood lipids in patients with hyperlipidemia and diabetes. The research for the treatment of prediabetes is in clinical phase II, and the research for the treatment of atherosclerosis and acute coronary syndrome (ACS) is in clinical phase III.

Compound CPI-0610 is a BRD4 inhibitor containing isoxazole structure developed by Constellation. Its $IC_{50}$ for BRD4-BD1 is 35 nM, and $IC_{50}$ for BRD4-BD2 is 6 nM, showing weak BD2 selectivity. This compound inhibits acute leukemia tumors by 41% when administered orally to mice at 60 mg/kg per day. It also shows good efficacy in patients with lymphoma, and is currently undergoing a phase I clinical trial.

The currently reported Abbv744 is the only BRD4-BD2 selective inhibitor for tumors, with a selectivity (BD2/BD1) >100 times. Preclinical data show that the BD2 selective inhibitor Abbv744 has better safety. It is currently used for the treatment of hematological tumors and solid tumors in clinical trial, and is in clinical phase I.

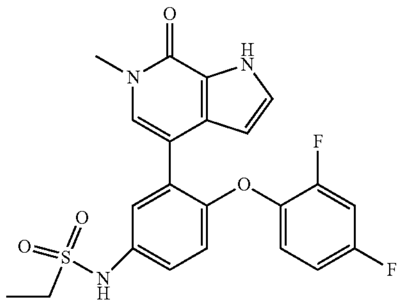

ABBV-075

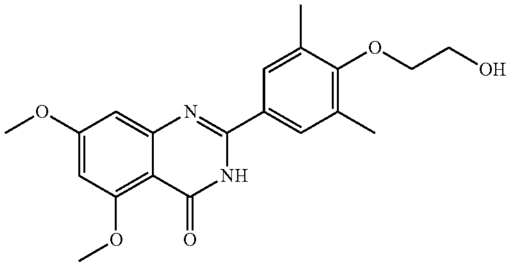

RVX-208

-continued

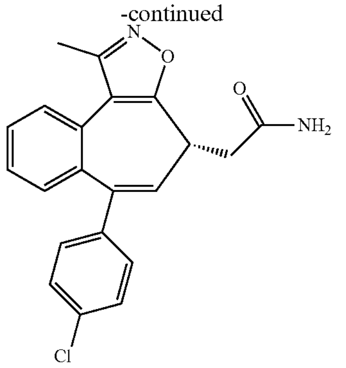

CPI-0610

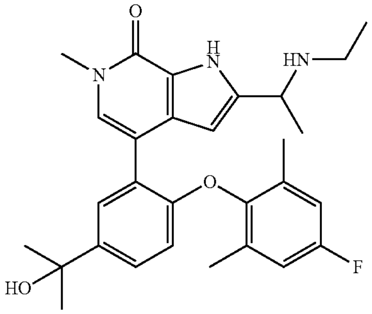

ABBV-744

However, mature and stable BRD4 inhibitors with good effectivity and low toxicity are still under research and development. In view of the broad prospects of BRD4 inhibitors as single or combined drugs in the field of tumors and other diseases, it remains critical to find more efficient and safer BRD4 inhibitors to meet patient needs.

SUMMARY OF THE INVENTION

The object of the present invention is to provide a compound with BRD4 inhibitory activity, preparation method and use thereof.

The first aspect of the present invention provides a compound of formula (I), deuterated compound, stereoisomer, racemate, geometric isomer, tautomer, prodrug, hydrate, solvate or pharmaceutically acceptable salt thereof:

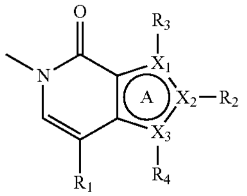

(I)

wherein, ring A is a five-membered aromatic heterocycle, and $X_1$, $X_2$ and $X_3$ are each independently C, N, O or S and are not C at the same time; preferably, one of $X_1$, $X_2$ and $X_3$ is N, and the other two are C;

$R_3$ is absent or a substituent on $X_1$; $R_2$ is absent or a substituent on $X_2$; and $R_4$ is absent or a substituent on $X_3$;

one of $R_1$ and $R_4$ is hydrogen, halogen or absent, and the other is selected from the group consisting of unsubstituted or substituted C1-C6 alkyl, unsubstituted or substituted C2-C6 alkenyl, unsubstituted or substituted C3-C6 cycloalkyl, unsubstituted or substituted 4-8 membered heterocycloalkyl, unsubstituted or substituted 5-12 membered aryloxy, unsubstituted or substituted amino, unsubstituted or substituted 5-12 membered heteroaryl, unsubstituted or substituted naphthyl, unsubstituted or substituted C1-C6 alkylaminoacyl, and unsubstituted or substituted C1-C6 alkylamido; wherein, the "substituted" refers to substitution with one or more substituents selected from the group consisting of =O, hydroxyl, halogen, unsubstituted or halogenated C1-C6 alkoxy, unsubstituted or halogenated C3-C8 cycloalkyl, C3-C6 cycloalkyloxy, C1-C6 ester group, C1-C6 alkoxycarbonyl, C1-C6 alkylcarbonyl, C1-C6 alkylaminoacyl, C1-C6 alkylamido, unsubstituted C1-C6 alkyl or C1-C6 alkyl substituted with one or more substituents selected from group A, unsubstituted C5-C10 aryl or C5-C10 aryl substituted with one or more substituents selected from group B, unsubstituted 5-8 membered heteroaryl or 5-8 membered heteroaryl substituted with one or more substituents selected from group B, unsubstituted 4-8 membered heterocycloalkylacyl or 4-8 membered heterocycloalkylacyl substituted with one or more substituents selected from group B, and unsubstituted C5-C8 aryloxy or C5-C8 aryloxy substituted with one or more substituents selected from group B; wherein the group A includes the following substituents: amino, nitro, cyano, hydroxyl, halogen, phenyl, unsubstituted or halogenated C3-C8 cycloalkyl, unsubstituted or halogenated C3-C6 cycloalkyloxy; the group B includes the following substituents: C1-C6 alkyl, nitro, cyano, halogen, halogenated C1-C6 alkyl, hydroxy, hydroxymethyl, amino, unsubstituted or halogenated C1-C6 alkoxy, C3-C6 cycloalkyloxy, unsubstituted or C1-C6 alkyl substituted 3-8-membered heterocycloalkyl, C1-C6 ester group, C1-C6 alkoxycarbonyl, C1-C6 alkylcarbonyl, C1-C6 alkylaminoacyl, C1-C6 alkylamido, —SO—(C1-C6 alkyl), —$SO_2$—(C1-C6 alkyl);

$R_2$ is selected from the group consisting of H, —COO—$R_6$, —CO—NH—$R_6$, —NH—CO—$R_6$, —$SO_2$—$NHR_6$, unsubstituted or substituted 5-8-membered heteroaryl, and unsubstituted or substituted C1-C6 alkyl; wherein, the "substituted" refers to substitution with one or more substituents selected from the group consisting of unsubstituted C1-C6 alkyl or C1-C6 alkyl substituted by one or more substituents selected from group C, halogen, hydroxy, C5-C8 aryl, 5-8 membered heteroaryl, 3-12 membered heterocycloalkyl, C1-C6 alkoxy, C3-C6 cycloalkyl, C3-C6 cycloalkyloxy, C1-C6 ester group, C1-C6 alkoxycarbonyl, nitro, cyano, C1-C6 alkylamido, and unsubstituted amino or amino substituted with one or more substituents selected from group D; the group C includes the following substituents: halogen, hydroxyl, C3-C6 cycloalkyl, 3-12-membered heterocycloalkyl, 3-12-membered heterocycloalkyl substituted with C1-C6 alkyl; the group D includes the following substituents: C1-C6 alkyl, halogenated C1-C6 alkyl, C1-C6 alkylamido, C3-C6 cycloalkyl; $R_6$ is selected from the group consisting of unsubstituted or halogenated C1-C6 alkyl, unsubstituted or halogenated C3-C6 cycloalkyl, unsubstituted 5-8 membered heteroaryl or 5-8 membered heteroaryl substituted with C1-C6 alkyl, and unsubstituted 5-8 membered heterocycloalkyl or 5-8 membered heterocycloalkyl substituted with C1-C6 alkyl;

$R_3$ is C1-C6 alkyl, halogen, unsubstituted amino or amino substituted by amino-protecting group (such as boc, Cbz, Fmoc, etc.), C1-C6 alkylamido, nitro, cyano, carboxyl or hydrogen, preferably hydrogen;

and the compound of formula (I) is not the following compound:

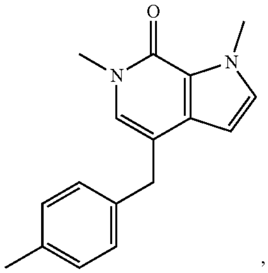
,
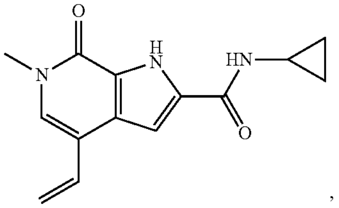
,
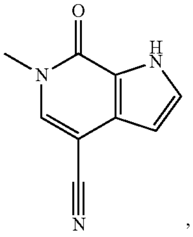
,
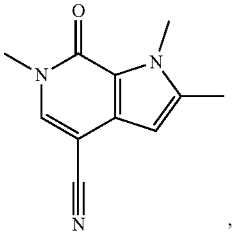
,
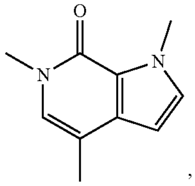
,

In another preferred embodiment, the compound is:

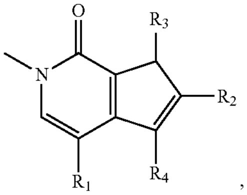
,
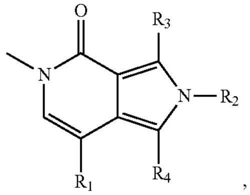
,
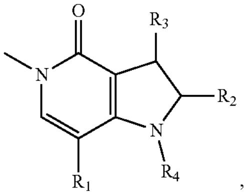
,
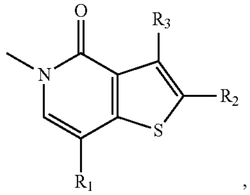
,

-continued

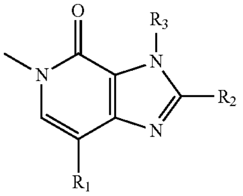
or
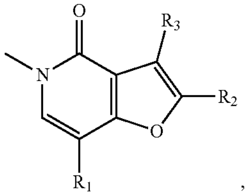
, wherein, the definitions of $R_1$, $R_2$, $R_3$ and $R_4$ are defined as above.

In another preferred embodiment, the compound is:

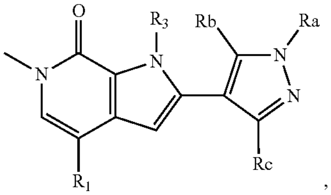
,
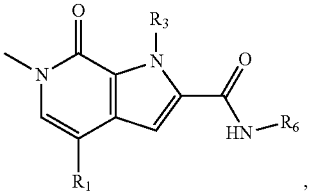
,
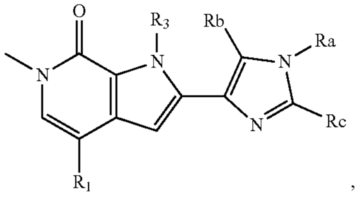
,
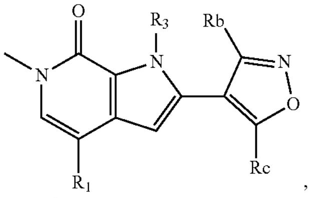
,
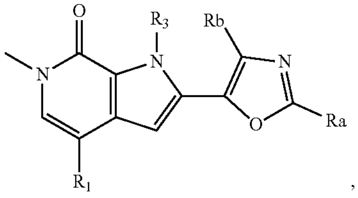
,
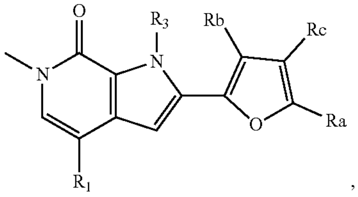
,
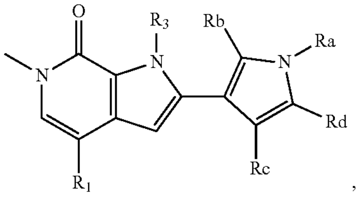
, -continued

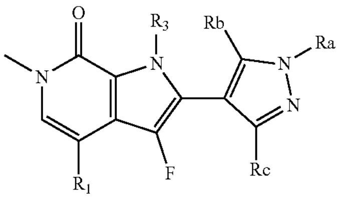

,

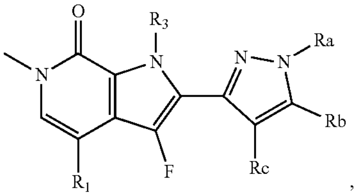

,

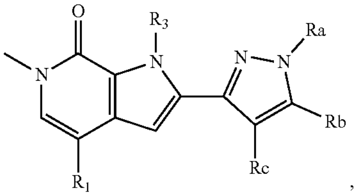

,

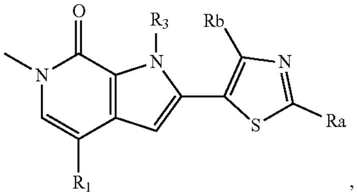

,

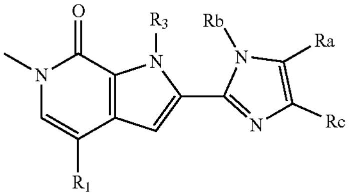

,

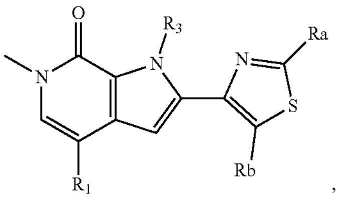

,

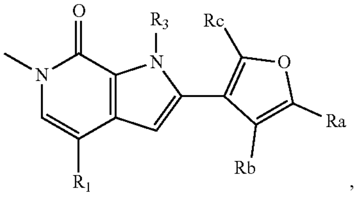

,

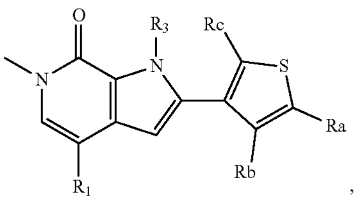

,

-continued

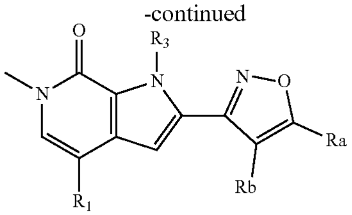

or

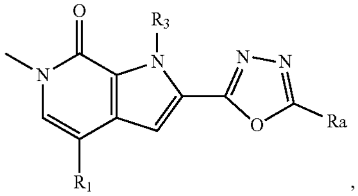

, wherein, $R_1$, $R_3$ and $R_6$ are defined as above; Ra, Rb, Rc and Rd are each independently selected from hydrogen, halogen, unsubstituted or halogenated C1-C6 alkyl, unsubstituted amino or amino substituted with one or more substituents selected from group D, C1-C6 alkylamido, nitro or 3-12-membered heterocycloalkyl; the group D includes the following substituents: C1-C6 alkyl, halogenated C1-C6 alkyl, C1-C6 alkylamido, C3-C6 cycloalkyl.

In another preferred embodiment, one of $R_1$ and $R_4$ is hydrogen or absent, and the other is selected from unsubstituted or substituted C1-C4 alkyl, unsubstituted or substituted C2-C4 alkenyl, unsubstituted or substituted C3-C6 cycloalkyl, unsubstituted or substituted N-containing 5-membered heterocycloalkyl, unsubstituted or substituted amino, unsubstituted or substituted N-containing 5-10 membered heteroaryl, unsubstituted or substituted naphthyl, or unsubstituted or substituted C1-C6 alkylaminoacyl;

wherein, the "substituted" refers to substitution with one or more substituents selected from =O, hydroxyl, halogen, C1-C4 alkoxy, C3-C6 cycloalkyl, C3-C6 cycloalkyl-O—, C1-C6 ester group, C1-C4 alkoxycarbonyl, C1-C4 alkylcarbonyl, C1-C4 alkylaminoacyl, C1-C4 alkylamido, unsubstituted C1-C4 alkyl or C1-C4 alkyl substituted with one or more substituents selected from group A, unsubstituted C5-C10 aryl or C5-C10 aryl substituted with one or more substituents selected from group B, unsubstituted 5-8 membered heteroaryl or 5-8 membered heteroaryl substituted with one or more substituents selected from group B, unsubstituted 4-6 membered heterocycloalkylacyl or 4-6 membered heterocycloalkylacyl substituted with one or more substituents selected from group B, or unsubstituted C6-C8 aryloxy or C6-C8 aryloxy substituted with one or more substituents selected from group B; when $R_1$ or $R_4$ is substituted C1-C4 alkyl or substituted C2-C4 alkenyl, the "substituted" refers to substitution with one or more substituents selected from halogen, hydroxyl, C1-C4 alkoxy, unsubstituted C5-C10 aryl or C5-C10 aryl substituted with one or more substituents selected from group B, unsubstituted 5-8-membered heteroaryl or 5-8 membered heteroaryl substituted with one or more substituents selected from group B, or unsubstituted C6-C8 aryloxy or C6-C8 aryloxy substituted with one or more substituents selected from group B;

the group A includes the following substituents: amino, nitro, cyano, hydroxyl, halogen, phenyl, unsubstituted or halogenated C3-C8 cycloalkyl, unsubstituted or halogenated C3-C8 cycloalkyloxy;

the group B includes the following substituents: C1-C4 alkyl, nitro, cyano, fluorine, chlorine, bromine, trifluoromethoxy, hydroxyl, hydroxymethyl, amino, C1-C4 alkoxy, C3-C6 cycloalkyloxy, unsubstituted 4-8-membered heterocycloalkyl or 4-8-membered heterocycloalkyl substituted with C1-C6 alkyl, C1-C6 ester group, C1-C6 alkoxycarbonyl, C1-C6 alkylcarbonyl, C1-C6 alkylaminoacyl, C1-C6 alkylamido, —SO—(C1-C6 alkyl), —$SO_2$—(C1-C6 alkyl).

In another preferred embodiment, the N-containing 5-membered heterocycloalkyl is

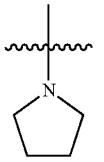
or
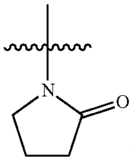
.

In another preferred embodiment, the N-containing 5-10-membered heteroaryl is

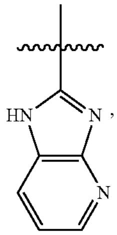
,
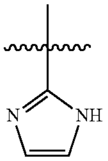
,
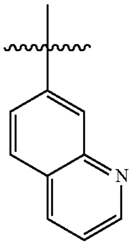
,
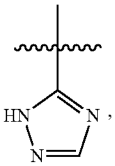
,
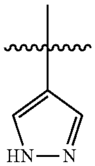
,
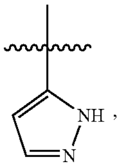
,
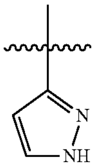
,
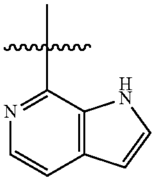
,
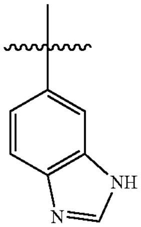
,
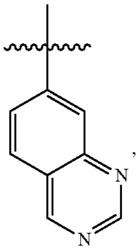
,
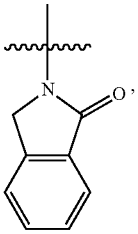
,
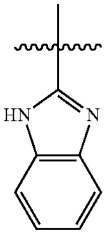
,
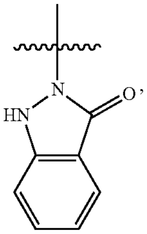

-continued

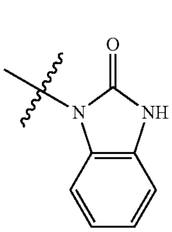
or
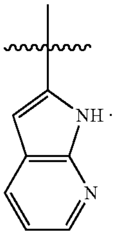
.

In another preferred embodiment, one of $R_1$ and $R_4$ is hydrogen, halogen or absent, and the other is selected from

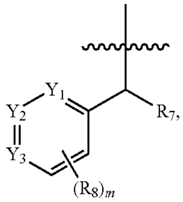
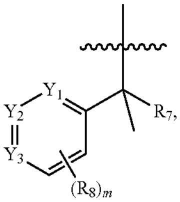
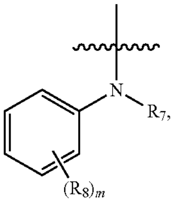
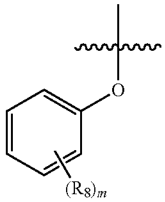
,
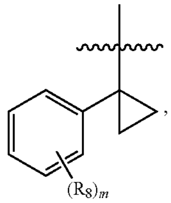
,
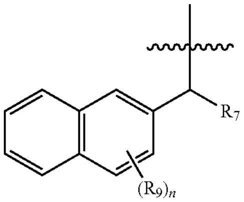
,
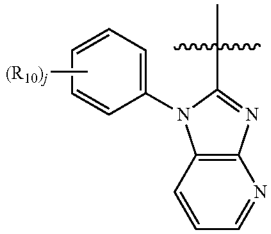
,
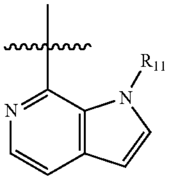
,
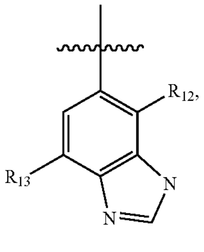
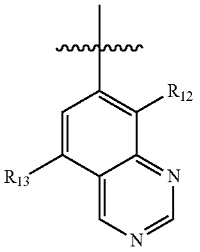
,
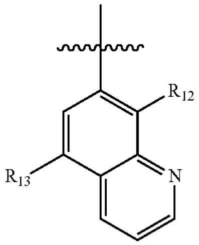
,
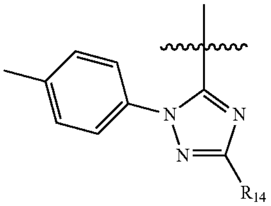
, -continued

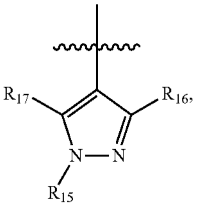
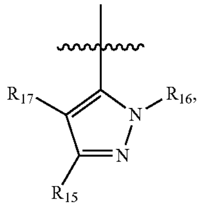
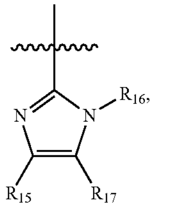
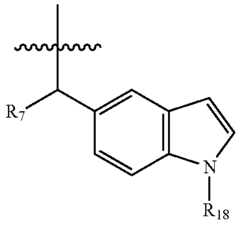
,
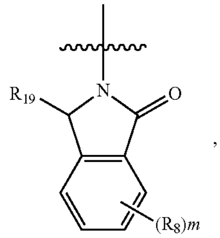
,
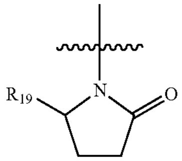
,
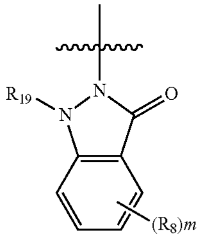
,
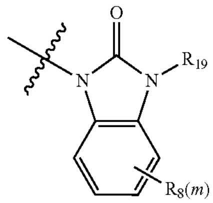
,
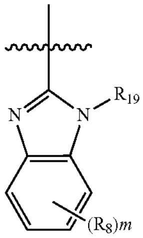
,
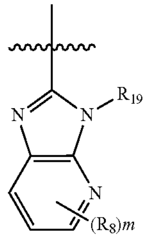
or
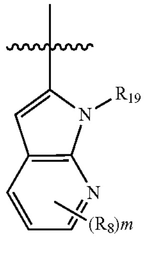
, wherein, $Y_1$, $Y_2$ and $Y_3$ are each selected from C or N and are not nitrogen at the same time;

$R_7$ is selected from hydrogen, unsubstituted or halogenated C1-C5 alkyl, unsubstituted or halogenated C3-C8 cycloalkyl, hydroxy, C1-C4 alkyl substituted with hydroxy, methoxy, halogen, phenyl, benzyl, phenoxy, phenoxy substituted with trifluoromethyl, trifluoromethoxy, phenoxy substituted with trifluoromethoxy, 5-8 membered heteroaryl or 3-8 membered heterocycloalkyl;

$R_8$ is a substituent on the phenyl or the six-membered heteroaryl, m is the number of the substituent $R_8$ and is selected from an integer of 0 to 4 (m is preferably 0, 1, 2); when m≥2, each $R_8$ is the same or different; the substituents represented by $R_8$ are each independently selected from hydrogen, C1-C6 alkyl, nitro, cyano, halogen, trifluoromethoxy, hydroxy, hydroxymethyl, amino, C1-C6 alkoxy, C3-C6 cycloalkyloxy, unsubstituted 3-8 membered heterocycloalkyl or 3-8 membered heterocycloalkyl substituted with C1-C6 alkyl;

$R_9$ is a substituent on the naphthyl, n is the number of the substituent $R_9$ and is selected from an integer of 0 to 4 (n is preferably 0, 1, 2); when n≥2, each $R_9$ is the same or different; the substituents represented by $R_9$ are each independently selected from the group consisting of C1-C6 alkyl, nitro, cyano, halogen, trifluoromethoxy, hydroxy, hydroxymethyl, amino, C1-C6 alkoxy, C3-C6 cycloalkyloxy, and unsubstituted 4-8 membered heterocycloalkyl or 4-8 membered heterocycloalkyl substituted with C1-C6 alkyl;

$R_{10}$ is a substituent on the phenyl, j is the number of the substituent $R_{10}$ and is selected from an integer of 0 to 4 (j is preferably 0, 1, 2); when j≥2, each $R_{10}$ is the same or different; the substituents represented by $R_{10}$ are each independently selected from C1-C6 alkyl, nitro, cyano, halogen, trifluoromethoxy, hydroxy, hydroxymethyl, amino, C1-C6 alkoxy or C3-C6 cycloalkyloxy;

$R_{11}$ is selected from hydrogen or C1-C6 alkyl;

$R_{12}$ and $R_{13}$ are each independently selected from hydrogen, C1-C6 alkyl, C3-C6 cycloalkyl, C3-C6 cycloalkyloxy, C1-C6 alkylcarbonyl, C1-C6 alkoxy, amino, hydroxyl or C1-C6 alkyl substituted with hydroxyl;

$R_{14}$ is selected from C1-C6 alkyl, C1-C6 ester group, C1-C6 alkoxycarbonyl, C1-C6 alkylaminoacyl or C1-C6 alkylamido;

$R_{15}$, $R_{16}$ and $R_{17}$ are each independently selected from hydrogen, C1-C6 alkyl, C1-C6 alkyl substituted with phenyl, C3-C6 cycloalkyl, C1-C6 alkyl substituted with cyclohexyl, phenyl, phenyl substituted with C1-C6 alkyl, hydroxy, hydroxymethyl, hydroxyethyl, trifluoromethoxy, C1-C6 alkoxy, C1-C6 alkylcarbonyl, C1-C6 ester group, C1-C6 alkoxycarbonyl, C1-C6 alkylaminoacyl, C1-C6 alkylamido or phenoxy;

$R_{18}$ is selected from hydrogen, C1-C6 alkyl or hydroxyl;

$R_{19}$ is selected from unsubstituted phenyl or phenyl substituted with one or more substituents selected from halogen, unsubstituted or halogenated C1-C6 alkyl, unsubstituted or halogenated C1-C6 alkoxy, hydroxyl, —SO—(C1-C6 alkyl) or —$SO_2$—(C1-C6 alkyl).

In another preferred embodiment, $R_2$ is selected from H, —COO—$R_6$, —CO—NH—$R_6$, —NH—CO—$R_6$, —$SO_2$—$NHR_6$, unsubstituted or substituted 5-8-membered heteroaryl, or unsubstituted or substituted C1-C4 alkyl; wherein, the "substituted" refers to substitution with one or more substituents selected from unsubstituted C1-C6 alkyl or C1-C6 alkyl substituted with one or more substituents selected from group C, halogen, hydroxy, amino, C6-C8 aryl, 5-6 membered heteroaryl, 5-8 membered heterocycloalkyl, C1-C4 alkoxy, C3-C6 cycloalkyl, C3-C6 cycloalkyloxy, C1-C6 ester group, C1-C4 alkoxycarbonyl, nitro, cyano, or C1-C4 alkylamido; $R_6$ is selected from unsubstituted or halogenated C1-C4 alkyl, unsubstituted or halogenated C3-C6 cycloalkyl, unsubstituted 5-6 membered heteroaryl or 5-6 membered heteroaryl substituted with C1-C6 alkyl, unsubstituted 5-6 membered heterocycloalkyl or 5-6 membered heterocycloalkyl substituted with C1-C6 alkyl; and the group C includes the following substituents: halogen, hydroxyl, 4-6 membered heterocycloalkyl, or 4-6 membered heterocycloalkyl substituted with C1-C4 alkyl.

In another preferred embodiment, the compound of formula (I) is selected from the following specific compounds:
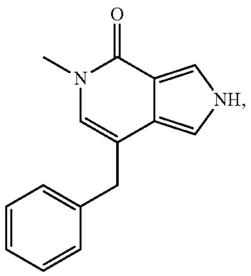
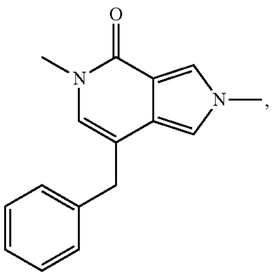
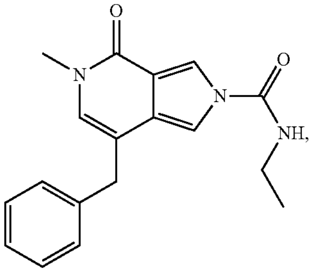
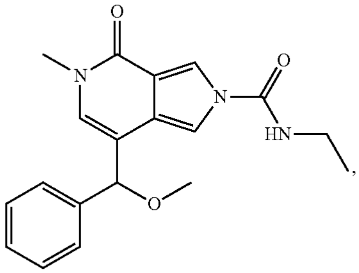
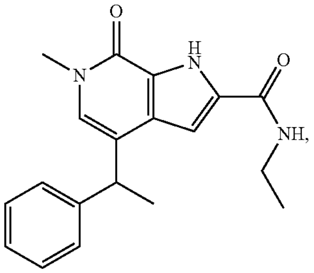
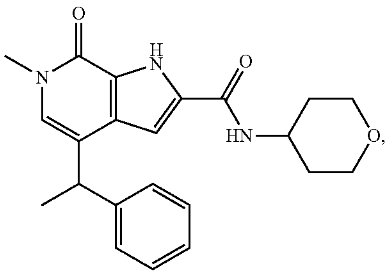
-continued
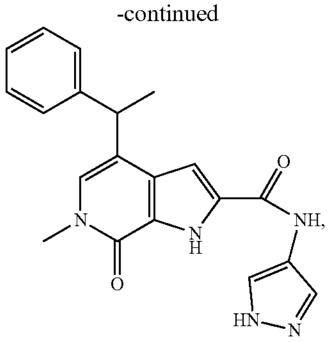
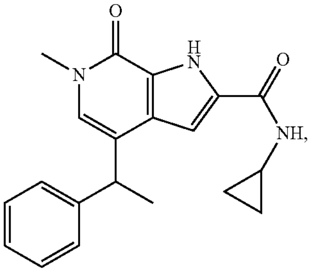
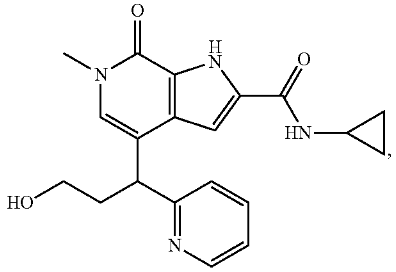
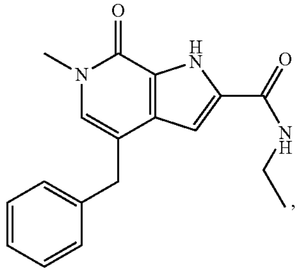
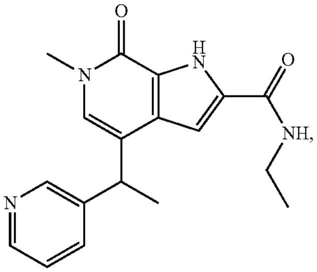
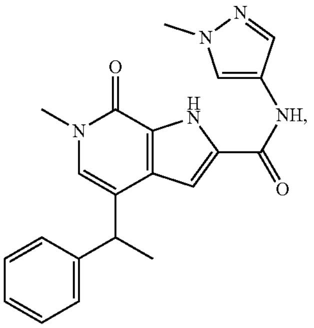

-continued
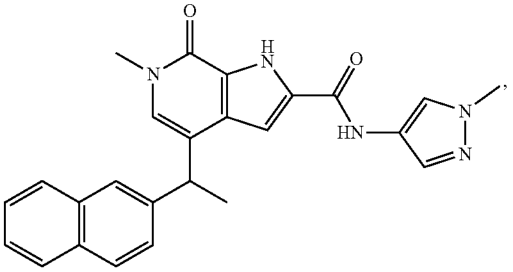
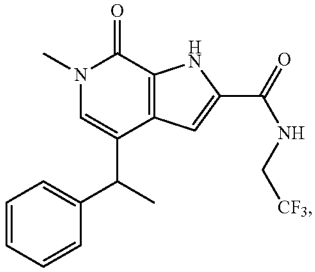
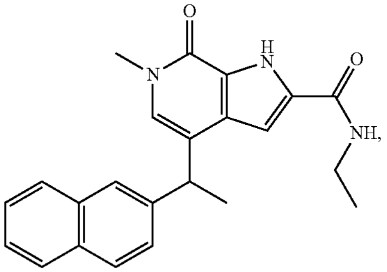
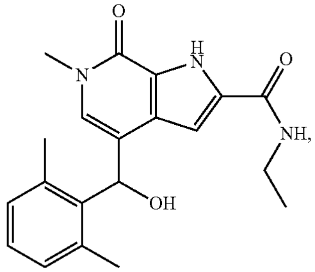
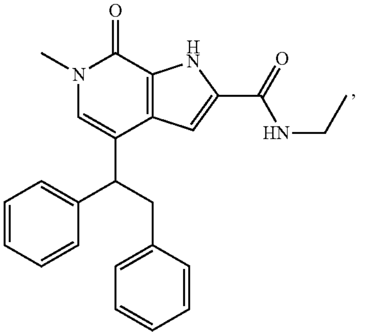
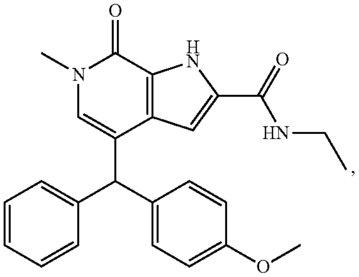
-continued
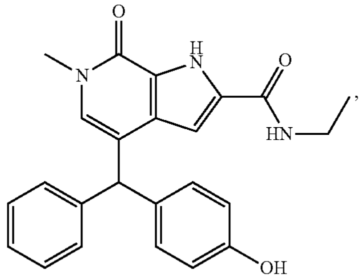
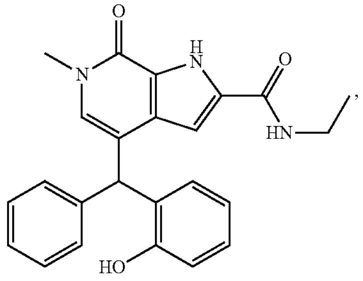
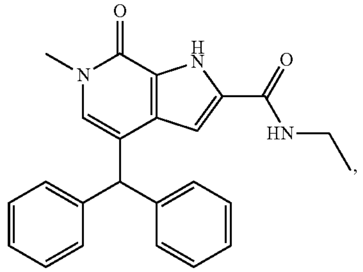
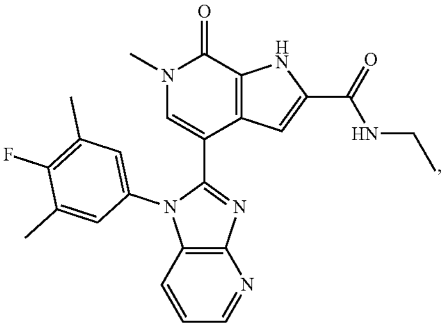
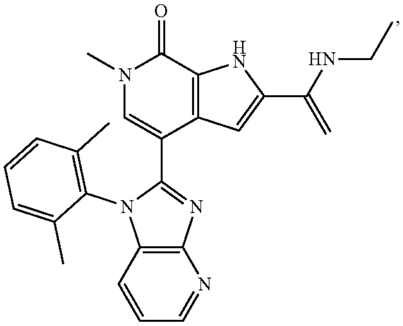

-continued
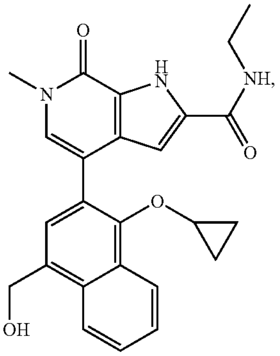
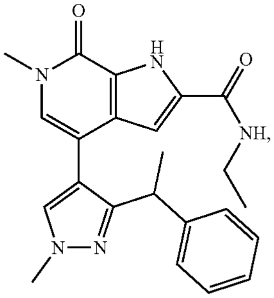
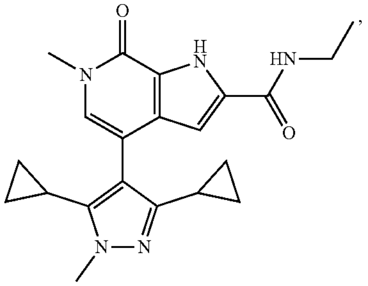
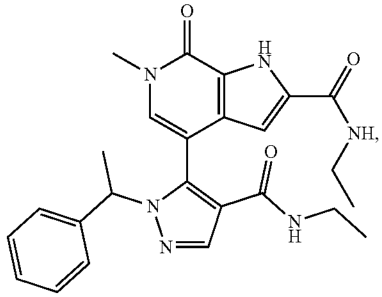
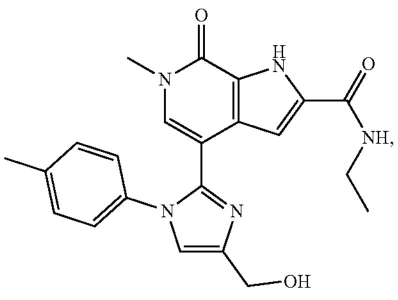
-continued
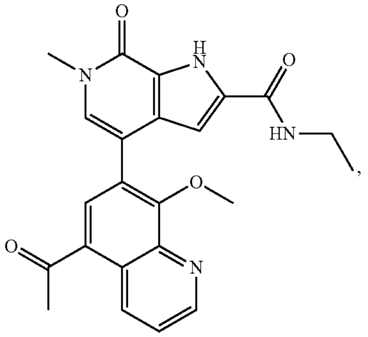
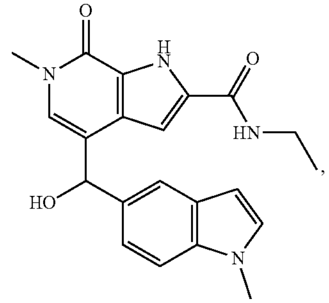
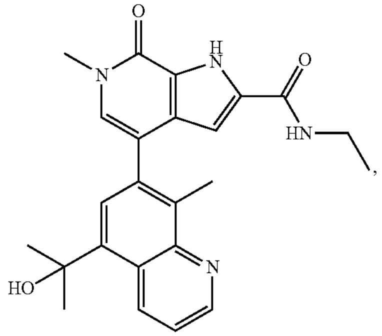
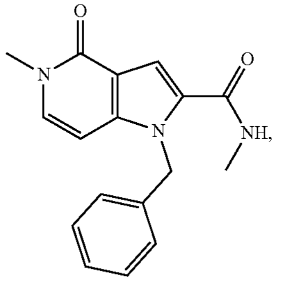
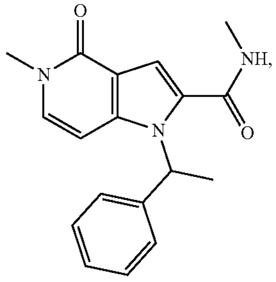

-continued
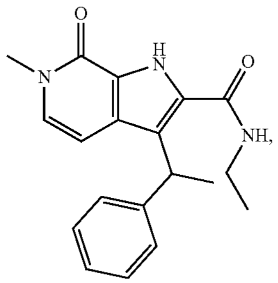
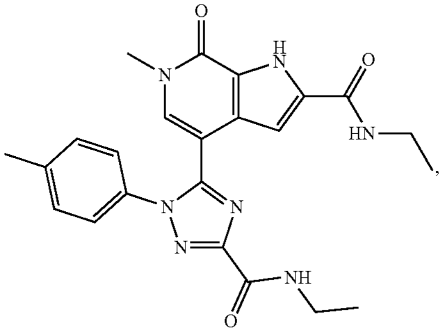
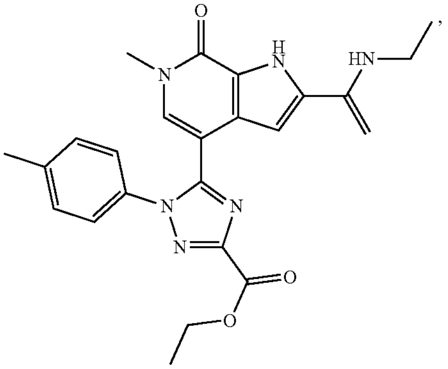
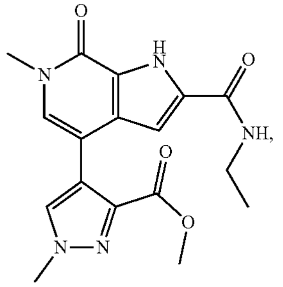
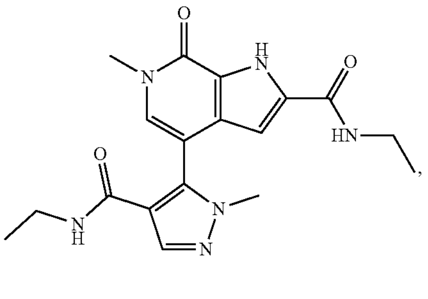
-continued
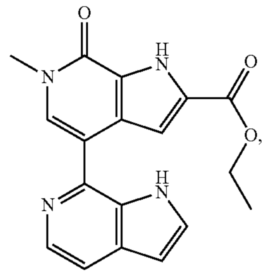
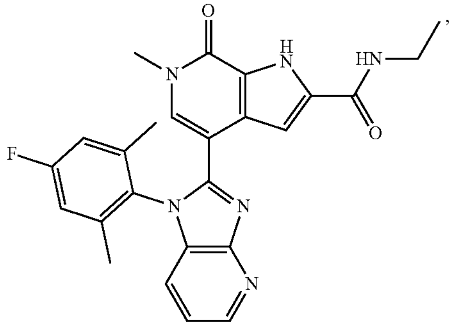
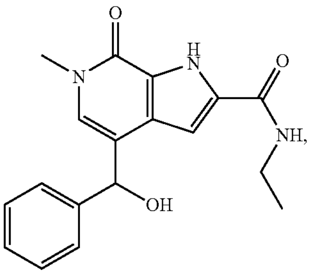
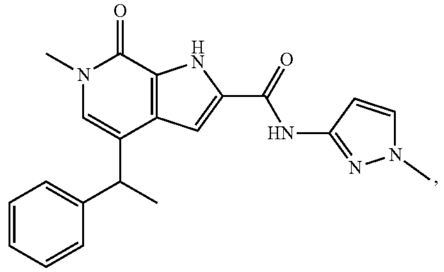
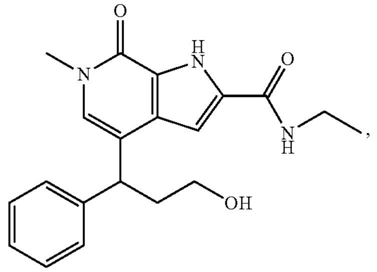
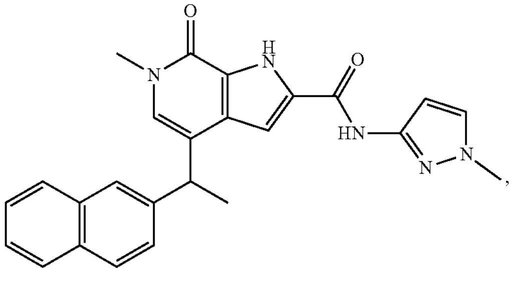

-continued
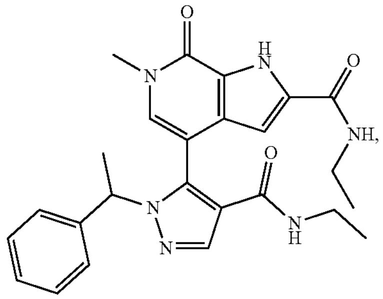
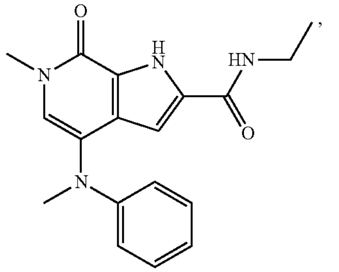
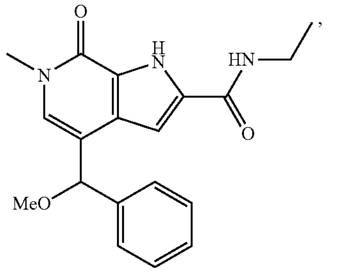
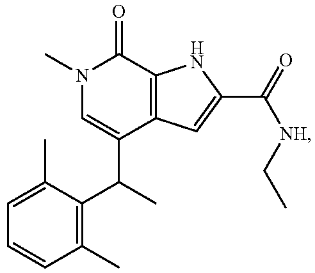
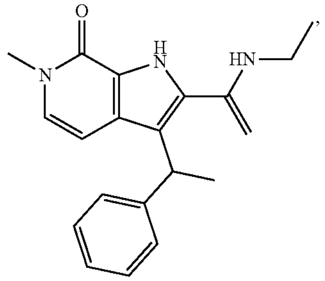
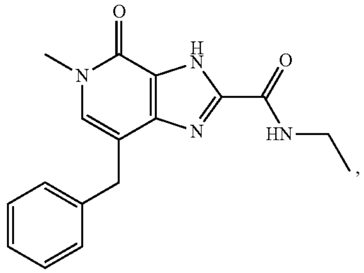
-continued
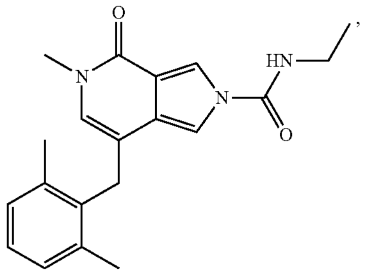
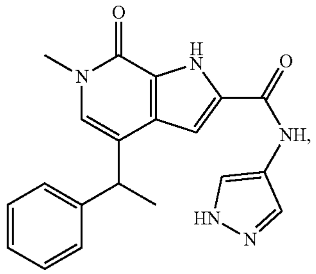
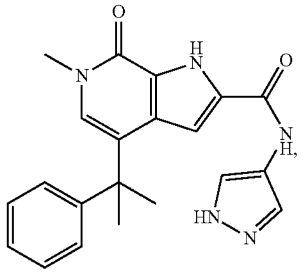
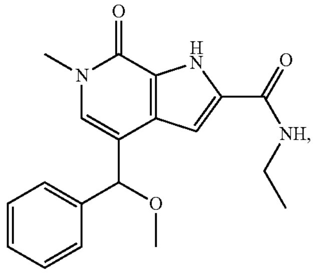
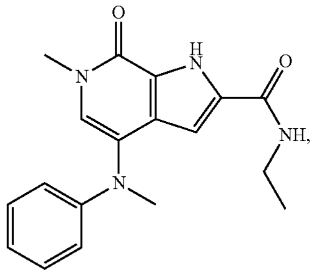
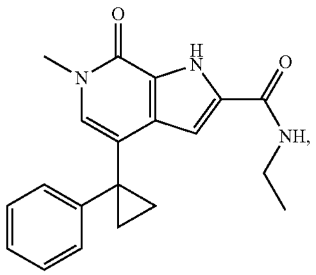

-continued
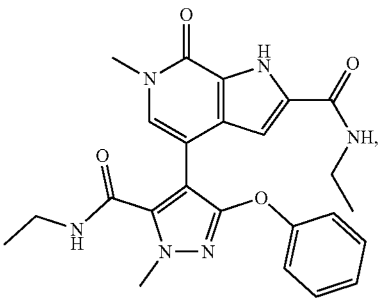
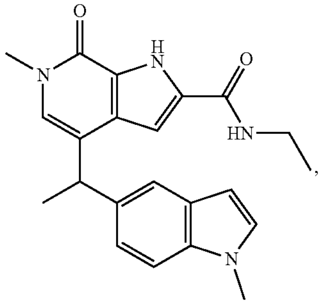
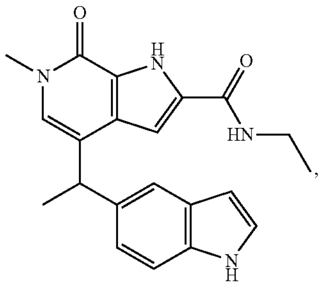
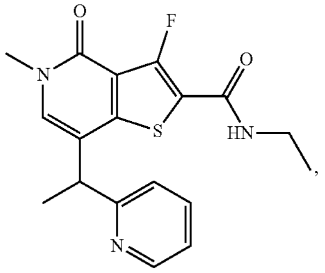
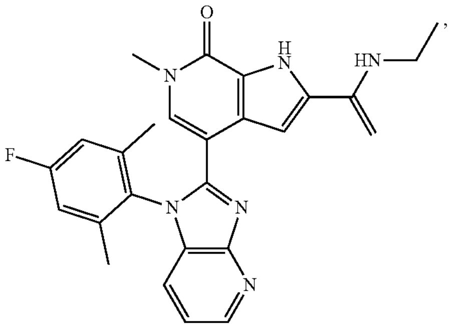
-continued
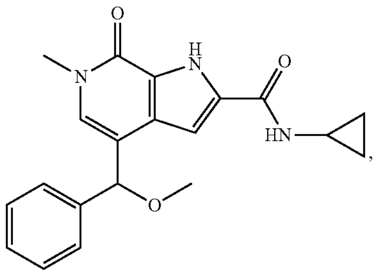
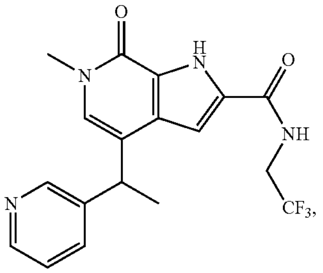
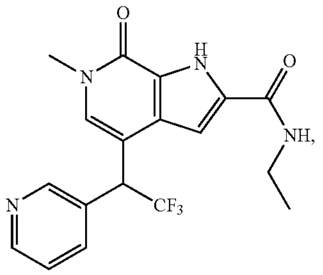
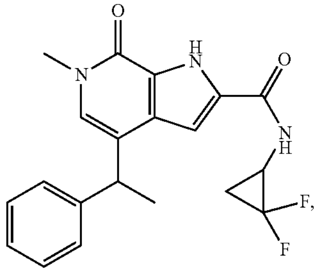
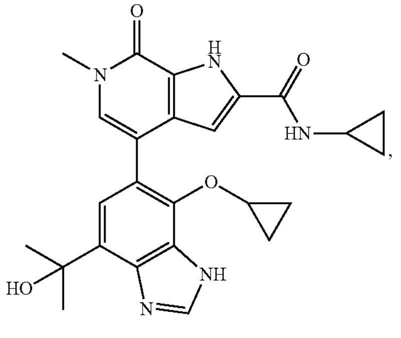

-continued
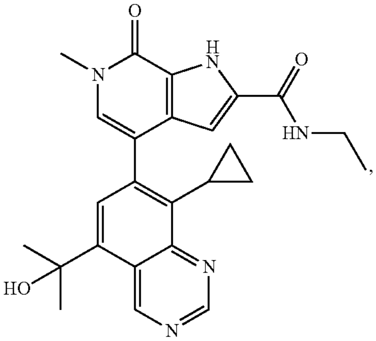,
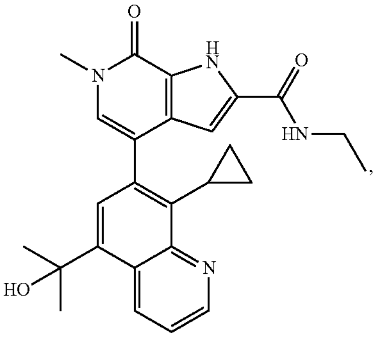,
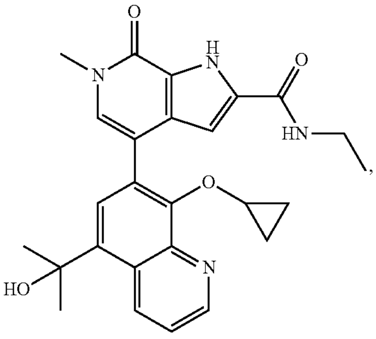,
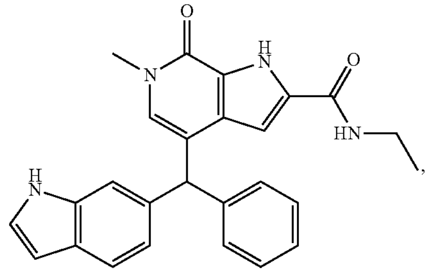,
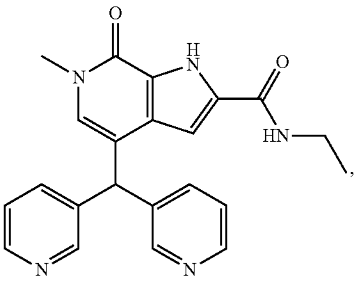,
-continued
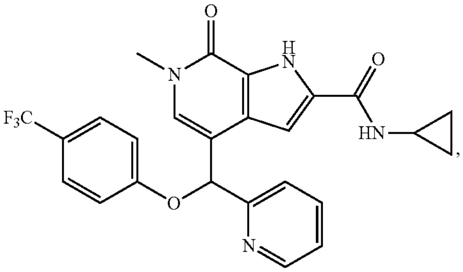,
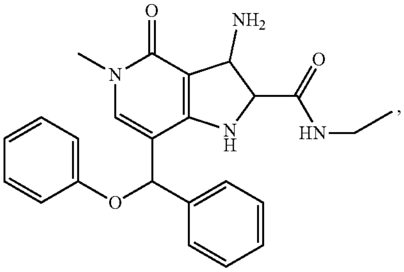,
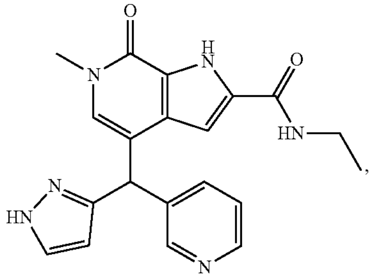,
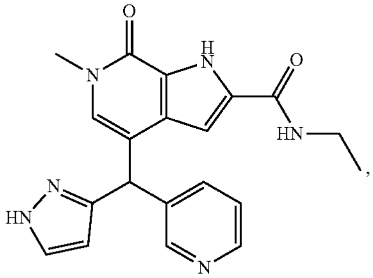,
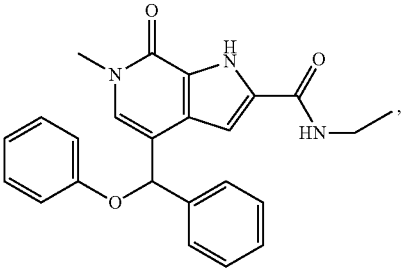,
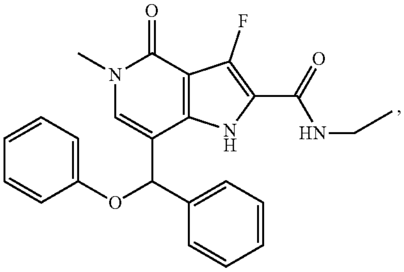, -continued
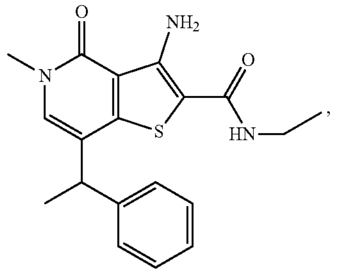
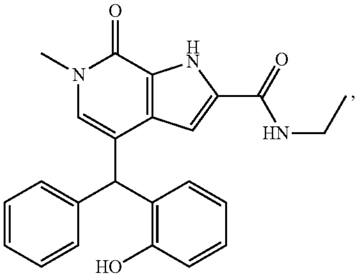
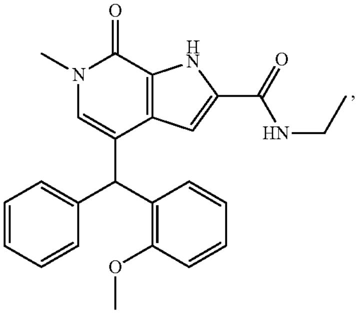
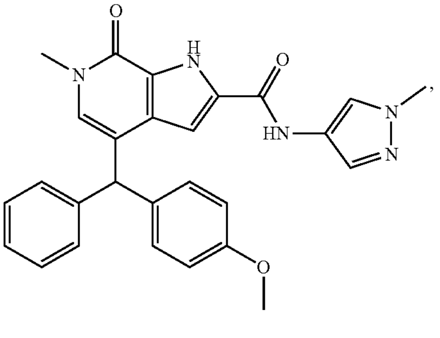
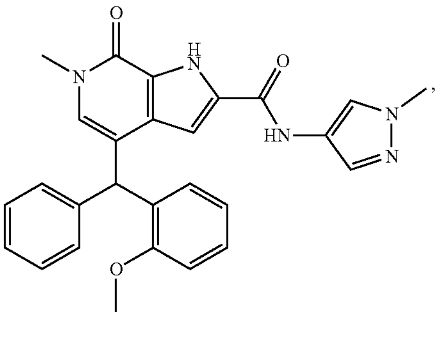
-continued
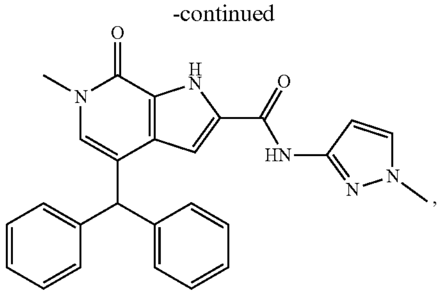
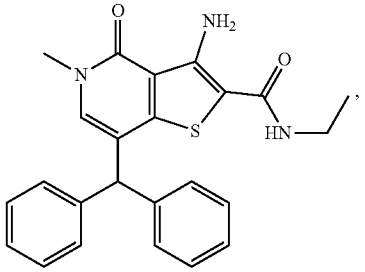
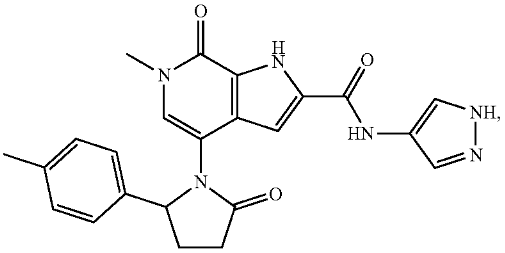
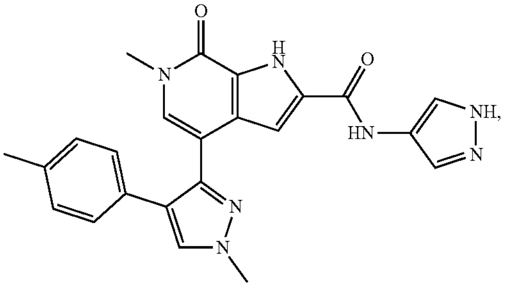
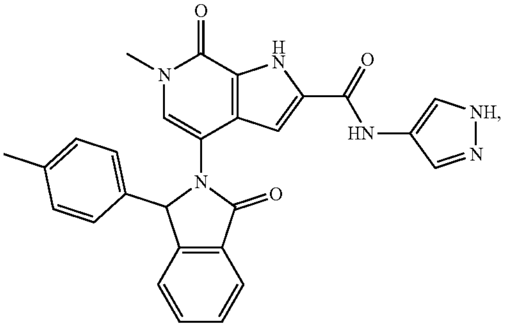
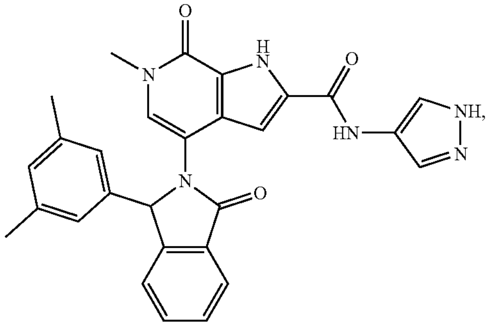

-continued
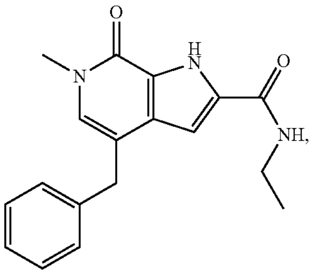
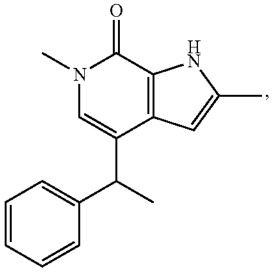
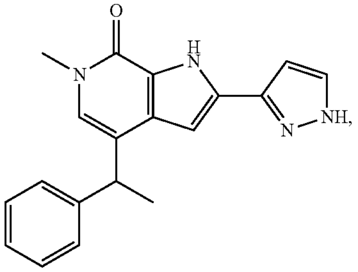
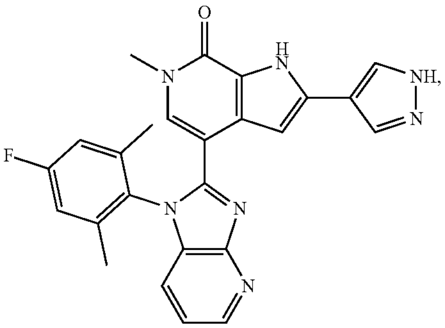
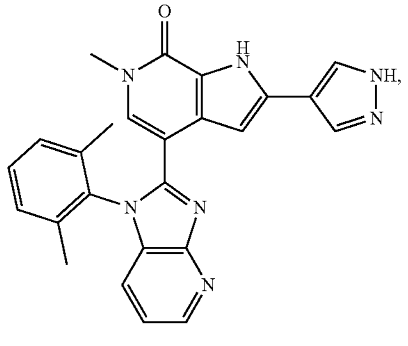
-continued
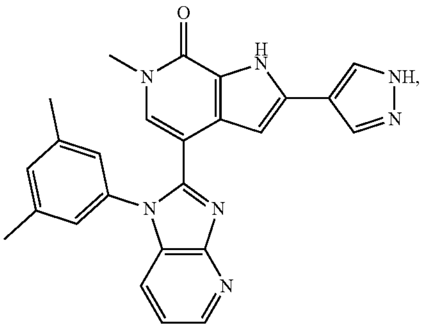
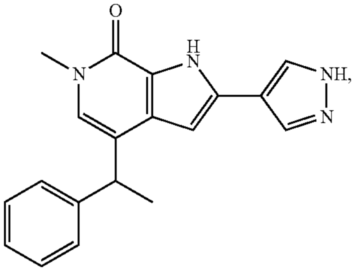
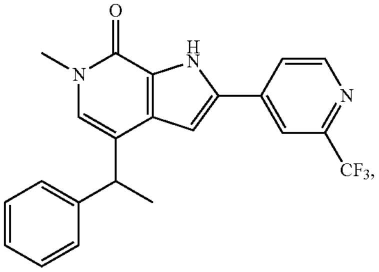
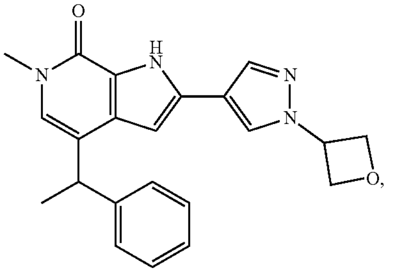
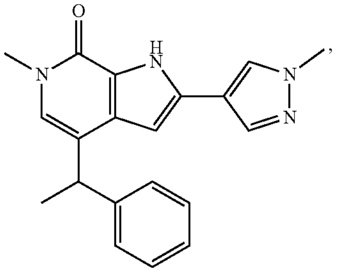
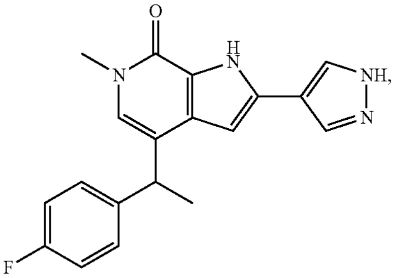

-continued
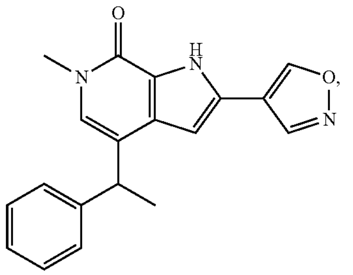
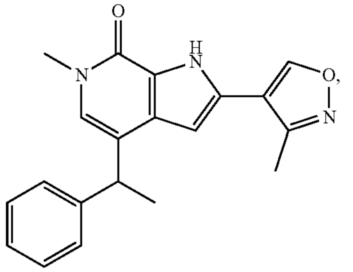
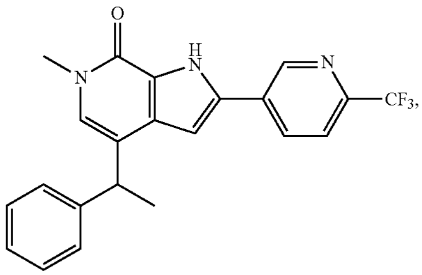
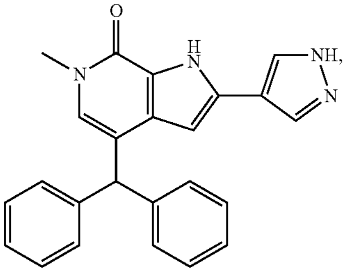
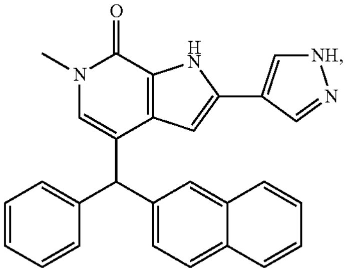
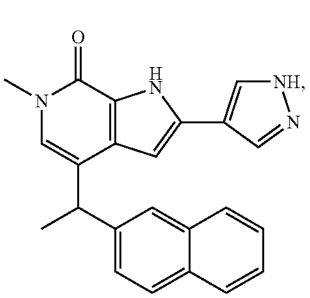
-continued
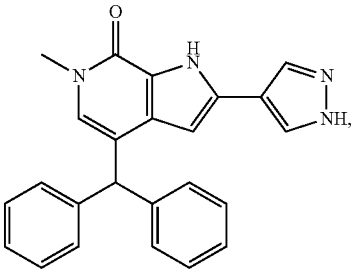
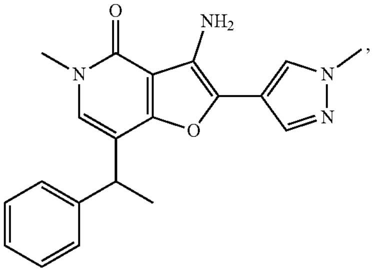
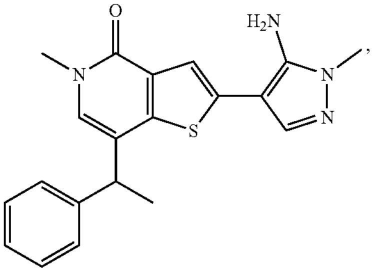
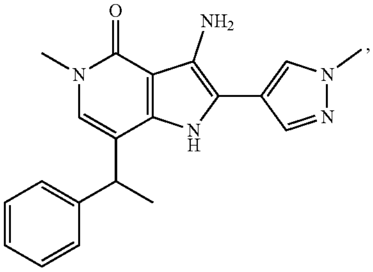
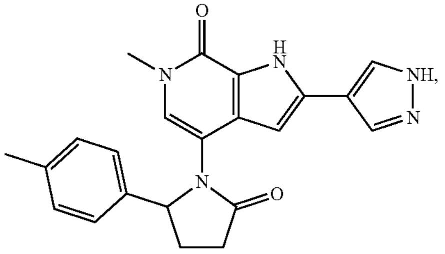
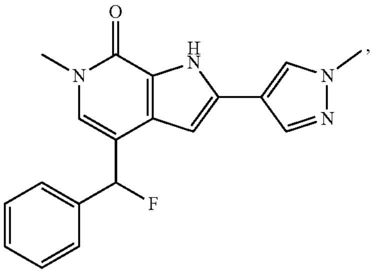

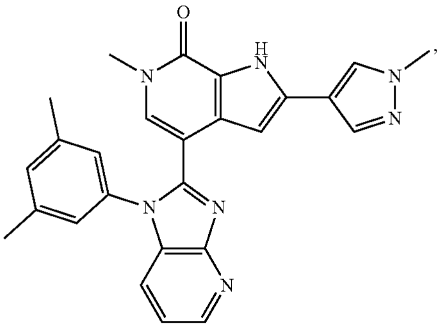
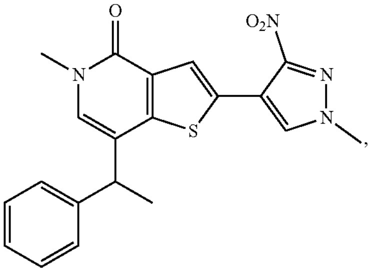
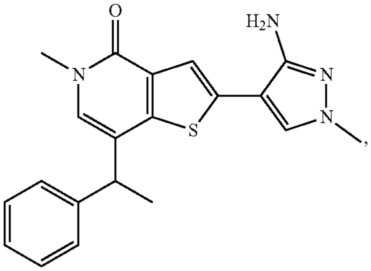
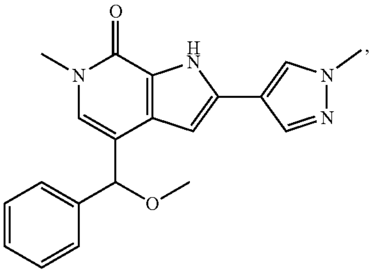
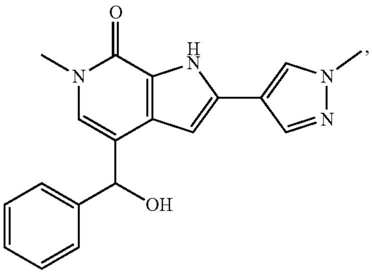
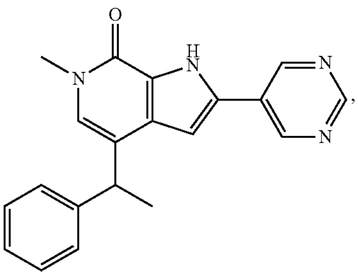
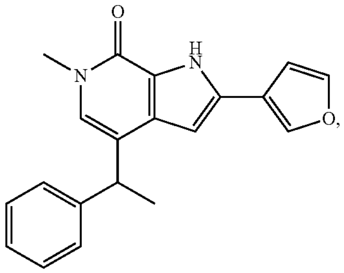
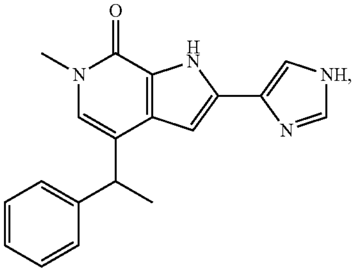
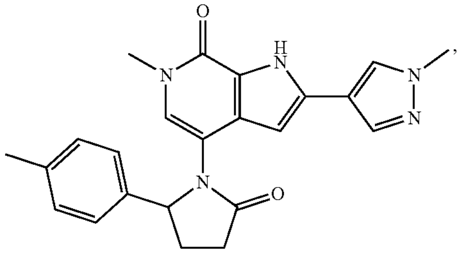
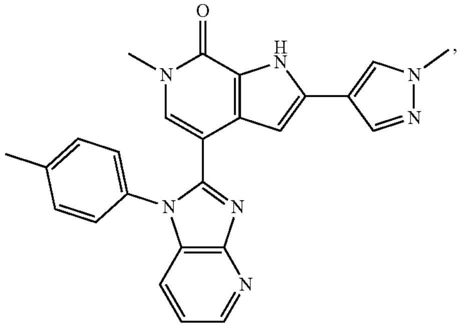
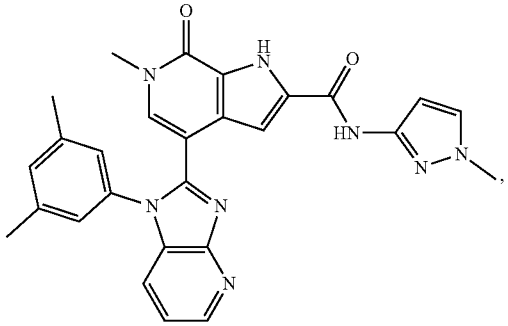

-continued
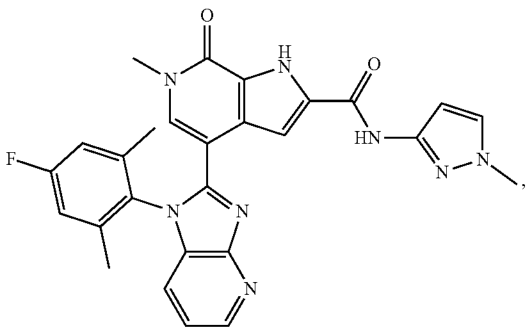
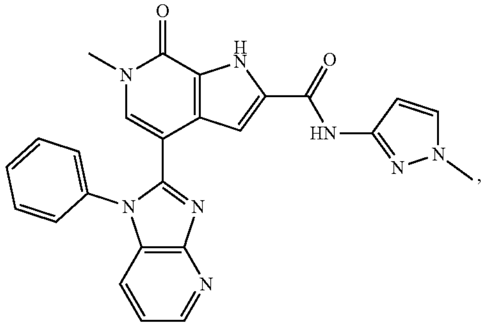
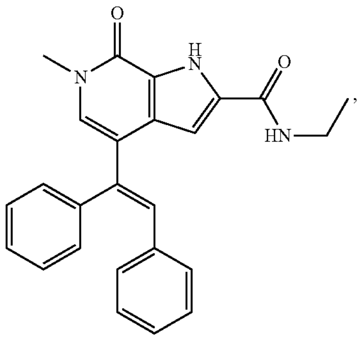
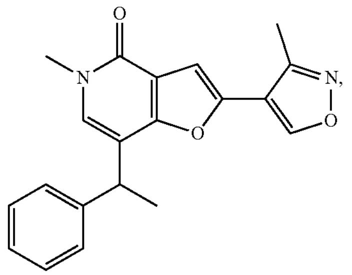
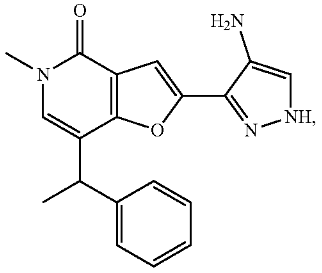
-continued
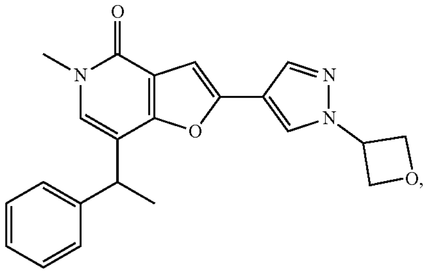
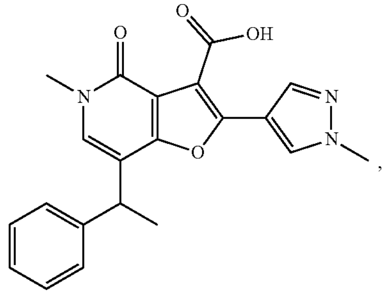
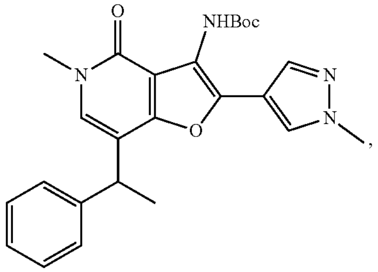
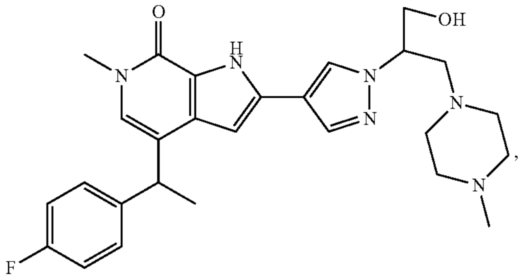
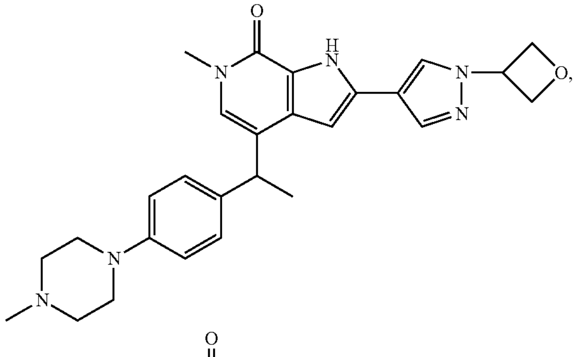
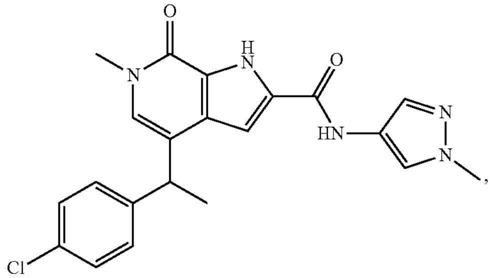

-continued

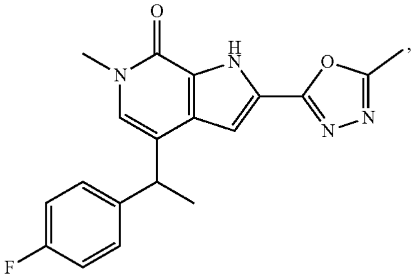
,

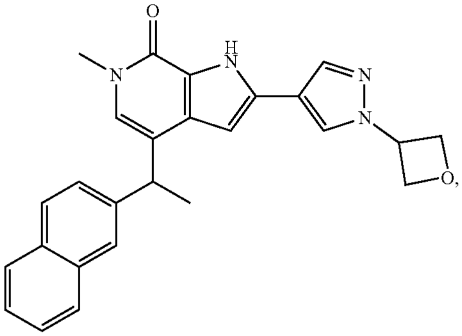
,

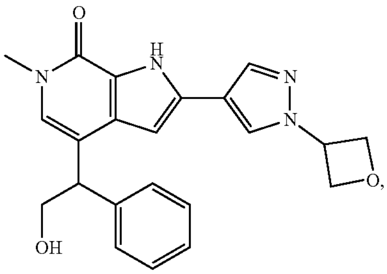
,

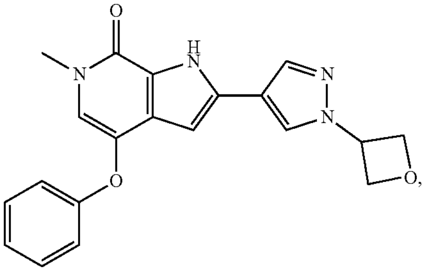
,

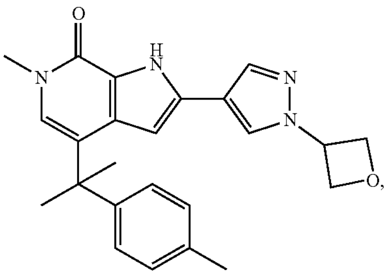
,

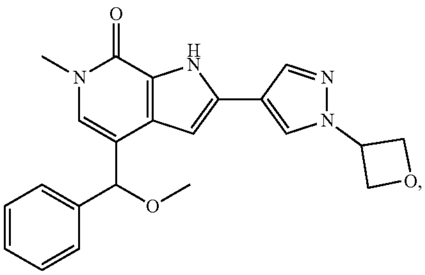
,

-continued

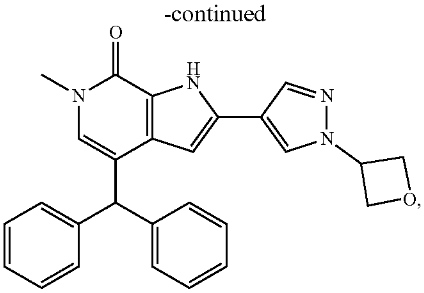
,

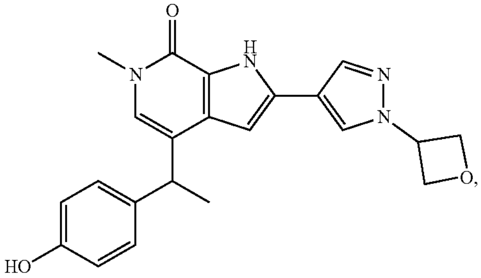
,

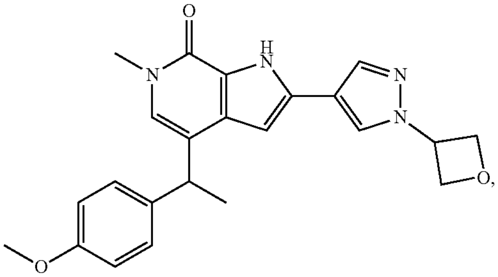
,

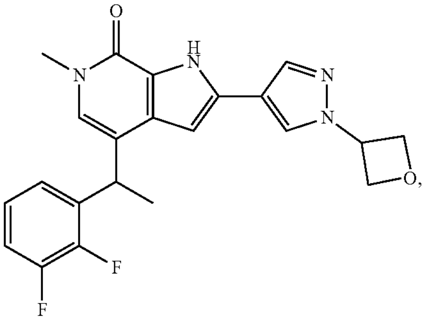
, or

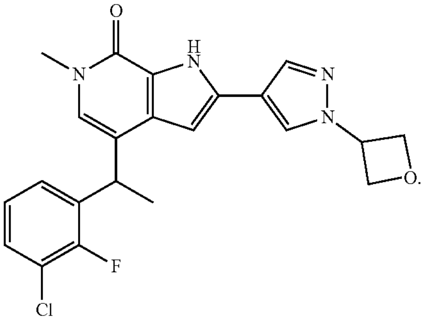
.

The compounds of the present invention possess asymmetric center, chiral axe and chiral plane, and may exist as racemates, R-isomers or S-isomers. Those skilled in the art can obtain the R-isomer and/or S-isomer from the racemate through resolution by conventional technical means.

The second aspect of the present invention provides a pharmaceutical composition comprising the compound, the deuterated compound, stereoisomer, racemate, geometric isomer, tautomer, prodrug, hydrate, solvate or pharmaceutically acceptable salt thereof according to the first aspect; and a pharmaceutically acceptable carrier or excipient.

The novel compounds provided by the present invention can be used alone or mixed with pharmaceutically acceptable auxiliary material (such as excipient, diluent, etc.) to prepare tablets, capsules, granules or syrups for oral administration. The pharmaceutical composition can be prepared according to conventional methods in pharmacy.

The third aspect of the present invention provides use of the compound, the deuterated compound, stereoisomer, racemate, geometric isomer, tautomer, prodrug, hydrate, solvate or pharmaceutically acceptable salt thereof according to the first aspect or the pharmaceutical composition according to the second aspect in the manufacture of a medicament for the treatment and/or prevention of a disease mediated by a bromodomain protein; or as a bromodomain protein inhibitor product.

In another preferred embodiment, the disease mediated by a bromodomain protein is selected from cancer, inflammatory disease, cardiovascular disease, viral infection, fibrotic disease, metabolic disease, acute rejection of transplanted organs, multiple organ dysfunction syndrome or Alzheimer's disease.

It should be understood that within the scope of the present invention, each foregoing technical feature of the present invention and each technical feature described specifically below (e.g., examples) may be combined with each other to form a new or preferred technical solution. Each feature disclosed in the specification may be replaced by any alternative feature serving the same, equivalent or similar purpose. Due to space limitations, those will not be redundantly repeated herein.

DETAILED DESCRIPTION

The inventors of the present application have conducted extensive and intensive research and have designed and synthesized a series of small molecule compounds with novel structure represented by general formula (I). These compounds or deuterated compounds, stereoisomers, racemates, geometric isomers, tautomers, prodrugs, hydrates, solvates, crystalline forms or pharmaceutically acceptable salts thereof and pharmaceutical compositions have high bromodomain protein inhibitory activity, especially the inhibitory activity targeting BRD4, and can be used to treat or/and prevent diseases mediated by bromodomain protein, providing a new treatment option for the treatment of diseases such as cancer and inflammation. On this basis, the present invention has been completed.

Term

The following terms and symbols used in this application have the meanings set forth below unless the context in which it is used dictates otherwise.

Said "deuterated compound" in the present invention refers to the form in which any hydrogen on the compound is deuterium, especially including the following compounds:

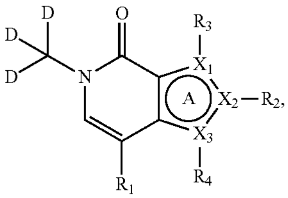

,

-continued

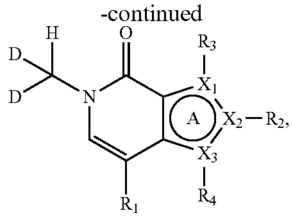

,

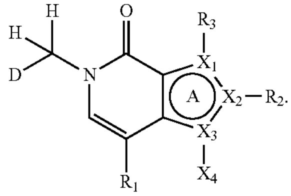

.

A dash ("-") not between two letters or symbols indicates the site of attachment of the substituent. For example, C1-C6 alkylcarbonyl- refers to a C1-C6 alkyl attached to the rest of the molecule through a carbonyl. However, when the site of attachment of the substituent will be apparent to those skilled in the art, e.g., halogen substituent, "-" may be omitted.

When the valence bond of a group has a wavy line "", such as in

"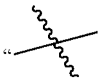", the wavy line indicates the site of attachment of the group to the rest of the molecule.

The term "halogen" as used herein refers to fluorine, chlorine, bromine, or iodine.

The term "alkyl" as used herein refers to straight or branched chain alkyl.

The term "heteroaryl" as used herein refers to a monocyclic aromatic hydrocarbon group having 5, 6 or 7 ring atoms, for example having 6 ring atoms, wherein one or more, e.g. 1, 2 or 3, e.g. 1 or 2 ring heteroatoms independently selected from N, O and S (e.g. N) are in the ring and the remaining ring atoms are carbon atoms; and

- a bicyclic aromatic hydrocarbon group (fused) having 8-12 ring atoms, for example having 9 or 10 ring atoms, wherein one or more, e.g. 1, 2, 3 or 4, e.g. 1 or 2 ring heteroatoms independently selected from N, O and S are in the ring, the remaining ring atoms are carbon atoms, and at least one ring is aromatic ring;
- when the total number of S atom and O atom in the heteroaryl exceeds 1, these S and O heteroatoms are not adjacent to each other;
- specifically, such as imidazolyl, pyridyl, pyrrolyl, thiazolyl, furanyl, oxazolyl, isoxazolyl, pyrazolyl, thienyl, pyrimidinyl, 1,2,4-triazolyl, etc.; preferably five-membered heteroaryl, such as imidazolyl, isoxazolyl, 1,2,4-triazolyl, benzoxazolyl, imidazopyridyl, triazolopyridyl, benzofuranyl, pyrazolopyrimidinyl, benzodioxolyl, indolyl, quinolyl, isoquinolyl and so on.

The term "heterocycloalkyl" as used herein refers to a heterocycloalkyl (including monocyclic ring, bridge ring, or spiro ring) containing at least 1 carbon atom and 1-4 heteroatoms selected from O, S and N, such as 3-12-membered heterocycloalkyl, 3-8-membered heterocycloalkyl, 3-6-membered heterocycloalkyl, etc.; such as oxetanyl, oxacyclohexyl, azetidinyl, oxiranyl, aziridinyl, thietanyl, 1,2-dithiocyclobutyl, 1,3-dithiocyclobutyl, azepanyl, oxepanyl, 3-azabicyclo[3.1.0]hexyl, 3,6-diazabicyclo[3.1.1]heptyl, 6-azabicyclo[3.1.1]heptyl, 3-azabicyclo[3.1.1]heptyl, 3-azabicyclo[4.1.0]heptyl, azabicyclo[2.2.2]hexyl, 2-azabicyclo[3.2.1]octyl, 8-azabicyclo[3.2.1]octyl, 2-azabicyclo[2.2.2]octyl, 8-azabicyclo[2.2.2]octyl, 7-oxabicyclo[2.2.1]heptyl, azaspiro[3.5]nonanyl, azaspiro[2.5]octyl, azaspiro[4.5]decyl, azaspiro[5.5]undecyl and so on.

As used herein, the terms “alkylcarbonyl” or “alkylacyl” refers to an alkyl attached to other group through a carbonyl, ie, alkyl-C(O)—, wherein alkyl is defined as herein. Similarly, “cycloalkylcarbonyl”, “cycloalkylacyl”, “heterocycloalkylcarbonyl” and “heterocycloalkylacyl” are all attached to other group through carbonyl.

The term “alkoxycarbonyl” or “alkyloxycarbonyl” as used herein refers to an alkoxy attached to other group through a carbonyl, ie, alkoxy-C(O)—.

The term “C1-C6 ester group” as used herein refers to the group C1-C6 alkyl-C(O)—O—, wherein alkyl is defined as above.

The term “alkylaminoacyl” as used herein refers to alkyl-NH—C(O)—. For example, C1-C6 alkylaminoacyl is C1-C6 alkyl-NH—C(O)—.

The term “alkylamido” as used herein refers to alkyl-C(O)—NH—. For example, C1-C6 alkylamido is C1-C6 alkyl-C(O)—NH—.

The term “C3-C6 cycloalkyloxy” or C3-C6 cycloalkoxy as used herein refers to C3-C6 cycloalkyl-O—.

The term “aryloxy” as used herein refers to aryl-O—.

“Substituted” as used herein is mono- or polysubstituted, such as di-, tri-, tetra- or penta-substitution.

The term “pharmaceutically acceptable salt” as used herein refers to a non-toxic, biologically tolerable acid addition salt or base addition salt of a compound of formula (I) suitable for administration to a subject, including but not limited to: acid addition salt of compounds of formula (I) with inorganic acids, such as hydrochloride, hydrobromide, carbonate, bicarbonate, phosphate, sulfate, sulfite, nitrate, etc.; and acid addition salt of compounds of formula (I) with organic acids, such as formate, acetate, malate, maleate, fumarate, tartrate, succinate, citrate, lactate, methanesulfonate, p-toluenesulfonate, 2-hydroxyethanesulfonate, benzoate, salicylate, stearate and salt formed with alkanedicarboxylic acids of formula $HOOC-(CH_2)_n-COOH$ (wherein n is 0-4). “Pharmaceutically acceptable salt” also includes base addition salt of a compound of formula (I) having acidic group with pharmaceutically acceptable cation such as sodium, potassium, calcium, aluminum, lithium and ammonium.

The compounds of the present invention may exist in the form of solvate. The term “solvate” means a solvent addition form comprising stoichiometric or non-stoichiometric amounts of solvent. If the solvent is water, the solvate formed is a hydrate, and when the solvent is ethanol, the solvate formed is an ethanolate.

The term “prodrug” as used herein refers to an active or inactive compound that is chemically modified into a compound of the present invention by in vivo physiological effect such as hydrolysis, metabolism, and the like after administration to an individual. The suitability and techniques involved in making and using prodrugs are well known to those skilled in the art. Exemplary prodrugs are, for example, esters of free carboxylic acids and S-acyl derivatives of thiols and O-acyl derivatives of alcohols or phenols. Suitable prodrugs are generally pharmaceutically acceptable ester derivatives that can be converted to the parent carboxylic acid by solvolysis under physiological conditions, such as lower alkyl esters, cycloalkyl esters, lower alkenyl esters, benzyl esters, mono- or di-substituted lower alkyl esters, such as ω-(amino, mono- or di-lower alkylamino, carboxyl, lower alkoxycarbonyl)-lower alkyl esters, α-(lower alkanoyloxy, lower alkoxycarbonyl or di-lower alkylaminocarbonyl)-lower alkyl esters, such as pivaloyloxymethyl ester and the like, which are conventionally used in the art.

It will be understood by those skilled in the art that some compounds of formula (I) may contain one or more chiral centers and therefore exist as two or more stereoisomers. Accordingly, the compound of the present invention may exist as individual stereoisomer (eg, enantiomer, diastereomer) and mixtures thereof in any ratio, such as racemate, and, where appropriate, it can exist in the form of its tautomer and geometric isomer.

The term “stereoisomer” as used herein refers to compounds that have the same chemical composition, but differ in the arrangement of atoms or groups in space. Stereoisomer includes enantiomer, diastereomer, conformer, and the like.

As used herein, the term “enantiomers” refers to two stereoisomers of a compound that are non-superimposable mirror images of each other.

The term “diastereomer” as used herein refers to a stereoisomer having two or more centers of chirality, whose molecules are not mirror images of each other. The mixture of diastereomers can be separated by high resolution analytical methods such as electrophoresis and chromatography such as HPLC.

The terms “racemic mixture” and “racemate” refer to an equimolar mixture of two enantiomers without optical activity.

The racemic mixture can be used in its own form or can be resolved into individual isomers for use. Stereochemically pure compounds can be obtained or a mixture of one or more isomers can be enriched by resolution.

The term “tautomer” or “tautomeric form” as used herein refers to structural isomers having different energy that are interconvertible via a low energy barrier. For example, proton tautomers (also known as proton transfer tautomers) include interconversions by migration of protons, such as keto-enol and imine-enamine isomerizations. Valence tautomers include interconversions through recombination of some of the bonding electrons.

As used herein, the term “geometric isomer” is an isomer caused by the inability of a double bond or a single bond of a ring carbon atom to rotate freely, also known as cis-trans isomer. Isomers with substituent groups on the same side of the plane are cis-isomers, and isomers on the opposite side of the plane are trans-isomers The term “treatment” as used herein refers to the administration of one or more drug substances to an individual suffering from a disease or having symptoms of the disease for the purpose of curing, relieving, alleviating, altering, treating, improving, ameliorating, or affecting the disease or symptoms of the disease.

The term “prevention” as used herein refers to the administration of one or more drug substances to an individual with a predisposition to the disease in order to prevent the individual from developing the disease.

Preparation Method

In another preferred embodiment, the preparation method of the compound of the present invention is selected from the following methods:

2)

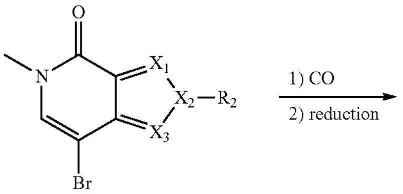

A1

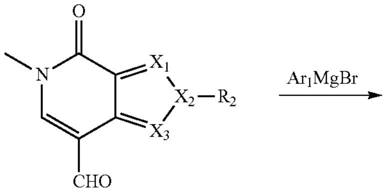

A2

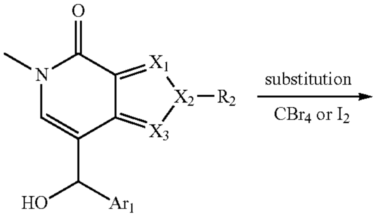

I-1-2

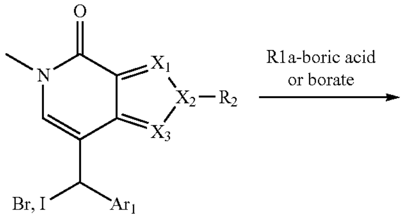

I-1-3

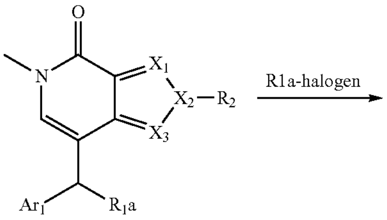

I-1-4

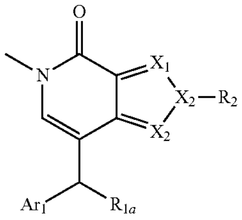

I-1-5

-continued

3)

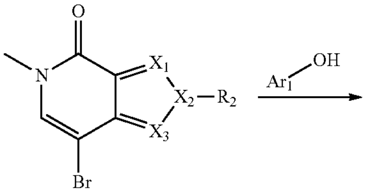

A1

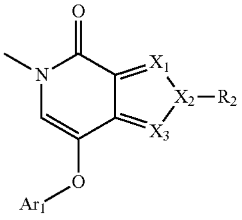

I-1-6

4)

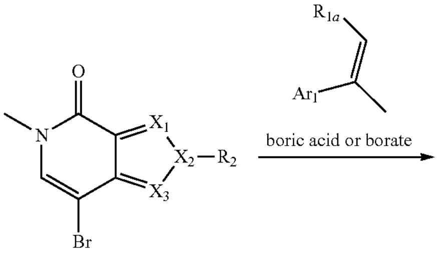

A1

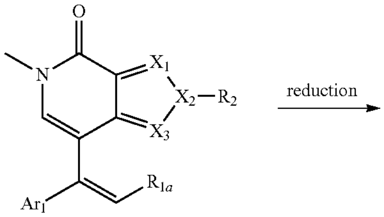

I-1-7

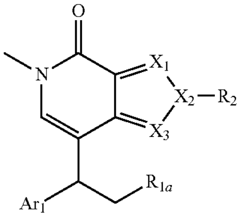

I-1-8 method 1), reacting compound A1 with $Ar_1$-NH—$R_{1a}$ via coupling to obtain compound I-1-1; or method 2), reacting compound A1 with CO via reduction to obtain compound A2;

reacting compound A2 with $Ar_1$-MgBr via coupling to obtain compound I-1-2;

reacting compound I-1-2 with $CBr_4$ or $I_2$ via substitution to obtain compound I-1-3;

reacting compound I-1-3 with $R_{1a}$-boronic acid or Ria-borate to obtain compound I-1-4; or reacting compound I-1-2 with $R_{1a}$-halogen via coupling to obtain compound I-1-5; or method 3), reacting compound A1 with $Ar_1$-OH via coupling to obtain compound I-1-6; or method 4), reacting compound A1 with

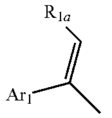

boronic acid or borate via coupling to obtain compound I-1-7;

reducing compound I-1-7 to obtain compound I-1-8, wherein, each substituent is defined as above; halogen is F, Cl, Br or I; $Ar_1$ is unsubstituted C5-C10 aryl or C5-C10 aryl substituted with one or more substituents selected from group B, or unsubstituted 5-8-membered heteroaryl or 5-8-membered heteroaryl substituted with one or more substituents selected from group B; $R_{1a}$ is selected from hydrogen, unsubstituted or halogenated C1-C6 alkoxy, unsubstituted or halogenated C3-C8 cycloalkyl, C3-C6 cycloalkyloxy, C1-C6 ester group, C1-C6 alkoxycarbonyl, C1-C6 alkylcarbonyl, C1-C6 alkylaminoacyl, C1-C6 alkylamido, unsubstituted C1-C6 alkyl or C1-C6 alkyl substituted with one or more substituents selected from group A, unsubstituted C5-C10 aryl or C5-C10 aryl substituted with one or more substituents selected from group B, unsubstituted 5-8 membered heteroaryl or 5-8 membered heteroaryl substituted with one or more substituents selected from group B, unsubstituted 4-8 membered heterocycloalkylacyl or 4-8 membered heterocycloalkylacyl substituted with one or more substituents selected from group B, or unsubstituted C5-C8 aryloxy or C5-C8 aryloxy substituted with one or more substituents selected from group B; wherein the "substituted" refers to substitution with one or more substituents selected from =O, hydroxy, halogen, C1-C4 alkoxy, C3-C6 cycloalkyl, C3-C6 cycloalkyl-O—, C1-C6 ester group, C1-C4 alkoxycarbonyl, C1-C4 alkylcarbonyl, C1-C4 alkylaminoacyl, C1-C4 alkylamido, unsubstituted C1-C4 alkyl or C1-C4 alkyl substituted with one or more substituents selected from group A, unsubstituted C5-C10 aryl or C5-C10 aryl substituted with one or more substituents selected from group B, unsubstituted 5-8 membered heteroaryl or 5-8 membered heteroaryl substituted with one or more substituents selected from group B, unsubstituted 4-6 membered heterocycloalkylacyl or 4-6 membered heterocycloalkylacyl substituted with one or more substituents selected from group B, or unsubstituted C6-C8 aryloxy or C6-C8 aryloxy substituted with one or more substituents selected from group B;

the group A includes the following substituents: amino, nitro, cyano, hydroxyl, halogen, phenyl, unsubstituted or halogenated C3-C8 cycloalkyl, unsubstituted or halogenated C3-C8 cycloalkyloxy;

the group B includes the following substituents: C1-C4 alkyl, nitro, cyano, fluorine, chlorine, bromine, trifluoromethoxy, hydroxyl, hydroxymethyl, amino, C1-C4 alkoxy, C3-C6 cycloalkyloxy, unsubstituted 4-8-membered heterocycloalkyl or 4-8-membered heterocycloalkyl substituted with C1-C6 alkyl, C1-C6 ester group, C1-C6 alkoxycarbonyl, C1-C6 alkylcarbonyl, C1-C6 alkylaminoacyl, C1-C6 alkylamido, —SO—(C1-C6 alkyl), —$SO_2$—(C1-C6 alkyl).

In another preferred embodiment, the preparation method of the compound of the present invention comprises the following steps:

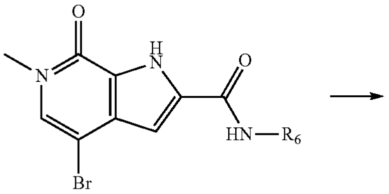

C1

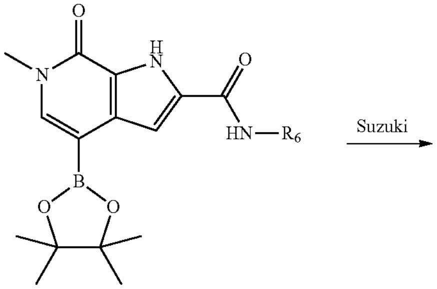

C2

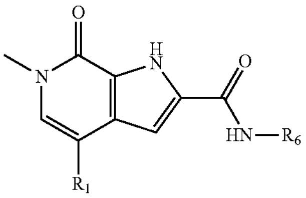

I-2

(a) reacting compound C1 with bis(pinacolato)diboron via Suzuki coupling to obtain boronate compound C2;

(b) reacting compound C2 with $R_1$—Br or $R_1$—I or $R_1$-OTf via Suzuki coupling and then subjecting a reduction reaction to obtain compound I-2;

wherein, each substituent is defined as above, and $R_1$ is not hydrogen, halogen or absent.

In another preferred embodiment, the preparation method of the compound of the present invention comprises the following steps:

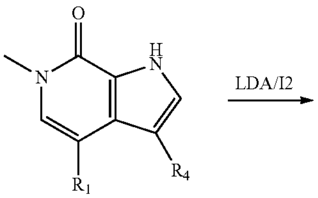

D1

-continued

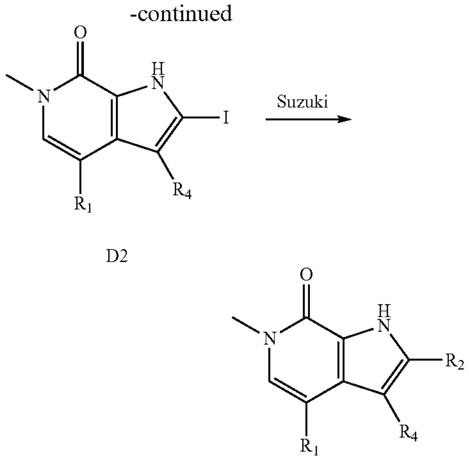

D2

I-3

(a) subjecting compound D1 to a dehydrogenation by LDA (lithium diisopropylamide) at low temperature and then iodination reaction to obtain compound D2;

(b) reacting compound D2 with $R_2$-boronic acid or $R_2$-borate via Suzuki coupling to obtain compound I-3, wherein, $R_1$ and $R_4$ are defined as above; $R_2$ is an unsubstituted or substituted 5-8-membered heteroaryl; the "substituted" refers to substitution with one or more substituents selected from C1-C6 alkyl, halogenated C1-C6 alkyl, halogen, hydroxy, C5-C8 aryl, 5-8 membered heteroaryl, 3-12 membered heterocycloalky, C1-C6 alkoxy, C3-C6 cycloalkyl, C3-C6 cycloalkylxyo, C1-C6 ester group, C1-C6 alkoxycarbonyl, nitro, cyano, C1-C6 alkylamido, or unsubstituted amino or amino substituted with one or more substituents selected from group D; the group D includes the following substituents: C1-C6 alkyl, halogenated C1-C6 alkyl, C1-C6 alkylamido, C3-C6 cycloalkyl.

Use

The compounds and pharmaceutical compositions of the present invention are used to manufacture a medicament for the treatment and/or prevention of disease mediated by bromodomain protein; or product used as bromodomain protein inhibitor.

In another preferred embodiment, the disease mediated by bromodomain protein is selected from cancer, inflammatory disease, cardiovascular disease, viral infection, fibrotic disease, metabolic disease, acute rejection of transplanted organs or multiple organ dysfunction syndrome or Alzheimer's disease.

The cancer refers to a physiological condition in mammals that is typically characterized by unregulated cell growth. For example, the cancer is selected from hematological malignancy, lung cancer, multiple myeloma, neuroblastoma, colon cancer, testicular cancer, or ovarian cancer. In particular, the cancer is selected from lung cancer (e.g. small cell lung cancer or non-small cell lung cancer), NUT midline cancer (e.g. BRD3-NUT midline cancer or BRD4-NUT midline cancer), leukemia, mixed lineage leukemia (MLL), acute myelocytic leukemia (AML), biphenotype B myelomonocytic leukemia or erythroleukemia. In particular, the cancer is selected from Burkitt lymphoma, breast cancer, colon cancer, neuroblastoma, glioblastoma multiforme, chronic lymphocytic leukemia or squamous cell carcinoma.

The inflammatory disease is a disease involving an inflammatory response to bacterial, viral, fungal, parasitic and/or protozoal infection.

In particular, the inflammatory disease is selected from osteoarthritis, acute gout, multiple sclerosis, inflammatory bowel disease (e.g. Crohn's disease and ulcerative colitis), neuroinflammation, asthma, chronic obstructive airway disease, pneumonia, myositis, eczema, dermatitis, acne, cellulitis, obliterative disease, thrombosis, alopecia, nephritis, vasculitis, retinitis, uveitis, scleritis, sclerosing cholangitis, hypophysitis, thyroiditis, infectious shock, systemic inflammatory response syndrome (SIRS), toxic shock syndrome, acute lung injury, ARDS (adult respiratory distress syndrome), acute renal failure, burn, pancreatitis (e.g. acute pancreatitis), postoperative syndrome, sarcoidosis, Herxheimer's reaction, encephalitis, myelitis, meningitis, or malaria. In particular, the inflammatory disease is acute or chronic pancreatitis. In particular, the inflammatory disease is burn. In particular, the inflammatory disease is inflammatory bowel disease. In particular, the inflammatory disease is neuroinflammation. In particular, the inflammatory disease is sepsis or sepsis syndrome. In particular, the inflammatory disease is graft versus host disease (GVHD).

The cardiovascular disease is selected from atherosclerosis develop, atherosclerosis, occlusion of arterial stents, heart failure (e.g. congestive heart failure), coronary artery disease, myocarditis, pericarditis, heart valve disease, stenosis, restenosis, in-stent stenosis, angina, myocardial infarction, acute coronary syndrome, coronary artery bypass grafting, cardiopulmonary bypass, endotoxemia, ischemia-reperfusion injury, cerebrovascular ischemia (stroke), renal reperfusion injury, embolism (e.g. pulmonary embolism, renal embolism, hepatic embolism, gastrointestinal embolism, or peripheral extremity embolism) or myocardial ischemia.

The viral infection is DNA viral infection (e.g. dsDNA viral infection, ssDNA viral infection, RNA viral infection, and dsRNA viral infections), RNA viral infection, reverse transcription (RT) viral infection, ssRNA-RT viral infection or dsDNART viral infection. In particular, the viral infection is a human immunodeficiency virus (HIV) infection such as acquired immunodeficiency syndrome (AIDS), human papilloma virus (HPV) infection, hepatitis C virus (HCV) infection, herpes virus infection (e.g. herpes simplex virus (HSV) infection), Ebola virus infection, severe acute respiratory syndrome (SARS) or influenza virus infection.

The fibrotic disease is selected from renal fibrosis, postoperative stricture, keloid formation, liver cirrhosis, biliary cirrhosis, cardiac fibrosis, scleroderma, or idiopathic pulmonary fibrosis.

The metabolic disease is selected from endocrine diseases (such as Addison's disease), diabetes (such as type I diabetes, type II diabetes or gestational diabetes), obesity, fatty liver (NASH or others), cachexia, hypercholesterolemia or disorder of lipid metabolism regulated by apolipoprotein A1 (APOA1).

The present invention also provides a method for non-therapeutic inhibition of the activity of a bromodomain protein, comprising contacting an effective amount of the compound represented by formula (I), deuterated compound, stereoisomer, racemate, geometric isomer, tautomer, prodrug, hydrate, solvate or pharmaceutically acceptable salt thereof or the pharmaceutical composition with a bromodomain protein, thereby inhibiting bromodomain protein.

The present invention is further described below with reference to specific examples. It should be understood that these examples are only used to illustrate the present invention and not to limit the scope of the present invention. The experimental methods without specific conditions in the following examples are usually performed according to conventional conditions (such as those described in Sambrook et al., Molecular Cloning: Laboratory Manual (New York: Cold Spring Harbor Laboratory Press, 1989)) or according to conditions recommended by the manufacturer. Unless stated otherwise, percentage and part are percentage by weight and part by weight. Unless otherwise stated, ratios of liquids are by volume.

Unless otherwise defined, all professional and scientific terms used in this application have the same meanings as those familiar to those skilled in the art. In addition, any methods and materials similar or equal to the contents described can be used in the method of the present invention. The preferred methods and materials described herein are for demonstration purposes only.

The experimental materials and reagents used in the following examples can be obtained from commercial sources unless otherwise specified.

In the following examples, $^1$H-NMR spectra were obtained by Bluker AVANCE III 400 Hz.

Mass spectra were recorded with Waters UPLC H-Class+ QDa (ESI), shimadzu LCMS-2020 and Agilent 12606120 (ESI) mass spectrometers; reverse-phase preparative HPLC was a Waters UV-guided fully automatic purification system (XBridge Prep C18 10 μm OBD column); and SFC preparation system model was Waters Prep-80.

In the text, the Chinese names of reagents represented by chemical formulas or English letter abbreviations are listed as follows:

AcOH acetic acid
$AcONH_4$ ammonium acetate
$AlMe_3$ trimethyl aluminum
$BF_3$-$Et_2O$ boron trifluoride-diethyl ether solution
BOC tert-butoxycarbonyl
$BOC_2O$ di-tert-butyl dicarbonate
$CD_3OD$ deuterated methanol
CDI N,N'-carbonyldiimidazole
CH3COOK or AcOK potassium acetate
conc. concentrated
DCM dichloromethane
DEA diethanolamine
DIAD diisopropyl azodicarboxylate
DIPEA or DIEA N,N-diisopropylethylamine
DMAP 4-dimethylaminopyridine or N,N-dimethyl-4-aminopyridine
DMEA N,N-dimethylethanolamine
DMF dimethylformamide
DMSO dimethyl sulfoxide
EA or EtOAc ethyl acetate
EDCI 1-ethyl-(3-dimethylaminopropyl)carbodiimide
EtOH ethanol
$Et_3N$ triethylamine
$Et_3SiH$ triethylsilane
EtI iodoethane
FA formic acid
HOBt 1-hydroxybenzotriazole
HPLC high performance liquid chromatography
$^i$PrOH or IPA isopropanol
LCMS liquid chromatography-mass spectrometry
MeCN, ACN or $CH_3CN$ acetonitrile
MeI or $Me_3I$ iodomethane
MW microwave
MeOH methanol
$N_2H_4$ hydrazine
NBS N-bromosuccinimide
Pd/C palladium/carbon
$Pd_2dba_3$ tris(dibenzylideneacetone)dipalladium
$Pd(dppf)Cl_2$ or $PdCl_2(dppf)$ 1,1'-bis(diphenylphosphino)ferrocene palladium dichloride
PE petroleum ether
PhMgBr phenylmagnesium bromide
$PPh_3$ triphenylphosphine
Py pyridine
r.t. or RT room temperature
RuPhos Palladacycle chloro(2-dicyclohexylphosphino-2',6'-diisopropoxy-1,1'-biphenyl)[2-(2-aminoethylphenyl)]palladium(II)
SEM 2-(trimethylsilyl)ethoxymethyl
SEMCl 2-(trimethylsilyl)ethoxymethyl chloride
SFC supercritical fluid chromatography
$^t$BuNC 2-isocyano-2-methylpropane
t-BuONa sodium tert-butoxide
$T_3P$ 1-propylphosphoric anhydride
TEA triethylamine
$Tf_2O$ trifluoromethanesulfonic anhydride
TLC thin layer chromatography
TFA or $CF_3COOH$ trifluoroacetic acid
THF tetrahydrofuran
TMSI trimethylsulfoxide iodide
X-Phos 2-dicyclohexylphosphino-2,4,6-triisopropylbiphenyl Synthesis Route of Intermediate 7

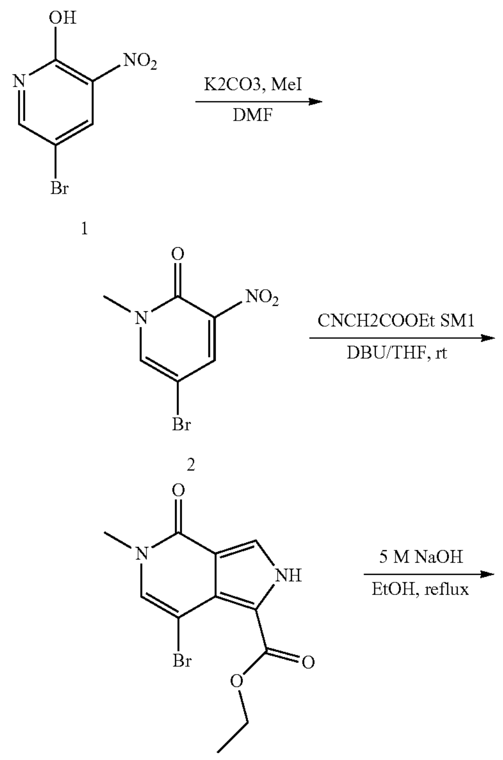

1
2
3

-continued

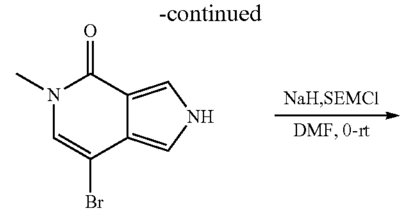

4

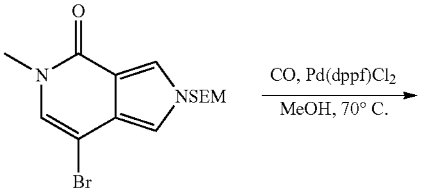

5

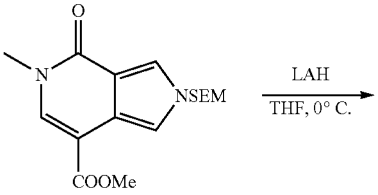

6

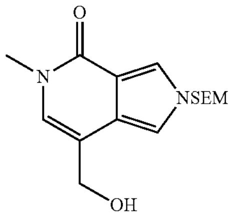

7

Step 1: Synthesis of 5-bromo-1-methyl-3-nitropyridin-2(1H)-one (Intermediate 2)

Intermediate 1 (7.0 g, 32 mmol), potassium carbonate (8.8 g, 64 mmol) and iodomethane (5.5 g, 38.4 mmol) were added successively to N,N-dimethylformamide (70 mL) at room temperature and reacted overnight. After the completion of the reaction monitored by TLC, the reaction solution was poured into ice water and extracted with ethyl acetate. The organic phase was washed with saturated brine, dried over anhydrous sodium sulfate, filtered, and the filtrate was concentrated, and separated by column (petroleum ether/ethyl acetate (v:v)=3/1) to obtain intermediate 2 as a yellow solid.

LCMS: m/z: 232.9 (M+H).

Step 2: Synthesis of ethyl 7-bromo-5-methyl-4-oxo-4,5-dihydro-2H-pyrrolo[3,4-c]pyridin-1-carboxylate (Intermediate 3)

Intermediate 2 (5.6 g, 24 mmol), ethyl isocyanoacetate (4 g, 36 mmol) and 1,8-diazacycloundecene, and diazabicyclo (7.3 g, 48 mmol) were successively added to tetrahydrofuran (56 mL) at 0° C. and reacted overnight at room temperature. After the completion of the reaction monitored by TLC, the reaction solution was poured into water and extracted with ethyl acetate. The organic phase was washed with saturated brine, dried over anhydrous sodium sulfate, filtered, and the filtrate was concentrated, and separated by column (petroleum ether/ethyl acetate (v:v)=1/2) to obtain intermediate 3 (4.6 g, yield: 64%) as a pale yellow solid.

LCMS: m/z 299.0 (M+H).

Step 3: Synthesis of 7-bromo-5-methyl-2,5-dihydro-4H-pyrrolo[3,4-c]pyridin-4-one (Intermediate 4)

Intermediate 3 (4.6 g, 15.4 mmol) and 5 M sodium hydroxide (15.4 mL, 77 mmol) were added to ethanol (50 mL) and refluxed overnight. After the completion of the reaction monitored by LC/MS (HHDED0032-129), the reaction solution was concentrated. The dry residue was dissolved in dichloromethane and the organic phase was washed with saturated brine, dried over anhydrous sodium sulfate, filtered, and concentrated to obtain intermediate 4 (3.0 g, yield: 86%) as a pale yellow solid.

LCMS: m/z 226.9 (M+H).

Step 4: Synthesis of 7-bromo-5-methyl-2-((2-(trimethylsilyl)ethoxy)methyl)-2,5-dihydro-4H-pyrrolo[3,4-c]pyridin-4-one (Intermediate 5)

60% sodium hydride (800 mg, 20.0 mmol) was added to a solution of intermediate 4 (3.0 g, 13.3 mmol) in N,N-dimethylformamide (20 mL) in an ice bath and reacted for 0.5 h in an ice bath. SEMCl (2.7 g, 16 mmol) was added dropwise to the reaction system, and the reaction was carried out in an ice bath for 0.5 h. After the completion of the reaction monitored by LC/MS, the reaction solution was poured into ice water and extracted with ethyl acetate. The organic phase was washed with saturated brine, dried over anhydrous sodium sulfate, filtered, and the filtrate was concentrated to obtain intermediate 5 (4.5 g, yield: 95%).

LCMS: m/z 357.0 (M+H).

Step 5: Synthesis of methyl 5-methyl-4-oxo-2-((2-(trimethylsilyl)ethoxy)methyl)-4,5-dihydro-2H-pyrrolo[3,4-c]pyridin-7-carboxylate (Intermediate 6)

Intermediate 5 (3.5 g, 9.8 mmol), triethylamine (3.0 g, 29.4 mmol) and 1,1-bis(diphenylphosphino)ferrocene palladium dichloride (358 mg, 0.49 mmol) were added successively to methanol (35 mL), replaced by carbon monoxide three times, and refluxed overnight. After the completion of the reaction monitored by TLC, the reaction solution was concentrated and the dry residue was dissolved in ethyl acetate. The organic phase was washed with saturated brine, dried over anhydrous sodium sulfate, filtered, and the filtrate was concentrated, and separated by column (petroleum ether, ethyl acetate (v:v)=2/1) to obtain intermediate 6 (2.5 g, yield: 75%) as a white solid.

LCMS: m/z 337.1 (M+H).

Step 6: Synthesis of 7-(hydroxymethyl)-5-methyl-2-((2-(trimethylsilyl)ethoxy)methyl)-2,5-dihydro-4H-pyrrolo[3,4-c]pyridin-4-one (Intermediate 7)

Intermediate 6 (2.5 g, 7.44 mmol) and lithium tetrahydroaluminum (707 mg, 18.6 mmol) were successively added to tetrahydrofuran (20 mL) in an ice bath and reacted at room temperature overnight. After the completion of the reaction monitored by LC/MS, the reaction solution was poured into ice water, extracted with dichloromethane, and the organic phase was washed with saturated brine, dried over anhydrous sodium sulfate, filtered, concentrated, and separated by column (petroleum ether/ethyl acetate (v:v)=1/2) to obtain intermediate 7 (1.0 g, yield: 43%) as a white solid.

LCMS: m/z 309.1 (M+H).

Example A1 and A2 Synthesis Route

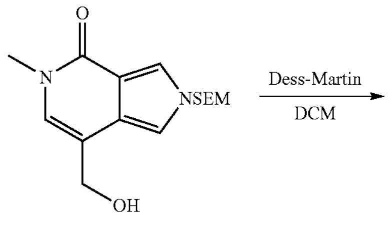

7

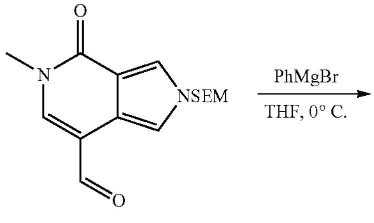

8

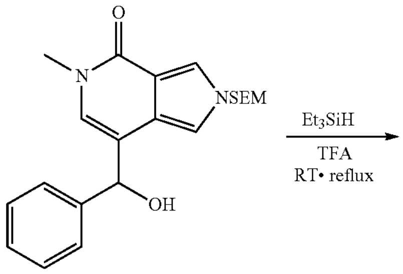

9

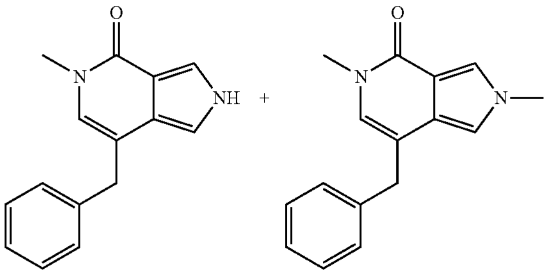

A1 A2

Step 1: Synthesis of (5-methyl-4-oxo-2-((2-(trimethylsilyl)ethoxy)methyl)-4,5-dihydro-2H-pyrrolo[3,4-c]pyridin-7-carbaldehyde) (Intermediate 8)

Dess-Martin oxidant (2.8 g, 6.5 mmol) was added to a solution of intermediate 7 (1.0 g, 3.25 mmol) in dichloromethane (10 mL) and reacted in an ice bath for 1 hour. After the completion of the reaction monitored by TLC, the reaction solution was poured into dichloromethane, washed with saturated brine, dried over anhydrous sodium sulfate, filtered, concentrated and separated by column (petroleum ether/ethyl acetate (v:v)=5/1) to obtain intermediate 8 (400 mg, yield: 40%).

Step 2: Synthesis of 7-(hydroxy(phenyl)methyl)-5-methyl-2-((2-(trimethylsilyl)ethoxy)methyl)-2,5-dihydro-4H-pyrrolo[3,4-c]pyridin-4-one (Intermediate 9)

At 0° C., phenylmagnesium bromide (3 mol/L, 0.7 mL, 1.97 mmol) was added dropwise to a solution of intermediate 8 (400 mg, 1.31 mmol) in THF (15 mL) under nitrogen protection and reacted for one hour. After the completion of the reaction monitored by TLC, the reaction solution was quenched with saturated ammonium chloride, extracted with ethyl acetate. The organic phase was washed with saturated brine, dried over anhydrous sodium sulfate, filtered, and the filtrate was concentrated, and separated by column (petroleum ether/ethyl acetate (v:v))=1:1) to obtain intermediate 9 (400 mg, yield: 79%) as a white solid.

LCMS: m/z 385.2 (M+H).

Step 3: Synthesis of 7-benzyl-2,5-dihydro-4H-pyrrolo[3,4-c]pyridin-4-one (A1) and 7-benzyl-5-methyl-2,5-dihydro-4H-pyrrolo[3,4-c]pyridin-4-one (A2)

Intermediate 9 (150 mg, 0.39 mmol) and triethylsilane (135 mg, 1.17 mmol) were added to trifluoroacetic acid (10 mL) and refluxed overnight. After the completion of the reaction monitored by TLC, the reaction solution was concentrated to dryness. The residue was dissolved in dichloromethane, washed with saturated aqueous sodium bicarbonate solution and saturated brine, dried over anhydrous sodium sulfate, filtered, and the filtrate was concentrated and separated by Prep-HPLC (dichloromethane/methanol (v:v)=10:1) to obtain 7-benzyl-2,5-dihydro-4H-pyrrolo[3,4-c]pyridin-4-one (A1) (55 mg, 60% purity). LCMS: m/z 239.0 (M+H). 7-benzyl-5-methyl-2,5-dihydro-4H-pyrrolo[3,4-c]pyridin-4-one (A2) (3 mg), white solid.

LCMS: m/z 253.3 (M+H). $^1$H-NMR (MeOD, 400 MHz): 7.44 (s, 1H), 7.27-7.23 (m, 4H), 7.19-7.17 (m, 1H), 6.77 (s, 1H), 6.64 (s, 1H), 3.85 (s, 2H), 3.82 (s, 3H), 3.47 (s, 3H).

Example A3 Synthesis Route

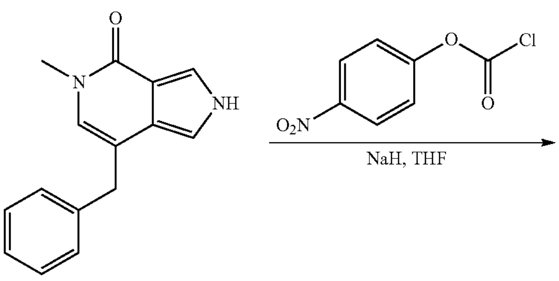

A1

-continued

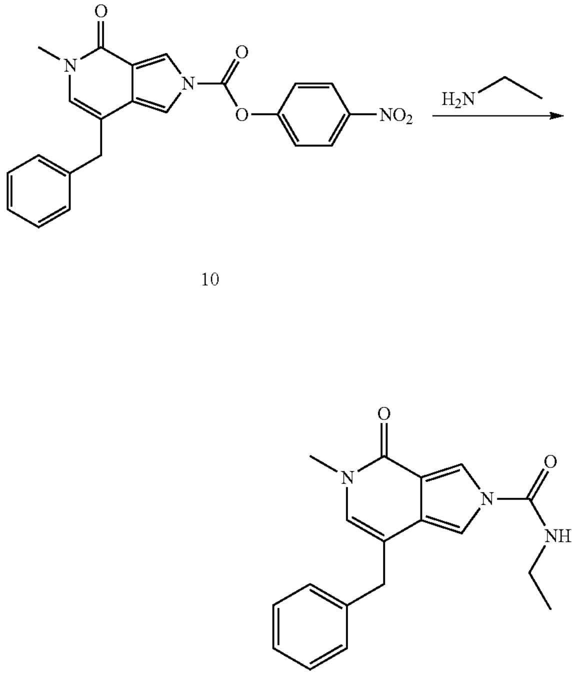

10

A3

Step 1: Synthesis of 4-nitrophenyl 7-benzyl-5-methyl-4-oxo-4,5-dihydro-2H-pyrrolo[3,4-c]pyridin-2-carboxylate (Intermediate 10)

In an ice bath, 60% sodium hydride (13 mg, 0.315 mmol) was added to a solution of intermediate A1 (50 mg, 0.21 mmol) in tetrahydrofuran (10 mL) and reacted for 0.5 h. p-nitrophenyl chloroformate (42 mg, 0.21 mmol) was added to the reaction system and reacted in an ice bath for 0.5 h. After the completion of the reaction monitored by TLC, the reaction solution was poured into ice water and extracted with ethyl acetate. The organic phase was washed with saturated brine, dried over anhydrous sodium sulfate, filtered, and the filtrate was concentrated to obtain intermediate 10 (60 mg, crude product) as a yellow oil, which was used directly in the next step.

Step 2: Synthesis of 7-benzyl-N-ethyl-5-methyl-4-oxo-4,5-dihydro-2H-pyrrolo[3,4-c]pyridin-2-carboxamide Intermediate 10 (60 mg, crude product) was added to ethylamine (3 mol/L solution in THF, 2 mL) and reacted at room temperature for 2 hours. After the completion of the reaction monitored by TLC, the reaction solution was concentrated by Prep-HPLC to obtain 2 mg of Example A3 (7-benzyl-N-ethyl-5-methyl-4-oxo-4,5-dihydro-2H-pyrrolo[3,4-c]pyridin-2-carboxamide) as a white solid.

LCMS: m/z 310.3 (M+H).

$^1$H-NMR (MeOD, 400 MHz): 8.03 (s, 1H), 7.37 (s, 1H), 7.37-7.25 (m, 4H), 7.20-7.17 (m, 1H), 6.70 (s, 1H), 3.86 (s, 2H), 3.38 (s, 3H), 3.49-3.41 (m, 2H), 1.24-1.19 (m, 3H).

Example A4 Synthesis Route

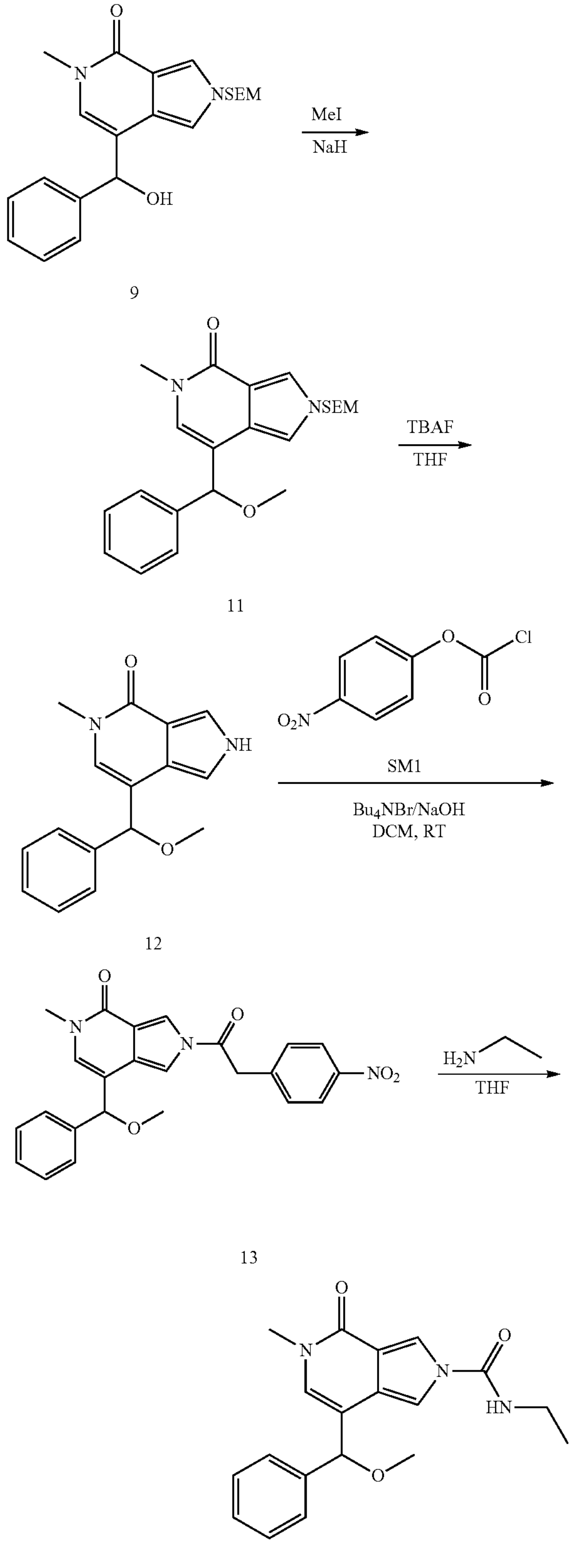

9

11

12

13

A4

Step 1: Synthesis of 7-(methoxy(phenyl)methyl)-5-methyl-2-((2-(trimethylsilyl)ethoxy)methyl)-2,5-dihydro-4H-pyrrolo[3,4-c]pyridin-4-one (Intermediate 11)

60% sodium hydride (62 mg, 1.56 mmol) was added to a solution of intermediate 9 (400 mg, 1.04 mmol) in N,N-dimethylformamide (3 mL) in an ice bath and reacted in an ice bath for 0.5 h. Iodomethane (162 mg, 1.144 mmol) was added dropwise to the reaction system and reacted at room temperature overnight. After the completion of the reaction monitored by LC/MS, the reaction solution was poured into ice water and extracted with ethyl acetate. The organic phase was washed with saturated brine, dried over anhydrous sodium sulfate, filtered, and the filtrate was concentrated to obtain intermediate 11 (400 mg, yield: 75%) as a pale yellow solid.

LCMS: m/z: 399.3 (M+H).

Step 2: Synthesis of 7-(methoxy(phenyl)methyl)-5-methyl-2,5-dihydro-4H-pyrrolo[3,4-c]pyridin-4-one (Intermediate 12)

Intermediate 11 (400 mg, 1 mmol) was added to tetrabutylammonium fluoride (1 mol/L, 15 mL) and reacted overnight at room temperature. After the completion of the reaction monitored by LC/MS (HHDED0032-130R3), the reaction solution was concentrated and the dry residue was dissolved in ethyl acetate. The organic phase was washed with saturated brine, dried over anhydrous sodium sulfate, filtered, and the filtrate was concentrated, and separated by column (dichloromethane/methanol (v:v)=30/1) to obtain intermediate 12 (230 mg, yield: 85%) as a yellow oil.

LCMS: m/z 269.0 (M+H).

Step 3: Synthesis of 4-nitrophenyl-7-(methoxy(phenyl)methyl)-5-methyl-4-oxo-4,5-dihydro-2H-pyrrolo[3,4-c]pyridin-2-carboxylate (Intermediate 13)

Intermediate 12 (217 mg, 0.81 mmol), sodium hydroxide (97 mg, 2.43 mmol), p-nitrophenyl chloroformate (163 mg, 0.81 mmol) and tetrabutylammonium bromide (13 mg, 0.041 mmol) were added to dichloromethane (5 mL) and reacted at room temperature for one hour. After the completion of the reaction monitored by TLC, the reaction solution was filtered and concentrated to obtain intermediate 13 (300 mg, crude product) as a yellow solid.

Step 4: Synthesis of (N-ethyl-7-(methoxy(phenyl)methyl)-5-methyl-4-oxo-4,5-dihydro-2H-pyrrolo[3,4-c]pyridin-2-carboxamide (A4)

Intermediate 13 (300 mg, crude product) was added to ethylamine (2 mol/L solution in THF, 3.5 mL) and reacted at room temperature for 2 hours. After the completion of the reaction monitored by TLC, the reaction solution was concentrated, and purified by Prep-TLC (dichloromethane/methanol (v:v)=20/1) to obtain compound A4 (N-ethyl-7-(methoxy(phenyl)methyl)-5-methyl-4-oxo-4,5-dihydro-2H-pyrrolo[3,4-c]pyridin-2-carboxamide, 100 mg) as a white solid.

A4 was subjected to SFC resolution to obtain A4-P1 (16 mg) and A4-P2 (18 mg).

A4-P1: LCMS: m/z 308.1 (M-MeO); $^1$H-NMR (DMSO, 400 MHz): 8.64-8.61 (m, 1H), 8.08 (s, 1H), 7.46-7.44 (m, 2H), 7.40 (s, 1H), 7.34-7.31 (m, 2H), 7.26-7.24 (m, 1H), 7.08 (s, 1H), 5.21 (s, 1H), 3.38 (s, 3H), 3.32-3.23 (m, 5H), 1.15-1.12 (m, 3H).

A4-P2: LCMS: m/z 308.1 (M-MeO); $^1$H-NMR (DMSO, 400 MHz): 8.65-8.62 (m 1H), 8.08 (s, 1H), 7.46-7.44 (m, 2H), 7.40 (s, 1H), 7.34-7.31 (m, 2H), 7.26-7.22 (m, 1H), 7.08 (s, 1H), 5.21 (s, 1H), 3.38 (s, 3H), 3.32-3.23 (m, 5H), 1.15-1.12 (m, 3H).

Intermediate 19: Synthesis Route of 4-bromo-2-(ethoxymethyl)-6-methyl-1,6-dihydro-7H-pyrrolo[2,3-c]pyridin-7-one (intermediate 19)

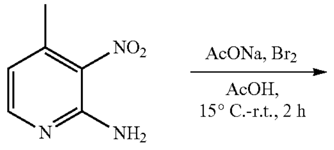

14

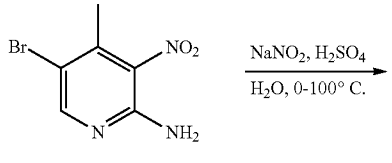

15

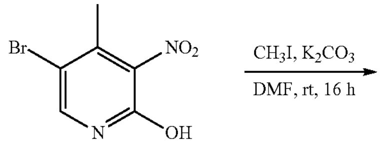

16

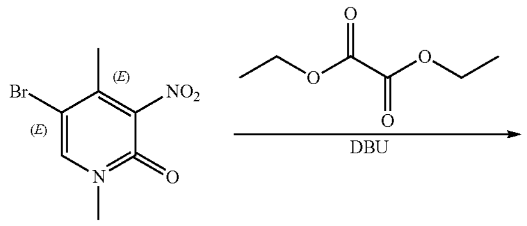

17

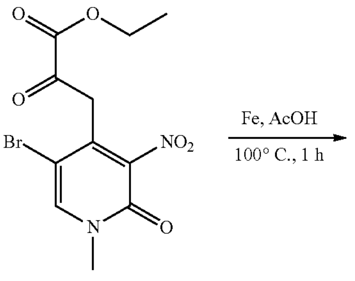

18

-continued

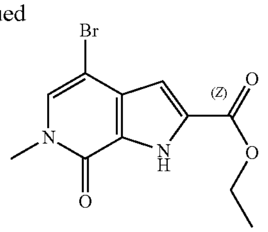

19

Step 1: Synthesis of 5-bromo-4-methyl-3-nitropyridin-2-amine (Intermediate 15)

Intermediate 14 (39.0 g, 0.25 mol), acetic acid (400 mL) and sodium acetate (41.8 g, 0.51 mol) were added in a dry 1000 mL three-necked flask at room temperature and then cooled to 15° C. A solution of liquid bromine (61 g) in acetic acid (100 mL) was added dropwise. The system temperature was maintained at 15° C. during the dropwise addition, and the dropwise addition was completed in 2 hours. After the completion of the reaction monitored by LCMS, the reaction solution was poured into ice water (2000 mL), and filtered to obtain a solid. The solid was dissolved in ethyl acetate (500 mL), washed with saturated sodium bicarbonate solution (300 mL), dried over anhydrous sodium sulfate and filtered. The filtrate was concentrated under reduced pressure, and the resulting product was dissolved in N,N-dimethylformamide (200 mL), poured into ice water (2000 mL) and filtered. The filter cake was dried to obtain 5-bromo-4-methyl-3-nitropyridin-2-amine (intermediate 15) (53.1 g, yellow solid), yield: 89.8%.

LCMS: m/z 231.8/233.8 (M+H).

Step 2: Synthesis of 5-bromo-4-methyl-3-nitropyridin-2-ol (Intermediate 16)

Intermediate 15 (25 g, 0.11 mmol) and a solution of sulfuric acid (25 mL) in water (600 mL) were added successively in a dry 1000 mL three-necked flask at room temperature and then cooled to 0° C. A solution of sodium nitrite (18.6 g) in water (600 mL) was added dropwise over two hours and then gradually raised to room temperature, heated to 100° C. and stirred for 2 hours. After the completion of the reaction monitored by LCMS, the reaction solution was poured into ice water (2000 mL) and filtered. The filter cake was dried to obtain 5-bromo-4-methyl-3-nitropyridin-2-ol (intermediate 16) (21.3 g, brown solid), yield: 77%.

LCMS: m/z 232.8/234.8 (M+H).

Step 3: Synthesis of 5-bromo-1,4-dimethyl-3-nitropyridin-2(1H)-one (Intermediate 17)

Intermediate 16 (41 g, 0.17 mol), N,N-dimethylformamide (400 mL), potassium carbonate (72.8 g, 0.53 mol) and iodomethane (50 g, 0.35 mol) were added successively in a dry 1000 mL round-bottomed flask and stirred for 18 h at room temperature. After the completion of the reaction monitored by LCMS, the reaction solution was poured into ice water (2000 mL) and filtered. The obtained solid was dried to obtain 5-bromo-1,4-dimethyl-3-nitropyridin-2(1H)-one (intermediate 17) (38 g, brown solid), yield: 87%.

LCMS: m/z 246.8/248.8 (M+H).

Step 4: Synthesis of ethyl 3-(5-bromo-1-methyl-3-nitro-2-oxo-1,2-dihydropyridin-4-yl)-2-carbonylpropionate (Intermediate 18)

Intermediate 17 (5.0 g, 0.02 mol) and dimethyl oxalate (200 mL) were added successively in a dry 500 mL three-necked flask at room temperature, replaced by nitrogen three times and cooled to minus 15° C. 1,8-diazabicycloundec-7-ene (12.3 g, 0.08 mol) was slowly added dropwise, gradually raised to room temperature, heated to 40° C. and stirred for 18 hours. The reaction was monitored by LCMS. The mixture was heated to 50° C. and stirred for 3 hours. Less intermediate 17 was remained. The reaction mixture was quenched with cold saturated aqueous sodium hydrogen sulfate (500 mL), diluted with ethyl acetate (500 mL), filtered to remove solid impurities in the mixture and then extracted with ethyl acetate (500 mL*3). The combined organic phases were dried over anhydrous sodium sulfate and filtered. The filtrate was concentrated under reduced pressure, directly poured into a silica gel column (wet method loading), washed with 4-5 column volumes of mixed solvent (petroleum ether:ethyl acetate (v:v)=5:1), washed with 4-5 column volumes of mixed solvent (petroleum ether:ethyl acetate (v:v)=2:1), and finally purified with petroleum ether:ethyl acetate (v:v=1:1) to obtain ethyl 3-(5-bromo-1-methyl-3-nitro-2-oxo-1,2-dihydropyridin-4-yl)-2-carbonylpropionate (Intermediate 18) (3.35 g, dark green solid), yield: 47.8%.

LCMS: m/z 346.7/348.7 (M+H).

Step 5: Synthesis of 4-bromo-2-(ethoxymethyl)-6-methyl-1,6-dihydro-7H-pyrrolo[2,3-c]pyridin-7-one (HHX-B38-int)

Intermediate 18 (12.86 g, 0.037 mol), iron powder (10.4 g, 0.18 mol) and acetic acid (200 mL) were added successively in a dry 500 mL round-bottomed flask at room temperature, heated to 100° C. and stirred for 1 hour. After the completion of the reaction monitored by LCMS, the reaction mixture was concentrated under reduced pressure, diluted with dichloromethane: methanol (v:v=5:1) solution, adjusted pH to 8-9 with saturated sodium bicarbonate solution and filtered. The filtrate was concentrated under reduced pressure and the obtained residue was purified by column chromatography method (dichloromethane: methanol (v:v) =15:1). The obtained crude product was added to ethyl acetate (50 mL), filtered, and the filter cake was dried to obtain 4-bromo-2-(ethoxymethyl)-6-methyl-1,6-dihydro-7H-pyrrolo[2,3-c]pyridin-7-one (Intermediate 19) (6.38 g, brown solid), yield: 57.6%.

LCMS: m/z 298.8/300.7 (M+H).

$^1$H NMR (400 MHz, DMSO-$d_6$) δ 13.25 (s, 1H), 7.63 (s, 1H), 6.83 (d, J=2.0 Hz, 1H), 4.30 (q, J=7.0 Hz, 2H), 3.51 (s, 3H), 1.32 (t, J=7.0 Hz, 3H).

Intermediate 20: Synthesis of 4-bromo-6-methyl-7-oxo-6,7-dihydro-1H-pyrrolo[2,3-c]pyridin-2-carboxylic acid (Intermediate 20)

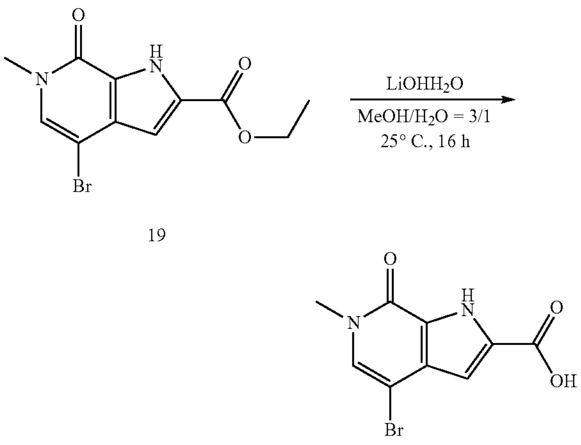

19

20

Intermediate 19 (500 mg, 1.67 mmol), methanol (10 mL), water (3 mL) and lithium hydroxide monohydrate (210 mg, 5.01 mmol) were added successively in a dry 25 mL round-bottomed flask at room temperature and stirred at room temperature for 16 hours. The mixture was concentrated under reduced pressure and the residue was acidified to pH 4 with 1 mol/mL aqueous hydrochloric acid solution. The mixture was filtered under reduced pressure, and the filter cake was dried to obtain 4-bromo-6-methyl-7-oxo-6,7-dihydro-1H-pyrrolo[2,3-c]pyridin-2-carboxylic acid 7 (Intermediate 20) (455 mg, yellow solid), yield: 100%.

LCMS: m/z 272.9 (M+H).

Intermediate 21: Synthesis of 4-bromo-N-ethyl-6-methyl-7-oxo-6,7-dihydro-1H-pyrrolo[2,3-c]pyridin-2-carboxamide (Intermediate 21)

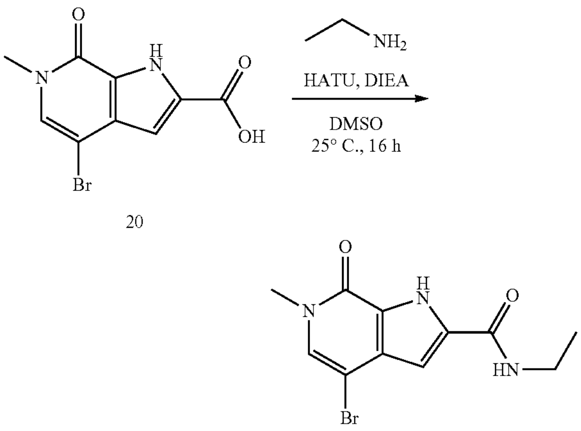

20

21

Intermediate 20 (455 mg, 1.68 mmol), dimethyl sulfoxide (10 mL), 2-(7-azobenzotriazole)-N,N,N',N'-tetramethylurea hexafluorophosphate (957 mg, 2.52 mmol) and N,N-diisopropylethylamine (0.83 mL, 5.04 mmol) were added successively in a dry 25 ml single-necked flask at room temperature and stirred at room temperature for 30 minutes. A solution of ethylamine in tetrahydrofuran (2.0 M, 1.26 mL, 2.52 mmol) was added. The mixture was stirred at room temperature and reacted for 16 hours. After the completion of the reaction monitored by TLC, 100 mL of water was poured into the mixture, which was then filtered under reduced pressure. The filter cake was dried to obtain 4-bromo-N-ethyl-6-methyl-7-oxo-6,7-dihydro-1H-pyrrolo[2,3-c]pyridin-2-carboxamide (intermediate 21) (440 mg, yellow solid), yield: 87.92%.

LCMS: m/z 298.0 (M+H).

Intermediate 22. Synthesis of N-ethyl-6-methyl-7-oxo-4-(4,4,5,5-tetramethyl-1,3,2-dioxaborolan-2-yl)-6,7-dihydro-1H-pyrrolo[2,3-c]pyridin-2-carboxamide (Intermediate 22)

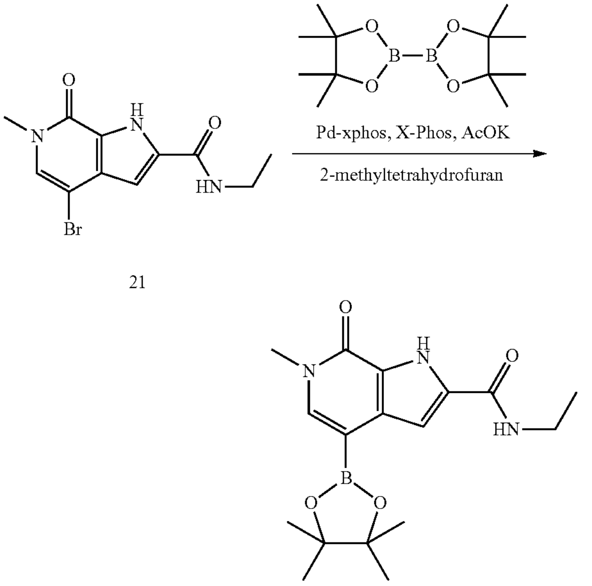

21

22

Intermediate 21 (200 mg, 0.67 mmol), 2-methyltetrahydrofuran (10 mL), bis(pinacolato)diboron (341 mg, 1.34 mmol), chloro(2-dicyclohexylphosphino-2',4',6'-triisopropyl-1,1'-biphenyl)[2-(2'-amino-1,1'-biphenyl)]palladium (II) (21 mg, 0.03 mmol), 2-dicyclohexyl phosphino-2,4,6-triisopropylbiphenyl (13 mg, 0.03 mmol) and anhydrous potassium acetate (198 mg, 2.01 mmol) were added successively in a dry 25 mL single-necked flask at room temperature, then heated to 75° C. and reacted for 16 hours. After the completion of the reaction monitored by LCMS, the mixture was filtered under reduced pressure, and the filtrate was concentrated under reduced pressure. The residue was washed with petroleum ether, and the filter cake was collected to give N-ethyl-6-methyl-7-oxo-4-(4,4,5,5-tetramethyl-1,3,2-dioxaborolan-2-yl)-6,7-dihydro-1H-pyrrolo[2,3-c]pyridin-2-carboxamide (intermediate 22, 120 mg) as a yellow solid, yield: 51.82%.

LCMS: m/z 346.1 (M+H).

Example A5 Synthesis Route

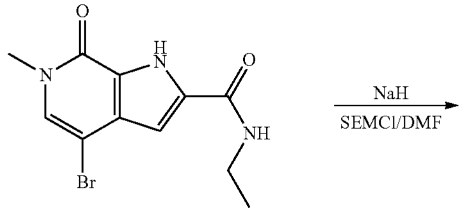

21

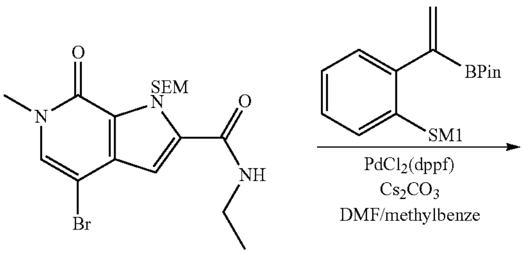

23

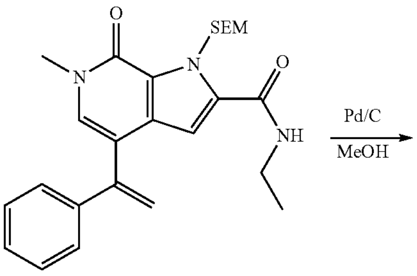

24

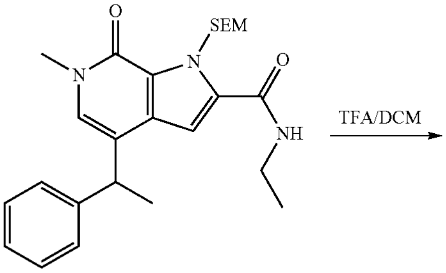

25

-continued

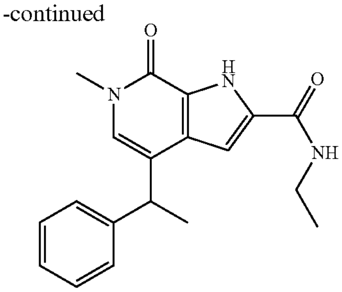

A5

Step 1: Synthesis of 4-bromo-N-ethyl-6-methyl-7-oxo-1-((2-(trimethylsilyl)ethoxy)methyl)-6,7-dihydro-1H-pyrrolo[2,3-c]pyridin-2-carboxamide (Intermediate 23)

In an ice bath, 60% sodium hydride (81 mg, 2.02 mmol) was added to a solution of intermediate 21 (300 mg, 1.01 mmol) in DMF (5 mL) and reacted at 0° C. for one hour. 2-chloromethoxyethyl-trimethylsilane (253 mg, 2.02 mmol) was added dropwise to the reaction system and then reacted at room temperature for 2 hours. After the completion of the reaction monitored by TLC, the reaction solution was poured into ice water and extracted with dichloromethane. The organic phase was washed with saturated brine, dried over anhydrous sodium sulfate, filtered and concentrated to obtain intermediate 23 (300 mg, yield 69%) as a white solid.

Step 2: Synthesis of N-ethyl-6-methyl-7-oxo-4-(1-phenylvinyl)-1-((2-(trimethylsilyl)ethoxy)methyl)-6,7-dihydro-1H-pyrrolo[2,3-c]pyridin-2-carboxamide (Intermediate 24)

Intermediate 23 (300 mg, 0.7 mmol), 1-styrylboronic acid pinacol ester (SM1, 177 mg, 0.77 mmol), 1,1-bis(diphenylphosphino)ferrocene)palladium dichloride (26 mg, 0.035 mmol) and cesium carbonate (683 mg, 2.1 mmol) were added successively to N,N-dimethylformamide/toluene (2 mL/10 mL) at room temperature, replaced by nitrogen three times and then reacted at 110° C. for 2 days. After the completion of the reaction monitored by TLC, the reaction solution was poured into water, extracted with dichloromethane, the organic phase was washed with saturated brine, dried over anhydrous sodium sulfate, filtered, and the filtrate was concentrated, and separated by column (petroleum ether/ethyl acetate (v:v)=5/1) to obtain intermediate 24 (162 mg, yield: 44%) as a white solid.

LCMS: m/z 452.4 (M+H).

Step 3: Synthesis of N-ethyl-6-methyl-7-oxo-4-(1-phenethyl)-1-((2-(trimethylsilyl)ethoxy)methyl)-6,7-dihydro-1H-pyrrolo[2,3-c]pyridin-2-carboxamide (Intermediate 25)

Intermediate 24 (70 mg, 0.16 mmol) and palladium/carbon (5 mg) were added to methanol (5 mL), replaced with hydrogen, and reacted at 0° C. for 3 hours. After the completion of the reaction monitored by LC/MS, the reaction solution was filtered, and the filtrate was concentrated to obtain intermediate 25 (70 mg, crude product) as a white solid.

LCMS: m/z 454.4 (M+H).

Step 4: Synthesis of N-ethyl-6-methyl-7-oxo-4-(1-phenethyl)-6,7-dihydro-1H-pyrrolo[2,3-c]pyridin-2-carboxamide (A5)

Intermediate 25 (70 mg, 0.155 mmol) and trifluoroacetic acid (5 mL) were added to dichloromethane (5 mL) and reacted overnight at room temperature. After the completion of the reaction monitored by TLC, the reaction solution was concentrated, and the residue was dissolved in dichloromethane, washed with saturated aqueous sodium bicarbonate solution and brine, dried over anhydrous sodium sulfate, concentrated and purified by Prep-TLC (dichloromethane: methanol (v:v)=10:1) to obtain compound A5 (N-ethyl-6-methyl-7-oxo-4-(1-phenethyl)-6,7-dihydro-1H-pyrrolo[2,3-c]pyridin-2-carboxamide), 23 mg, yield: 46%. LCMS: m/z 324.2 (M+H).

A5 was subjected to SFC resolution to obtain A5-P1 (4 mg) and A5-P2 (4 mg).

The spectral data of A5-P1 are as follows: LCMS: m/z 324.2 (M+H).

$^1$H-NMR (MeOD, 400 MHz): 7.21-7.15 (m, 4H), 7.08-7.04 (m, 1H), 6.98 (s, 1H), 6.69 (s, 1H), 4.17-4.11 (m, 1H), 3.55 (s, 3H), 3.29-3.23 (m, 2H), 1.55 (d, J=8.0 Hz, 3H), 1.11-1.07 (m, 3H)

The spectral data of A5-P2 are as follows: LCMS: m/z 324.2 (M+H). $^1$H-NMR (MeOD, 400 MHz): 7.21-7.15 (m, 4H), 7.08-7.04 (m, 1H), 6.98 (s, 1H), 6.69 (s, 1H), 4.17-4.11 (m, 1H), 3.55 (s, 3H), 3.29-3.23 (m, 2H), 1.55 (d, J=8 Hz, 31H), 1.11-1.07 (m, 3H).

Example A6 Synthesis Route

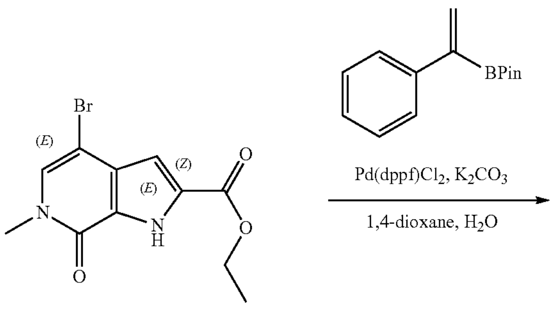

19

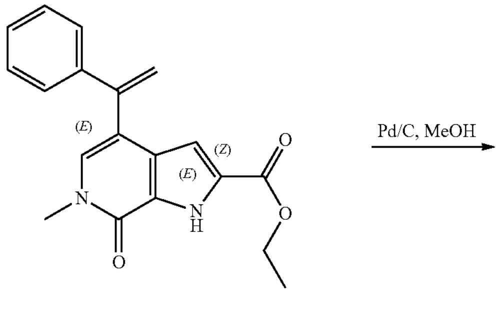

26

-continued

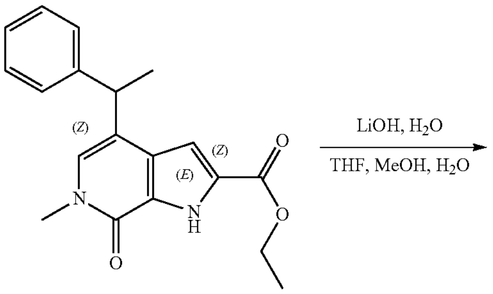

27

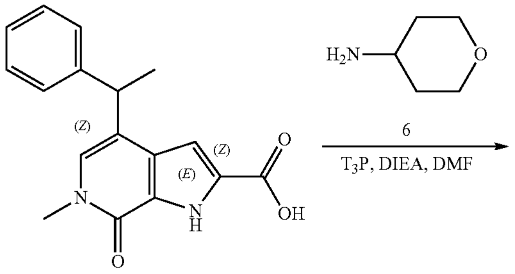

28

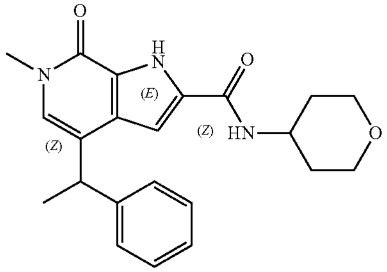

A6

Step 1: Synthesis of ethyl 6-methyl-7-carbonyl-4-(1-phenylvinyl)-6,7-dihydro-1H-pyrrolo[2,3-c]pyridin-2-carboxylate (Intermediate 26)

Intermediate 19 (120 mg, 0.4 mmol), intermediate 2 (120 mg, 0.52 mmol), potassium carbonate (166 mg, 1.2 mmol), 1,4-dioxane (40 mL), and distilled water (6 mL) were added successively to a dry 100 mL round-bottomed flask at room temperature and then [1,1'-bis(triphenylphosphino)ferrocene]dichloropalladium dichloromethane complex (33 mg, 0.04 mol) was added. The mixture was replaced by nitrogen three times, heated to 80° C., and stirred for 18 hours. After the completion of the reaction monitored by LCMS, the mixture was concentrated under reduced pressure, and the obtained residue was purified by column chromatography (pure ethyl acetate) to obtain ethyl 6-methyl-7-carbonyl-4-(1-phenylvinyl)-6,7-dihydro-1H-pyrrolo[2,3-c]pyridin-2-carboxylate (intermediate 26) (60 mg, pale yellow oil), yield: 46.5%.

LCMS: m/z 322.9 (M+H).

Step 2: Synthesis of ethyl 6-methyl-7-carbonyl-4-(1-phenylethyl)-6,7-dihydro-1H-pyrrolo[2,3-c]pyridin-2-carboxylate (Intermediate 27)

Intermediate 26 (40 mg, 0.12 mmol), methanol (40 mL) and aqueous palladium on carbon (40 mg) were added successively to a dry 100 mL round-bottomed flask at room temperature and stirred under 1 atmosphere of hydrogen for 4 hours. After the completion of the reaction monitored by LCMS, the mixture was filtered, and the filtrate was concentrated to obtain ethyl 6-methyl-7-carbonyl-4-(1-phenylethyl)-6,7-dihydro-1H-pyrrolo[2,3-c]pyridin-2-carboxylate (Intermediate 27) (40 mg, off-white solid), yield: 99%.

LCMS: m/z 324.9 (M+H).

Step 3: Synthesis of 6-methyl-7-carbonyl-4-(1-phenylethyl)-6,7-dihydro-1H-pyrrolo[2,3-c]pyridin-2-carboxylic acid (Intermediate 28)

Intermediate 27 (40 mg, 0.12 mmol), lithium hydroxide monohydrate (16 mg, 0.37 mmol), distilled water (5 mL), methanol (5 mL) and tetrahydrofuran (20 mL) were added successively to a dry 100 mL round-bottomed flask at room temperature and stirred at room temperature for 18 hours. After the completion of the reaction monitored by LCMS, the mixture was concentrated under reduced pressure, distilled water (10 mL) was added to dissolve the obtained residue and the pH was adjusted to 4-5 with 2N aqueous hydrochloric acid. The mixture was filtered, and the filter cake was dried to obtain 6-methyl-7-carbonyl-4-(1-phenylethyl)-6,7-dihydro-1H-pyrrolo[2,3-c]pyridin-2-carboxylic acid (intermediate 28) (26.6 mg, pale yellow solid), yield: 80%.

LCMS: m/z 296.9 (M+H).

Step 4: Synthesis of 6-methyl-7-carbonyl-4-(1-phenylethyl)-N-(tetrahydro-2H-pyran-4-yl)-6,7-dihydro-1H-pyrrolo[2,3-c]pyridin-2-carboxamide (A6)

Intermediate 28 (30 mg, 0.09 mmol), intermediate 6 (21 mg, 0.21 mmol), N,N-dimethylformamide (10 mL), 1-propylphosphoric acid cyclic anhydride (258 mg, 0.39 mmol) and N,N-diisopropylethylamine (51 mg, 0.39 mmol) were added successively to a dry 100 mL round-bottomed flask at room temperature and stirred at room temperature for 18 hours. After the completion of the reaction monitored by LCMS, the pH was adjusted to 8-9 with saturated aqueous sodium bicarbonate solution and then saturated brine (30 mL) was added. The mixture was extracted with ethyl acetate (20 mL*3) and the combined organic phases were washed with saturated brine (30 mL*3), dried over anhydrous sodium sulfate and filtered.

The filtrate was concentrated under reduced pressure, and the residue was purified by pre-HPLC to give 6-methyl-7-carbonyl-4-(1-phenylethyl)-N-(tetrahydro-2H-pyran-4-yl)-6,7-dihydro-1H-pyrrolo[2,3-c]pyridin-2-carboxamide (A6) (12 mg, white solid), yield: 29%.

LCMS: m/z 379.8 (M+H).

A6 was subjected to chiral resolution to obtain A6-P1 (4.3 mg, white solid) and A6-P2 (4.2 mg, white solid).

Resolution Conditions:

Chiral column: OJ-H;

Mobile phase: 70% carbon dioxide+30% ethanol (0.2% diethylamine)

Flow rate: 40 g/min

The spectral data of A6-P1 are as follows:

LCMS: m/z 380.0 (M+H).

$^1$H NMR (400 MHz, CD3OD) δ 7.34-7.23 (m, 4H), 7.19-7.14 (m, 1H), 7.08 (d, J=0.8 Hz, 1H), 6.86 (s, 1H), 4.24 (q, J=7.2 Hz, I H), 4.09-4.02 (m, 1H), 3.98-3.95 (m, 2H), 3.65 (s, 3H), 3.53-3.47 (m, 2H), 1.88-1.85 (m, 2H), 1.69-1.56 (m, 5H).

The spectral data of A6-P2 are as follows:

LCMS: m/z 380.0 (M+H).

$^1$H NMR (400 MHz, CD3OD) δ 7.32-7.24 (m, 4H), 7.19-7.14 (m, 1H), 7.08 (d, J=0.8 Hz, I H), 6.86 (s, 1H), 4.24 (q, J=7.2 Hz, 1H), 4.08-4.03 (m, 1H), 3.98-3.95 (m, 2H), 3.65 (s, 3H), 3.53-3.47 (m, 2H), 1.89-1.84 (m, 2H), 1.68-1.59 (m, 5H).

Example A7 Synthesis Route

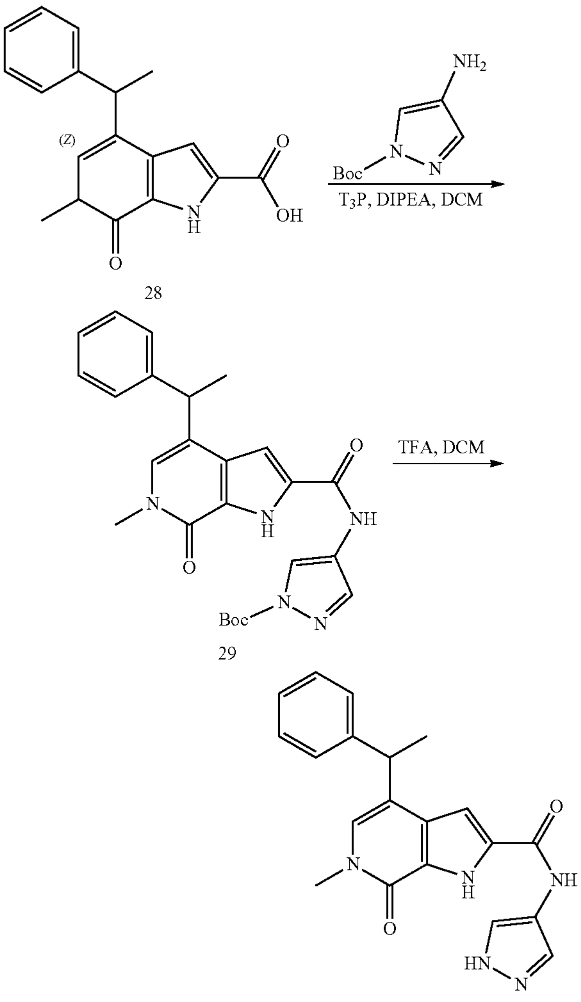

28

29

A7

Step 1: Synthesis of tert-butyl 4-(6-methyl-7-carbonyl-4-(1-phenylethyl)-6,7-dihydro-1H-pyrrolo[2,3]pyridin-2-carboxamido)-1H-pyrazol-1-carboxylate (Intermediate 29)

Intermediate 28 (51 mg, 0.17 mmol), tert-butyl 3-aminopyrazolecarboxylate (31 mg, 0.17 mmol), N,N-diisopropylethylamine (44 mg, 0.34 mmol) and dichloromethane (10 mL) were added successively to a dry 50 mL single-necked flask at room temperature and then 1-propylphosphoric anhydride (50% solution in ethyl acetate, 216 mg, 0.34 mmol). The reaction mixture was stirred at room temperature for 2 hours. Water (5 mL) was added and the mixture was extracted with dichloromethane (10 mL×2). The combined organic phases were concentrated under reduced pressure, and the residue was purified by column chromatography (dichloromethane: methanol (v:v)=20:1) to give tert-butyl 4-(6-methyl-7-carbonyl-4-(1-phenylethyl)-6,7-dihydro-1H-pyrrolo [2,3]pyridine-2-carboxamido)-1H-pyrazol-1-carboxylate (intermediate 29) (21 mg, yellow solid), yield: 27%.

LCMS: m/z 362.2 (M+H-Boc);

Step 2: Synthesis of 6-methyl-7-carbonyl-4-(1-phenylethyl)-N-(1H-pyrazol-4-yl)-6,7-dihydro-1H-pyrrolo[2,3]pyridin-2-carboxamide (A7)

Intermediate 29 (21 mg, 0.045 mmol), trifluoroacetic acid (1 mL) and dichloromethane (10 mL) were added successively to a dry 50 mL single-necked flask at room temperature and stirred at room temperature for 4 hours. The mixture was concentrated under reduced pressure and the residue was purified by reverse phase preparation to obtain 6-methyl-7-carbonyl-4-(1-phenylethyl)-N-(1H-pyrazol-4-yl)-6,7-dihydro-1H-pyrrolo[2,3]pyridin-2-carboxamide (A7) (2.3 mg, white solid), yield: 14%.

The spectral data of A7 are as follows: LCMS: m/z 362.2 (M+H). $^1$H NMR (400 MHz, $CD_3OD$) δ 7.96-7.87 (m, 2H), 7.35-7.25 (m, 4H), 7.18 (t, J=7.8 Hz, 1H), 7.12 (s, 1H), 6.95 (s, 1H), 4.28 (q, J=7.6 Hz 1H), 3.67 (s, 3H), 1.68 (d, J=7.2 Hz, 3H).

Example A8 Synthesis Route

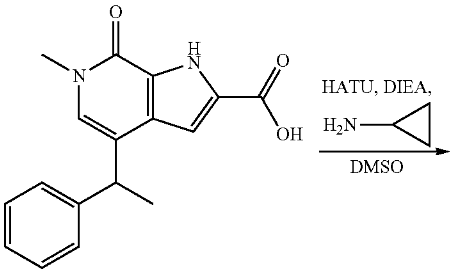

28

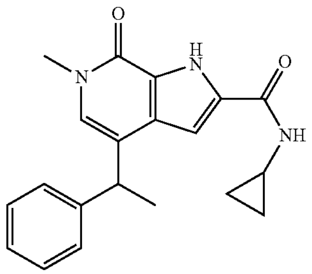

A8

Step 1: Synthesis of N-cyclopropyl-6-methyl-7-oxo-4-(1-phenethyl)-6,7-dihydro-1H-pyrrolo[2,3-c]pyridin-2-carboxamide (A8)

Intermediate 28 (100 mg, 0.337 mmol), cyclopropylamine (57.8 mg, 1.01 mmol), HATU (192 mg, 0.506 mmol), N,N-diisopropylethylamine (262 mg, 2.02 mmol) and 5 mL of dimethyl sulfoxide were added successively to a 50 mL single-necked flask at room temperature and reacted at room temperature for two hours. After the completion of the reaction monitored by TLC, the reaction solution was diluted with water and extracted twice with ethyl acetate. The organic phase was collected, washed with saturated brine, dried over anhydrous sodium sulfate and filtered. The filtrate was concentrated under reduced pressure and purified by column chromatography (dichloromethanol:methanol (v:v)=15:1) to obtain 80 mg crude product, which was then subjected to chiral resolution to give the product A8 (P1: 26 mg, white solid; P2; 27 mg, white solid). The resolution method was the same as that for A6-P1 and A6-P2.

The spectral data of A8-P1 are as follows:

LCMS: m/z 336.4 (M+H). $^1$H-NMR (DMSO, 400 MHz): 12.05 (brs, 1H), 8.31 (d, J=3.6 Hz, 1H), 7.32-7.25 (m, 4H), 7.18-7.15 (m, 2H), 6.67 (s, 1H), 4.18-4.14 (m, 1H), 3.55 (s, 3H), 2.80-2.76 (m, 1H), 1.57 (d, J=7.2 Hz, 3H), 0.72-0.69 (m, 2H), 0.52-0.49 (m, 2H).

The spectral data of A8-P2 are as follows:

LCMS: m/z 336.4 (M+H). $^1$H-NMR (DMSO, 400 MHz): 12.05 (brs, 1H), 8.31 (d, J=4.0 Hz, 1H), 7.32-7.25 (m, 4H), 7.17-7.14 (m, 2H), 6.67 (s, 1H), 4.18-4.16 (m, 1H), 3.55 (s, 3H), 2.79-2.77 (m, 1H), 1.57 (d, J=7.2 Hz, 3H), 0.71-0.68 (m, 2H), 0.52-0.48 (m, 2H).

Example A9 Synthesis Route

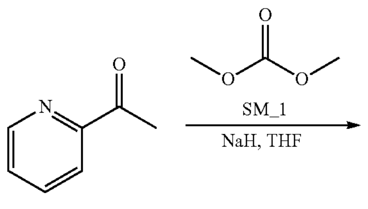

30

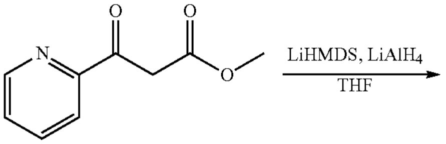

31

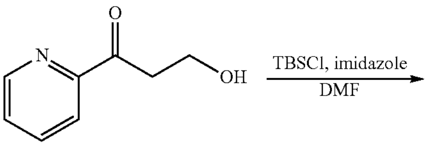

32

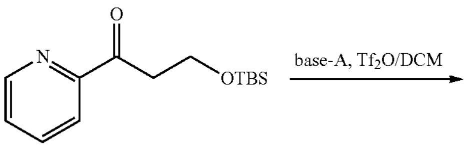

33

-continued

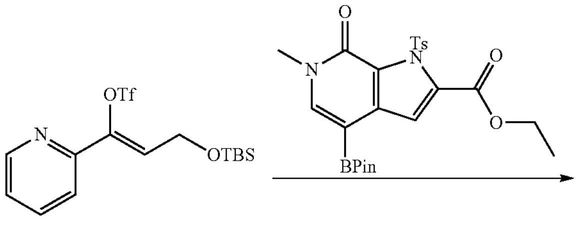

34

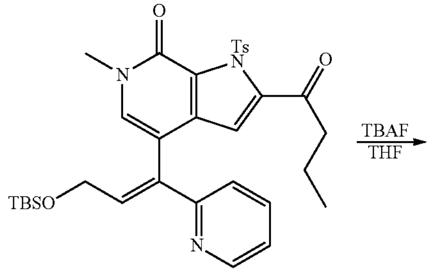

35

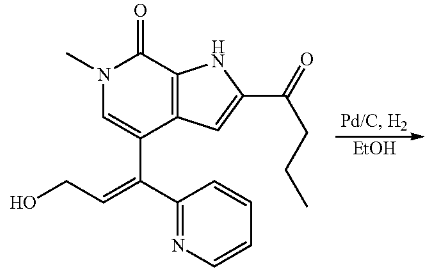

36

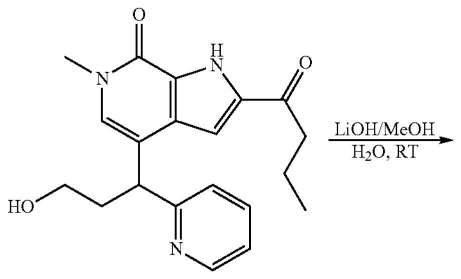

37

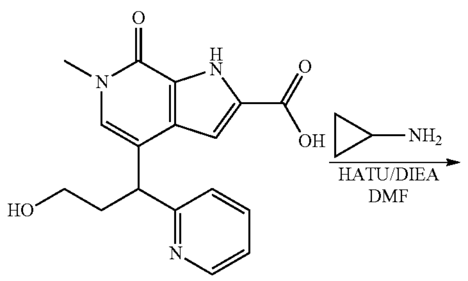

38

-continued

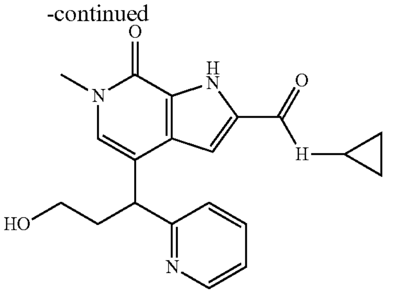

A9

Step 1: Synthesis of methyl pyridine 2-formyl acetate (31)

Tetrahydrofuran (200 mL), sodium hydride (3.6 g, 89.25 mmol), intermediate 30 (4.32 g, 35.70 mmol) and dimethyl carbonate (12 mL, 142.80 mmol) were added to a dry 500 mL round-bottomed flask at room temperature and heated to reflux for 4 hours. Then the mixture was stirred and reacted at room temperature for 16 hours. The mixture was quenched by adding acetic acid (20 mL) in an ice bath, diluted with water (200 mL) and extract with ethyl acetate (200 mL×3). The combined organic phases were washed with saturated aqueous sodium chloride solution (300 mL), dried over anhydrous sodium sulfate and filtered, and the filtrate was concentrated under reduced pressure to obtain methyl pyridine-2-formyl acetate (intermediate 31) (3.5 g, yellow liquid), yield: 54.0%.

Step 2: Synthesis of 3-hydroxy-1-(2-pyridin)-1-propanone (Intermediate 32)

Intermediate 31 (8.0 g, 44.69 mmol) and lithium hexamethyldisilazide (45.7 mL, 44.69 mmol) were added successively to a dry 250 mL round-bottomed flask and stirred at 0° C. for 30 minutes. Then lithium aluminum tetrahydride (3.40 g, 89.38 mmol) was added, and the mixture was stirred at 0° C. for 4 hours. After the completion of the reaction monitored by TLC, water (2.3 mL) was added and the mixture was filtered and washed with ethyl acetate (200 mL). The filtrate was dried over anhydrous sodium sulfate, filtered, and the filtrate was concentrated under reduced pressure to obtain 3-hydroxy-1-(2-pyridin)-1-propanone (intermediate 32) (9.1 g, crude product, yellow liquid), which was used directly in the following step. LCMS: m/z 152.2 (M+H).

Step 3: Synthesis of 3-((tert-butyldimethylsilyl)oxy)-1-(pyridin-2-yl)propan-1-one (Intermediate 33)

Intermediate 32 (4.20 g, 27.8 mmol), N,N-dimethylformamide (50 mL), imidazole (1.89 g, 83.4 mmol) and tert-butylchlorodimethylsilane (4.2 g, 41.7 mmol) were successively added to a dry 100 mL single-necked flask at room temperature, stirred at room temperature and reacted for 16 hours. After the reaction was completed, water (200 mL) was added. The mixture was extracted with ethyl acetate (100 mL×2). The organic phases were collected, dried over anhydrous sodium sulfate, filtered, and the filtrate was concentrated under reduced pressure to obtain 3-((tert-butyldimethylsilyl)oxy)-1-(pyridin-2-yl)propan-1-one (intermediate 33) (1.2 g, yellow liquid), two-step yield: 35.29%.

Step 4: Synthesis of 3-((tert-butyldimethylsilyl)oxy)-1-(pyridin-2-yl)prop-1-en-1-yltrifluoromethanesulfonic acid (Intermediate 34)

In an ice bath, intermediate 33 (530 mg, 2.0 mmol), dichloromethane (20 ml), 2,6-di-tert-butyl-4-methylpyridine (615 mg, 3 mmol) and trifluoromethanesulfonic anhydride (677 mg, 2.4 mmol) were added successively to a dry 100 mL single-necked flask at room temperature, stirred and reacted for 3 hours. After the reaction was completed, water (50 mL) was added. The mixture was extracted with ethyl acetate (50 mL×3). The organic phases were collected, dried over anhydrous sodium sulfate and filtered. The filtrate was concentrated under reduced pressure, and the concentrate was subjected to column chromatography (petroleum ether/ethyl acetate (v:v)=10/1) to obtain 3-((tert-butyldimethylsilyl)oxy)-1-(pyridin-2-yl)prop-1-en-1-yltrifluoro methanesulfonic acid (intermediate 34) (300 mg, yellow liquid), yield: 38.0%. LCMS: m/z 398.1 (M+H).

Step 5: Synthesis of 4-(3-((tert-butyldimethylsilyl)oxy)-1-(pyridin-2-yl)prop-1-en-1-yl)-6-methyl-7-oxo-1-tosyl-6,7-dihydro-1H-pyrrolo[2,3-c]pyridin-2-carboxylate (Intermediate 35)

Intermediate 34 (300 mg, 0.6 mmol), ethyl 6-methyl-7-oxo-4-(4,4,5,5-tetramethyl-1,3,2-dioxaborolan-2-yl)-1-p-tolyl-6,7-dihydro-1H-pyrrolo[2,3-c]pyridin-2-carboxylate (262 mg, 0.66 mmol), tris(dibenzylideneacetone)dipalladium (55 mg, 0.06 mmol), 1,3,5,7-tetramethyl-6-phenyl-2,4,8-trioxa-6-phosphaadamantane (53 mg, 0.18 mmol), sodium carbonate (191 mg, 1.8 mmol), 1,4-dioxane (20 mL) and water (5 mL) were added successively to a dry 100 mL single-necked flask at room temperature, stirred at 50° C. and reacted for 3 hours. After the reaction was completed, the mixture was concentrated under reduced pressure, and the concentrate was subjected to column chromatography (petroleum ether/ethyl acetate (v:v)=10/1) to obtain ethyl 4-(3-((tert-butyl dimethylsilyl)oxy)-1-(pyridin-2-yl)prop-1-en-1-yl)-6-methyl-7-oxo-1-tosyl-6,7-dihydro-1H-pyrrolo[2,3-c]pyridin-2-carboxylate 35 (200 mg, yellow solid), yield: 53.0%.

LCMS: m/z 622.3 (M+H).

Step 6: Synthesis of ethyl 4-(3-hydroxy-1-(pyridin-2-yl)prop-1-en-1-yl)-6-methyl-7-oxo-6,7-dihydro-1H-pyrrolo[2,3-c]pyridin-2-carboxylate (Intermediate 36)

Intermediate 35 (180 mg, 0.6 mmol), tetrabutylammonium fluoride (1 mL, 1 mmol) and tetrahydrofuran (5 mL) were added successively to a dry 25 mL single-necked flask at room temperature, stirred and reacted for 3 hours. After the reaction was completed, the mixture was concentrated under reduced pressure, and the concentrate was subjected to column chromatography (petroleum ether/ethyl acetate=2/1) to obtain ethyl 4-(3-hydroxy-1-(pyridin-2-yl)prop-1-ene-1-yl)-6-methyl-7-oxo-6,7-dihydro-1H-pyrrolo[2,3-c]pyridin-2-carboxylate (intermediate 36) (55 mg, yellow solid), yield: 54.0%. LCMS: m/z 354.2 (M+H).

$^1$H NMR (400 MHz, $CDCl_3$) δ 10.43 (s, 1H), 8.60 (d, J=3.9 Hz, 1H), 7.59 (t, J=7.3 Hz, 1H), 7.21-7.10 (m, 2H), 7.05 (m, 1H), 6.95 (s, 1H), 6.51 (d, J=1.8 Hz, 1H), 4.37-4.23 (m, 4H), 3.65 (s, 3H), 3.00-2.93 (m, 1H), 1.32 (t, J=7.1 Hz, 3H).

Step 7: Synthesis of ethyl 4-(3-hydroxy-1-(pyridin-2-yl)propyl)-6-methyl-7-oxo-6,7-dihydro-1H-pyrrolo[2,3-c]pyridin-2-carboxylate (Intermediate 37)

Intermediate 36 (50 mg, 0.14 mmol), palladium on carbon (50 mg) and ethanol (10 mL) were added successively to a dry 50 mL single-necked flask at room temperature, stirred under a hydrogen balloon and reacted for 3 hours. After the reaction was completed, the mixture was filtered and the filtrate was concentrated under reduced pressure to obtain ethyl 4-(3-hydroxy-1-(pyridin-2-yl) propyl)-6-methyl-7-oxo-6,7-dihydro-1H-pyrrolo[2,3-c]pyridin-2-carboxylate (intermediate 37) (38 mg, yellow solid), yield: 76%.

LCMS: m/z 356.2 (M+H).

Step 8: Synthesis of 4-(3-hydroxy-1-(pyridin-2-yl)propyl)-6-methyl-7-oxo-6,7-dihydro-1H-pyrrolo[2,3-c]pyridin-2-carboxylic acid (Intermediate 38)

Intermediate 37 (38 mg, 0.11 mmol), lithium hydroxide (0.33 mL, 0.33 mmol; 1 mol/L), methanol (2 mL) and water (1 mL) were added successively to a dry 25 mL single-necked flask at room temperature, stirred and reacted for 6 hours. The mixture was concentrated under reduced pressure and the pH was adjusted to 3-4. The mixture was concentrated under reduced pressure and the concentrate was subjected to reverse preparative chromatography to obtain 4-(3-hydroxy-1-(pyridin-2-yl)propyl)-6-methyl-7-oxo-6,7-dihydro-1H-pyrrolo[2,3-c]pyridin-2-carboxylic acid (intermediate 38) (25 mg, white solid), yield: 71%. LCMS: m/z 328.2 (M+H).

Step 9: Synthesis of N-cyclopropyl-4-(3-hydroxy-1-(pyridin-2-yl)propyl)-6-methyl-7-oxo-6,7-dihydro-1H-pyrrolo[2,3-c]pyridin-2-carboxamide (A9)

Intermediate 38 (25 mg, 0.076 mmol), cyclopropylamine (22 mg, 0.382 mmol), N,N-diisopropylethylamine (50 mg, 0.382 mmol) and N,N-dimethylformamide (1 mL) were added successively to a dry 25 mL single-necked flask at room temperature and then 2-(7-azobenzotriazole)-N,N,N',N'-tetramethylurea hexafluorophosphate (44 mg, 0.11 mmol) was added. The mixture was stirred at room temperature and reacted for 2 hours. After the reaction was completed, the mixture was purified by high-performance liquid phase reverse preparative column to obtain N-cyclopropyl-4-(3-hydroxy-1-(pyridin-2-yl)propyl)-6-methyl-7-oxo-6,7-dihydro-1H-pyrrolo[2,3-c]pyridin-2-carboxamide (A9) (2 mg, white solid), yield: 12.5%. LCMS: m/z 367.3 (M+H).

1H NMR (400 MHz, DMSO) δ 12.02 (s, 1H), 8.51 (d, J=3.9 Hz, 1H), 8.33 (d, J=3.8 Hz, 1H), 7.67 (td, J=7.7, 1.8 Hz, 1H), 7.33 (d, J=7.9 Hz, 1H), 7.25-7.10 (m, 2H), 6.89 (s, 1H), 4.48 (t, J=5.1 Hz, 1H), 4.26 (t, J=7.5 Hz, 1H), 3.51 (s, 3H), 3.42-3.32 (m, 2H), 2.83-2.76 (m, 1H), 2.39-2.31 (m, 1H), 2.25-2.16 (m, 1H), 0.76-0.64 (m, 2H), 0.57-0.46 (m, 2H).

Example A10 Synthesis Route

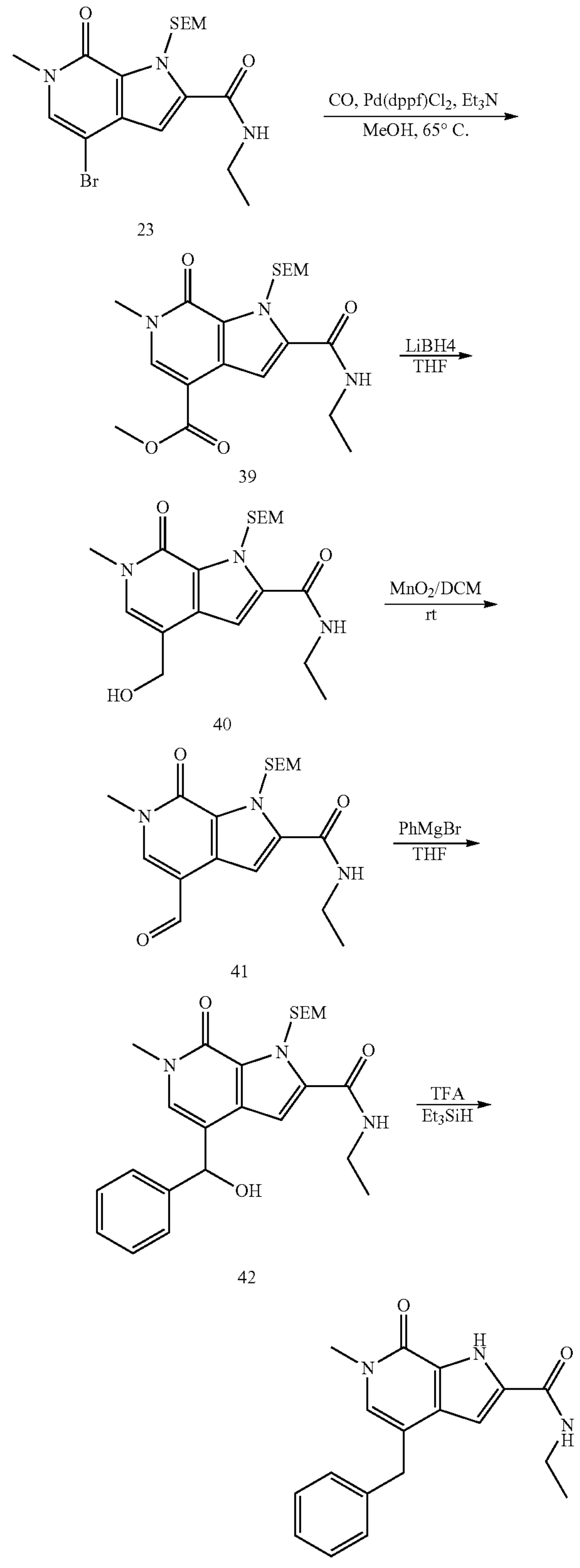

23

39

40

41

42

A10

Step 1: Synthesis of methyl 2-(ethylcarbamoyl)-6-methyl-7-oxo-1-((2-(trimethylsilyl)ethoxy)methyl)-6,7-dihydro-1H-pyrrolo[2,3-c]pyridin-4-carboxylate (Intermediate 39)

Intermediate 23 (800 mg, 1.87 mmol), triethylamine (567 mg, 5.61 mmol), 1,1-bis(diphenylphosphino)ferrocene)palladium dichloride (137 mg, 0.187 mmol) were added successively to methanol (50 mL), replaced by carbon monoxide three times, and refluxed overnight. After the completion of the reaction monitored by TLC, the reaction solution was concentrated to dryness and the residue was dissolved in ethyl acetate. The organic phase was washed with saturated brine, dried over anhydrous sodium sulfate, filtered, and the filtrate was concentrated, and separated by column (petroleum ether/ethyl acetate (v:v)=4/1) to obtain intermediate 39 (540 mg, yield: 70%) as a pale yellow solid. LCMS: m/z 380.2 (M-Et).

Step 2: Synthesis of N-ethyl-4-(hydroxymethyl)-6-methyl-7-oxo-1-((2-(trimethylsilyl)ethoxy)methyl)-6,7-dihydro-1H-pyrrolo [2,3-c]pyridin-2-carboxamide (Intermediate 40)

Intermediate 39 (540 mg, 1.33 mmol) and lithium borohydride (146 mg, 6.65 mmol) were successively added to THF (10 mL) and reacted at 50° C. overnight. After the completion of the reaction monitored by LC/MS, the reaction solution was poured into ice water and extracted with ethyl acetate. The organic phase was washed with saturated brine, dried over anhydrous sodium sulfate, filtered, and concentrated to obtain intermediate 40 (277 mg, yield: 55%) as a white solid.

LCMS: m/z 380.2 (M+H).

Step 3: Synthesis of N-ethyl-4-formyl-6-methyl-7-oxo-1-((2-(trimethylsilyl)ethoxy)methyl)-6,7-dihydro-1H-pyrrolo[2,3-c]pyridin-2-carboxamide (Intermediate 41)

Intermediate 40 (277 mg, 0.73 mmol) and manganese dioxide (635 mg, 7.3 mmol) were added to dichloromethane (15 mL) and reacted overnight at room temperature. After the completion of the reaction monitored by LC/MS (HHC16015-038R), the reaction solution was filtered, and the filtrate was concentrated to obtain intermediate 41 (240 mg, yield: 87%).

LCMS: m/z 378.2 (M+H).

Step 4: Synthesis of N-ethyl-4-(hydroxy(phenyl)methyl)-6-methyl-7-oxo-1-((2-(trimethylsilyl)ethoxy)methyl)-6,7-dihydro-1H-pyrrolo[2,3-c]pyridin-2-carboxamide (Intermediate 42)

Phenylmagnesium bromide (3 mol/L, 0.64 mL, 1.92 mmol) was added dropwise to a solution of intermediate 41 (240 mg, 0.64 mmol) in tetrahydrofuran (20 mL) at 0° C. under the protection of nitrogen and reacted for one hour. After the completion of the reaction monitored by TLC, the reaction solution was quenched with saturated ammonium chloride and extracted with ethyl acetate. The organic phase was washed with saturated brine, dried over anhydrous sodium sulfate, filtered, and the filtrate was concentrated and separated by Prep-TLC (dichloromethane/methanol (v:v)=20:1) to obtain intermediate 42 (240 mg, yield: 82%) as a white solid. LCMS: m/z 456.2 (M+H).

Step 5: Synthesis of 4-benzyl-N-ethylamino-6-methyl-7-oxo-6,7-dihydro-1H-pyrrolo[2,3-c]pyridin-2-carboxamide Intermediate 42 (50 mg, 0.11 mmol) and triethylsilane (38 mg, 0.33 mmol) were added to TFA (5 mL) and reacted at 50° C. for 2 days. After the completion of the reaction monitored by LC/MS (HHC16015-040C), the reaction solution was concentrated to dryness, the residue was dissolved in dichloromethane, washed with saturated aqueous sodium bicarbonate solution and saturated brine, dried over anhydrous sodium sulfate, filtered, and the filtrate was concentrated and separated by Prep-HPLC (dichloromethane/methanol (v:v)=15:1) to obtain compound A10 (7 mg, yield: 20%).

LCMS: m/z 310.2 (M+H).

$^1$H-NMR (DMSO, 400 MHz): 12.16 (br, 1H), 8.32 (br, 1H), 7.29 (br, 4H), 7.15 (br, 2H), 6.78 (s, 1H), 3.88 (s, 2H), 3.50 (s, 3H), 3.26 (br, 2H), 1.13 (br, 3H).

Example A11 Synthesis Route

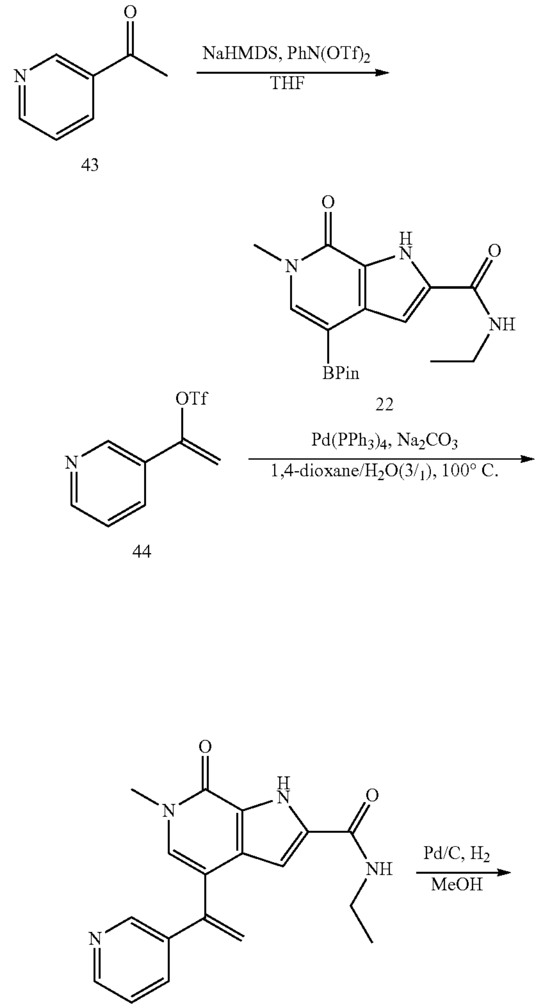

43

22

44

45

-continued

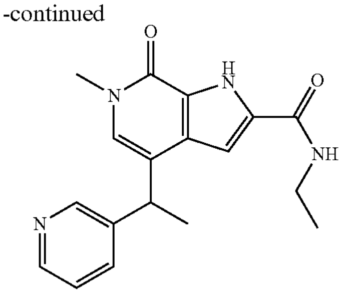

A11

Step 1: Synthesis of 1-(pyridin-3-yl)vinyl trifluoromethanesulfonate (Intermediate 44)

Intermediate 43 (3.00 g, 24.76 mmol) and tetrahydrofuran (60 mL) were added successively to a dry 100 mL three-necked flask at room temperature and replaced by nitrogen 3 times. The system was cooled to −70° C., and sodium bis(trimethylsilyl)amide (2M, 18.57 mL, 37.15 mmol) was slowly added dropwise, stirred at −40° C. and reacted for 1 hour. A solution of N-phenylbis(trifluoromethanesulfonyl)imide (8.85 g, 24.76 mmol) in tetrahydrofuran (15 mL) was slowly added, stirred at 0° C. and reacted for 4 h. After the completion of the reaction monitored by TLC, the reaction was quenched with methanol/ethyl acetate (1/10, 33 mL) at −70° C. and the mixture was concentrated under reduced pressure. The residue was purified by silica gel column (petroleum ether:ethyl acetate (v:v)=5:1) to give 1-(pyridin-3-yl)vinyl trifluoromethanesulfonate (intermediate 44) (1.8 g, yellow oil), purity: 50%.

$^1$H-NMR ($CDCl_3$, 400 MHz): 8.73-8.72 (m, 1H), 8.68-8.66 (m, 1H), 7.65-7.57 (m, 2H), 8.32 (d, J=4.8 Hz, 1H), 5.75 (d, J=4.8 Hz, 1H).

Step 2: Synthesis of N-ethyl-6-methyl-7-oxo-4-(1-(pyridin-3-yl)vinyl)-6,7-dihydro-1H-pyrrolo[2,3-c]pyridin-2-carboxamide (Intermediate 45)

Intermediate 44 (150 mg, 0.43 mmol), intermediate 22 (440 mg, 1.74 mmol), 1,4-dioxane (3 ml), water (1 mL), palladium tetrakistriphenylphosphine (50 mg, 0.04 mmol) and sodium carbonate (115 mg, 1.09 mmol) were added successively to a dry 25 mL single-necked flask at room temperature, heated to 100° C. and reacted for 2 hours.

After the reaction was completed, the mixture was concentrated under reduced pressure, and the residue was purified with a preparative plate (dichloromethane:methanol (v:v)=10:1) to obtain N-ethyl-6-methyl-7-oxo-4-(1-(pyridin-3-yl)vinyl)-6,7-dihydro-1H-pyrrolo[2,3-c]pyridin-2-carboxamide (intermediate 45) (110 mg, yellow solid), yield: 78.53%. LCMS: m/z 323.1 (M+H).

Step 3: Synthesis of N-ethyl-6-methyl-7-oxo-4-(1-(pyridin-3-yl)ethyl)-6,7-dihydro-1H-pyrrolo[2,3-c]pyridin-2-carboxamide (A11)

Intermediate 45 (110 mg, 0.34 mmol), methanol (5 mL) and palladium on carbon (11 mg) were added successively to a dry 25 mL single-necked flask at room temperature and replaced by hydrogen 3 times. The mixture was stirred at room temperature and reacted for 16 hours. After the completion of the reaction monitored by TLC, the reaction solution was filtered, and the filtrate was concentrated under reduced pressure. The residue was purified by preparative plate (dichloromethane:methanol (v:v)=10:1) to give N-ethyl-6-methyl-7-oxo-4-(1-(pyridin-3-yl) ethyl)-6,7-dihydro-1H-pyrrolo[2,3-c]pyridin-2-carboxamide A11 (30 mg, white solid), yield: 27.2%. The final intermediate was subjected to SFC resolution to give A11-P1 (15 mg) and A11-P2 (15 mg).

The spectral data of A11-P1 are as follows: LCMS: m/z 325.2 (M+H). RT=0.731 min (2.50 min).

$^1$H-NMR (DMSO, 400 MHz): 12.12 (s, 1H), 8.60 (d, J=1.6 Hz, 1H), 8.39-8.37 (m, 1H), 8.29-8.26 (m, 1H), 7.67 (d, J=7.6 Hz, 1H), 7.30-7.27 (m, 1H), 7.23 (s, 1H), 6.70 (s, 1H), 4.26-4.20 (m, 1H), 3.55 (s, 3H), 3.25-3.20 (m, 2H), 1.60 (d, J=7.2 Hz, 3H), 1.10 (t, J=7.2 Hz, 3H).

The spectral data of A11-P2 are as follows: LCMS: m/z 335.2 (M+H). $^1$H-NMR (DMSO, 400 MHz): 12.14 (s, 1H), 8.60 (d, J=2.0 Hz, 1H), 8.39-8.37 (m, I H), 8.26 (d, J=4.4 Hz, 1H), 7.67 (d, J=7.6 Hz, 1H), 7.30-7.27 (m, 1H), 7.21 (s, 1H), 6.69 (s, 1H), 4.25-4.20 (m, 1H), 3.54 (s, 3H), 3.27-3.20 (m, 2H), 1.61-1.56 (m, 3H), 1.10 (t, J=7.2 Hz, 3H).

Example A12 Synthesis Route

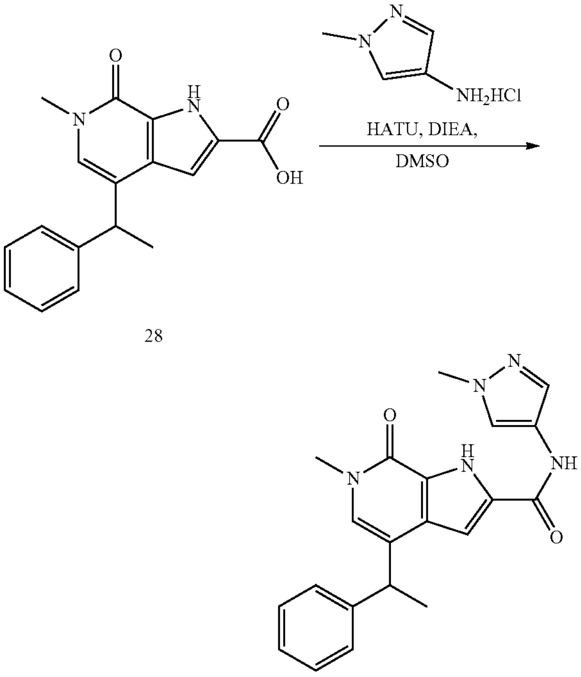

28

A12

Intermediate 28 (200 mg, 0.67 mmol), dimethyl sulfoxide (3 mL), 2-(7-azobenzotriazole)-N, dimethyl sulfoxide (3 mL), 2-(7-azobenzotriazole)-N,N,N',N'-tetramethylurea hexafluorophosphate (385 mg, 1.01 mmol) and N,N-diisopropylethylamine (0.67 mL, 4.04 mmol) were added successively to a dry 25 mL single-necked flask at room temperature and stirred at room temperature for 30 minutes. The free form of intermediate 1-methyl 4-aminopyrazole hydrochloride (135 mg, 1.01 mmol) was added and the mixture was stirred at room temperature and reacted for 16 hours. After the completion of the reaction monitored by TLC, the reaction mixture was concentrated under reduced pressure. The residue was purified by preparative plate (dichloromethane:methanol (v:v)=10:1) to give 6-methyl-N-(1-methyl-1H-pyrazol-4-yl)-7-oxo-4-(1-phenethyl)-6,7-dihydro-1H-pyrrolo[2,3-c]pyridin-2-carboxamide A12 (52 mg, yellow solid), yield: 20.50%. The final intermediate was subjected to SFC resolution to give A12-P1 (29 mg) and A12-P2 (23 mg).

The spectral data of Example A12-P1 are as follows: LCMS: m/z 376.2 (M+H). $^1$H-NMR (DMSO, 400 MHz): 12.21 (s, 1H), 10.27 (s, 1H), 7.96 (s, 1H), 7.50 (s, 1H), 7.34-7.26 (m, 4H), 7.20-7.14 (m, 2H), 6.82 (s, 1H), 4.22-4.17 (m, 1H), 3.81 (s, 3H), 3.55 (s, 3H), 1.60-1.57 (m, 3H).

The spectral data of Example A12-P2 are as follows: LCMS: m/z 376.1 (M+H). $^1$H-NMR (DMSO, 400 MHz): 12.24-12.19 (m, 1H), 10.26 (s, 1H), 7.96 (s, 1H), 7.50 (s, 1H), 7.33-7.26 (m, 4H), 7.20-7.15 (m, 2H), 6.82 (s, 1H), 4.22-4.17 (m, 1H), 3.81 (s, 3H), 3.55 (s, 3H), 1.59 (d, J=7.2 Hz, 3H).

Example A13 Synthesis Route

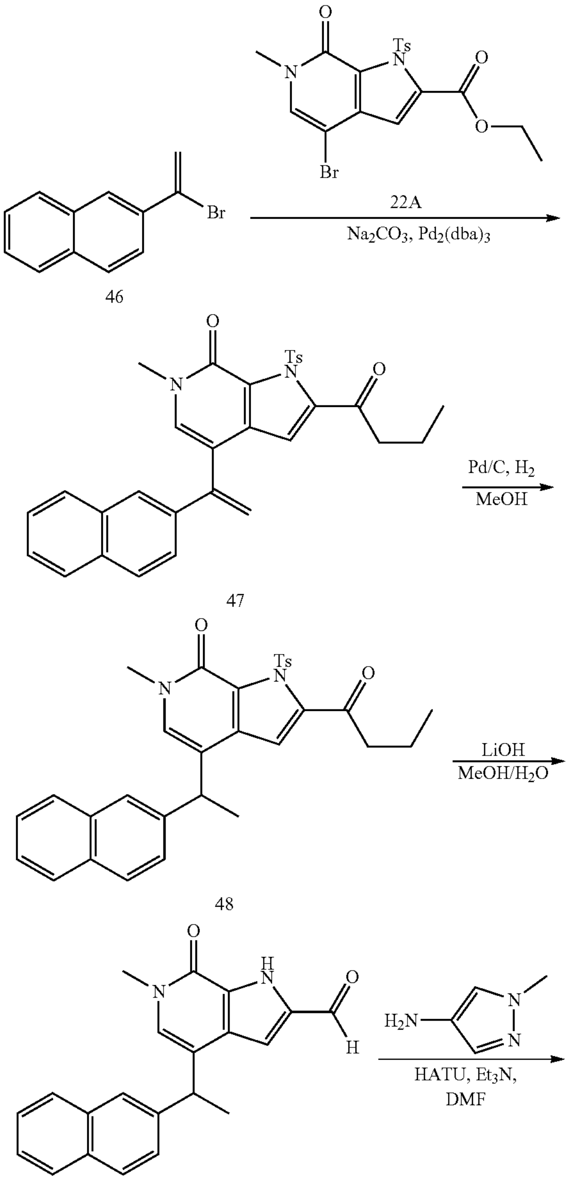

46

47

48

49

-continued

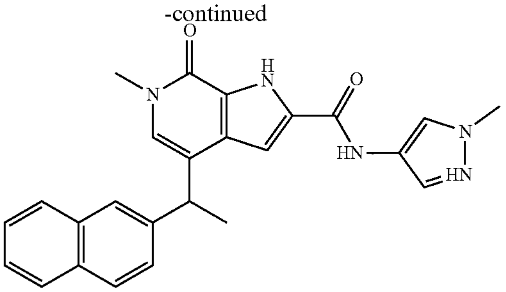

A13

Step 1: Synthesis of ethyl 6-methyl-4-(1-naphthalen-2-yl)vinyl)-7-oxo-1-methylbenzenesulfonyl-6,7-dihydro-1H-pyrrolo[2,3-c]pyridin-2-carboxylic acid (Intermediate 47)

Intermediate 22A (180 mg, 0.773 mmol), intermediate 46 (464 mg, 0.930 mmol), sodium carbonate (246 mg, 2.31 mmol), 1,1'-bisdiphenylphosphinoferrocene palladium dichloride (70 mg, 0.077 mmol) and adamantane (67 mg, 0.23 mmol) were added successively to a 50 mL three-necked flask containing 10 mL of 1,4-dioxane and 2.5 mL of water at room temperature and reacted at 100° C. under the protection of $N_2$ for two hours. After the completion of the reaction monitored by TLC, the reaction solution was diluted with water, extracted twice with ethyl acetate, the organic phase was collected, washed with saturated brine, dried over anhydrous sodium sulfate, filtered, and the filtrate was concentrated under reduced pressure. The crude product was purified by column chromatography (petroleum ether: ethyl acetate (v:v)=1:1) to give product 47 (145 mg, yellow solid), yield: 32.2%.

LCMS: m/z 527.1 (M+H).

Step 2: Synthesis of ethyl 6-methyl-4-(1-naphthalen-2-yl)ethyl)-7-oxo-1-p-tosyl-6,7-dihydro-1H-pyrrolo[2,3-c]pyridin-2-carboxylic acid (Intermediate 48)

Intermediate 47 (145 mg, 0.276 mmol) and Pd/C (15 mg, Wt 10%) were successively added to a 100 mL single-necked flask containing 10 mL of methanol at room temperature and reacted at room temperature overnight under a hydrogen atmosphere. After the completion of the reaction monitored by TLC, the reaction system was filtered, and the filtrate was concentrated to obtain a crude product (intermediate 48) (130 mg, yellow solid), yield: 89.2%.

LCMS: m/z 529.2 (M+H).

Step 3: Synthesis of 6-methyl-4-(1-naphthalen-2-yl)ethyl)-7-6-oxo-2,3-dihydro-1H-pyrrolo[2,3-c]pyridin-2-carboxylic acid (Intermediate 49)

Intermediate 48 (130 mg, 0.25 mmol), sodium hydroxide (29.5 mg, 0.73 mmol), 12 mL of methanol and 4 mL of water were added successively to a dry 100 mL single-necked flask at room temperature and reacted at 60° C. for 3 hours. After the completion of the reaction monitored by TLC, the reaction solution was concentrated, a small amount of water was added to the residue, and the pH was adjusted to 5-6 with 4 moles of hydrochloric acid. The mixture was filtered and the filter cake was dried to give intermediate 49 (80 mg, white solid), yield: 82.3%. LCMS: m/z 347.1 (M+H).

Step 4: 6-methyl-7-oxo-4-(1-phenethyl)-N-(1H-pyrazol-4-yl)-6,7-dihydro-1H-pyrrolo[2,3-c]pyridin-2-carboxamide (A13)

Intermediate 49 (80 mg, 0.23 mmol), HATU (132 mg, 0.34 mmol), N,N-diisopropylethylamine (179 mg, 1.39 mmol) and 1-methyl-1H-pyrazol-4-amine (93 mg, 0.69 mmol) were added successively to a 50 mL single-necked flask containing 5 mL of dimethyl sulfoxide at room temperature and reacted for one hour. After the completion of the reaction monitored by TLC, the reaction solution was diluted with water, extracted twice with ethyl acetate, the organic phase was collected, washed with saturated brine, dried over anhydrous sodium sulfate, filtered, and the filtrate was concentrated under reduced pressure. The crude product was purified by column chromatography (dichloromethane: methanol=20:1) to give the product A13 (16 mg, white solid), yield: 16.3%.

The spectral data of Example A13 are as follows: LCMS: m/z 426.4 (M+H). $^1$H-NMR (DMSO, 400 MHz): 12.26 (s, 1H), 10.25 (s, 1H), 7.93 (s, 1H), 7.88-7.82 (m, 4H), 7.49-7.44 (m, 4H), 7.27 (s, 1H), 6.83 (s, 1H), 4.41-4.35 (m, 1H), 3.80 (s, 3H), 3.59 (s, 3H), 1.69 (d, J=6.8 Hz, 3H).

Example A14 Synthesis Route

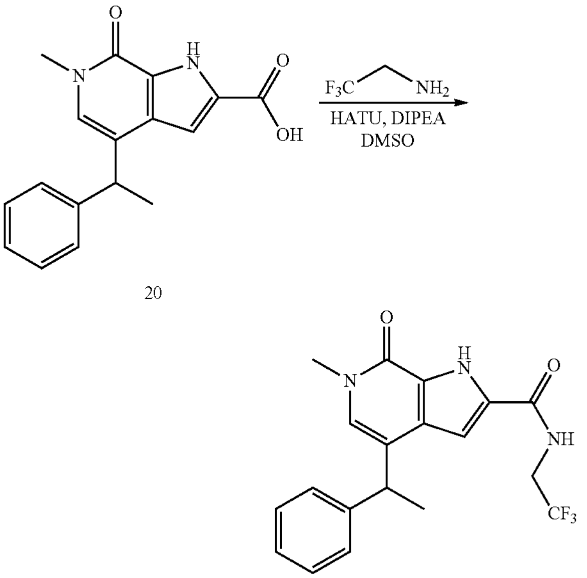

20

A14

Intermediate 20 (120 mg, 0.41 mmol) was dissolved in dimethyl sulfoxide (5 mL), and then 2-(7-oxobenzotriazole)-N,N,N',N'-tetramethylurea hexafluorophosphate (232 mg, 0.61 mmol), N,N-diisopropylethylamine (159 mg, 1.23 mmol) and 2,2,2-trifluoroethylamine (60 mg, 0.61 mmol) were added successively to the system and reacted at room temperature for 16 hours. When LCMS showed that the starting material was consumed and new intermediate was formed, the reaction system was poured into water (10 mL), extracted three times with ethyl acetate (10 mL), and the combined organic phases were washed with saturated aqueous sodium chloride solution (10 mL) and water three times, dried over anhydrous sodium sulfate and filtered. The concentrated organic phase was separated by prep-TLC (dichloromethane/methanol=20/1) to obtain compound A14 (115 mg, yield: 74.4%) as a yellow solid. The resulting intermediate was subjected to SFC resolution to give A14-P1 (17 mg) and A14-P2 (24 mg).

The spectral data of A14-P1 are as follows:

LCMS: m/z 378.3 (M+H).

$^{1}$H NMR (400 MHz, DMSO) δ 12.28 (s, 1H), 8.81 (s, 1H), 7.26-7.18 (m, 4H), 7.14-7.07 (m, 2H), 6.75 (s, 1H), 4.14-3.96 (m, 3H), 3.48 (s, 3H), 1.51 (d, J=7.2 Hz, 3H).

$^{19}$F NMR (377 MHz, DMSO) δ −70.56 (s).

The spectral data of A14-P2 are as follows:

LCMS: m/z 378.3 (M+H).

$^{1}$H NMR (400 MHz, DMSO) δ 8.97 (s, 1H), 7.34-7.25 (m, 4H), 7.20-7.14 (m, 2H), 6.85 (s, 1H), 4.25-4.03 (m, 3H), 3.55 (s, 3H), 1.58 (d, J=7.2 Hz, 3H).

$^{19}$F NMR (377 MHz, DMSO) δ −70.28 (s).

Synthesis Route of Intermediate 55

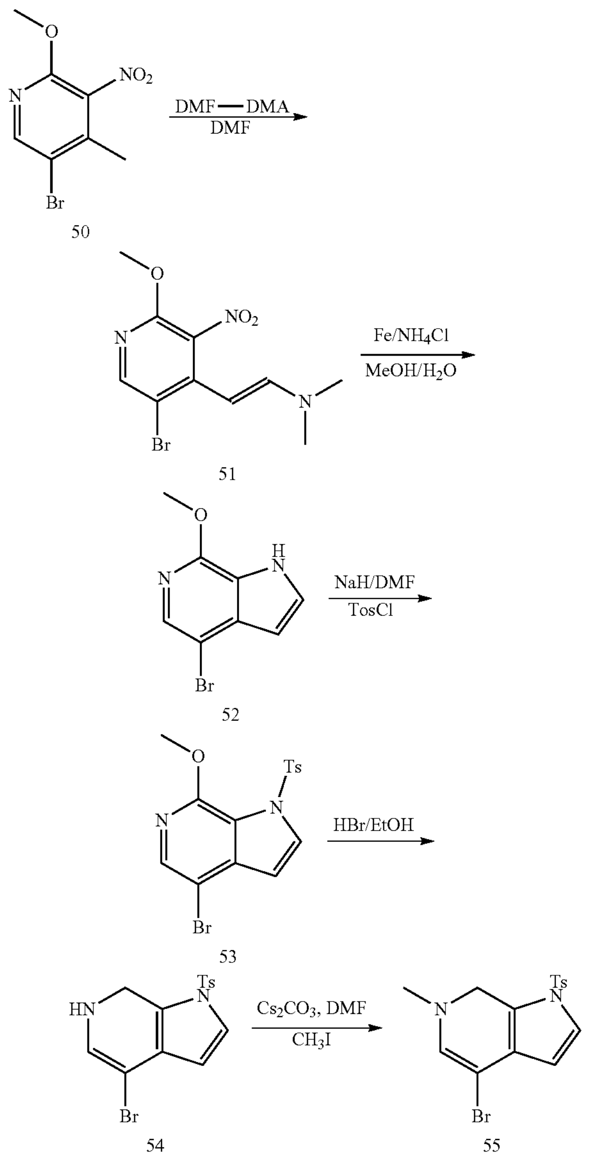

50, 51, 52, 53, 54, 55

Step 1: (E)-2-(5-bromo-2-methoxy-3-nitropyridin-4-yl)-N,N-dimethylvinyl-1-amine (Intermediate 51)

Compound 1 (1.5 g, 6 mmol) and 15 mL of DMF were added to a dry 50 mL three-necked flask, heated to 80° C., and then 7 mL (48 mmol) of DMF-DMA was slowly added dropwise. After the dropwise addition, the temperature was raised to 95° C., and the reaction was carried out overnight. After the completion of the reaction monitored by TLC, the reaction mixture was cooled to room temperature, added to cold water, and filtered to obtain (E)-2-(5-bromo-2-methoxy-3-nitropyridin-4-yl)-N,N-dimethylvinyl-1-amine, 1.2 g of boric acid.

Step 2: Synthesis of 4-bromo-7-methoxy-6,7-dihydro-1H-pyrrolo[2,3-c]pyridine (Intermediate 52)

Intermediate 51 (40 g, 0.14 mol), iron powder (39 g, 0.7 mol), ammonium chloride (37 g, 0.7 mol), 800 mL methanol and 100 mL water were successively added to a dry 2000 mL three-necked flask, refluxed at 90° C. overnight, filtered while it was still hot, and separated by column chromatography to obtain intermediate 52 (18 g, 0.08 mol).

Step 3: Synthesis of 1-p-tosyl-N-4-bromo-7-methoxy-6,7-dihydro-1H-pyrrolo[2,3-c]pyridine (Intermediate 53)

Compound 52 (18 g, 0.08 mol) and 70 mL of DMF were added to a dry 250 mL three-necked flask, NaH (9.6 g, 0.24 mol) was slowly added in an ice bath and reacted for 1 h, and then a solution of TosCl (23 g, 0.12 mol) in DMF was added. After the addition, the reaction was carried out at room temperature for 2 h and then quenched with saturated ammonium chloride solution. The mixture was subjected to column chromatography to obtain intermediate 53 (25 g, 0.07 mol).

Step 4: Synthesis of 1-N-p-tosyl-4-bromo-6-methyl-7-oxo-6,7-dihydro-1H-pyrrolo[2,3-c]pyridine (Intermediate 54)

Intermediate 53 (14 g, 0.04 mol), HBr (70 mL, 40% aqueous solution) and 40 mL ethanol were added to a dry 250 mL three-necked flask and reacted at 90° C. for 2 h. The mixture was cooled to room temperature and filtered to obtain intermediate 54 (12 g, 0.03 mol).

Step 5: Synthesis of 4-bromo-6-methyl-7-oxo-6,7-dihydro-1H-pyrrolo[2,3-c]pyridine (Intermediate 55)

Compound 5 (12 g, 0.04 mol), cesium carbonate (16 g, 0.05 mol) and 100 mL of DMF were added successively to a dry 250 mL three-necked flask, and methyl iodide (22 g, 0.16 mol) was added at room temperature, and the reaction was carried out overnight at room temperature. The mixture was quenched with water, extracted, and separated by column chromatography to obtain intermediate 55 (8.5 g, 0.03 mol).

Example A15 Synthesis Route

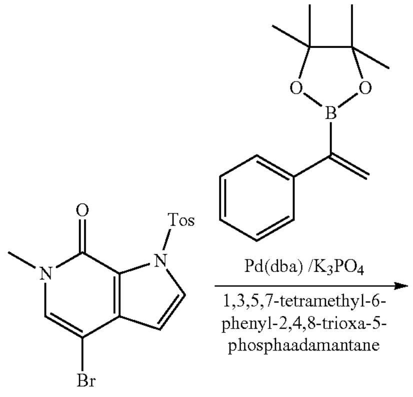

55

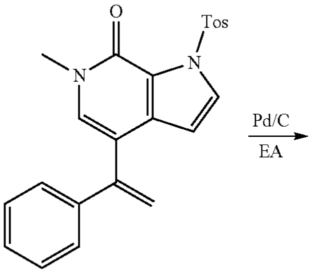

56

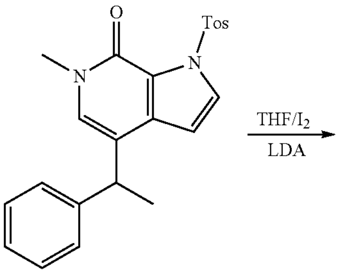

57

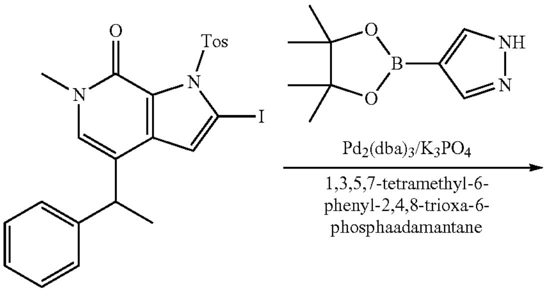

58

-continued

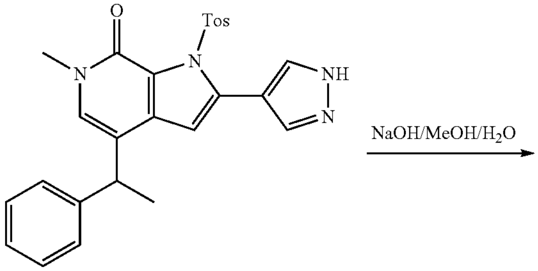

59

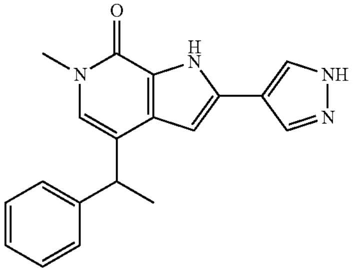

A15

Step 1: Synthesis of 6-methyl-4-(1-phenylvinyl)-1-tosyl-1,6-dihydro-7H-pyrrolo[2,3-c]pyridin-7-one (Intermediate 56)

4-bromo-6-methyl-1-p-tosyl-1,6-dihydro-7H-pyrrolo[2,3-c]pyridin-7-one (intermediate 55) (1 g, 2.63 mmol), 4,4,5,5-tetramethyl-2-(1-phenylvinyl)-1,3,2-dioxaborolane (604 mg, 2.63 mmol), $Pd_2(dba)_3$ (241 mg, 0.26 mmol), $K_3PO_4$ (1.2 g, 5.26 mmol), 1,3,5,7-tetramethyl-6-phenyl-2,4,8-trioxa-6-phosphaadamantane (77 mg, 0.26 mmol), 8 mL of 1,4-dioxane and 2 mL of $H_2O$ were added successively to a dry 50 mL three-necked flask and reacted at 70° C. under the protection of nitrogen for 12 h. After the completion of the reaction monitored by TLC, the mixture was filtered, the filter cake was washed with a large amount of ethyl acetate, the filtrate was dried by rotary evaporation, then 100 mL of water was slowly added to the crude product. The mixture was extracted with ethyl acetate (100 mL×3), the organic phases were combined and washed with saturated brine (50 mL×3), dried over anhydrous sodium sulfate, filtered, and the filtrate was concentrated under reduced pressure to obtain a crude product, which was then subjected to column chromatography to obtain 600 mg of 6-methyl-4-(1-phenylvinyl)-1-tosyl-1,6-dihydro-7H-pyrrolo[2,3-c]pyridin-7-one (intermediate 56).

LCMS: m/z 405.1 (M+H).

Step 2: Synthesis of 6-methyl-4-(1-phenethyl)-1-p-tosyl-1,6-dihydro-7H-pyrrolo[2,3-c]pyridin-7-one (57)

6-methyl-4-(1-phenylvinyl)-1-tosyl-1,6-dihydro-7H-pyrrolo[2,3-c]pyridin-7-one (intermediate 56) (600 mg, 1.49 mmol) and 40 mL of ethyl acetate were added successively to a dry 100 mL three-necked flask, replaced by hydrogen, and then 220 mg of Pd/C was added. After replacement by hydrogen, the mixture was reacted overnight. After the completion of the reaction monitored by TLC, the mixture was filtered and the filter cake was washed with a large amount of ethyl acetate. The filtrate was dried by rotary evaporation to obtain 600 mg of 6-methyl-4-(1-phenethyl)-1-p-tosyl-1,6-dihydro-7H-pyrrolo[2,3-c]pyridin-7-one (intermediate 57).

LCMS: m/z 407.1 (M+H).

Step 3: Synthesis of 2-iodo-6-methyl-4-(1-phenethyl)-1-p-tosyl-1,6-dihydro-7H-pyrrolo[2,3-c]pyridin-7-one (Intermediate 58)

6-methyl-4-(1-phenethyl)-1-p-tosyl-1,6-dihydro-7H-pyrrolo[2,3-c]pyridin-7-one (57) (250 mg, 0.615 mmol) and 4 mL of THF were added successively to a dry 100 mL three-necked flask and LDA (0.9 mL, 1.8 mmol) was slowly added at −70° C. and reacted at −70° C. for 40 minutes. Then iodine (460 mg, 1.8 mmol) was added and reacted for ten minutes. After the completion of the reaction monitored by TLC, the reaction mixture was quenched by adding saturated ammonium chloride and extracted with ethyl acetate (50 mL×3). The combined organic phases were washed with saturated brine (50 mL×3), dried over anhydrous sodium sulfate and filtered. The filtrate was concentrated under reduced pressure to obtain a crude product, which was subjected to column chromatography to obtain 130 mg of 2-iodo-6-methyl-4-(1-phenethyl)-1-p-tosyl-1,6-dihydro-7H-pyrrolo[2,3-c]pyridin-7-one (intermediate 58).

LCMS: m/z 533.0 (M+H).

Step 4: Synthesis of 6-methyl-4-(1-phenethyl)-2-(1H-pyrazol-4-yl)-1-tosyl-1,6-dihydro-7H-pyrrolo[2,3-c]pyridin-7-one (Intermediate 59)

2-iodo-6-methyl-4-(1-phenethyl)-1-p-tosyl-1,6-dihydro-7H-pyrrolo[2,3-c]pyridin-7-one (intermediate 58) (50 mg, 0.1 mmol), 4-(4,4,5,5-tetramethyl-1,3,2-dioxaborolan-2-yl)-1H-pyrazole (6) (60 mg, 0.3 mmol), $Pd_2(dba)_3$ (9 mg, 0.01 mmol), $K_3PO_4$ (53 mg, 0.25 mmol), 1,3,5,7-tetramethyl-6-phenyl-2,4,8-trioxa-6-phosphaadamantane (3 mg, 0.01 mmol), 4 mL of 1,4-dioxane and 1 mL of $H_2O$ were added successively to a dry 50 mL three-necked flask and reacted at 70° C. for 12 h under the protection of nitrogen. After the completion of the reaction monitored by TLC, the reaction mixture was filtered, the filter cake was washed with a large amount of ethyl acetate, the filtrate was dried by rotary evaporation, and then 50 mL of water was added. The mixture was extracted with ethyl acetate (50 mL×3), and the organic phases were combined and washed with saturated brine (50 mL×3), dried over anhydrous sodium sulfate, filtered, and the filtrate was concentrated under reduced pressure to obtain a crude product, which was subjected to column chromatography to obtain 30 mg of 6-methyl-4-(1-phenethyl)-2-(1H-pyrazol-4-yl)-1-tosyl-1,6-dihydro-7H-pyrrolo[2,3-c]pyridin-7-one (intermediate 59). LCMS: m/z 473.0 (M+H).

Step 5: Synthesis of 6-methyl-4-(1-phenethyl)-2-(1H-pyrazol-4-yl)-1,6-dihydro-7H-pyrrolo[2,3-c]pyridin-7-one (A15)

6-methyl-4-(1-phenethyl)-2-(1H-pyrazol-4-yl)-1-tosyl-1,6-dihydro-7H-pyrrolo[2,3-c]pyridin-7-one (7) (30 mg, 0.064 mmol), methanol (2 mL) and water (0.5 mL) were added successively to a dry 50 mL three-necked flask and then sodium hydroxide (7 mg, 0.18 mmol) was added and reacted at 80° C. for 2 h. After the completion of the reaction monitored by TLC, the mixture was concentrated under reduced pressure to obtain a crude product, which was subjected to column chromatography to obtain 7 mg of 6-methyl-4-(1-phenethyl)-2-(1H-pyrazol-4-yl)-1,6-dihydro-7H-pyrrolo[2,3-c]pyridin-7-one (A15).

LCMS: m/z 319.0 (M+H). $^1$H-NMR (DMSO, 400 MHz): δ 12.92 (s, 1H), 11.99 (s, 1H), 8.23 (s, 1H), 7.96 (s, 1H), 7.34 (d, J=7.4 Hz, 2H), 7.27 (t, J=7.6 Hz, 2H), 7.15 (t, J=7.2 Hz, 1H), 7.09 (s, 1H), 6.33 (d, J=1.8 Hz, 1H), 4.16 (q, J=7.1 Hz, 1H), 3.53 (s, 3H), 1.59 (d, J=7.2 Hz, 3H).

Example A16 Synthesis Route

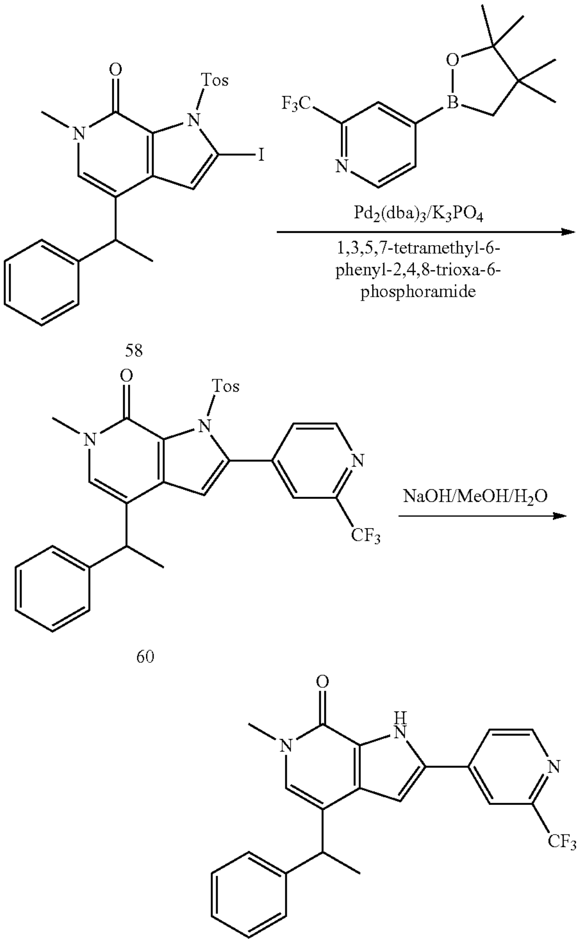

58

60

A16

Step 1: Synthesis of 6-methyl-4-(1-phenethyl)-1-tosyl-2-(2-(trifluoromethyl)pyridin-4-yl)-1,6-dihydro-7H-pyrrolo[2,3-c]pyridin-7-one (Intermediate 60)

2-iodo-6-methyl-4-(1-phenethyl)-1-p-tosyl-1,6-dihydro-7H-pyrrolo[2,3-c]pyridin-7-one (intermediate 58) (50 mg, 0.1 mmol), 4-(4,4,5,5-tetramethyl-1,3,2-dioxaborolan-2-yl)-2-(trifluoromethyl)pyridine (82 mg, 0.3 mmol), $Pd_2(dba)_3$ (9 mg, 0.01 mmol), $K_3PO_4$ (53 mg, 0.25 mmol), 1,3,5,7-tetramethyl-6-phenyl-2,4,8-trioxa-6-phosphaadamantane (3 mg, 0.01 mmol), 4 mL of 1,4-dioxane and 1 mL of $H_2O$ were added successively to a dry 50 mL three-necked flask and reacted at 70° C. for 12 h under the protection of nitrogen. After the completion of the reaction monitored by TLC, the reaction mixture was filtered, the filter cake was washed with a large amount of ethyl acetate, the filtrate was dried by rotary evaporation, and then 50 mL of water was added. The mixture was extracted with ethyl acetate (50 mL×3), and the organic phases were combined and washed with saturated brine (50 mL×3), dried over anhydrous sodium sulfate and filtered. The filtrate was concentrated under reduced pressure to obtain a crude product which was subjected to column chromatography to obtain 40 mg of 6-methyl-4-(1-phenethyl)-1-tosyl-2-(2-(trifluoromethyl)pyridin-4-yl)-1,6-dihydro-7H-pyrrolo[2,3-c]pyridin-7-one (intermediate 60).

LCMS: m/z 552.0 (M+H).

Step 2: Synthesis of 6-methyl-4-(1-phenethyl)-2-(2-(trifluoromethyl)pyridin-4-yl)-1,6-dihydro-7H-pyrrolo[2,3-c]pyridin-7-one (A16)

6-methyl-4-(1-phenethyl)-1-tosyl-2-(2-(trifluoromethyl) pyridin-4-yl)-1,6-dihydro-7H-pyrrolo[2,3-c]pyridin-7-one (60) (40 mg, 0.73 mol), 2 mL methanol and 0.5 mL water were added successively to a dry 50 mL three-necked flask and then sodium hydroxide (8 mg, 0.22 mmol) was added and reacted at 80° C. for 2 h. After the completion of the reaction monitored by TLC, the mixture was concentrated under reduced pressure to obtain a crude product, which was subjected to column chromatography to obtain 12 mg of 6-methyl-4-(1-phenethyl)-2-(2-(trifluoromethyl) pyridin-4-yl)-1,6-dihydro-7H-pyrrolo[2,3-c]pyridin-7-one (A16).

The spectrogram data of Example A16 is as follows:

LCMS: m/z 398.0 (M+H).

$^1$H-NMR (DMSO, 400 MHz): δ 12.77 (s, 1H), 8.71 (d, J=5.2 Hz, 1H), 8.49 (d, J=0.9 Hz, I H), 8.15 (dd, J=5.2, 1.4 Hz, 1H), 7.39 (d, J=7.2 Hz, 2H), 7.27 (dd, J=14.8, 7.2 Hz, 2H), 7.19-7.12 (m, 3H), 4.21 (q, J=7.2 Hz, 1H), 3.54 (s, 3H), 1.61 (d, J=7.2 Hz, 3H).

Example A17 Synthesis Route

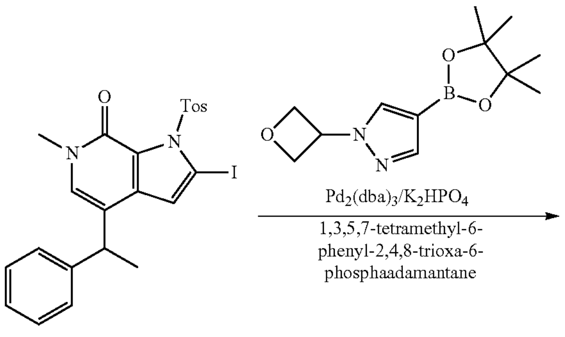

58

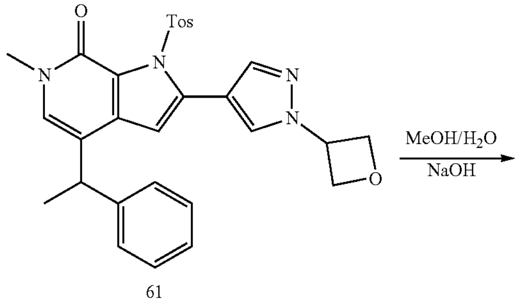

61

-continued

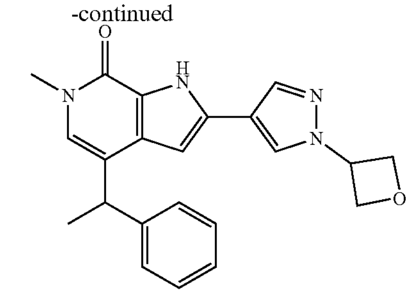

A17

Step 1: Synthesis of 6-methyl-2-(1-(oxetan-3-yl)-1H-pyrazol-4-yl)-4-(1-phenethyl)-1-tosyl-1,6-dihydro-7H-pyrrolo[2,3-c]pyridin-7-one (Intermediate 61)

2-iodo-6-methyl-4-(1-phenethyl)-1-p-tosyl-1,6-dihydro-7H-pyrrolo[2,3-c]pyridin-7-one (intermediate 58) (130 mg, 0.24 mmol), 1-methyl-4-(4,4,5,5-tetramethyl-1,3,2-dioxaborolan-2-yl)-1H-pyrazole (92 mg, 0.37 mmol), $Pd_2(dba)_3$ (22 mg, 0.024 mmol), $K_2HPO_4$ (63 mg, 0.36 mmol), 1,3,5,7-tetramethyl-6-phenyl-2,4,8-trioxa-6-phosphaadamantane (7 mg, 0.024 mmol), 4 mL of 1,4-dioxane and 1 mL of $H_2O$ were added successively to a dry 50 mL three-necked flask and reacted at 50° C. for 12 h under the protection of nitrogen. After the completion of the reaction monitored by TLC, the reaction mixture was filtered, the filter cake was washed with a large amount of ethyl acetate, the filtrate was dried by rotary evaporation, and then 50 mL of water was added. The mixture was extracted with ethyl acetate (50 mL×3), and the organic phases were combined and washed with saturated brine (50 mL×3), dried over anhydrous sodium sulfate, filtered, and the filtrate was concentrated under reduced pressure to obtain a crude product, which was subjected to column chromatography to obtain 40 mg of 6-methyl-2-(1-(oxetan-3-yl)-1H-pyrazol-4-yl)-4-(1-phenethyl)-1-tosyl-1,6-dihydro-7H-pyrrolo[2,3-c]pyridin-7-one (intermediate 61).

LCMS: m/z 529.1 (M+H).

Step 2: Synthesis of 6-methyl-2-(1-(oxetan-3-yl)-1H-pyrazol-4-yl)-4-(1-phenethyl)-1,6-dihydro-7H-pyrrolo[2,3-c]pyridin-7-one (A17)

6-methyl-2-(1-(oxetan-3-yl)-1H-pyrazol-4-yl)-4-(1-phenethyl)-1-tosyl-1,6-dihydro-7H-pyrrolo[2,3-c]pyridin-7-one (intermediate 61) (40 mg, 0.076 mmol), methanol (2 mL) and water (0.5 ml) were added successively to a dry 50 mL three-necked flask and then cesium carbonate (74 mg, 0.23 mmol) was added and reacted at 70° C. for 12 h. After the completion of the reaction monitored by TLC, the reaction mixture was concentrated under reduced pressure to obtain a crude product, which was subjected to column chromatography to obtain 18 mg of 6-methyl-2-(1-(oxetan-3-yl)-1H-pyrazol-4-yl)-4-(1-phenethyl)-1,6-dihydro-7H-pyrrolo[2,3-c]pyridin-7-one (A17).

LCMS: m/z 375.0 (M+H).

$^1$H-NMR (DMSO, 400 MHz): δ 12.07 (s, 1H), 8.37 (s, 1H), 8.08 (s, 1H), 7.34 (d, J=7.2 Hz, 2H), 7.27 (t, J=7.6 Hz, 2H), 7.14 (dd, J=14.8, 7.5 Hz, 2H), 6.34 (d, J=2.1 Hz, 1H), 5.61-5.50 (m, 1H), 4.93 (t, J=7.1 Hz, 2H), 4.86 (t, J=6.4 Hz, 2H), 4.15 (q, J=7.3 Hz, 1H), 3.53 (s, 3H), 1.59 (d, J=7.2 Hz, 3H).

Example A18 Synthesis Route

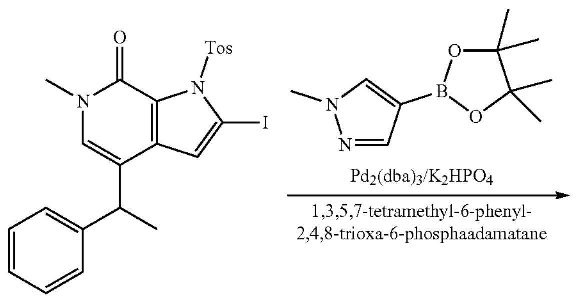

58

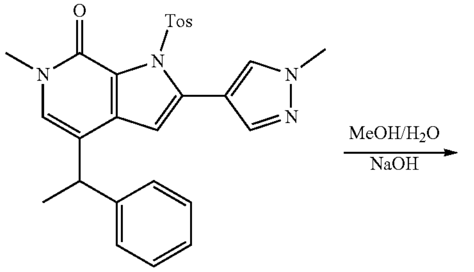

62

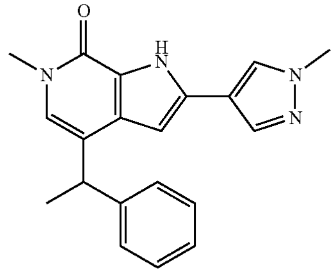

A18

Step 1: Synthesis of 6-methyl-2-(1-methyl-1H-pyrazol-4-yl)-4-(1-phenethyl)-1-tosyl-1,6-dihydro-7H-pyrrolo[2,3-c]pyridin-7-one (Intermediate 62)

2-iodo-6-methyl-4-(1-phenethyl)-1-p-tosyl-1,6-dihydro-7H-pyrrolo[2,6-dihydro-7H-pyrrolo[2,3-c]pyridin-7-one (intermediate 58) (130 mg, 0.24 mmol), 1-methyl-4-(4,4,5,5-tetramethyl-1,3,2-dioxaborolan-2-yl)-LH-pyrazole (76 mg, 0.37 mmol), $Pd_2(dba)_3$ (22 mg, 0.024 mmol), $K_2HPO_4$ (63 mg, 0.36 mmol), 1,3,5,7-tetramethyl-6-phenyl-2,4,8-trioxa-6-phosphaadamantane (7 mg, 0.024 mmol), 4 mL of 1,4-dioxane and 1 mL of $H_2O$ were added successively to a dry 50 mL three-necked flask and reacted at 50° C. for 12 h under the protection of nitrogen. After the completion of the reaction monitored by TLC, the reaction mixture was filtered, the filter cake was washed with a large amount of ethyl acetate, the filtrate was dried by rotary evaporation, and then 50 mL of water was added. The mixture was extracted with ethyl acetate (50 mL×3), and the organic phases were combined and washed with saturated brine (50 mL×3), dried over anhydrous sodium sulfate, filtered. The filtrate was concentrated under reduced pressure to obtain a crude product, which was subjected to column chromatography to obtain 57 mg of 6-methyl-2-(1-methyl-1H-pyrazol-4-yl)-4-(1-phenethyl)-1-tosyl-1,6-dihydro-7H-pyrrolo[2,3-c]pyridin-7-one (intermediate 62). LCMS: m/z 487.1 (M+H).

Step 2: Synthesis of 6-methyl-2-(1-methyl-1H-pyrazol-4-yl)-4-(1-phenethyl)-1,6-dihydro-7H-pyrrolo[2,3-c]pyridin-7-one (A18)

6-methyl-2-(1-methyl-1H-pyrazol-4-yl)-4-(1-phenethyl)-1-tosyl-1,6-dihydro-7H-pyrrolo[2,3-c]pyridin-7-one (intermediate 62) (57 mg, 0.18 mmol), methanol (2 mL) and water (0.5 mL) were added successively to a dry 50 mL three-necked flask and then sodium hydroxide (22 mg, 0.54 mmol) was added and reacted at 80° C. for 2 h. After the completion of the reaction monitored by TLC, the mixture was concentrated under reduced pressure to obtain a crude product, which was subjected to column chromatography to obtain 9.7 mg of 6-methyl-2-(1-methyl-1H-pyrazol-4-yl)-4-(1-phenethyl)-1,6-dihydro-7H-pyrrolo[2,3-c]pyridin-7-one (A18).

LCMS: m/z 333.0 (M+H). $^1$H-NMR (DMSO, 400 MHz): δ 12.02 (s, 1H), 8.13 (s, 1H), 7.90 (s, 1H), 7.36-7.30 (m, 2H), 7.26 (t, J=7.6 Hz, 2H), 7.16 (d, J=7.2 Hz, 1H), 7.10 (s, 1H), 6.28 (d, J=2.1 Hz, 1H), 4.15 (q, J=7.2 Hz, 1H), 3.83 (s, 3H), 3.53 (s, 3H), 1.58 (d, J=7.2 Hz, 3H).

Example A19 Synthesis Route

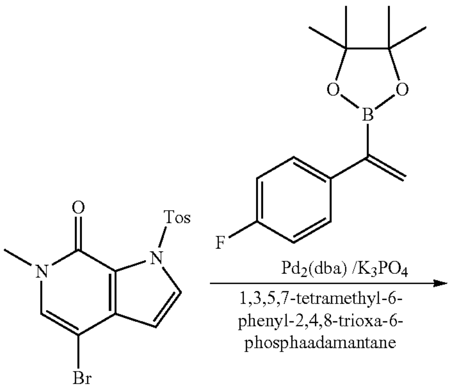

55

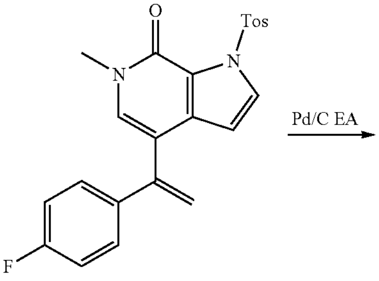

63

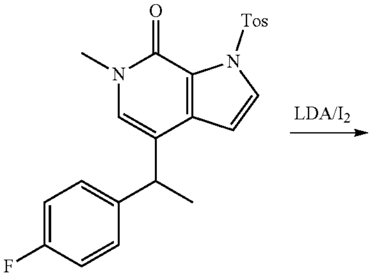

64

-continued

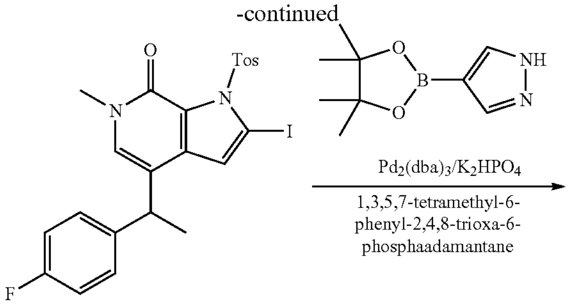

65

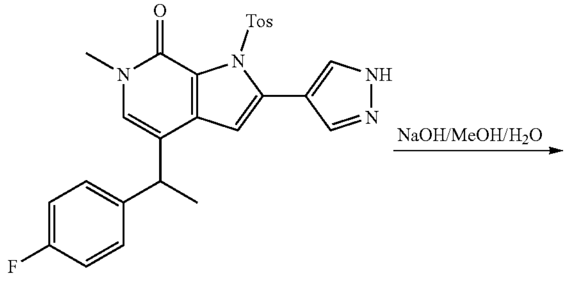

66

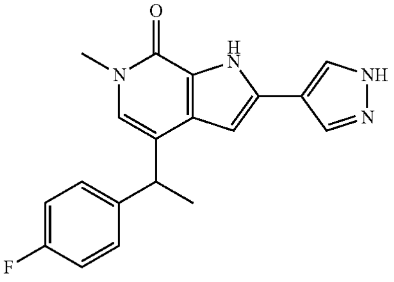

A19

Step 1: Synthesis of 4-(1-(4-fluorophenyl)vinyl)-6-methyl-1-p-tosyl-1,6-dihydro-7H-pyrrolo[2,3-c]pyridin-7-one (Intermediate 63)

4-bromo-6-methyl-1-p-tosyl-1,6-dihydro-7H-pyrrolo[2,3-c]pyridin-7-one (intermediate 55) (307 mg, 0.81 mmol), 2-(1-(4-fluorophenyl) vinyl)-4,4,5,5-tetramethyl-1,3,2-dioxaborolane (200 mg, 0.81 mmol), $Pd_2(dba)_3$ (73 mg, 0.08 mmol), $K_3PO_4$ (342 mg, 1.62 mmol), 1,3,5,7-tetramethyl-6-phenyl-2,4,8-trioxa-6-phosphaadamantane (24 mg, 0.08 mmol), 4 mL of 1,4-dioxane and 1 mL of $H_2O$ were added successively to a dry 50 mL three-necked flask and reacted at 70° C. for 12 h under the protection of nitrogen. After the completion of the reaction monitored by TLC, the reaction mixture was filtered, and the filter cake was washed with a large amount of ethyl acetate. The filtrate was dried by rotary evaporation, and then 100 mL of water was added slowly to the crude product. The mixture was extracted with ethyl acetate (100 mL×3), the organic phases were combined and washed with saturated brine (50 mL×3), dried over anhydrous sodium sulfate and filtered. The filtrate was concentrated under reduced pressure to obtain a crude product which was subjected to column chromatography to obtain 210 mg of 4-(1-(4-fluorophenyl)vinyl)-6-methyl-1-p-tosyl-1,6-dihydro-7H-pyrrolo[2,3-c]pyridin-7-one (Intermediate 63).

LCMS: m/z 405.1 (M+H).

Step 2: Synthesis of 4-(1-(4-fluorophenyl)ethyl)-6-methyl-1-p-tosyl-1,6-dihydro-7H-pyrrolo[2,3-c]pyridin-7-one (Intermediate 64)

4-(1-(4-fluorophenyl)vinyl)-6-methyl-1-p-tosyl-1,6-dihydro-7H-pyrrolo[2,3-c]pyridin-7-one (intermediate 63) (210 mg, 0.50 mmol) and 40 mL of ethyl acetate were added successively to a dry 100 mL three-necked flask, replaced by hydrogen and then 80 mg of Pd/C was added. After replacement by hydrogen, the reaction was carried out overnight. After the completion of the reaction monitored by TLC, the reaction mixture was filtered, and the filter cake was washed with a large amount of ethyl acetate. The filtrate was dried by rotary evaporation to obtain 200 mg of 4-(1-(4-fluorophenyl)ethyl)-6-methyl-1-p-tosyl-1,6-dihydro-7H-pyrrolo[2,3-c]pyridin-7-one (Intermediate 64).

LCMS: m/z 407.1 (M+H).

Step 3: Synthesis of 4-(1-(4-fluorophenyl)ethyl)-2-iodo-6-methyl-1-p-tosyl-1,6-dihydro-7H-pyrrolo[2,3-c]pyridin-7-one (Intermediate 65)

4-(1-(4-fluorophenyl)ethyl)-6-methyl-1-p-tosyl-1,6-dihydro-7H-pyrrolo[2,3-c]pyridin-7-one (intermediate 64) (200 mg, 0.47 mmol) and 4 mL of THF were added successively to a dry 100 mL three-necked flask and LDA (0.7 mL, 1.41 mmol) was slowly added at −70° C. and reacted for 40 minutes. Then iodine (360 mg, 1.41 mmol) was added and reacted for ten minutes. After the completion of the reaction monitored by TLC, the reaction mixture was quenched by adding saturated ammonium chloride and extracted with ethyl acetate (50 mL×3). The combined organic phases were washed with saturated brine (50 mL×3), dried over anhydrous sodium sulfate and filtered. The filtrate was concentrated under reduced pressure to obtain a crude product, which was subjected to column chromatography to obtain 210 mg of 4-(1-(4-fluorophenyl)ethyl)-2-iodo-6-methyl-1-p-tosyl-1,6-dihydro-7H-pyrrolo[2,3-c]pyridin-7-one (intermediate 65).

LCMS: m/z 533.0 (M+H).

Step 4: Synthesis of 4-(1-(4-fluorophenyl)ethyl)-6-methyl-2-(1H-pyrazol-4-yl)-1-tosyl-1,6-dihydro-7H-pyrrolo[2,3-c]pyridin-7-one (Intermediate 66)

4-(1-(4-fluorophenyl)ethyl)-2-iodo-6-methyl-1-p-tosyl-1,6-dihydro-7H-pyrrolo[2,3-c]pyridin-7-one (intermediate 65) (210 mg, 0.38 mmol), 4-(4,4,5,5-tetramethyl-1,3,2-dioxaborolan-2-yl)-1H-pyrazole (111 mg, 0.57 mmol), $Pd_2(dba)_3$ (35 mg, 0.038 mmol), $K_2HPO_4$ (100 mg, 0.57 mmol), 1,3,5,7-tetramethyl-6-phenyl-2,4,8-trioxa-6-phosphaadamantane (11 mg, 0.038 mmol), 4 mL of 1,4-dioxane and 1 mL of $H_2O$ were added successively to a dry 50 mL three-necked flask and reacted at 50° C. for 12 h under the protection of nitrogen. After the completion of the reaction monitored by TLC, the reaction mixture was filtered, and the filter cake was washed with a large amount of ethyl acetate. The filtrate was dried by rotary evaporation, and then 50 mL of water was added. The mixture was extracted with ethyl acetate (50 mL×3), and the organic phases were combined and washed with saturated brine (50 mL×3), dried over anhydrous sodium sulfate, filtered. The filtrate was concentrated under reduced pressure to obtain a crude product, which was subjected to column chromatography to obtain 90 mg of 4-(1-(4-fluorophenyl)ethyl)-6-methyl-2-(1H-pyrazol-4-yl)-1-tosyl-1,6-dihydro-7H-pyrrolo[2,3-c]pyridin-7-one (intermediate 66).

LCMS: m/z 491.0 (M+H).

Step 5: Synthesis of 4-(1-(4-fluorophenyl)ethyl)-6-methyl-2-(1H-pyrazol-4-yl)-1,6-dihydro-7H-pyrrolo[2,3-c]pyridin-7-one (A19)

4-(1-(4-fluorophenyl)ethyl)-6-methyl-2-(1H-pyrazol-4-yl)-1-tosyl-1,6-dihydro-7H-pyrrolo[2,3-c]pyridin-7-one (intermediate 66) (90 mg, 0.18 mmol), methanol (2 mL) and water (0.5 mL) were added successively to a dry 50 mL three-necked flask and then sodium hydroxide (22 mg, 0.54 mmol) was added and reacted at 80° C. for 2 h. After the completion of the reaction monitored by TLC, the mixture was concentrated under reduced pressure to obtain a crude product, which was subjected to column chromatography to obtain 25 mg of 4-(1-(4-fluorophenyl)ethyl)-6-methyl-2-(1H-pyrazol-4-yl)-1,6-dihydro-7H-pyrrolo[2,3-c]pyridin-7-one (A19).

LCMS: m/z 337.1 (M+H). $^1$H-NMR (DMSO, 400 MHz): δ 12.92 (s, 1H), 12.00 (s, 1H), 8.23 (s, 1H), 7.96 (s, 1H), 7.42-7.25 (m, 2H), 7.16-6.95 (m, 3H), 6.32 (d, J=2.1 Hz, 1H) 4.17 (q, J=7.2 Hz, 1H), 3.53 (s, 3H), 1.58 (d, J=7.2 Hz, 3H).

Example A20 Synthesis Route

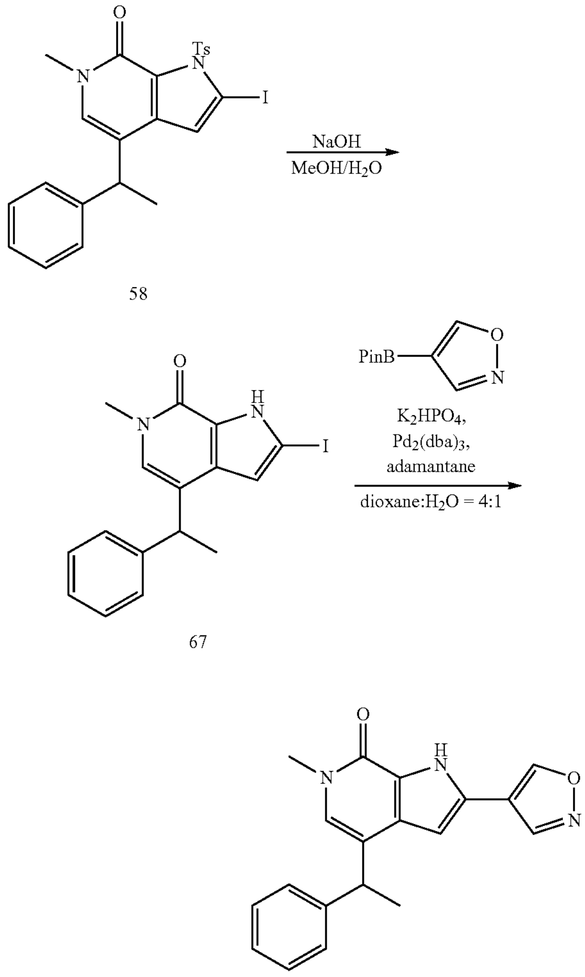

58

67

A20

Step 1: 2-iodo-6-methyl-4-(1-phenethyl)-1H-pyrrolo[2,3-c]pyridin-7(6H)-one (Intermediate 67)

Intermediate 58 (150 mg, 0.28 mmol), sodium hydroxide (56.4 mg, 1.41 mmol), 9 mL of methanol and 3 mL of water were added successively to a dry 50 mL single-necked flask and reacted at 60° C. for 2 hours. After the completion of the reaction monitored by TLC, the reaction mixture was cooled to room temperature. Water was added to the reaction solution and then a white solid was precipitated, filtered, and the filter cake was dried to obtain the product (intermediate 67) (90 mg, white solid) as a crude product.

LCMS: m/z 379.2 (M+H).

Step 2: 2-(isoxazol-4-yl)-6-methyl-4-(1-phenethyl)-1H-pyrrolo[2,3-c]pyridin-7(6H)-one (A20)

Intermediate 5 (70 mg, 0.132 mmol), 4-(4,4,5,5-tetramethyl-1,3,2-dioxolan-2-yl)isoxazole (28.4 mg, 0.146 mmol), dipotassium hydrogen phosphate (45 mg, 0.198 mmol), tris(dibenzylideneindenacetone)dipalladium (6.0 mg, 0.007 mmol) and adamantane (3.9 mg, 0.013 mmol) were added successively to a dry 25 mL three-necked flask containing 3.2 mL of 1,4-dioxane and 0.8 mL of water at room temperature and reacted at 50° C. for 3 h. After the completion of the reaction monitored by TLC, the reaction solution was diluted with water, extracted twice with ethyl acetate, and the organic phase was collected, washed with saturated brine, dried over anhydrous sodium sulfate, filtered. The filtrate was concentrated under reduced pressure and subjected to preparative chromatography to give product A20 (7 mg, white solid), yield: 11.8%.

LCMS: m/z 320.1 (M+H).

$^1$H-NMR (DMSO, 400 MHz): 12.33 (s, 1H), 9.34 (s, 1H), 9.15 (s, 1H), 7.35-7.14 (m, 6H), 6.58 (s, 1H), 4.19-4.14 (m, 1H), 3.55 (s, 3H), 1.60 (d, J=7.2 Hz, 3H).

Example A21 Synthesis Route

Example A21 was synthesized according to Example A20 and using 4-(4,4,5,5-tetramethyl-1,3,2-dioxolan-2-yl)-3-methylisoxazole as raw material and the structure is as follows:

A21

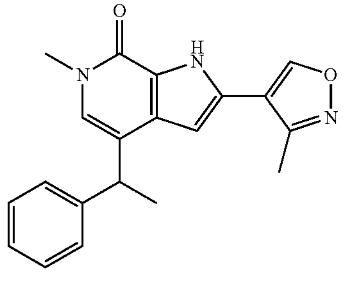

The product A21 (81 mg, white solid) was obtained and subjected to chiral resolution to give the product (P1: 32 mg, white solid; P2; 33 mg, white solid), yield: 45.7%.

LCMS: m/z 334.4 (M+H). $^1$H-NMR (DMSO, 400 MHz): 12.22 (s, 1H), 9.21 (s, 1H), 7.37-7.14 (m, 6H), 6.31 (s, 1H), 4.24-4.19 (m, 1H), 3.55 (s, 3H), 2.33 (s, 3H), 1.59 (d, J=7.6 Hz, 3H).

The data of A21-P1 are as follows:

LCMS: m/z 334.1 (M+H). $^1$H-NMR (DMSO, 400 MHz): 12.21 (s, 1H), 9.22 (s, 1H), 7.37-7.35 (m, 2H), 7.29-7.25 (m, 2H), 7.17-7.15 (m, 2H), 6.31 (s, 1H), 4.24-4.21 (m, 1H), 3.55 (s, 3H), 2.33 (s, 3H), 1.59 (d, J=7.2 Hz, 3H).

The data of A21-P2 are as follows:

LCMS: m/z 334.1 (M+H). $^1$H-NMR (DMSO, 400 MHz): 12.22 (s, 1H), 9.22 (s, 1H), 7.37-7.35 (m, 2H), 7.29-7.25 (m, 2H), 7.17-7.15 (m, 2H), 6.32 (s, 1H), 4.24-4.19 (m, 1H), 3.55 (s, 3H), 2.33 (s, 3H), 1.59 (d, J=7.6 Hz, 3H).

Example A22 Synthesis Route

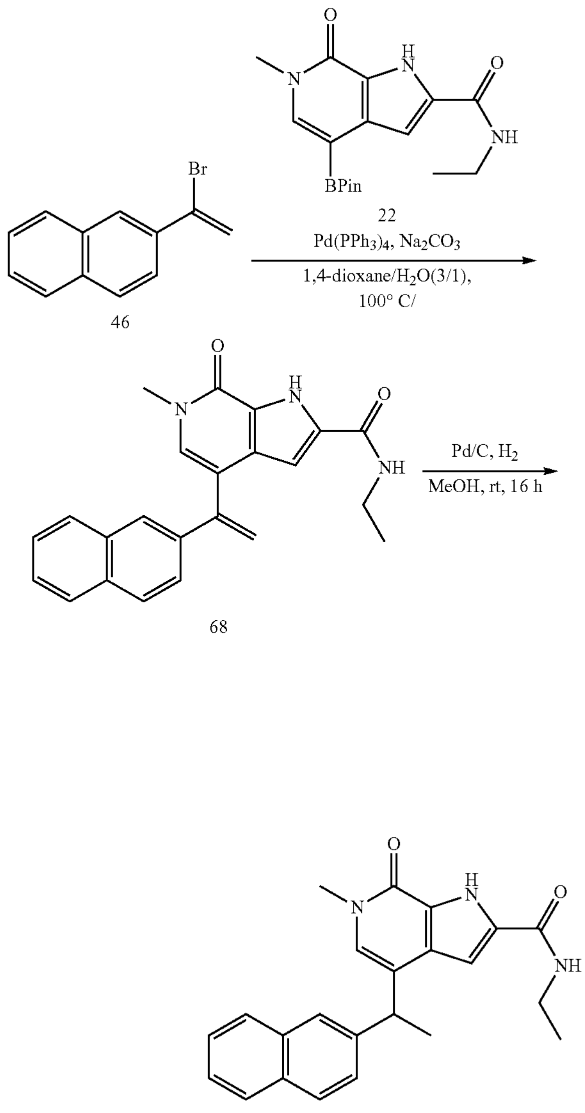

22

46

68

A22

Step 1: Synthesis of N-ethyl-6-methyl-4-(1-(naphthalen-2-yl)ethenyl)-7-oxo-6,7-dihydro-1H-pyrrolo [2,3-c]pyridin-2-carboxamide (Intermediate 68)

Intermediate 46 (150 mg, 0.43 mmol), intermediate 3 (122 mg, 0.52 mmol), 1,4-dioxane (3 ml), water (1 mL), palladium tetrakistriphenylphosphine (50 mg, 0.04 mmol) and sodium carbonate (115 mg, 1.09 mmol) were added successively to a dry 25 mL single-necked flask at room temperature, heated to 100° C. and reacted for 2 hours. After the reaction was completed, the reaction mixture was concentrated under reduced pressure, and the residue was purified by preparative plate (dichloromethane:methanol (v:v) =20:1) to obtain N-ethyl-6-methyl-4-(1-(naphthalen-2-yl) vinyl)-7-oxo-6,7-dihydro-1H-pyrrolo[2,3-c]pyridin-2-carboxamide (intermediate 68) (120 mg, white solid), yield: 74.35%.

$^1$H-NMR (DMSO, 400 MHz): 8.28-8.26 (m, 1H), 7.93-7.86 (m, 4H), 7.58-7.49 (m, 3H), 7.32 (s, 1H), 6.28 (d, J=2.4 Hz, I H), 5.72 (d, J=2.4 Hz, 1H), 4.34 (d, J=0.8 Hz, 1H), 3.57 (s, 3H), 3.21-3.15 (m, 2H), 1.06 (d, J=6.8 Hz, 3H).

Step 2: Synthesis of N-ethyl-6-methyl-4-(1-(naphthalen-2-yl)ethyl)-7-oxo-6,7-dihydro-1H-pyrrolo[2,3-c]pyridin-2-carboxamide (A22)

Intermediate 68 (110 mg, 0.30 mmol), methanol (10 mL) and palladium on carbon (11 mg) were added successively to a dry 25 mL single-necked flask at room temperature and replaced by hydrogen 3 times. The mixture was stirred at room temperature and reacted for 16 hours. After the completion of the reaction monitored by TLC, the reaction mixture was filtered, and the filtrate was concentrated under reduced pressure. The residue was purified by preparative plate (dichloromethane:methanol (v:v)=20:1) to give N-ethyl-6-methyl-4-(1-(naphthalen-2-yl)ethyl)-7-oxo-6,7-dihydro-1H-pyrrolo[2,3-c]pyridin-2-carboxamide (Compound A22) (41 mg, white solid), yield: 37.10%. The final intermediate was subjected to SFC resolution to give A22-P1 (20 mg) and A22-P2 (21 mg).

The spectral data of A22-P1 are as follows:

LCMS: m/z 374.1 (M+H). $^1$H-NMR (DMSO, 400 MHz): 12.11 (s, 1H), 8.25-8.23 (m, 1H), 7.86-7.80 (m, 4H), 7.49-7.42 (m, 3H), 7.24 (s, 1H), 6.67 (s, 1H), 4.34 (d, J=7.2 Hz, 1H), 3.57 (s, 3H), 3.23-3.16 (m, 2H), 1.66 (d, J=7.2 Hz, 3H), 1.07 (t, J=7.2 Hz, 3H).

The spectral data of A22-P1 are as follows:

LCMS: m/z 374.1 (M+H).

$^1$H-NMR (DMSO, 400 MHz): 12.10 (s, 1H), 8.26-8.23 (m, 1H), 7.86-7.80 (m, 4H), 7.49-7.42 (m, 3H), 7.25 (s, 1H), 6.67 (s, 1H), 4.34 (d, J=7.2 Hz, 1H), 3.57 (s, 3H), 3.23-3.16 (m, 2H), 1.66 (d, J=6.8 Hz, 3H), 1.07 (t, J=7.2 Hz, 3H).

Example A23 Synthesis Route

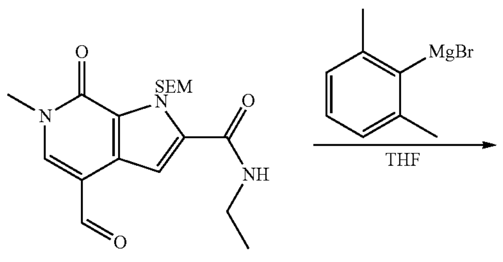

41

-continued

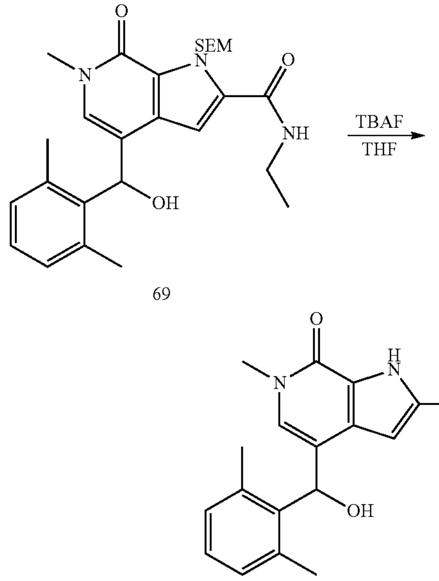

69

A23

Step 1: Synthesis of (4-(2,6-dimethylphenyl)(hydroxy)methyl)-N-ethyl-6-methyl-7-oxo-1-(2-(trimethylsilyl)ethoxy)methyl)-6,7-dihydro-1H-pyrrolo[2,3-c]pyridin-2-carboxamide (Intermediate 69)

Intermediate 41 (190 mg, 0.503 mmol) and 10 mL tetrahydrofuran were successively added to a dry 25 mL three-necked flask at room temperature, replaced by nitrogen three times, and 6 mL of dimethylphenyl Grignard reagent was added at 0° C. and reacted overnight at room temperature. After the completion of the reaction monitored by TLC, the reaction mixture was extracted twice with ethyl acetate, and the organic phase was collected, washed with saturated brine, dried over anhydrous sodium sulfate, and filtered. The filtrate was concentrated under reduced pressure to obtain (4-(2,6-dimethylphenyl)(hydroxy)methyl)-N-ethyl-6-methyl-7-oxo-1-(2-(trimethylsilyl) ethoxy)methyl)-6,7-dihydro-1H-pyrrolo[2,3-c]pyridin-2-carboxamide (intermediate 69) (270 mg, yellow oil) as a crude product.

LCMS: m/z 484.3 (M+H).

Step 2: Synthesis of (4-(2,6-dimethylphenyl)(hydroxy)methyl)-N-ethyl-6-methyl-7-oxo-6,7-dihydro-1H-pyrrolo[2,3-c]pyridin-2-carboxamide (A23)

Intermediate 69 (20 mg) was added to a 50 mL single-necked flask containing 5 mL of tetrabutylammonium fluoride at room temperature and reacted at 60° C. overnight. After the completion of the reaction monitored by TLC, the reaction solution was diluted with water, extracted twice with ethyl acetate, and the organic phase was collected, washed with saturated brine, dried over anhydrous sodium sulfate, and filtered. The filtrate was concentrated under reduced pressure and purified by Prep-HPLC to give (4-(2,6-dimethylphenyl)(hydroxy)methyl)-N-ethyl-6-methyl-7-oxo-6,7-dihydro-1H-pyrrolo[2,3-c]pyridin-2-carboxamide (Compound A23) (9 mg, white solid), yield: 61.6%.

LCMS: m/z 354.4 (M+H).

$^1$H-NMR (DMSO, 400 MHz): 12.19 (s, 1H), 8.35-8.33 (m, 1H), 7.17-7.13 (m, 1H), 7.06 (d, J=7.6 Hz, 2H), 6.97 (s, 1H), 6.42 (s, 1H), 6.22-6.21 (m, 1H), 5.89 (d, J=4.4 Hz, 1H), 3.53 (s, 3H), 3.33-3.28 (m, 2H), 2.35 (s, 6H), 1.18-1.15 (m, 3H).

Example A24 Synthesis Route

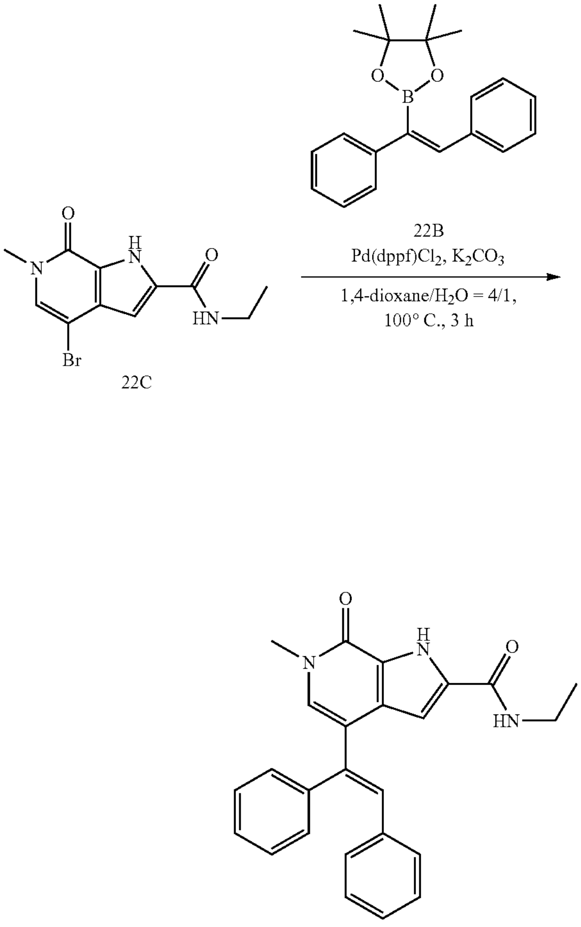

22C

A24

Intermediate 22C (160 mg, 0.54 mmol), intermediate 22B (214 mg, 0.70 mmol), 1,4-dioxane (2 mL), water (0.5 mL), [1,1'-bis(diphenylphosphino)ferrocene]palladium dichloride (39 mg, 0.05 mmol) and potassium carbonate (148 mg, 1.07 mmol) were successively added to a dry 25 mL single-necked flask at room temperature, heated to 100° C., and reacted for 3 hours under the protection of $N_2$. After the reaction was completed, the reaction mixture was concentrated under reduced pressure, and the residue was purified by prep-TLC (dichloromethane:methanol (v:v)=10:1) to obtain (E)-4-(1,2-diphenylvinyl)-N-ethyl-6-methyl-7-oxo-6,7-dihydro-1H-pyrrolo[2,3-c]pyridin-2-carboxamide (A24) (113.8 mg, yellow solid), yield: 53.38%.

LCMS: m/z 398.2 (M+H). $^1$H-NMR (DMSO, 400 MHz): 12.24 (s, 1H), 8.32 (t, J=5.2 Hz, 1H), 7.36-7.34 (m, 3H), 7.22-7.08 (m, 6H), 7.03 (d, J=6.8 Hz, 2H), 6.96 (s, 1H), 6.40 (s, 1H), 3.52 (s, 3H), 3.26-3.19 (m, 2H), 1.09 (t, J=7.2 Hz, 3H).

Example A25 Synthesis Route

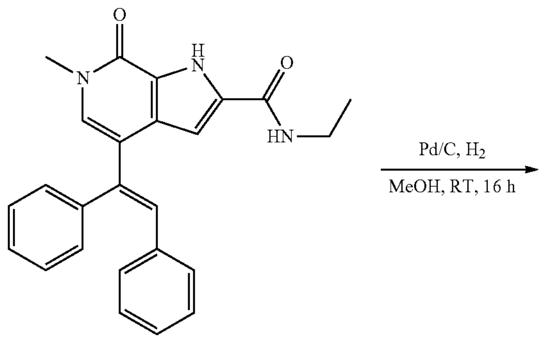

A24

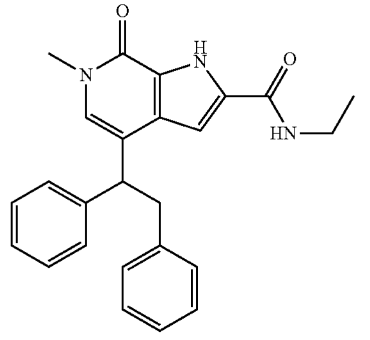

A25

Intermediate A24 (110 mg, 0.28 mmol), methanol (15 mL) and palladium on carbon (11 mg) were added successively to a dry 25 mL single-necked flask at room temperature, and replaced by hydrogen 3 times. The mixture was stirred at room temperature and reacted for 16 hours. After the completion of the reaction monitored by TLC, the reaction solution was filtered, and the filtrate was concentrated under reduced pressure. The residue was purified by preparative plate (dichloromethane:methanol (v:v)=10:1) to give N-ethyl-6-methyl-4-(1-(naphthalen-2-yl)ethyl)-7-oxo-6,7-dihydro-1H-pyrrolo[2,3-c]pyridin-2-carboxamide HHX-M63 (37 mg, yellow solid), yield: 33.5%. The final intermediate was subjected to SFC resolution to give A25-P1 (16 mg) and A25-P2 (21 mg).

The spectral data of A25-P1 are as follows:

LCMS: m/z 400.1 (M+H). $^1$H-NMR (DMSO, 400 MHz): 12.11 (s, 1H), 8.30 (t, J=5.2 Hz, 1H), 7.34 (d, J=8.4 Hz, 3H), 7.25-7.08 (m, 8H), 6.92 (s, 1H), 4.37-4.33 (m, 1H), 3.51 (s, 3H), 3.45-3.40 (m, 2H), 3.30-3.22 (m, 2H), 1.11 (t, J=7.2 Hz, 3H).

The spectral data of A25-P2 are as follows:

LCMS: m/z 400.1 (M+H). $^1$H-NMR (DMSO, 400 MHz): 8.23 (s, 1H), 7.34-7.32 (m, 2H), 7.24-7.09 (m, 9H), 6.82 (s, 1H), 4.33-4.29 (m, 1H), 3.49 (s, 3H), 3.45 (m, 2H), 3.29-3.23 (m, 2H), 1.10 (t, J=7.2 Hz, 3H).

Example A26 Synthesis Route

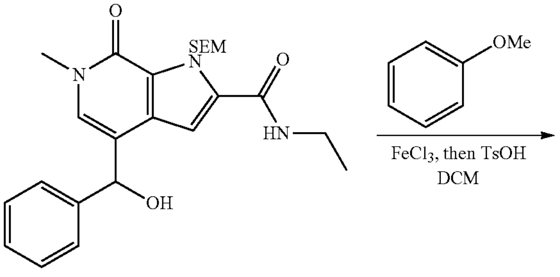

42

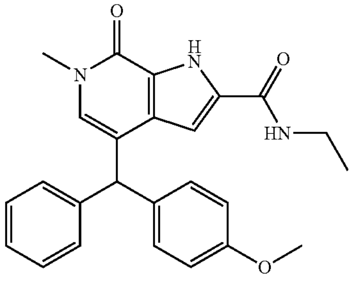

A26

Intermediate 42 (100 mg, 0.21 mmol), anisole (70 mg, 0.65 mmol) and anhydrous $FeCl_3$ (4 mg, 0.02 mmol) were added successively to a 50 mL single-necked flask containing anhydrous dichloromethane (8 mL) at room temperature and reacted for 3 hours at room temperature under nitrogen protection. TsOH·$H_2O$ (50 mg, 0.2 mmol) and anisole (70 mg, 0.65 mmol) were added to the system and stirred at room temperature for 3 h. After the completion of the reaction monitored by LCMS, the reaction mixture was concentrated and separated by prep-TLC (DCM/MeOH=10/1) to obtain A26 (16 mg, white solid), yield: 7%.

$^1$H-NMR (d-DMSO, 400 Hz): 12.17 (s, 1H), 8.29-8.26 (m, 1H), 7.34-7.30 (m, 2H), 7.24-7.19 (m, 3H), 7.11 (d, J=8.8 Hz, 2H), 6.88 (d, J=8.8 Hz, 2H), 6.52 (s, I H), 6.48 (s, 1H), 5.54 (s, 1H), 3.73 (s, 3H), 3.42 (s, 3H), 3.27-3.21 (m, 2H), 1.10 (t, J=7.2 Hz, 3H).

Synthesis Route of Intermediate 74

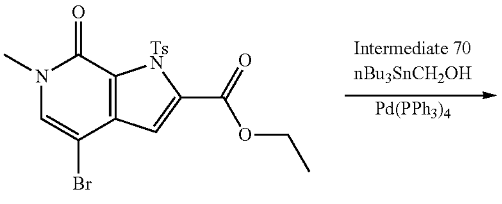

22D

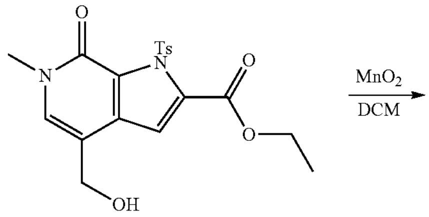

71

-continued

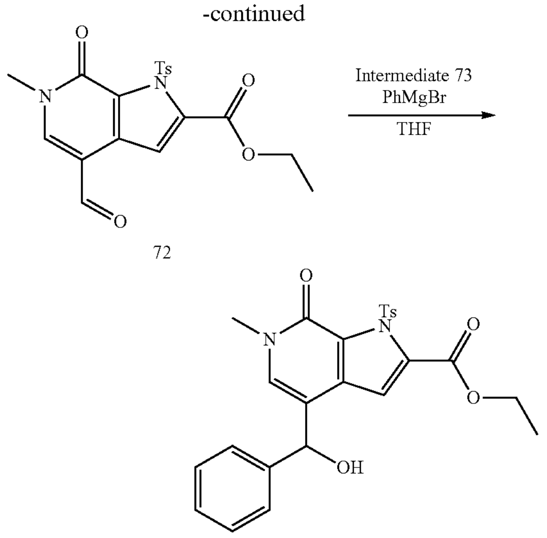

72

74

Step 1: Synthesis of ethyl 4-(hydroxymethyl)-6-methyl-7-oxo-1-tosyl-6,7-dihydro-1H-pyrrolo[2,3-c]pyridin-2-carboxylate (Intermediate 71)

Ethyl 4-bromo-6-methyl-7-oxo-1-tosyl-6,7-dihydro-1H-pyrrolo[2,3-c]pyridin-2-carboxylate (intermediate 22D) (2.0 g, 4.4 mmol), (tributylstannyl)methanol (intermediate 70, 2.1 g, 6.6 mmol) and tetrakistriphenylphosphonium palladium (508 mg, 0.44 mmol) were added successively to a 100 mL three-necked round-bottomed flask containing 30 mL of 1,4-dioxane, replaced by nitrogen three times, heated to 80° C. and reacted overnight. After the completion of the reaction monitored by TLC, the system was filtered, concentrated and separated by column chromatography (ethyl acetate) to obtain the product 71 (550 mg, yield: 30%) as a white solid. LCMS: m/z 405.2 (M+H).

Step 2: Ethyl 4-formyl-6-methyl-7-oxo-1-tosyl-6,7-dihydro-1H-pyrrolo[2,3-c]pyridin-2-carboxylate (Intermediate 72)

Intermediate 71 (550 mg, 1.36 mmol) and manganese dioxide (1.2 g, 13.6 mmol) were added successively to a 50 mL single-necked flask containing 20 mL of dichloromethane at room temperature and reacted at room temperature overnight. After the completion of the reaction monitored by TLC, the reaction solution was filtered and concentrated to obtain intermediate 72 (475 mg, yield: 86%) as a white solid. LCMS: m/z 403.1 (M+H).

Step 3: Ethyl 4-(hydroxy(phenyl)methyl)-6-methyl-7-oxo-1-tosyl-6,7-dihydro-1H-pyrrolo[2,3-c]pyridin-2-carboxylate (Intermediate 74)

PhMgBr (intermediate 73) and intermediate 72 (300 mg, 0.75 mmol) were added to a 50 mL three-necked flask containing 10 mL of tetrahydrofuran, the reaction system was cooled to 0° C., and phenylmagnesium bromide (3 mol/L, 0.28 mL, 0.825 mmol) was added dropwise under nitrogen protection. After the addition, the mixture was reacted at room temperature for one hour. After the completion of the reaction monitored by TLC, the reaction solution was quenched with saturated aqueous ammonium chloride solution, extracted with ethyl acetate, and the organic phase was washed with saturated brine, dried over anhydrous sodium sulfate, filtered, concentrated, and separated by Prep-TLC (dichloromethane/methanol (v:v)=15/1) to obtain intermediate 74 (300 mg, yield: 83%) as a white solid.

Example A27 and A28 Synthesis Route

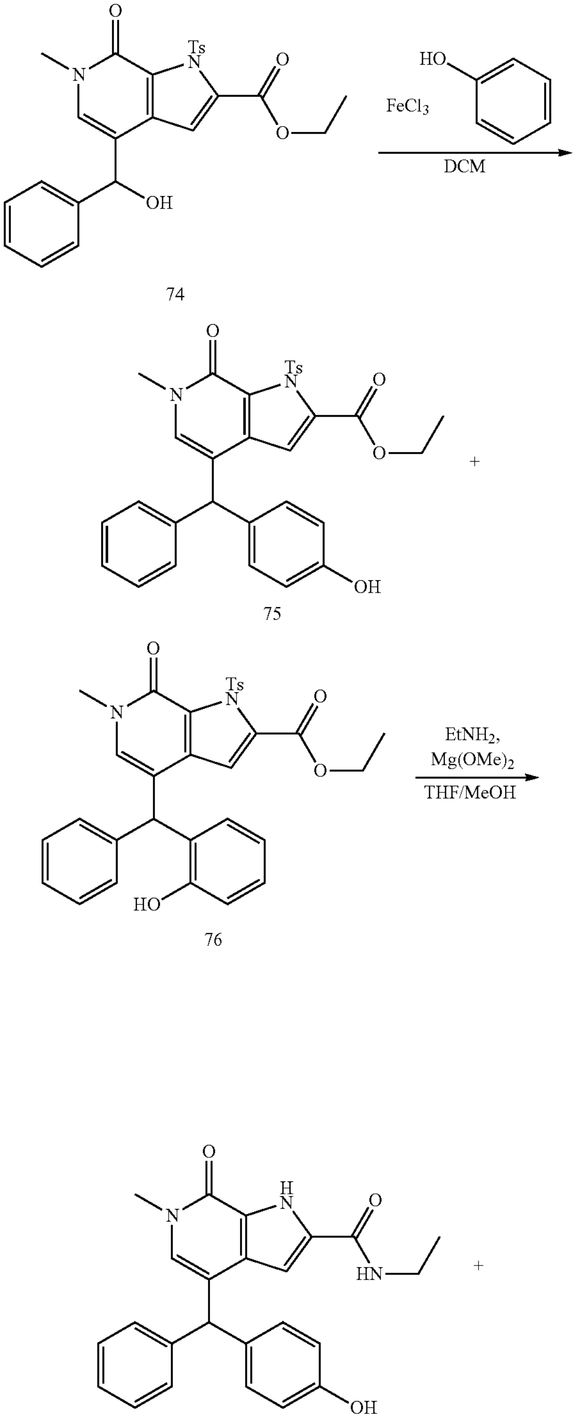

74

75

76

A27

-continued

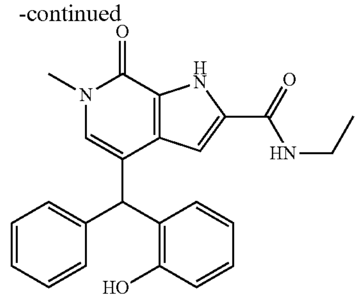

A28

Step 1: Synthesis of ethyl 4-((4-hydroxyphenyl)(phenyl)methyl)-6-methyl-7-oxo-1-tolyl-6,7-dihydro-1H-pyrrolo[2,3-c]pyridin-2-carboxylate (75) and ethyl 4-((2-hydroxyphenyl)(phenyl)methyl)-6-methyl-7-oxo-1-tolyl-6,7-dihydro-1H-pyrrolo[2,3-c]pyridin-2-carboxylate (Intermediate 76)

Intermediate 74 (200 mg, 0.42 mmol), phenol (40 mg, 0.45 mmol), ferric chloride (6.7 mg, 0.021 mmol) and 6 mL of dichloromethane were successively added to a 50 mL single-necked flask at room temperature and reacted for two hours. After the completion of the reaction monitored by TLC, the reaction solution was diluted with water, extracted twice with dichloromethane, and the organic phase was collected, washed with saturated brine, dried over anhydrous sodium sulfate, filtered. The filtrate was concentrated under reduced pressure. The crude product was purified by column chromatography (petroleum ether:ethyl acetate (v:v)=1:1) to give intermediate 75 (80 mg, white solid) and intermediate 76 (30 mg, orange solid).

LCMS: m/z 557.2 (M+H).

Example A27 Synthesis Route

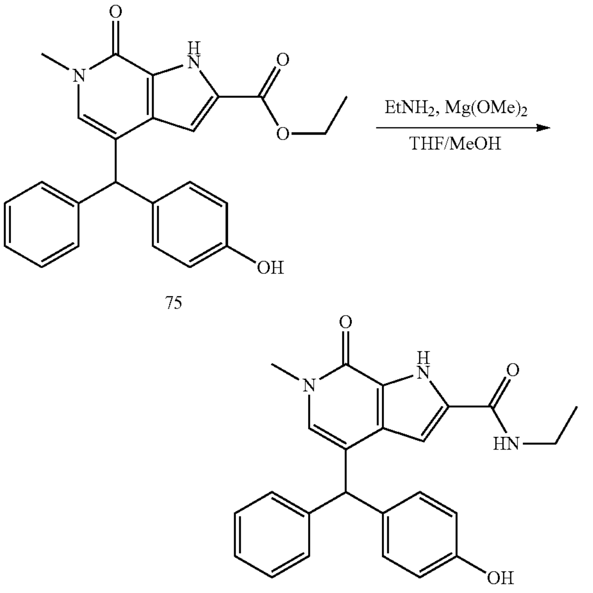

75

A27

Intermediate 75 (80 mg, 0.144 mmol), a solution of ethylamine in tetrahydrofuran (0.58 mL, 1.151 mmol) and 7% magnesium methoxide (37 mg, 0.432 mmol) were added successively to a 100 mL airtight container at room temperature and reacted at 55° C. for 15 hours. After the completion of the reaction monitored by TLC, the reaction solution was concentrated to dryness and the crude product was purified by Prep-HPLC to obtain the product A27 (16 mg, white solid), yield: 27.7%.

LCMS: m/z 402.3 (M+H). $^1$H-NMR (DMSO, 400 MHz): 12.20 (s, 1H), 9.34 (s, 1H), 8.33 (m, 1H), 7.36-7.23 (m, 5H), 7.04 (d, J=8.4 Hz, 2H), 6.75 (d, J=8.8 Hz, 2H), 6.57 (s, 1H), 6.52 (s, 11H), 5.53 (s, 1H), 3.47 (s, 3H), 3.30-3.27 (m, 2H), 1.17-1.14 (m, 3H).

Example A28

A method similar to that in A27 was used and intermediate 75 was replaced by intermediate 76 as starting material to synthesize compound A28, 3 mg, white solid, yield: 13.8%.

A28

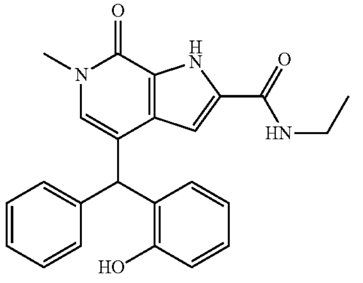

The spectral data of A28 are as follows:

LCMS: m/z 402.2 (M+H).

$^1$H-NMR ($CDCl_3$, 400 MHz): 7.20-7.17 (m, 2H), 7.12 (d, J=7.2 Hz, 1H), 7.06 (d, J=7.2 Hz, 2H), 6.98-6.96 (m, 1H), 6.73-6.69 (m, 2H), 6.65-6.63 (m, 1H), 6.58 (s, 1H), 6.26 (s, 1H), 5.87 (s, 1H), 3.39 (s, 3H), 3.26-3.23 (m, 2H), 1.09-1.05 (m, 3H).

Synthesis Route of Example A29

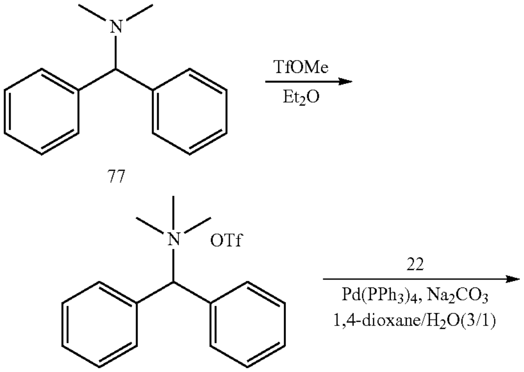

77

78

-continued

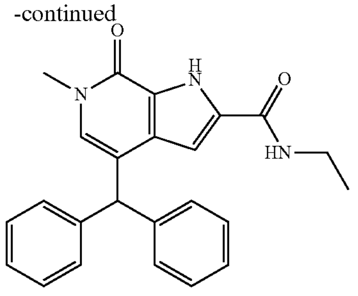

A29

Step 1: Diphenylmethyltrimethyl-1,4-azatrifluoromethanesulfonate (Intermediate 78)

Intermediate 77 (900 mg, 4.26 mmol) and methyl trifluorosulfonate (699 mg, 4.26 mmol) were successively added to a 100 mL single-necked round-bottomed flask containing 10 mL of anhydrous diethyl ether at 0° C. and the reaction system was stirred at 0° C. for 3 hours. After the completion of the reaction monitored by TLC, the mixture was filtered, and the filter cake was washed with anhydrous diethyl ether to obtain the product 78 (500 mg, yield: 31%) as a white solid.

LCMS: m/z 375.1 (M-OTf).

Step 2: 4-diphenylmethyl-N-ethylamino-6-methyl-7-oxo-6,7-dihydro-1H-pyrrolo[2,3-c]pyridin-2-carboxamide (A29)

Intermediate 78 (100 mg, 0.26 mmol) and intermediate 22 (120 mg, 0.34 mmol), sodium carbonate (57 mg, 1.57 mmol) and a catalytic amount of $Pd(PPh_3)_4$ were successively added to a 50 mL three-necked flask containing mixed solvent of dioxane/water (v:v)=3/1 (5 mL) at room temperature and reacted at 70° C. for 3 hours under nitrogen protection. After the completion of the reaction monitored by LCMS, the reaction solution was diluted with water, extracted with EA, and the organic phases were combined, washed with saturated sodium chloride solution, dried over anhydrous sodium sulfate, filtered, concentrated and subjected to prep-TLC (DCM/MeOH (v:v)=15/1) to obtain the intermediate A29 (45 mg, white solid), yield: 45%.

The spectral data of A29 are as follows:

$^1$H-NMR (d-DMSO, 400 Hz): 12.23 (s, 1H), 8.35-8.32 (m, I H), 7.39-7.35 (m, 4H), 7.30-7.25 (m, 6H), 6.58 (s, 1H), 6.55 (s, 1H), 5.65 (s, 1H), 3.43 (s, 3H), 3.31-3.24 (m, 2H), 1.15 (t, J=7.2 Hz, 3H).

Example A30 Synthesis Route

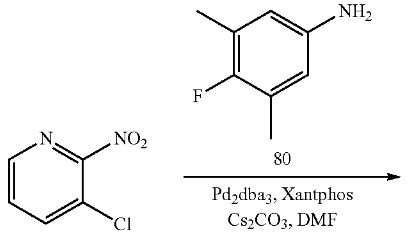

80

79

-continued

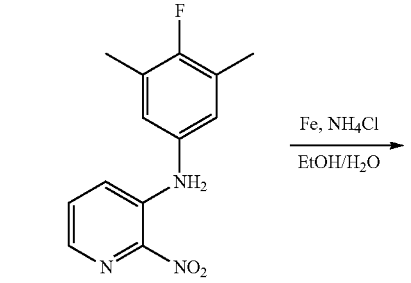

81

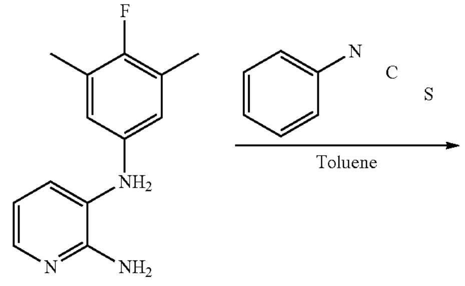

82

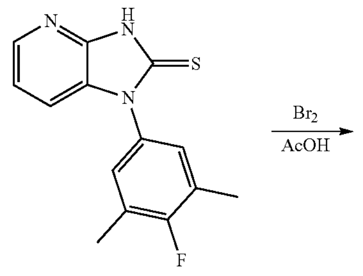

83

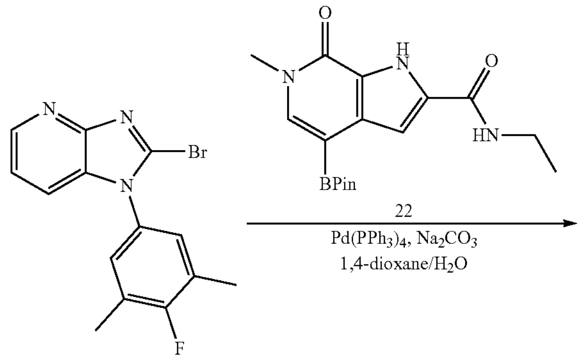

22

84

-continued

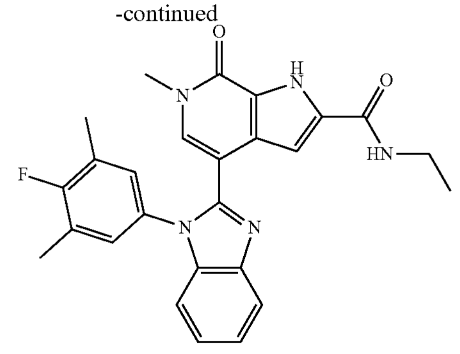

A30

Step 1: Synthesis of N-(4-fluoro-3,5-dimethylphenyl)-2-nitro-pyridin-3-amine (Intermediate 81)

Intermediate 79 (500 mg, 3.15 mmol), 4-fluoro-3,5-dimethylaniline (438 mg, 3.15 mmol), 4,5-bisdiphenylphosphine-9,9-dimethylxanthene (365 mg, 0.63 mmol), tris (dibenzylideneacetone) dipalladium (289 mg, 0.315 mmol), cesium carbonate (2054 mg, 6.3 mmol) and N,N-dimethylacetamide (20 mL) were successively added to a dry 50 mL round-bottomed flask at room temperature and heated to 100° C. overnight. The reaction mixture was diluted with water (100 mL), extracted with ethyl acetate (200 mL×3), and the organic phases were combined, washed with saturated aqueous sodium chloride solution (300 mL), dried over anhydrous sodium sulfate, filtered. The filtrate was concentrated under reduced pressure. The concentrate was subjected to column chromatography (petroleum ether/ethyl acetate (v:v)=5/1) to obtain N-(4-fluoro-3,5-dimethylphenyl)-2-nitro-pyridin-3-amine (Intermediate 81) (200 mg, yellow solid), yield: 24.0%.

LCMS: m/z 262.0 (M+H).

Step 2: Synthesis of N-3-(4-fluoro-3,5-dimethylphenyl)pyridin-2,3-diamine (Intermediate 82)

Intermediate 81 (370 mg, 1.42 mmol), iron powder (397.6 mg, 7.1 mmol), ammonium chloride (383.4 mg, 7.1 mmol), ethanol (20 mL) and water (5 mL) were successively added to a dry 50 mL round-bottomed flask at 0° C. and stirred at 70° C. for 2 hours. After the completion of the reaction monitored by TLC, the reaction mixture was filtered and the filtrate was concentrated under reduced pressure. The concentrate was subjected to column chromatography (petroleum ether/ethyl acetate (v:v)=2/1) to obtain N-3-(4-fluoro-3,5-dimethylphenyl)pyridin-2,3-diamine (intermediate 82) (200 mg, pale yellow solid), yield: 60.9%.

LCMS: m/z 232.1 (M+H).

Step 3: Synthesis of 1-(4-fluoro-3,5-dimethylphenyl)-1,3-dihydro-2H-imidazo[4,5-b]pyridin-2-thione (Intermediate 83)

Intermediate 82 (180 mg, 0.78 mmol), phenyl thioisocyanate (212 mg, 1.56 mmol) and toluene (10 mL) were added successively to a dry 25 mL single-necked bottle at room temperature, heated to 120° C. and stirred to react for 16 hours. After the reaction was completed, the reaction mixture was filtered, and the filter cake was dried under reduced pressure to obtain 1-(4-fluoro-3,5-dimethylphenyl)-1,3-dihydro-2H-imidazo [4,5-b]pyridin-2-thione (intermediate 83) (120 mg, brown solid), yield: 56.3%.

LCMS: m/z 274.2 (M+H).

Step 4: Synthesis of 2-bromo-1-(4-fluoro-3,5-dimethylphenyl)-1H-imidazo[4,5-b]pyridin (Intermediate 84)

In an ice bath, intermediate 83 (120 mg, 0.34 mmol), hydrobromic acid (86 mg, 0.51 mmol, 48%), bromine (218 mg, 1.36 mmol) and acetic acid (15 mL) were successively added to a dry 100 mL single-necked flask at room temperature and stirred in an ice bath and reacted for 2 hours. After the reaction was completed, water (20 mL) and ammonia water (30 mL) were added, and the mixture was extracted with ethyl acetate (50 mL×3). The organic phase was collected, dried over anhydrous sodium sulfate and filtered. The filtrate was concentrated under reduced pressure, and the concentrate was subjected to column chromatography (dichloromethane/methanol=20/1) to obtain 2-bromo-1-(4-fluoro-3,5-dimethyl phenyl)-1H-imidazo[4,5-b]pyridine (intermediate 84) (64 mg, yellow solid), yield: 42.8%.

LCMS: m/z 320.1 (M+H).

Step 5: Synthesis of N-ethyl-4-(1-(4-fluoro-3,5-dimethylphenyl)-1H-imidazo[4,5-b]pyridin-2-yl)-6-methyl-7-oxo-6,7-dihydro-1H-pyrrolo[2,3-c]pyridin-2-carboxamide (A30)

Intermediate 84 (50 mg, 0.16 mmol), N-ethyl-6-methyl-7-oxo-4-(4,4,5,5-tetramethyl-1,3,2-dioxaborolan-2-yl)-6,7-dihydro-1H-pyrrolo[2,3-c]pyridin-2-carboxamide (65 mg, 0.18 mmol), palladium tetrakistriphenylphosphine (19 mg, 0.016 mmol), sodium carbonate (34 mg, 0.32 mmol), dioxane (6 mL) and water (1.5 mL) were successively added to a dry 25 mL single-necked flask at room temperature. The mixture was heated to 100° C. and stirred, and the reaction was carried out for 2 hours. After the reaction was completed, the solvent was concentrated under reduced pressure, and the concentrate was purified by preparative thin layer chromatography to obtain N-ethyl-4-(1-(4-fluoro-3,5-dimethylphenyl)-1H-imidazo[4,5-b]pyridin-2-yl)-6-methyl-7-oxo-6,7-dihydro-1H-pyrrolo[2,3-c]pyridin-2-carboxamide (A30) (34 mg, white solid), yield: 45.9%.

LCMS: m/z 459.3 (M+H). 1H NMR (400 MHz, DMSO) δ 12.41 (s, 1H), 8.50 (d, J=3.7 Hz, 1H), 8.4-8.39 (m, 1H), 7.65 (d, J=7.9 Hz, 1H), 7.34-7.24 (m, 5H), 3.37 (s, 3H), 3.30-3.23 (m, 2H), 2.28 (s, 6H), 1.13 (t, J=7.2 Hz, 3H).

Synthesis Route of Intermediate 85

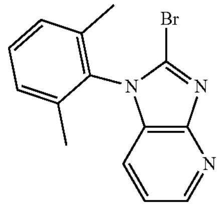

85

Intermediate 85 was synthesized following the same route with reference to the synthesis of intermediate 84, wherein intermediate 80 was replaced by 3,5-dimethylaniline.

Example A31 Synthesis Route

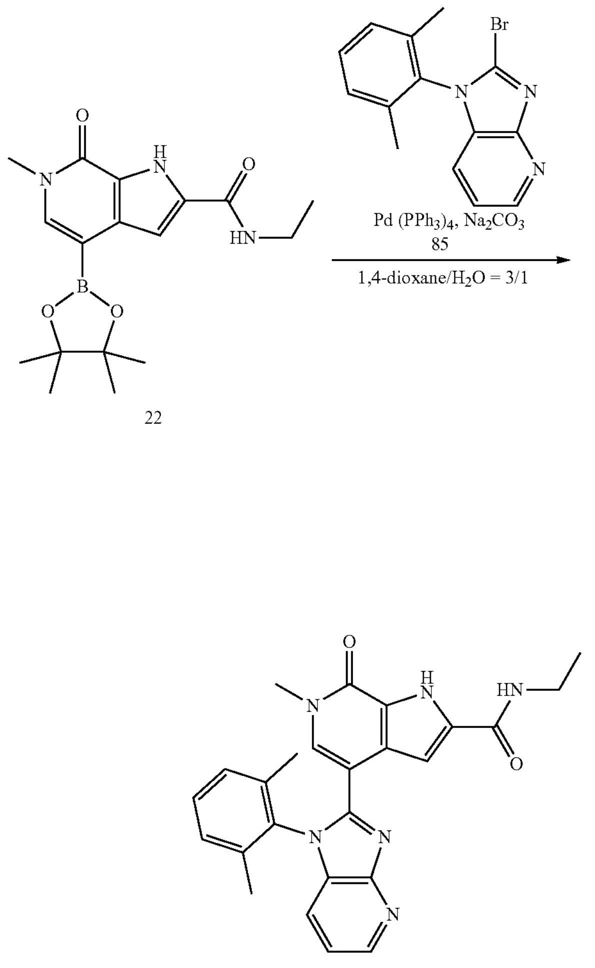

22

85

A31

Intermediate 22 (750 mg, 2.17 mmol), intermediate 85 (788 mg, 2.61 mmol), 1,4-dioxane (6 mL), water (2 mL), tetrakis(triphenylphosphine)palladium (251 mg, 0.22 mmol) and sodium carbonate (576 mg, 5.43 mmol) were successively added to a 25 mL single-necked flask at room temperature, heated to 103° C. and reacted for 2 hours. After the reaction was completed, the reaction mixture was concentrated under reduced pressure, and the residue was purified by preparative plate (dichloromethane:methanol (v:v) 20:1) to obtain 4-(1-(2,6-dimethylphenyl)-1H-imidazo[4,5-b]pyridin-2-yl)-N-ethyl-6-methyl-7-oxo-6,7-dihydro-1H-pyrrolo[2,3-c]pyridin-2-carboxamide (A31) (315 mg, white solid), yield: 32.90%.

The spectral data of Example A31 are as follows: LCMS: m/z 441.2 (M+H).

$^1$H-NMR (MeOD, 400 MHz): 12.38 (s, 1H), 8.51 (m, 1H), 8.45-8.42 (m, 1H), 7.66-7.64 (m, 1H), 7.32-7.27 (m, 2H), 7.22-7.21 (d, J=4.4 Hz, 1H), 7.19-7.18 (d, J=4.4 Hz, 1H), 7.13 (m, 1H), 3.37 (s, 3H), 3.29-3.25 (m, 2H), 2.31 (s, 6H), 1.14 (t, J=7.2 Hz, 3H).

Example A32 Synthesis Route

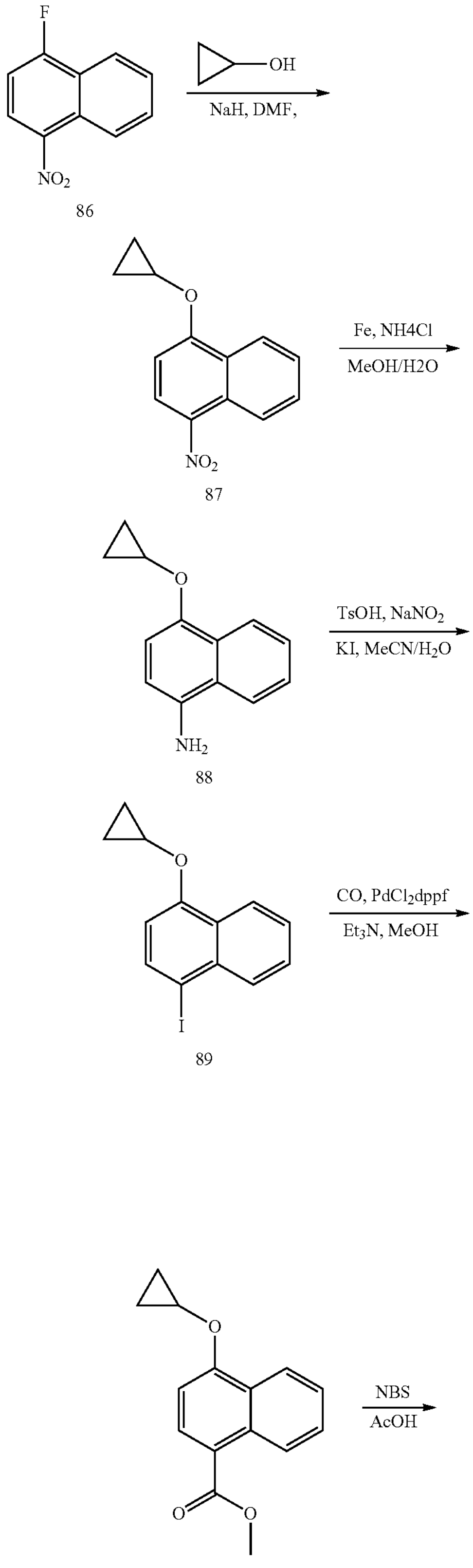

86

87

88

89

90

-continued

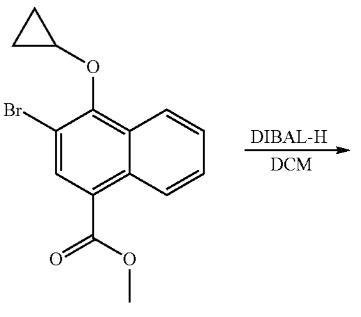

91

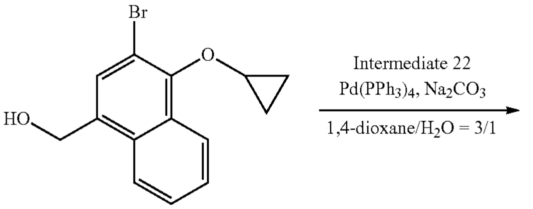

92

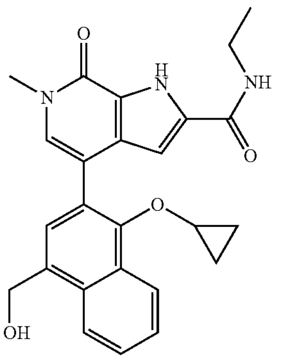

A32

Step 1: Synthesis of 1-cyclopropoxy-4-dinitronaphthalene (Intermediate 87)

Sodium hydride (132 mg, 3.31 mmol) was added to a 50 mL three-necked flask containing dry N,N-dimethylformamide (10 mL), cooled to 0° C., and then a solution of intermediate 86 (160 mg, 2.76 mmol) in N,N-dimethylformamide was slowly added and reacted at 0° C. for 30 minutes. A solution of cyclopropanol (580 mg, 3.03 mmol) in N,N-dimethylformamide was slowly added and reacted overnight at room temperature. After the completion of the reaction monitored by TLC, the system was quenched with saturated ammonium chloride solution, diluted with water, extracted with ethyl acetate, and the organic phase was washed with saturated sodium chloride, dried over anhydrous sodium sulfate, filtered, and concentrated. The crude product was purified by column (petroleum ether/ethyl acetate (v:v)=10/1) to obtain intermediate 87 (500 mg, yellow solid), yield: 60%.

$^1$H-NMR ($CDCl_3$, 400 MHz): 8.77 (d, J=8.8 Hz, 1H), 8.42 (d, J=8.8 Hz, 1H), 8.28 (d, J=8.4 Hz, 1H), 7.75-7.71 (m, 1H), 7.59-7.55 (m, 1H), 7.23 (d, J=8.8 Hz, 1H), 4.04-3.99 (m, 1H), 0.98-0.93 (m, 4H).

Step 2: Synthesis of 4-cyclopropoxynaphthyl-1-amine (Intermediate 88)

Intermediate 87 (100 mg, 0.436 mmol), reduced iron powder (122 mg, 2.18 mmol) and ammonium chloride (128 mg, 2.40 mmol) were successively added to a 50 mL single-necked flask containing a mixed solution of methanol/water (v:v, 7/1) at room temperature and reacted at 70° C. for 2 hours. After the completion of the reaction monitored by TLC, the reaction solution was filtered, and the filtrate was diluted with water, extracted with ethyl acetate. The organic phase was washed with saturated sodium chloride solution, dried over anhydrous sodium sulfate, filtered, concentrated and purified by prep-TLC (petroleum ether/ethyl acetate (v:v)=10/1) to obtain intermediate 88 (60 mg, brown solid), yield: 86%.

LCMS: m/z 200.1 ($M-H_2O$);

Step 3: Synthesis of 1-cyclopropoxy-4-iodonaphthalene (Intermediate 89)

Intermediate 88 (140 mg, 0.703 mmol) and p-toluenesulfonic acid monohydrate (400 mg, 2.1 mmol) were added successively to a 50 mL single-necked flask containing acetonitrile (5 mL) at room temperature and then stirred at 0° C. for 10 minutes. An aqueous solution of sodium nitrite (97 mg, 1.41 mmol) and potassium iodide (291 mg, 1.75 mmol) was added dropwise and the reaction system was stirred at room temperature for 1 hour. After the completion of the reaction monitored by TLC, the reaction solution was diluted with water and extracted with ethyl acetate. The organic phase was washed with saturated sodium chloride solution, dried over anhydrous sodium sulfate, filtered, concentrated and purified by prep-TLC (petroleum ether/ethyl acetate (v:v)=10/1) to obtain intermediate 89 (100 mg, colorless oil), yield: 46%.

$^1$H-NMR ($CDCl_3$, 400 MHz): 8.14 (d, J=8.8 Hz, 1H), 8.02-7.95 (m, 2H), 7.58-7.54 (m, 1H), 7.49-7.45 (m, 1H), 6.98 (d, J=8.4 Hz, 1H), 3.90-3.87 (m, 1H), 0.88-0.87 (m, 4H).

Step 4: Synthesis of methyl 4-cyclopropoxy-1-naphthoate (Intermediate 90)

89 (100 mg, 0.322 mmol), triethylamine (0.13 mL, 0.967 mmol) and 1,1'-bisdiphenylphosphinoferrocene palladium dichloride (20 mg) were added successively to a 50 mL single-necked flask containing methanol (5 mL) at room temperature and then stirred at 70° C. under carbon monoxide for 2 hours. After the completion of the reaction monitored by TLC, the reaction solution was concentrated and purified by prep-TLC (petroleum ether/ethyl acetate (v:v)=5/1) to give intermediate 90 (80 mg, colorless oil), yield: 100%.

$^1$H-NMR ($CDCl_3$, 400 MHz): 9.01 (d, J=8.8 Hz, 1H), 8.26-8.22 (m, 2H), 7.63-7.59 (m, 1H), 7.51-7.48 (m, 1H), 7.20 (d, J=8.0 Hz, 1H), 3.99-3.97 (m, 4H), 0.92-0.91 (m, 4H).

Step 5: Synthesis of methyl 3-bromo-4-cyclopropoxy-1-naphthoate (Intermediate 91)

Intermediate 90 (77 mg, 0.318 mmol) and N-bromosuccinimide (62 mg, 0.35 mmol) were successively added to a 50 mL single-necked flask containing glacial acetic acid (5 mL) at room temperature and stirred at 70° C. for 2 hours. After the completion of the reaction monitored by TLC, the reaction solution was diluted with water and extracted with EA. The organic phase was washed with saturated sodium bicarbonate solution, water and saturated sodium chloride solution successively, dried over anhydrous sodium sulfate, and filtered. The filtrate was concentrated and purified by prep-TLC (petroleum ether/ethyl acetate (v:v)=5/1) to obtain intermediate 91 (60 mg, colorless oil), yield: 67%.

LCMS: m/z 321.1, 323.1 (M+H).

Step 6: Synthesis of (3-bromo-4-cyclopropylnaphthalen-1-yl)methanol (Intermediate 92)

Intermediate 91 (80 mg, 0.25 mmol) and dichloromethane (2 mL) were successively added to a dry 25 mL three-necked flask at room temperature and replaced by nitrogen 3 times. The system was cooled to 0° C., and diisobutylaluminum hydride (0.33 mL, 0.50 mmol) was slowly added dropwise. The mixture was stirred at room temperature and reacted for 16 hours. After the completion of the reaction monitored by TLC, the reaction mixture was quenched with saturated aqueous ammonium chloride solution, and extracted with dichloromethane (20 mL×2). The organic phase was collected, dried over anhydrous sodium sulfate, filtered, and the filtrate was concentrated under reduced pressure to give the product (3-bromo-4-cyclopropylnaphthalen-1-yl)methanol (intermediate 92) (50 mg, yellow oil), yield: 68.47%.

LCMS: m/z 275.0 (M−$H_2O$).

Step 7: Synthesis of 4-(1-cyclopropyl-4-(hydroxymethyl)naphthalen-2-yl)-N-ethyl-6-methyl-7-oxo-6,7-dihydro-1H-pyrrolo[2,3-c]pyridin-2-carboxamide (A32)

The intermediate N-ethyl-6-methyl-7-oxo-4-(4,4,5,5-tetramethyl-1,3,2-dioxaborolan-2-yl)-6,7-dihydro-1H-pyrrolo[2,3-c]pyridin-2-carboxamide (40 mg, 0.12 mmol), intermediate 22 (50 mg, 0.17 mmol), 1,4-dioxane (3 mL), water (1 mL), palladium tetrakistriphenylphosphine (13 mg, 0.01 mmol) and sodium carbonate (31 mg, 0.22 mmol) were added successively to a dry 25 mL single-necked flask, heated to 100° C. and reacted for 2 h. After the reaction was completed, the reaction mixture was concentrated under reduced pressure, and the residue was purified by high-performance liquid phase reverse preparative column to obtain 4-(1-cyclopropyl-4-(hydroxymethyl)naphthalen-2-yl)-N-ethyl-6-methyl-7-oxo-6,7-dihydro-1H-pyrrolo[2,3-c]pyridin-2-carboxamide (A32) (13 mg, white solid), yield: 26.0%.

LCMS: m/z 432.1 (M+H).

$^1$H-NMR (DMSO, 400 MHz): 12.03 (s, 1H), 8.10 (t, J=5.2 Hz, 1H), 7.89-7.85 (m, 2H), 7.35-7.33 (m, 2H), 7.30 (s, 1H), 7.19 (s, 1H), 6.53 (d, J=2.0 Hz, 1H), 5.08-5.05 (m, 1H), 4.71 (d, J=4.8 Hz, 2H), 3.43-3.39 (m, 1H), 3.76 (s, 3H), 3.02-2.97 (m, 2H), 0.86 (t, J=7.2 Hz, 2H), 0.27 (t, J=7.2 Hz, 2H), 0.05-0.00 (m, 2H).

Example A33 Synthesis Route

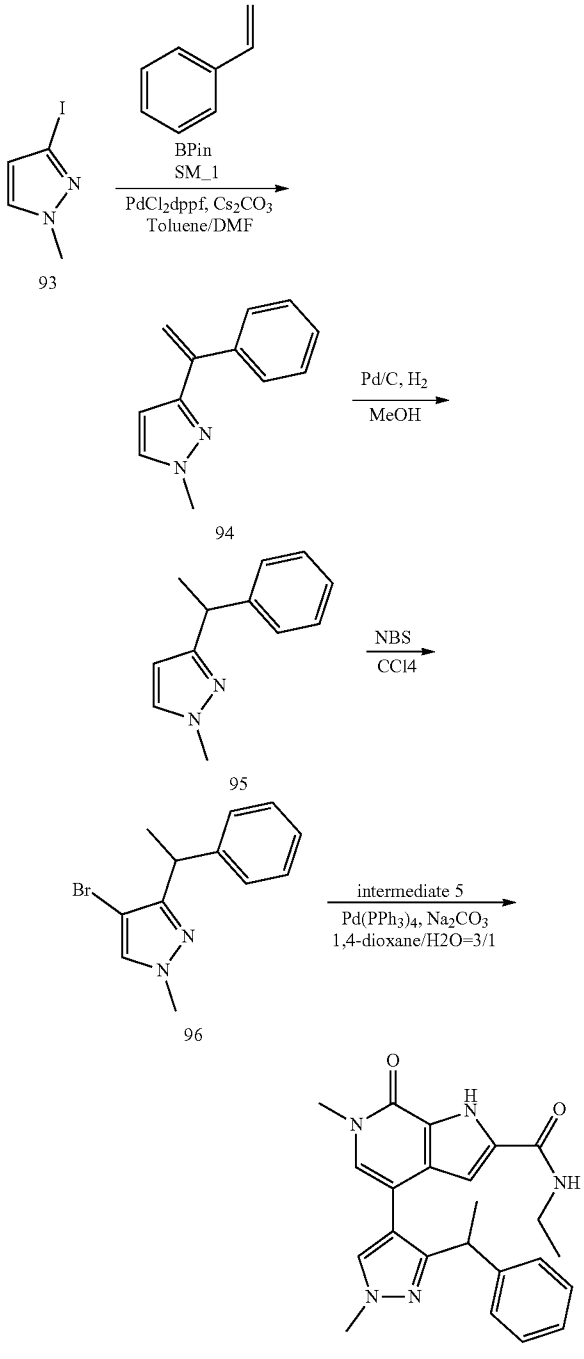

93

94

95

96

A33

Step 1: Synthesis of 1-methyl-3-(1-phenylvinyl)-1H-pyrazole (Intermediate 94)

Intermediate 93 (199 mg, 0.956 mmol), intermediate 1-styrylboronic acid pinacol ester (200 mg, 0.869 mmol), toluene/DMF (5 mL, v:v, 20/1), 1,1'-bisdiphenylphosphinoferrocene palladium dichloride (10 mg, 0.01 mmol) and cesium carbonate (424 mg, 1.3 mmol) were successively added to a dry 25 mL single-necked flask at room temperature, heated to 100° C. and reacted under nitrogen for 2 hours. After the reaction was completed, the reaction mixture was concentrated under reduced pressure, and the residue was used to obtain intermediate 94 (100 mg, yellow oil), yield: 63%.

LCMS: m/z 185.2 (M+H).

Step 2: Synthesis of 1-methyl-3-(1-phenylethyl)-1H-pyrazole (Intermediate 95)

Intermediate 94 (30 mg, 0.09 mmol) and palladium/carbon (20 mg) were successively added to a dry 25-mL single-necked flask at room temperature and reacted overnight under hydrogen at room temperature. After the completion of the reaction monitored by LCMS, the reaction mixture was filtered, and the filtrate was concentrated under reduced pressure to obtain intermediate 95 (100 mg, crude product).

LCMS: m/z 187.2 (M+H).

Step 3: Synthesis of 4-bromo-1-methyl-3-(1-phenylethyl)-1H-pyrazole (Intermediate 96)

Intermediate 95 (90 mg, 0.48 mmol), intermediate N-bromosuccinimide (94 mg, 0.532 mmol) and carbon tetrachloride (5 mL) were added successively to a dry 25 mL single-necked flask and reacted at room temperature for 1 hour. After the completion of the reaction monitored by TLC, the reaction solution was filtered, and the filtrate was concentrated and separated by prep-TLC (petroleum ether/ethyl acetate (v:v)=10/1)) to obtain intermediate 96 (80 mg, white solid), yield: 63%.

$^1$H-NMR (MeOD, 400 MHz): 7.32-7.25 (m, 5H), 7.19-7.15 (m, 1H), 4.23-4.18 (m, 2H), 3.86 (s, 3H), 1.65 (d, J=7.6 Hz, 3H).

Step 4: Synthesis of N-ethyl-6-methyl-4-(1-methyl-3-(1-phenylethyl)-1H-pyrazol-4-yl)-7-oxo-6,7-dihydro-1H-pyrrolo[2,3c]pyridin-2-carboxamide (A33)

Intermediate 96 (30 mg, 0.09 mmol), intermediate 5 (46 mg, 0.17 mmol), 1,4-dioxane (3 ml), water (1 mL), tetrakis (triphenylphosphine)palladium (10 mg, 0.01 mmol) and sodium carbonate (23 mg, 0.22 mmol) were added successively to a dry 25 mL single-necked flask at room temperature, heated to 100° C. and reacted for 2 hours. After the reaction was completed, the reaction mixture was concentrated under reduced pressure, and the residue was purified by high-performance liquid phase reverse preparative column to obtain N-ethyl-6-methyl-4-(1-methyl-3-(1-phenylethyl)-1H-pyrazol-4-yl)-7-oxo-6,7-dihydro-1H-pyrrolo[2,3c]pyridin-2-carboxamide (A33) (5 mg, brown solid), yield: 14.26%.

LCMS: m/z 404.3 (M+H).

$^1$H-NMR (MeOD, 400 MHz): 7.68 (s, 1H), 7.19-7.15 (m, 2H), 7.11-7.06 (m, 3H), 6.75 (s, 1H), 6.51 (s, 1H), 4.20-4.16 (m, 1H), 3.97 (s, 3H), 3.44 (s, 3H), 3.42-3.36 (m, 2H), 1.60 (d, J=7.6 Hz, 3H), 1.23-1.20 (m, 3H).

Example A34 Synthesis Route

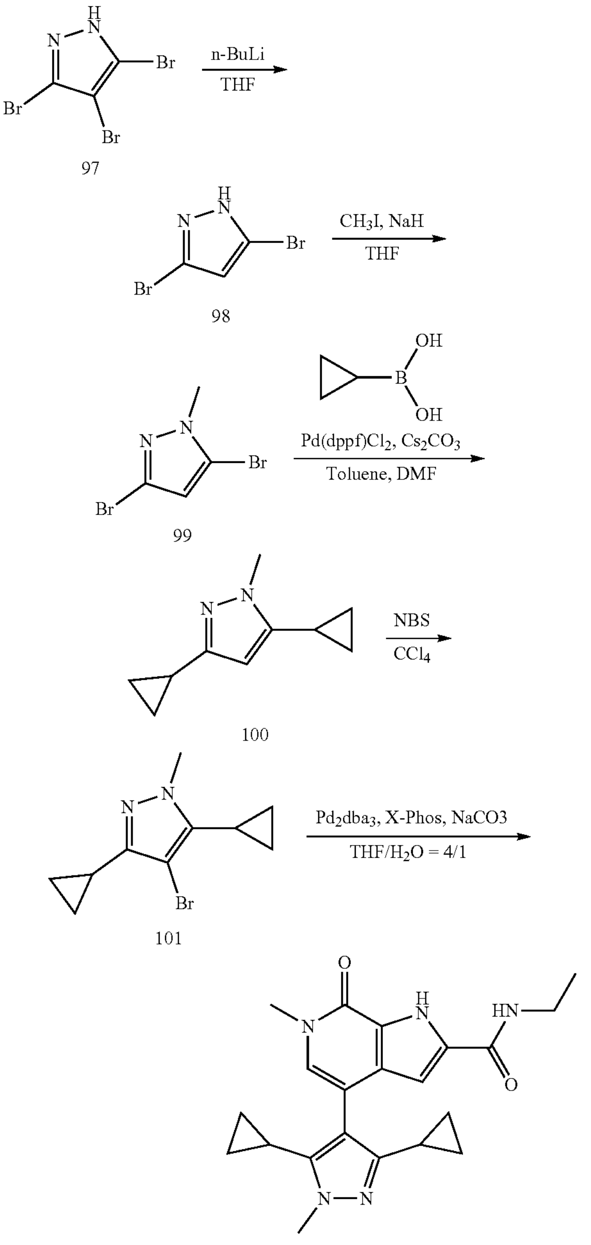

97

98

99

100

101

A34

Step 1: Synthesis of 3,5-dibromo-1H-pyrazole (Intermediate 98)

Intermediate 97 (2.00 g, 6.56 mmol) and tetrahydrofuran (30 mL) were added successively to a dry 100 mL three-necked flask at room temperature. The system was cooled to −78° C. and n-butyllithium (2.5M, 5.25 mL, 13.12 mmol) was added slowly, then stirred at −78° C. and reacted for 30 minutes. The reaction system was added slowly with methanol:tetrahydrofuran=2:3 (10 mL), then warmed to room temperature, stirred for 1.5 hours. The reaction mixture was concentrated under reduced pressure. The residue was diluted with 25 mL of ethyl acetate and washed with 3 mL of 0.5 mol/mL aqueous hydrochloric acid. The organic phase was collected, dried over anhydrous sodium sulfate, filtered, and the filtrate was concentrated under reduced pressure to obtain 3,5-dibromo-1H-pyrazole (Intermediate 98) (1.33 g, yellow solid), yield: 89.73%.

$^1$H-NMR (DMSO, 400 MHz): 6.18 (s, 1H).

Step 2: Synthesis of 3,5-dibromo-1-methyl-1H-pyrazole (Intermediate 99)

Sodium hydride (60% wt, 353 mg, 8.83 mmol), tetrahydrofuran (20 mL) and intermediate 98 (1.33 g, 5.89 mmol) were added successively to a dry 50 mL three-necked flask at 0° C. and stirred at 0° C. for 30 minutes. Iodomethane (0.55 mL, 8.83 mmol) was added, stirred at room temperature and reacted for 2 hours. After the completion of the reaction monitored by TLC, the mixture was poured into 50 mL of water, and extracted with ethyl acetate (20 mL×2). The organic phase was collected, dried over anhydrous sodium sulfate, filtered, and the filtrate was concentrated under reduced pressure. The residue was purified with silica gel column (petroleum ether:ethyl acetate (v:v)=5:1) to give 3,5-dibromo-1-methyl-1H-pyrazole (intermediate 99) (630 mg, yellow oil), yield: 44.60%.

$^1$H-NMR ($CDCl_3$, 400 MHz): 6.30 (s, 1H), 3.85 (s, 3H).

Step 3: Synthesis of 3,5-dicyclopropyl-1-methyl-1H-pyrazole (Intermediate 100)

Intermediate 99 (530 mg, 2.21 mmol), toluene (25 mL), N,N-dimethylformamide (2.5 mL), cyclopropylboronic acid (569 mg, 6.63 mmol), [1,1'-bis(diphenylphosphino)ferrocene]palladium dichloride (323 mg, 0.44 mmol) and cesium carbonate (2880 mg, 8.84 mmol) were added successively to a dry 100 mL single-necked flask at room temperature, heated to 100° C. and reacted for 3 hours. After the reaction was completed, the reaction mixture was concentrated under reduced pressure. The residue was purified with silica gel column (petroleum ether:ethyl acetate (v:v=)=3:1) to give 3,5-dicyclopropyl-1-methyl-1H-pyrazole (intermediate 100) (160 mg, yellow solid), yield: 44.64%.

$^1$H-NMR ($CDCl_3$, 400 MHz): 5.47 (s, 1H), 3.80 (s, 3H), 1.88-1.71 (m, 1H), 1.69-1.59 (m, 1H), 0.94-0.83 (m, 4H), 0.67-0.61 (m, 4H).

Step 4: Synthesis of 4-bromo-3,5-dicyclopropylmethyl-1-methyl-1H-pyrazole (Intermediate 101)

Intermediate 100 (160 mg, 0.99 mmol), carbon tetrachloride (3 mL) and N-bromosuccinimide (176 mg, 0.99 mmol) were added successively to a dry 25 mL single-necked flask at room temperature, stirred at room temperature and reacted for 16 hours. After the completion of the reaction monitored by TLC, the reaction mixture was poured into 20 mL of water, and extracted with ethyl acetate (100 mL×2). The organic phase was collected, dried over anhydrous sodium sulfate, filtered, and the filtrate was concentrated under reduced pressure to obtain 4-bromo-3,5-dicyclopropylmethyl-1-methyl-1H-pyrazole (intermediate 101) (160 mg, yellow solid), yield: 67.28%.

$^1$H-NMR ($CDCl_3$, 400 MHz): 3.80 (s, 3H), 1.85-1.79 (m, 1H), 1.62-1.57 (m, 1H), 1.02-0.98 (m, 2H), 0.90-0.84 (m, 6H).

Step 5: Synthesis of 4-(3,5-dicyclopropyl-1-methyl-1H-pyrazol-4-yl)-N-ethyl-6-methyl-7-oxo-6,7-dihydro-1H-pyrrolo[2,3-c]pyridin-2-carboxamide (A34)

Intermediate 101 (100 mg, 0.29 mmol), intermediate 5 (70 mg, 0.29 mmol), tetrahydrofuran (4 mL), water (1 mL), tris(dibenzylideneacetone) dipalladium (27 mg, 0.03 mmol), 2-dicyclohexylphosphino-2,4,6-triisopropylbiphenyl (14 mg, 0.03 mmol) and sodium carbonate (123 mg, 1.16 mmol) were added successively to a dry 25 mL single-necked flask at room temperature, heated to 75° C. and reacted for 16 hours. After the reaction was completed, the reaction mixture was purified by high-performance liquid phase reverse preparative column to obtain 4-(3,5-dicyclopropyl-yl-1-methyl-7-oxo-6,7-dihydro-1H-pyrrolo[2,3-c]pyridin-2-carboxamide (A34) (4.1 mg, brown solid), yield: 3.72%.

LCMS: m/z 380.3 (M+H). $^1$H-NMR (MeOD, 400 MHz): 7.11 (s, 1H), 6.78 (s, 1H), 3.88 (s, 3H), 3.68 (s, 3H), 3.41-3.36 (m, 2H), 1.83-1.79 (m, 1H), 1.69-1.65 (m, 1H), 1.20 (t, J=7.2 Hz, 3H), 0.78-0.76 (m, 6H), 0.42-0.34 (m, 2H).

Example A35 Synthesis Route

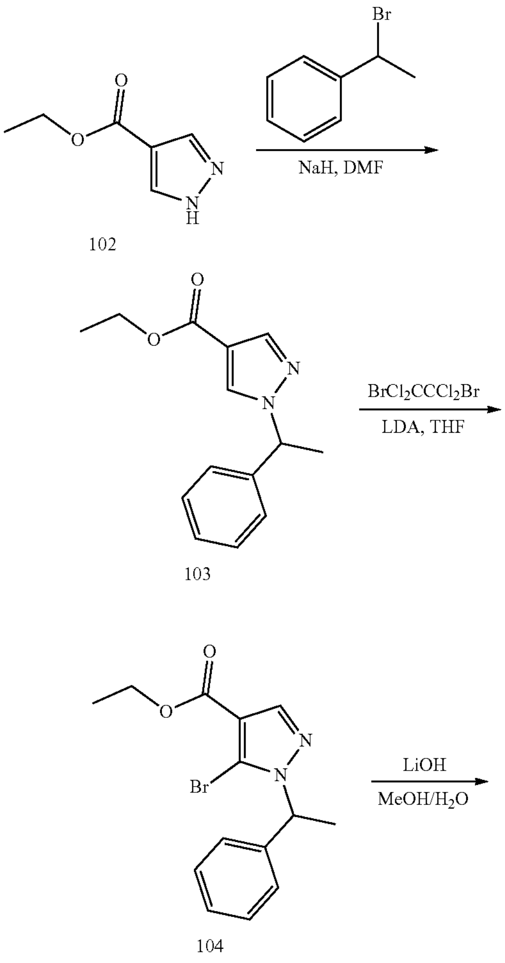

102

103

104

-continued

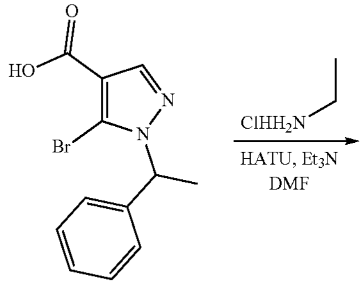

105

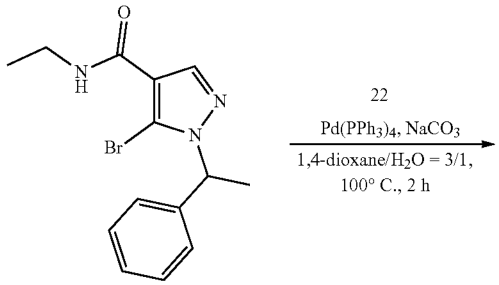

106

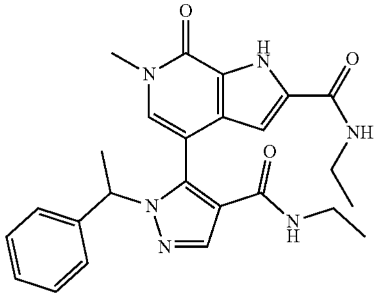

A35

Step 1: Synthesis of ethyl 1-(1-phenylethyl)-1H-pyrazol-4-carboxylate (Intermediate 103)

NaH (342 mg, 8.56 mmol) and anhydrous N,N-dimethylformamide (15 mL) were added to a dry 50 mL three-necked flask at room temperature, then cooled to 0° C. and a solution of intermediate 102 (1.0 g, 7.14 mmol) in N,N-dimethylformamide was added and reacted for 30 minutes at this temperature. A solution of (1-bromoethyl)benzene (1.58 g, 8.56 mmol) in N,N-dimethylformamide was added and stirred at room temperature for 2 hours. After the completion of the reaction monitored by TLC, the system was quenched with saturated ammonium chloride solution, diluted with water, and extracted with ethyl acetate. The organic phase was washed with saturated sodium chloride solution, dried over anhydrous sodium sulfate, filtered, concentrated and purified by column (petroleum ether/ethyl acetate (v:v)=10/1)) to obtain intermediate 103 (1.7 g, white solid), yield: 99%.

$^1$H-NMR ($CDCl_3$, 400 MHz): 7.93 (s, 1H), 7.89 (s, 1H), 7.37-7.26 (m, 3H), 7.23-7.21 (m, 2H), 5.53-5.49 (m, 1H), 4.30-4.24 (m, 2H), 1.90 (d, J=7.2 Hz, 3H), 1.35-1.31 (m, 3H).

Step 2: Synthesis of ethyl 5-bromo-1-(1-phenylethyl)-1H-pyrazol-4-carboxylate (Intermediate 104)

Intermediate 103 (100 mg, 0.409 mmol) and anhydrous THF were added to a dry 50 mL three-necked flask at room temperature, cooled to −78° C., and then n-butyllithium (0.256 mL, 0.409 mmol) was slowly added and reacted for 60 minutes at this temperature. A solution of 1,1,2,2-tetrachloro-1,2-dibromoethane (147 mg, 0.45 mmol) in tetrahydrofuran was slowly added and stirred at room temperature for 2 hours. After the completion of the reaction monitored by TLC, the system was quenched with saturated ammonium chloride solution, diluted with water and extracted with ethyl acetate. The organic phase was washed with saturated sodium chloride solution, dried over anhydrous sodium sulfate, filtered, concentrated and purified by prep-TLC (petroleum ether/ethyl acetate (v:v)=10/1) to give intermediate 104 (1.7 g, yellow oil), yield: 38%.

$^1$H-NMR ($CDCl_3$, 400 MHz): 7.95 (m, 1H), 7.27-7.17 (m, 5H), 5.72-5.67 (m, 1H), 4.26-4.21 (m, 2H), 1.85 (d, J=7.2 Hz, 3H), 1.29-1.25 (m, 3H).

Step 3: Synthesis of 5-bromo-1-(1-phenylethyl)-1H-pyrazol-4-carboxylic acid (Intermediate 105)

Intermediate 104 (1.8 g, 5.59 mmol), lithium hydroxide (441 mg, 11.2 mmol), 15 mL of methanol and 5 mL of water were successively added to a dry 50 mL three-necked flask at room temperature and reacted overnight at room temperature. After the completion of the reaction monitored by TLC, the methanol was removed from the system by rotary evaporation, a small amount of water was added, and the pH was adjusted to 3-4 with 4 moles of hydrochloric acid. The mixture was filtered and dried to give intermediate 105 (1.6 g, white solid), yield: 88%.

LCMS: m/z 295.0 (M+H).

Step 4: Synthesis of 5-bromo-N-ethyl-1-(1-phenylethyl)-1H-pyrazol-4-carboxamide (Intermediate 106)

Intermediate 105 (1.6 g, 5.4 mmol), 2-(7-oxobenzotriazole)-N,N,N',N'-tetramethylurea hexafluorophosphate (2.46 g, 6.5 mmol), triethylamine (1.64 g, 16 mmol) and ethylamine hydrochloride (570 mg, 7.0 mmol) were successively added to a 100 mL single-necked flask containing 20 mL N,N-dimethylformamide at room temperature and reacted for two hours. After the completion of the reaction monitored by TLC, the reaction solution was diluted with water, extracted twice with ethyl acetate, and the organic phase was collected, washed with saturated brine, dried over anhydrous sodium sulfate, filtered. The filtrate was concentrated under reduced pressure. The crude product was purified by column chromatography (petroleum ether:ethyl acetate (v:v)=3:1) to obtain intermediate 106 (1.6 g, yellow solid), yield: 91.7%.

$^1$H-NMR (MeOD, 400 MHz): 7.98 (s, 1H), 7.33-7.21 (m, 5H), 5.87-5.82 (m, 1H), 3.37-3.31 (m, 2H), 1.88 (d, J=6.0 Hz, 3H), 1.20-1.17 (m, 3H).

Step 5: Synthesis of N-ethyl-4-(4-(ethylcarbamoyl)-1-(1-phenylethyl)-1H-pyrazol-5-yl)-6-methyl-7-oxo-6,7-dihydro-1H-pyrrolo[2,3-c]pyridin-2-carboxamide (A35)

N-ethyl-6-methyl-7-oxo-4-(4,4,5,5-tetramethyl-1,3,2-dioxaborolan-2-yl)-6,7-dihydro-1H-pyrrolo[2,3-c]pyridin-2-carboxamide (intermediate 22, 30 mg, 0.09 mmol), intermediate 106 (56 mg, 0.17 mmol), tetrahydrofuran (3 mL), water (1 mL), palladium tetrakistriphenylphosphine (10 mg, 0.01 mmol) and sodium carbonate (23 mg, 0.22 mmol) were added successively to a dry 25 mL single-necked flask at room temperature, heated to 100° C. and reacted for 2 hours. After the reaction was completed, the reaction mixture was concentrated under reduced pressure, and the residue was purified by high-performance liquid phase reverse preparative column to obtain N-ethyl-4-(4-(ethylcarbamoyl)-1-(1-phenylethyl)-1H-pyrazol-5-yl)-6-methyl-7-oxo-6,7-dihydro-1H-pyrrolo[2,3-c]pyridin-2-carboxamide (A35) (5.3 mg, white solid), yield: 13.24%.

LCMS: m/z 461.4 (M+H).

$^1$H-NMR (MeOD, 400 MHz): 8.13-8.05 (m, 1H), 7.36-7.24 (m, 3H), 7.10-7.03 (m, 2H), 6.95-6.93 (m, 1H), 6.67 (d, J=3.2 Hz, 1H), 5.61-5.29 (m, 1H), 3.69-3.45 (s, 3H), 3.41-3.34 (m, 2H), 3.24-3.08 (m, 2H), 1.89-1.84 (m, 3H), 1.22-1.12 (m, 3H), 1.02-0.90 (m, 3H).

Example A36 Synthesis Route

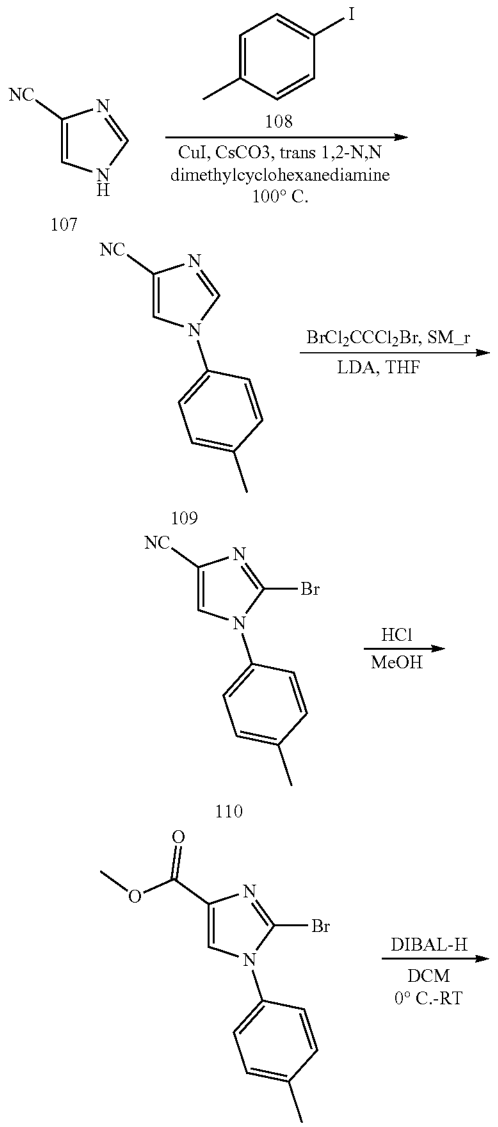

107

109

110

111

-continued

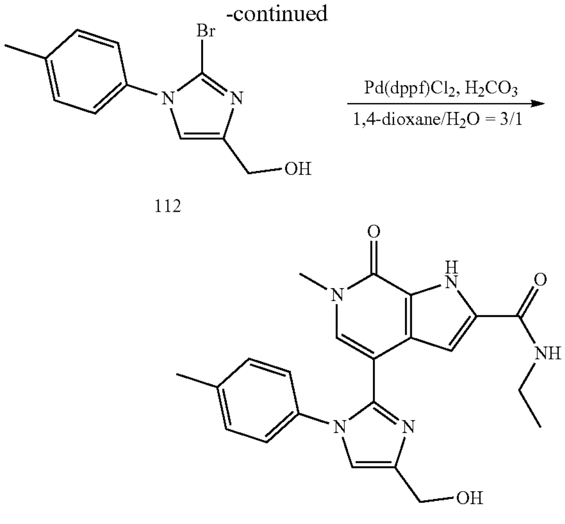

112

A36

Step 1: Synthesis of 1-(p-tolyl)-1H-imidazol-4-carbonitrile (Intermediate 109)

Intermediate 107 (1.0 g, 10.74 mmol), intermediate 108 (2.8 mg, 12.89 mmol), cesium carbonate (7.0 g, 21.43 mmol), trans-1,2-N,N-dimethylcyclohexanediamine (100 mg) and cuprous iodide (100 mg) were added successively to a 50 mL single-necked flask containing DMF (10 mL) at room temperature and reacted at 100° C. overnight under nitrogen protection. After the completion of the reaction monitored by TLC, the reaction system was diluted with water, extracted with EA, and the organic phase was washed with water and saturated sodium chloride, dried, filtered, concentrated and purified by column (petroleum ether/ethyl acetate (v:v)=1/1) to obtain intermediate 109 (1.0 g, white solid), yield: 51%.

Step 2: Synthesis of 2-bromo-1-(p-tolyl)-1H-imidazol-4-carbonitrile (Intermediate 110)

Intermediate 109 (1.0 g, 5.46 mmol) was added to a 50 mL three-necked flask containing dry THF (10 mL) at room temperature, cooled to −78° C. under nitrogen protection, and lithium diisopropylamide (2.73 mL, 5.46 mmol) was added dropwise and reacted at this temperature for 1 hour. A solution of 1,1,2,2-tetrachloro-1,2-dibromoethane (1.95 g, 6.01 mmol) in THF was added dropwise thereto and stirred at room temperature for 2 hours. After the completion of the reaction monitored by TLC, the reaction mixture was quenched with saturated ammonium chloride solution, diluted with water and extracted with ethyl acetate. The organic phase was washed with water and saturated sodium chloride solution, dried over anhydrous sodium sulfate, filtered, concentrated, and purified by column (petroleum ether/ethyl acetate=5/1) to obtain intermediate 110 (240 mg, white solid), yield: 17%.

LCMS: m/z 262.0 264.0 (M+H).

Step 3: Synthesis of methyl 2-bromo-1-(p-tolyl)-1H-imidazol-4-carboxylate (Intermediate 111)

Intermediate 110 (35 mg, 0.133 mmol) was added at room temperature to a 50 mL single-necked flask containing hydrochloric acid methanol (3 mL) and reacted overnight at 65° C. After the completion of the reaction monitored by TLC, the reaction mixture was diluted with water, and the pH was adjusted to 10 with saturated aqueous sodium carbonate solution, extracted with ethyl acetate. The organic phase was washed with water and saturated sodium chloride solution, dried over anhydrous sodium sulfate, filtered, concentrated and purified by prep-TLC (petroleum ether/ ethyl acetate (v:v)=5/1) to obtain intermediate 111 (35 mg, white solid), yield: 89%.

$^1$H-NMR ($CDCl_3$, 400 MHz): 7.74 (s, 1H), 7.32 (d, J=8.0 Hz, 2H), 7.25-7.23 (m, 2H), 3.92 (s, 3H), 2.44 (s, 3H).

Step 4. Synthesis of (2-bromo-1-(p-tolyl)-1H-imidazol-4-yl)methanol (Intermediate 112)

Intermediate 111 (160 mg, 0.54 mmol) and dichloromethane (5 mL) were successively added to a dry 25 mL three-necked flask at room temperature and replaced by nitrogen 3 times. The system was cooled to 0° C., and diisobutylaluminum hydride (0.72 mL, 1.08 mmol) was slowly added dropwise. The mixture was stirred at room temperature and reacted for 16 hours. After the completion of the reaction monitored by TLC, the reaction mixture was quenched with saturated aqueous ammonium chloride solution and extracted with ethyl acetate (20 mL×2). The organic phase was collected, dried over anhydrous sodium sulfate, filtered, and the filtrate was concentrated under reduced pressure. The residue was purified by preparative plate (petroleum ether ethyl acetate (v:v)=1:1) to give (2-bromo-1-(p-tolyl)-1H-imidazol-4-yl)methanol (intermediate 112) (100 mg, white solid), yield: 69.05%.

LCMS: n/z 267.0 (M+H).

Step 5: Synthesis of N-ethyl-4-(4-(hydroxymethyl)-1-(p-tolyl)-1H-imidazol-2-yl)-6-methyl-7-oxo-6,7-dihydro-1H-pyrrolo[2,3-c]pyridin-2-carboxamide (A36)

Intermediate 112 (60 mg, 0.17 mmol), intermediate 22 (70 mg, 0.26 mmol), 1,4-dioxane (3 ml), water (1 mL), [1,1'-bis(diphenylphosphino)ferrocene]palladium dichloride (13 mg, 0.02 mmol) and potassium carbonate (48 mg, 0.34 mmol) were successively added to a dry 25 mL single-necked flask at room temperature, heated to 100° C. and reacted for 2 hours. After the reaction was completed, the reaction mixture was concentrated under reduced pressure, and the residue was purified by high-performance liquid phase reverse preparative column to obtain N-ethyl-4-(4-(hydroxymethyl)-1-(p-tolyl)-1H-imidazol-2-yl)-6-methyl-7-oxo-6,7-dihydro-1H-pyrrolo[2,3-c]pyridin-2-carboxamide (A36) (5 mg, white solid), yield: 7.10%.

LCMS: m/z 406.21 (M+H). $^1$H-NMR (DMSO, 400 MHz): 12.25-12.17 (m, 1H), 8.29 (t, J=5.2 Hz, 1H), 7.31 (s, 1H), 7.21-7.17 (m, 4H), 7.10 (s, 1H), 6.70 (s, 1H), 5.01 (t, J=5.6 Hz, 1H), 4.48-4.45 (m, 2H), 3.40 (s, 3H), 3.27-3.19 (m, 2H), 2.28 (s, 3H), 1.10 (t, J=7.6 Hz, 3H).

Example A37 Synthesis Route

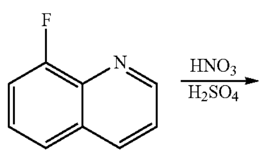

113

-continued

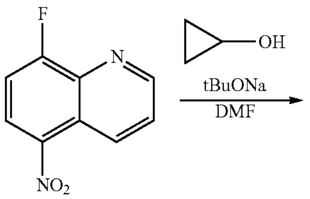

114

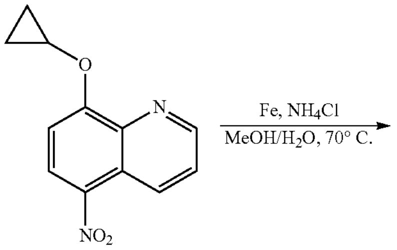

115

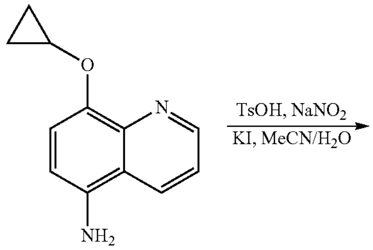

116

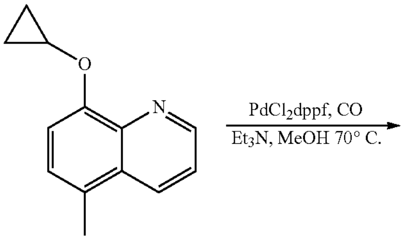

117

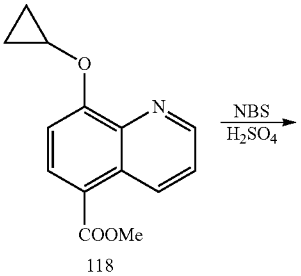

118

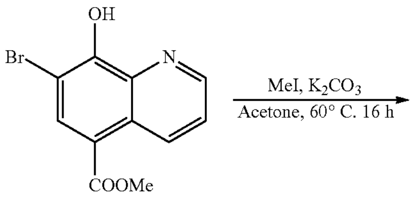

119

-continued

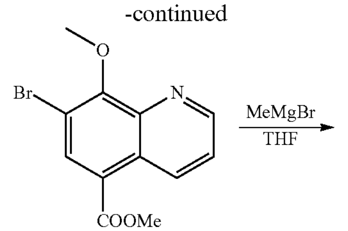

120

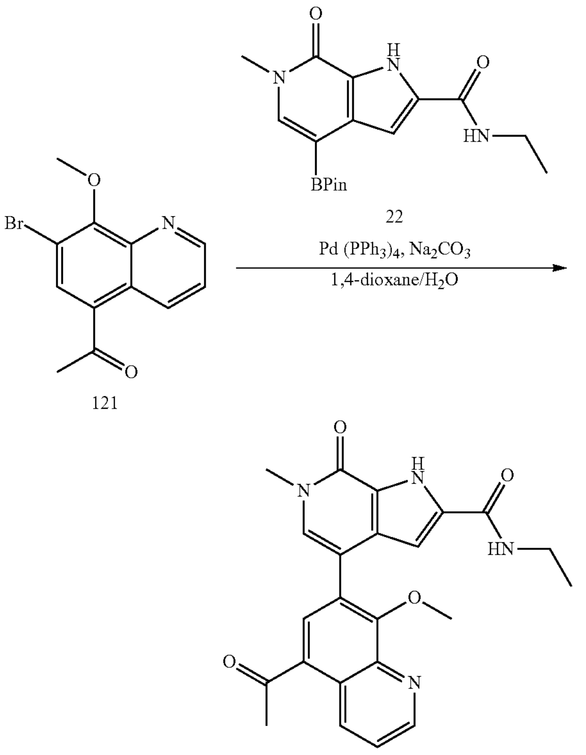

22

121

A37

Step 1: Synthesis of 5-nitro-8-fluoroquinoline (Intermediate 114)

Intermediate 113 (5 g, 34 mmol), concentrated sulfuric acid (17.5 mL) and concentrated nitric acid (7.5 mL) were successively added to a dry 50 mL three-necked flask at 0° C. in an ice bath, then the ice bath was removed and the mixture was reacted at room temperature for 4 hours. After the completion of the reaction monitored by TLC, the reaction solution was quenched with ice cubes, and the pH was adjusted to 7 with potassium carbonate. The aqueous phase was extracted five times with dichloromethane, dried, concentrated and then purified by column (petroleum ether/ethyl acetate (v:v)=1/1) to obtain 5-nitro-8-fluoroquinoline (intermediate 114) (3.9 g, yellow solid), yield: 69.2%.

LCMS: m/z 193.1 (M+H).

Step 2: Synthesis of 5-nitro-8-cyclopropoxy-quinoline (Intermediate 115)

Intermediate 114 (1.9 g, 9.9 mmol), N,N-dimethylformamide (20 mL), cyclopropanol (861 mg, 14.8 mmol) and sodium tert-butoxide (1.42 g, 14.8 mmol) were successively added to a dry 25 mL three-necked flask at 0° C. in an ice bath under nitrogen protection. The mixture was stirred at 0° C. in an ice bath and reacted for 6 hours. After the completion of the reaction monitored by TLC, the reaction mixture was quenched with water, and the aqueous phase was extracted three times with ethyl acetate, dried, concentrated and purified by column (petroleum ether/ethyl acetate=3/1) to obtain 5-nitro-8-cyclopropoxy-quinoline (intermediate 115) (1.3 g, yellow solid), yield: 57%.

LCMS: m/z 231.1 (M+H).

Step 3: Synthesis of 5-amino-8-cyclopropoxy-quinoline (Intermediate 116)

Intermediate 115 (1.3 g, 5.7 mmol), methanol (30 mL), iron powder (1.58 g, 28.3 mmol) and ammonium chloride (1.51 g, 28.3 mmol) were successively added to a dry 100 mL round-bottomed flask at room temperature, then heated to 75° C. and reacted for 6 hours. After the completion of the reaction monitored by TLC, the reaction mixture was filtered and concentrated under reduced pressure to remove the organic solvent to obtain 5-amino-8-cyclopropoxy-quinoline (intermediate 116) (800 mg, yellow solid), yield: 70.8%.

LCMS: m/z 201.2 (M+H).

Step 4: Synthesis of 5-iodo-8-cyclopropoxy-quinoline (Intermediate 117)

Intermediate 116 (800 mg, 4 mmol), acetonitrile (15 mL), water (15 mL), p-toluenesulfonic acid monohydrate (4.56 g, 24 mmol) and sodium nitrite (304 mg, 4.4 mmol) were successively added to a dry 100 mL single-necked flask at room temperature and stirred at 0° C. for 30 minutes. Then potassium iodide (1.99 g, 12 mmol) was added and the mixture was stirred at room temperature and reacted for 6 hours. After the completion of the reaction monitored by TLC, the reaction mixture was filtered and extracted three times with ethyl acetate, dried, filtered and concentrated. The residue was purified by column (petroleum ether/ethyl acetate (v:v)=10/1) to give 5-iodo-8-cyclopropoxy-quinoline (Intermediate 117) (720 mg, yellow solid), yield: 57.7%.

LCMS: m/z 312.0 (M+H).

Step 5: Synthesis of methyl 5-carboxylate-8-cyclopropoxyquinoline (Intermediate 118)

Intermediate 117 (1.1 g, 3.73 mmol), methanol (20 mL), 1,1'-bis(diphenylphosphino)ferrocene palladium chloride (549 mg, 0.75 mmol) and triethylamine (753 mg, 7.46 mmol) were successively added to a dry 100 mL single-necked flask at room temperature and replaced by carbon monoxide three times. The mixture was stirred at 75° C. and reacted for 12 hours. After the completion of the reaction monitored by TLC, the reaction mixture was filtered and concentrated. The residue was purified by column (petroleum ether/ethyl acetate=5/1) to give methyl 5-carboxylate-8-cyclopropoxyquinoline (Intermediate 118) (645 mg, yellow solid), yield: 72.1%.

LCMS: m/z 228.2 (M+H).

Step 6: Synthesis of methyl 5-carboxylate-7-bromo-8-hydroxyquinoline (Intermediate 119)

Intermediate 118 (900 mg, 3.7 mmol), concentrated sulfuric acid (10 mL), N-bromosuccinimide (791 mg, 4.4 mmol) were successively added to a dry 50 mL single-necked flask at room temperature, stirred at room temperature and reacted for 6 hours. After the completion of the reaction monitored by TLC, the reaction mixture was quenched with ice cubes, and the pH of the system was adjusted to 9 with sodium bicarbonate, extracted three times with ethyl acetate, dried, filtered and concentrated. The residue was purified by column (ethyl acetate) to give methyl 5-carboxylate-7-bromo-8-hydroxyquinoline (intermediate 119) (600 mg, yellow solid), yield: 57.7%.

LCMS: m/z 282.2 (M+H).

Step 7: Synthesis of methyl 7-bromo-8-methoxyquinolin-5-carboxylate (Intermediate 120)

Intermediate 119 (250 mg, 0.89 mmol), acetone (10 mL) and potassium carbonate (244 mg, 1.77 mmol) were successively added to a dry 50 mL single-necked flask at room temperature and stirred at room temperature for 30 minutes, and then iodomethane (0.11 mL, 1.77 mmol) was added, heated to 60° C. and reacted for 16 hours. After the completion of the reaction monitored by TLC, the reaction mixture was concentrated under reduced pressure. The residue was purified by preparative plate (petroleum ether:ethyl acetate (v:v)=3:1) to give methyl 7-bromo-8-methoxyquinoline-5-carboxylate (intermediate 120) (130 mg, white solid), yield: 49.54%.

$^1$H-NMR (DMSO, 400 MHz): 9.23 (d, J=8.8 Hz, 1H), 9.03 (s, 1H), 8.38 (s, 1H), 7.77-7.74 (m, 1H), 4.20 (s, 3H), 3.94 (s, 3H).

Step 8: Synthesis of 1-(7-bromo-8-methoxyquinolin-5-yl)ethan-1-one (Intermediate 121)

Intermediate 120 (100 mg, 0.34 mmol) and tetrahydrofuran (5 mL) were successively added to a dry 25 mL three-necked flask at room temperature and replaced by nitrogen three times. Methylmagnesium bromide (3M, 0.23 mL, 0.68 mmol) was added slowly at 0° C. and the mixture was stirred at 0° C. and reacted for 2 hours. After the completion of the reaction monitored by TLC, the reaction mixture was quenched with 1 mL of methanol and concentrated under reduced pressure. The residue was purified by preparative plate (petroleum ether:ethyl acetate (v:v)=5:1) to give 1-(7-bromo-8-methoxyquinolin-5-yl)ethan-1-one (intermediate 121) (60 mg, white solid), yield: 63.43%.

$^1$H-NMR (DMSO, 400 MHz): 9.18 (d, J=8.8 Hz, 1H), 9.04 (s, 1H), 8.34 (s, 1H), 7.76-7.73 (m, 1H), 3.95 (s, 3H), 2.91 (s, 3H).

Example A37 Synthesis Route

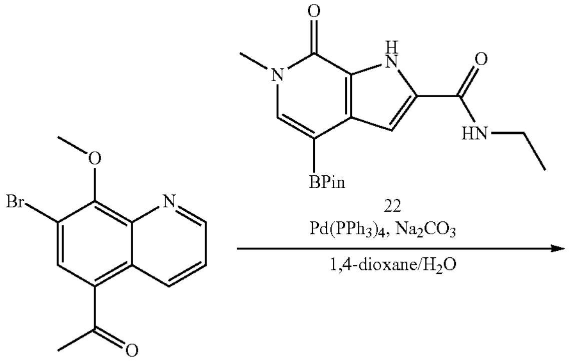

22

121

-continued

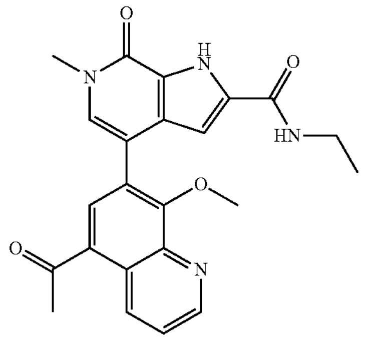

A37

Intermediate 121 (55 mg, 0.16 mmol), intermediate 22 (44 mg, 0.16 mmol), 1,4-dioxane (3 mL), water (1 mL), palladium tetrakistriphenylphosphine (18 mg, 0.02 mmol) and sodium carbonate (42 mg, 0.40 mmol) were successively added to a dry 25 mL three-necked flask at room temperature, heated to 100° C. and reacted for 2 hours. After the reaction was completed, the reaction mixture was concentrated under reduced pressure, and the residue was purified by preparative plate (dichloromethane:methanol (v:v) 10:1) to obtain 4-(5-acetyl-8-methoxyquinolin-7-yl)-N-ethyl-6-methyl-7-oxo-6,7-dihydro-1H-pyrrolo[2,3-c]pyridin-2-carboxamide (A37) (17 mg, white solid), yield: 25.50%.

LCMS: m/z 419.2 (M+H). $^1$H-NMR (DMSO, 400 MHz): 12.36 (brs, 1H), 9.29-9.26 (m, 1H), 9.09-9.08 (m, 1H), 8.33-8.31 (m, 1H), 8.17 (s, 1H), 7.76-7.73 (m, 1H), 7.42 (s, 1H), 6.58 (s, 1H), 3.93 (s, 3H), 3.61 (s, 3H), 3.26-3.19 (m, 2H), 2.71 (s, 3H), 1.08 (t, J=7.2 Hz, 3H).

Example A38

A38

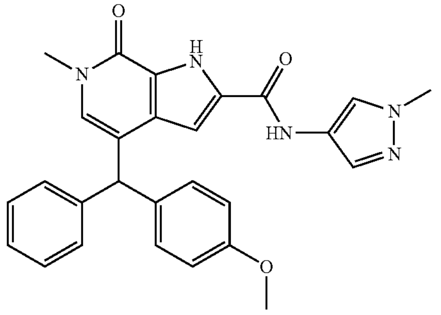

4-((4-methoxyphenyl)(phenyl)methyl)-6-methyl-N-(1-methyl-1H-pyrazol-4-yl)-7-oxo-6,7-dihydro-1H-pyrrolo[2,3-c]pyridin-2-carboxamide (A38) was obtained by using a synthesis method similar to that of Example A29.

The spectrogram data of Example A38 are as follows:

LCMS: m/z 468.3 (M+H). $^1$H-NMR (MeOD, 400 Hz): 7.98 (s, 1H), 7.56 (s, 1H), 7.31-7.30 (m, 2H), 7.20-7.18 (m, 3H), 7.11-7.09 (m, 2H), 6.89-6.87 (m, 2H), 6.80 (s, 1H), 6.41 (s, 1H), 5.60 (s, 1H), 3.86 (s, 3H), 3.77 (s, 3H), 3.51 (s, 3H).

Example A39 Synthesis Route

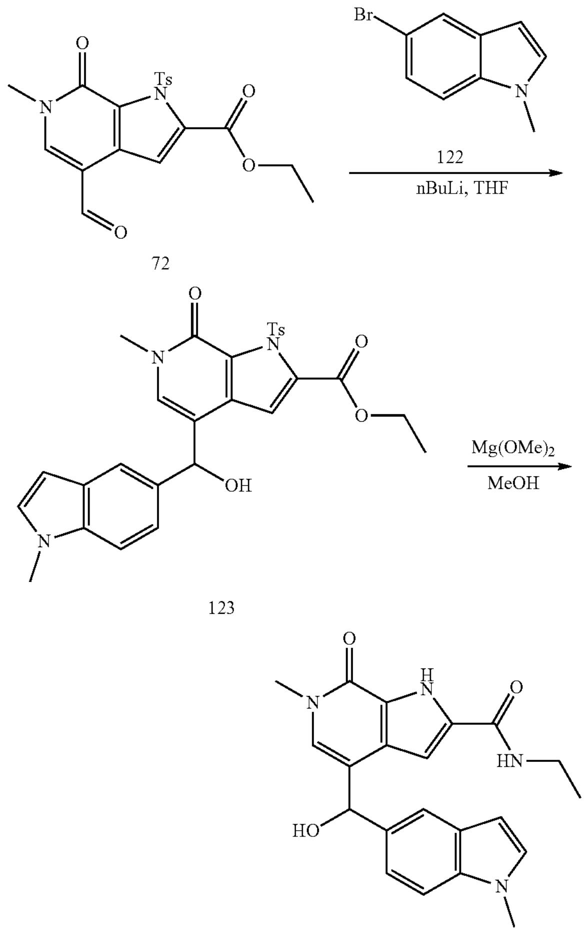

72

123

A39

Step 1: Synthesis of 4-(hydroxy(1-methyl-1H-indol-5-yl)methyl)-6-methyl-7-oxo-1-tosyl-6,7-dihydro-1H-pyrrolo[2,3-c]pyridin-2-carboxylic acid (Intermediate 123)

Intermediate 72 (80 mg, 0.2 mmol) was added to a 25-mL three-necked round-bottomed flask containing 8 mL of anhydrous THF, cooled to −78° C. under nitrogen protection, and n-butyllithium (0.14 mL, 0.22 mmol, 1.6N) was added dropwise to the reaction system and then stirred at −78° C. for 30 minutes.

At −78° C., a solution of intermediate 122 (63 mg, 0.3 mmol) in tetrahydrofuran (2 mL) was added dropwise to the reaction system, and reacted at −78° C. for one hour. After the completion of the reaction monitored by LC/MS, the system was quenched with saturated ammonium chloride solution, diluted with water and extracted with ethyl acetate. The organic phase was washed with saturated sodium chloride, dried over anhydrous sodium sulfate, filtered, concentrated and separated by prep-TLC (ethyl acetate) to give intermediate 123 (30 mg, yield: 28%) as a white solid.

LCMS: m/z 534.2 (M+H).

Step 2: N-ethyl-4-(hydroxy(1-methyl-1H-indol-5-yl)methyl)-6-methyl-7-oxo-6,7-dihydro-1H-pyrrolo[2,3-c]pyridin-2-carboxamide (A39)

Intermediate 123 (30 mg, 0.06 mmol), a solution of magnesium methoxide (7%, 2 mL) in methanol and a solution of ethylamine in tetrahydrofuran (1 mol/L, 2 mL) were successively added to the stuffy jar at room temperature, and reacted at 50° C. overnight. The reaction solution was concentrated and separated by prep-TLC (dichloromethane/methanol (v:v)=10/1) to obtain A39 (1 mg, white solid), yield: 4%.

LCMS: m/z 379.2 (M+H).

$^1$H-NMR (MeOD, 400 Hz): 7.65 (s, 1H), 7.34-7.32 (m, 1H), 7.25-7.22 (m, 1H), 7.19 (s, 1H), 7.14 (s, 1H), 6.83 (s, 1H), 6.41 (s, 1H), 5.98 (s, 1H), 3.78 (s, 3H), 3.64 (s, 3H), 3.36-3.30 (m, 2H), 1.18-1.15 (t, J=7.2 Hz, 3H).

Example A40 Synthesis Route

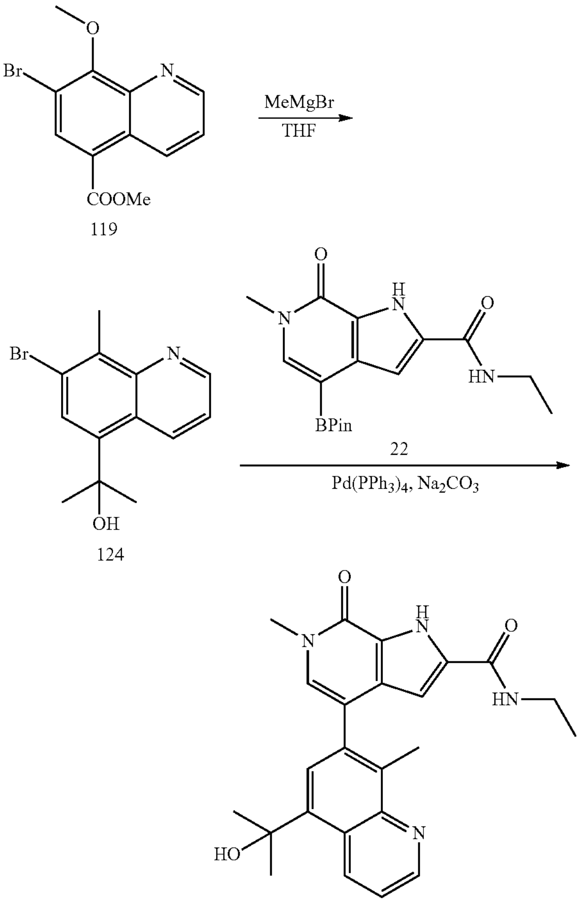

119

124

A40

Step 1: Synthesis of 2-(7-bromo-8-methylquinolin-5-yl)propan-2-ol (Intermediate 124)

Intermediate 119 (80 mg, 0.27 mmol) and tetrahydrofuran (5 mL) were successively added to a dry 25 mL three-necked flask at room temperature and replaced by nitrogen 3 times and methylmagnesium bromide (3M, 0.0 mL, 2.70 mmol)

was added slowly at 0° C. The mixture was stirred at ° C. and reacted for 2 hours. After the completion of the reaction monitored by TLC, the reaction mixture was quenched with 1 mL of methanol and concentrated under reduced pressure. The residue was purified by preparative plate (petroleum ether:ethyl acetate (v:v)=2:1) to give 2-(7-bromo-8-methylquinolin-5-yl)propan-2-ol (intermediate 124) (32 mg, white solid), yield: 42.28%.

1H-NMR (DMSO, 400 MHz): 9.24 (d, J=8.8 Hz, 1H), 8.92 (s, 1H), 7.73 (s, 1H), 7.57-7.55 (m, 1H), 5.51 (d, J=2.8 Hz, 1H), 2.81 (d, J=2.4 Hz, 1H), 1.67 (s, 6H).

Step 2: Synthesis of N-ethyl-4-(5-(2-hydroxypropan-2-yl)-8-methylquinolin-7-yl)-6-methyl-7-oxo-6,7-dihydro-1H-pyrrolo[2,3-c]pyridin-2-carboxamide (A40)

Intermediate 124 (40 mg, 0.12 mmol), intermediate 22 (32 mg, 0.12 mmol), 1,4-dioxane (3 ml), water (1 mL), palladium tetrakistriphenylphosphine (13 mg, 0.01 mmol) and sodium carbonate (31 mg, 0.29 mmol) were successively added to a dry 25 mL three-necked flask at room temperature, heated to 100° C. and reacted for 2 hours. After the reaction was completed, the reaction mixture was concentrated under reduced pressure, and the residue was purified by preparative plate (dichloromethane:methanol (v:v) =10:1) to obtain N-ethyl-4-(5-(2-hydroxypropan-2-yl)-8-methylquinolin-7-yl)-6-methyl-7-oxo-6,7-dihydro-1H-pyrrolo[2,3-c]pyridin-2-carboxamide (A40) (14 mg, white solid), yield: 28.87%.

LCMS: m/z 419.2 (M+H). $^1$H-NMR (DMSO, 400 MHz): 12.33 (s, 1H), 9.35-9.32 (m, 1H), 8.96-8.94 (m, 1H), 8.33 (d, J=5.2 Hz, 1H), 7.56-7.53 (m, 1H), 7.50 (s, 1H), 7.31 (s, 1H), 6.56 (s, 1H), 5.43 (s, 1H), 3.61 (s, 3H), 3.24-3.21 (m, 2H), 2.60 (s, 3H), 1.70 (s, 6H), 1.08 (t, J=7.2 Hz, 3H).

Intermediate 126 Synthesis Route

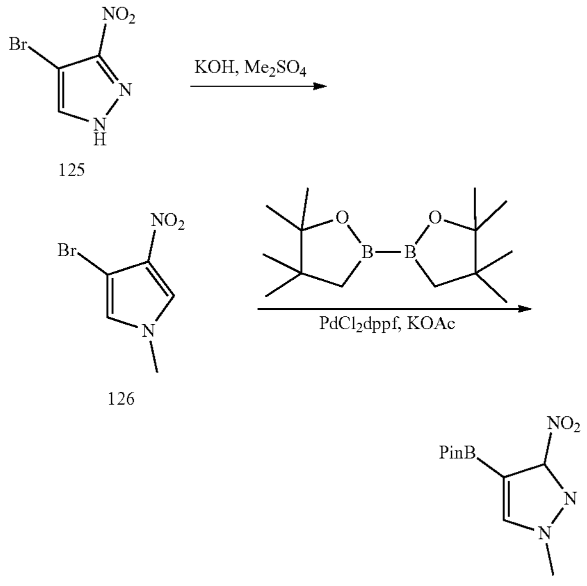

125

126

127

Step 1: Synthesis of 4-bromo-1-methyl-3-nitro-1H-pyrazole (Intermediate 126)

Intermediate 125 (500 mg, 2.62 mmol) and potassium hydroxide (147 mg, 2.62 mmol) were successively added to a 50 mL single-necked flask containing 10 mL of water at room temperature and dimethyl sulphate (297 mg, 2.36 mmol) was added slowly thereto at 0° C. The reaction was carried out at room temperature for 16 hours. After the completion of the reaction monitored by LCMS, the reaction mixture was filtered, and the filter cake was washed twice with water to obtain intermediate 126 (270 mg, white solid), yield: 51%.

$^1$H-NMR ($CDCl_3$, 400 MHz): 7.55 (s, 1H), 4.01 (s, 3H).

Step 2: Synthesis of 1-methyl-3-nitro-4-(4,4,5,5-tetramethyl-1,3,2-dioxaborolan-2-yl)-1H-pyrazole (Intermediate 127)

Intermediate 126 (600 mg, 2.91 mmol), bis(pinacolato) diboron (1.1 g, 4.37 mmol), anhydrous potassium acetate (855 mg, 8.73 mmol) and 1,1'-bisdiphenylphosphinoferrocene palladium dichloride (100 mg) were successively added to a 50 mL three-necked flask containing dry 1,4-dioxane at room temperature, heated to 90° C. under nitrogen protection and reacted for 16 hours. After the completion of the reaction monitored by LCMS, the reaction solution was diluted with water and extracted with ethyl acetate. The organic phase was washed with water and saturated sodium chloride solution successively, dried over anhydrous sodium sulfate, filtered, concentrated and purified by column (petroleum ether/ethyl acetate (v:v)=1/1) to obtain intermediate 127 (600 mg, containing part of the product without bromine, white solid).

1H-NMR ($CDCl_3$, 400 MHz): 7.55 (s, 1H), 4.02 (s, 3H), 1.26 (s, 12H).

Example A41 and A42 Synthesis Route

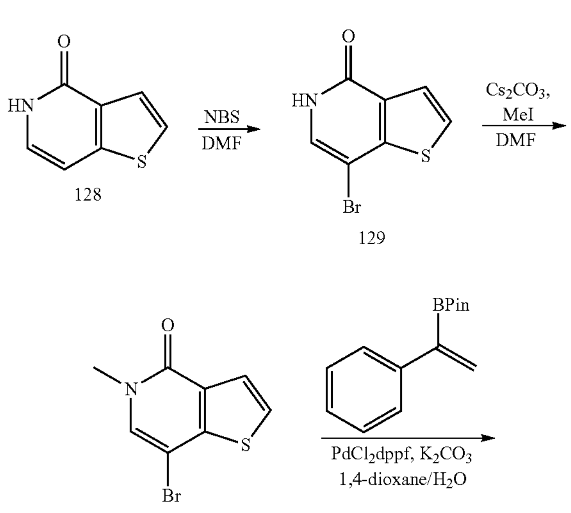

128

129

130

-continued

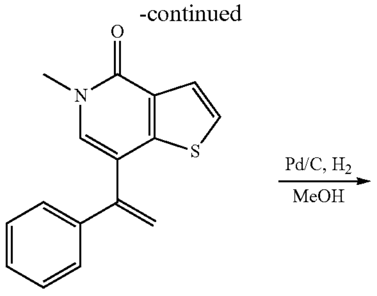

131

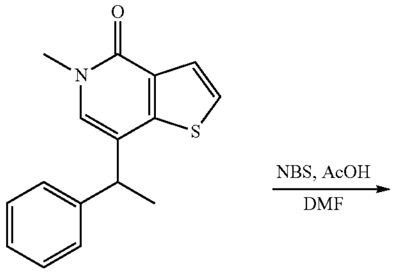

132

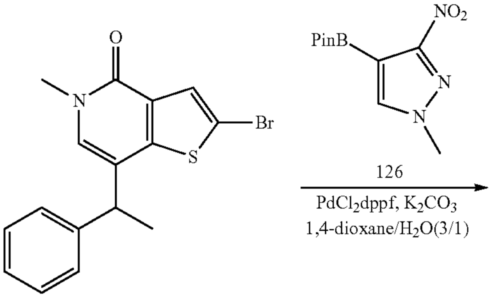

133

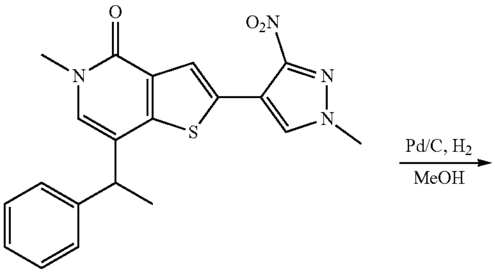

A41

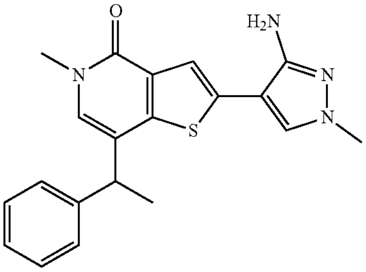

A42

Step 1: Synthesis of 7-bromothieno[3,2-c]pyridin-4(5H)-one (Intermediate 129)

Intermediate 128 (2.7 g, 17.8 mmol) was added to a 100 mL single-necked flask containing 30 mL of N,N-dimethylformamide at 0° C. in an ice bath, followed by the slow addition of N-bromosuccinimide (3.5 g, 19.58 mmol) and then reacted at room temperature for 16 hours after removing the ice bath. After the completion of the reaction monitored by LCMS, the reaction system was diluted with water and extracted with ethyl acetate three times. The organic phase was washed with water and saturated sodium chloride solution successively, dried over anhydrous sodium sulfate, filtered and concentrated to obtain a crude product 129 (2.7 g, white solid), yield: 68%.

LCMS: m/z 232.1 (M+H).

Step 2: Synthesis of 7-bromo-5-methylthieno[3,2-c]pyridin-4(5H)-one (Intermediate 130)

Intermediate 129 (2.2 g, 9.56 mmol) and cesium carbonate (4.66 g, 14.34 mmol) were successively added to a 100 mL single-necked flask containing dry N,N-dimethylformamide at 0° C. in an ice bath, and then a solution of iodomethane (1.2 mL, 19.12 mmol) in N,N-dimethylformamide was added dropwise.

The mixture was reacted at room temperature for 1 hour. After the completion of the reaction monitored by TLC, the reaction system was diluted with water, and the aqueous phase was extracted three times with ethyl acetate, dried, concentrated and purified by column (petroleum ether/ethyl acetate=3/1) to obtain intermediate 130 (2.0 g, white solid), yield: 87%.

1H-NMR ($CDCl_3$, 400 MHz): 7.75 (d, J=5.6 Hz, 1H), 7.37 (d, J=5.2 Hz, 1H), 7.31 s, 1H), 7.15 (s, 1H), 3.62 (s, 3H).

Step 3: Synthesis of 5-methyl-7-(1-phenylethenyl)thieno[3,2-c]pyridin-4(5H)-one (Intermediate 131)

Intermediate 130 (1.2 g, 4.91 mmol), styryl borate (1.35 g, 5.90 mmol), anhydrous potassium carbonate (2.03 g, 14.73 mmol), 1,1'-bisdiphenylphosphinoferrocene palladium dichloride (100 mg) and dioxane:water (20 mL, 3/1) were successively added to a dry 100 mL three-necked round-bottomed flask at room temperature, heated to 100° C. under nitrogen protection and reacted for 2 hours. After the completion of the reaction monitored by TLC, the reaction system was cooled to room temperature, diluted with water, and extracted with ethyl acetate. The organic phase was washed with water and saturated sodium chloride solution successively, dried over anhydrous sodium sulfate, filtered, concentrated and purified by column (petroleum ether/ethyl acetate) (v:v)=3/1) to give intermediate 131 (1.1 g, white solid), yield: 85%.

1H-NMR ($CDCl_3$, 400 MHz): 7.66 (d, J=5.2 Hz, 1H), 7.40-7.33 (m, 5H), 7.23 (d, J=5.2 Hz, 1H), 7.15 (s, 1H), 5.58 (d, J=8.8 Hz, 2H), 3.64 (s, 3H).

Step 4: Synthesis of 5-methyl-7-(1-phenylethyl)thieno[3,2-c]pyridin-4(5H)-one (Intermediate 132)

Intermediate 131 (1.1 g, 4.12 mmol) and palladium carbon (100 mg) were successively added to a 100 mL single-necked flask containing methanol (20 mL) at room temperature and stirred under hydrogen protection at room temperature for 4 hours. After the completion of the reaction monitored by TLC, the reaction mixture was filtered and the filtrate was concentrated to obtain a crude product 132 (1.1 g, yellow solid), which was directly used in the next step, yield: 100%.

LCMS: m/z 270.2 (M+H).

Step 5: Synthesis of 2-bromo-5-methyl-7-(1-phenylethyl)thieno[3,2-c]pyridin-4(5H)-one (Intermediate 133)

Intermediate 132 (1.0 g, 3.71 mmol) and 10 drops of acetic acid were successively added to a 100 mL single-necked flask containing N,N-dimethylformamide at room temperature, then N-bromosuccinimide (661 mg, 3.71 mmol) was slowly added. The mixture was stirred at 60° C. and reacted for 10 minutes. After the completion of the reaction monitored by TLC, the reaction system was cooled to room temperature, diluted with water and extracted with ethyl acetate. The organic phase was washed successively with water and saturated sodium chloride solution, dried over anhydrous sodium sulfate, filtered and concentrated. The residue was purified by column (petroleum ether/ethyl acetate (v:v)=3/1) to obtain intermediate 133 (980 mg, yellow solid), yield: 73%.

1H-NMR ($CDCl_3$, 400 MHz): 7.58 (s, 1H), 7.34-7.30 (m, 2H), 7.26-7.21 (m, 3H), 7.00 (s, 1H), 4.03-3.98 (m, 1H), 3.62 (s, 3H), 1.67 (d, J=7.2 Hz, 3H).

Step 6: Synthesis of 5-methyl-2-(1-methyl-3-nitro-1H-pyrazol-4-yl)-7-(1-phenylethyl)thieno[3,2-c]pyridin-4(5H)-one (A41)

Intermediate 133 (180 mg, 0.517 mmol), 1-methyl-3-nitro-4-(4,4,5,5-tetramethyl-1,3,2-dioxaborolan-2-yl)-1H-pyrazole (intermediate 124, 400 mg, 1.56 mg mol), anhydrous potassium carbonate (142 mg, 1.03 mmol) and 1,1'-bisdiphenylphosphinoferrocene palladium dichloride (100 mg) were successively added to a 50 mL three-necked flask containing mixed solvent of dioxane/water (3/1, 8 mL) at room temperature and reacted under nitrogen protection at 100° C. for 16 hours. After the completion of the reaction monitored by TLC, the reaction system was cooled to room temperature, diluted with water and extracted with ethyl acetate. The organic phase was washed with water and saturated sodium chloride solution successively, dried over anhydrous sodium sulfate, filtered and concentrated. The residue was purified by prep-TLC (ethyl acetate) to give the product A40 (55 mg, yellow solid), yield: 27%.

1H-NMR (d-DMSO, 400 MHz): 8.43 (s, 1H), 7.79 (s, I H), 7.69 (s, 1H), 7.33-7.28 (m, 4H), 7.22-7.19 (m, 1H), 4.10-4.08 (m, 1H), 3.95 (s, 3H), 3.59 (s, 3H), 1.61 (d, J=7.2 Hz, 3H).

Step 7 Synthesis of 2-(3-amino-1-methyl-1H-pyrazol-4-yl)-5-methyl-7-(1-phenylethyl)thieno[3,2-c]pyridin-4(5H)-one (A41)

5-methyl-2-(1-methyl-3-nitro-1H-pyrazol-4-yl)-7-(1-phenylethyl)thieno[3,2-c]pyridin-4(5H)-one (40 mg, 0.1 mmol) and palladium on carbon (10 mg) were successively added to a dry 50 mL single-necked flask at room temperature and stirred at room temperature for 30 minutes. After the completion of the reaction monitored by TLC, the reaction mixture was filtered, and the filtrate was concentrated and purified by prep-TLC (dichloromethane/methanol=20:1) to obtain product A42 (12 mg, white solid), yield: 33%.

1H-NMR (MeOD, 400 MHz): 7.55 (s, 1H), 7.44 (s, 1H), 7.41 (s, 1H), 7.29-7.25 (m, 4H), 7.21-7.19 (m, 1H), 4.15-4.13 (m, 1H), 3.68 (s, 3H), 3.67 (s, 3H), 1.67 (d, J=7.2 Hz, 3H).

Example A43 Synthesis Route

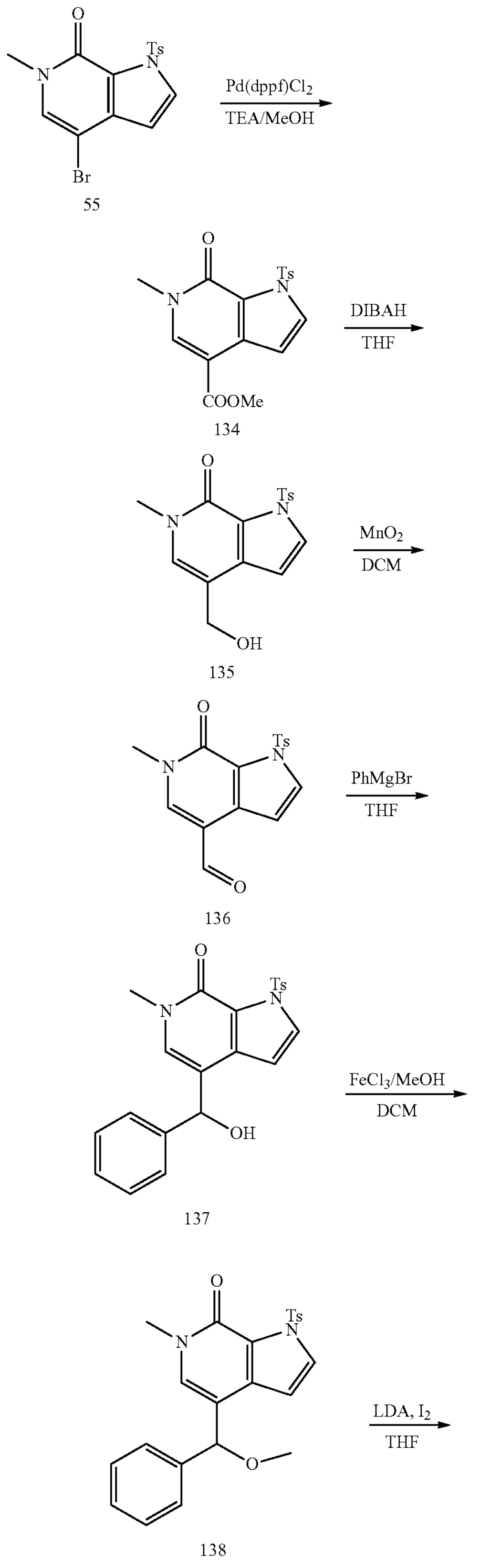

-continued

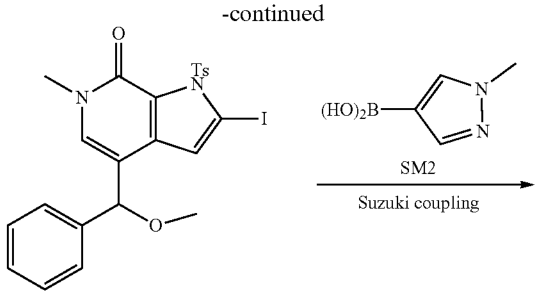

139

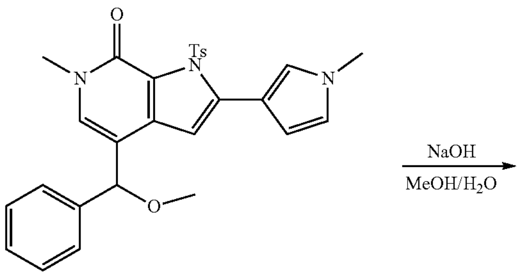

140

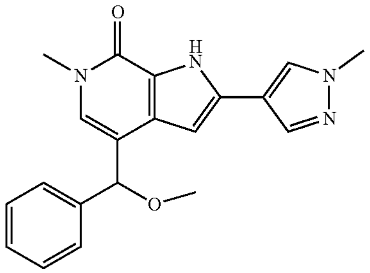

A43

Step 1: Methyl 6-methyl-7-oxo-1-tosyl-6,7-dihydro-1H-pyrrolo[2,3-c]pyridin-4-carboxylate (Intermediate 134)

The compound 4-bromo-6-methyl-1-p-tosyl-1,6-dihydro-7H-pyrrolo[2,3-c]pyridin-7-one (1.5 g, 3.95 mmol), triethylamine (1.2 g, 11.85 mmol) and [1,1'-bis(diphenylphosphino) ferrocene]palladium dichloride (288 mg, 0.395 mmol) were successively added to a 50 mL three-necked round-bottomed flask containing 20 mL methanol, replaced by carbon monoxide three times, heated to reflux and reacted overnight. After the completion of the reaction monitored by TLC, the system was filtered, concentrated and separated by column chromatography (ethyl acetate/petroleum ether (v:v) =1:1) to obtain intermediate 134 (1.2 g, yield: 84%) as a white solid.

LCMS: m/z 361.1 (M+H).

Step 2: 4-(hydroxymethyl)-6-methyl-1-p-tosyl-1,6-dihydro-7H-pyrrolo[2,3-c]pyridin-7-one Diisobutylaluminum hydride (1 mol/L in toluene, 5 mL, 5 mmol) was added dropwise to a solution of methyl 6-methyl-7-oxo-1-tosyl-6,7-dihydro-1H-pyrrolo[2,3-c]pyridin-4-carboxylate (900 mg, 2.5 mmol) in tetrahydrofuran (15 mL) under nitrogen protection at −50° C. and reacted at −50° C. for half an hour. After the completion of the reaction monitored by LC/MS, the reaction solution was poured into ice water and extracted with ethyl acetate. The organic phase was washed with saturated aqueous sodium chloride solution, dried over anhydrous sodium sulfate, filtered and concentrated to obtain intermediate 135 (800 mg, yield: 96%) as a white solid.

LCMS: m/z 333.1 (M+H).

Step 3: 6-methyl-7-oxo-1-p-tosyl-6,7-dihydro-1H-pyrrolo[2,3-c]pyridin-4-carbaldehyde 4-(hydroxymethyl)-6-methyl-1-p-tosyl-1,6-dihydro-7H-pyrrolo[2,3-c]pyridin-7-one (800 mg, 2.4 mmol) and manganese dioxide (1.2 g, 24 mmol) were successively added to a 50 mL single-necked flask containing 20 mL of dichloromethane at room temperature and reacted at room temperature overnight. After the completion of the reaction monitored by TLC, the reaction solution was filtered and concentrated to obtain intermediate 136 (770 mg, yield: 96%) as a white solid.

Step 4: Synthesis of 4-(hydroxy(phenyl)methyl)-6-methyl-1-p-tosyl-1,6-dihydro-7H-pyrrolo[2,3-c]pyridin-7-one (Intermediate 137)

6-methyl-7-oxo-1-p-tosyl-6,7-dihydro-1H-pyrrolo[2,3-c] pyridin-4-carboxaldehyde (770 mg, 2.33 mmol) was added to a 50 mL three-necked flask containing 10 mL of tetrahydrofuran, the reaction system was cooled to 0° C., and phenylmagnesium bromide (3 mol/L, 1.2 mL, 3.5 mmol) was added dropwise under nitrogen protection and then reacted at 0° C. for one hour. After the completion of the reaction monitored by TLC, the reaction solution was quenched with saturated aqueous ammonium chloride solution and extracted with ethyl acetate, and the organic phase was washed with saturated brine, dried over anhydrous sodium sulfate, filtered, concentrated, and separated by column chromatography (petroleum ether/ethyl acetate (v:v) =1/1) to intermediate 137 (770 mg, yield: 80%) as a white solid.

LCMS: m/z 409.1 (M+H).

Step 5: Synthesis of 4-(methoxy(phenyl)methyl)-6-methyl-1-p-tosyl-1,6-dihydro-7H-pyrrolo[2,3-c]pyridin-7-one (Intermediate 138)

4-(hydroxy(phenyl)methyl)-6-methyl-1-p-tosyl-1,6-dihydro-7H-pyrrolo[2,3-c]pyridin-7-one (440 mg, 1.1 mmol), ferric trichloride (232 mg, 1.43 mmol) and methanol (0.1 mL) were successively added to a 50 mL three-necked flask containing 10 mL of dichloromethane at room temperature and reacted at room temperature for half an hour. After the completion of the reaction monitored by TLC, the reaction solution was filtered, concentrated and separated by column chromatography (petroleum ether/ethyl acetate (v:v)=2/1) to obtain intermediate 138 (400 mg, yield: 87%) as a white solid.

LCMS: m/z 423.2 (M+H). 1H-NMR ($CDCl_3$,400 Hz): 8.00 (d, J=8.4 Hz, 2H), 7.81 (d, J=3.6 Hz, 1H), 7.36-7.35 (m, 4H), 7.32-7.26 (m, 4H), 6.88 (s, 1H), 6.40 (d, J=3.6 Hz, 1H), 3.48 (s, 3H), 3.37 (s, 3H), 2.39 (s, 3H).

Step 6: 2-iodo-4-(methoxy(phenyl)methyl)-6-methyl-1-p-tosyl-1,6-dihydro-7H-pyrrolo[2,3-c]pyridin-7-one (139)

4-(methoxy(phenyl)methyl)-6-methyl-1-p-tosyl-1,6-dihydro-7H-pyrrolo[2,3-c]pyridin-7-one (400 mg, 0.95 mmol) was added to a 50 mL three-necked flask containing 10 mL of tetrahydrofuran at room temperature, the reaction system was cooled to −78° C., and lithium diisopropylamide (2 mol/L, 0.7 mL, 1.43 mmol) was added dropwise under nitrogen protection and then reacted for half an hour at −78° C. after addition. A solution of iodine (267 mg, 1.05 mmol) in tetrahydrofuran (2 mL) was added dropwise to the reaction system under the protection of nitrogen at −78° C., and the reaction was carried out at −78° C. for one hour after addition. After the completion of the reaction monitored by LC/MS, the reaction solution was quenched with saturated aqueous ammonium chloride solution, extracted with ethyl acetate, and the organic phase was washed with saturated aqueous sodium sulfite solution and brine, dried over anhydrous sodium sulfate, filtered and concentrated to obtain intermediate 139 (350 mg, yield: 67%) as a white solid.

LCMS: m/z 549.1 (M+H).

Step 7: 4-(methoxy(phenyl)methyl)-6-methyl-2-(1-methyl-1H-pyrazol-4-yl)-1-tosyl-1,6-dihydro-7H-pyrrolo[2,3-c]pyridin-7-one (Intermediate 140)

2-iodo-4-(methoxy(phenyl)methyl)-6-methyl-1-p-tosyl-1,6-dihydro-7H-pyrrolo[2,3-c]pyridin-7-one (350 mg, 0.64 mmol), (1-methyl-1H-pyrazol-4-yl)boronic acid (88 mg, 0.704 mmol), tris(dibenzylideneacetone)dipalladium (58 mg, 0.064 mmol), dipotassium hydrogen phosphate trihydrate (292 mg, 1.28 mmol) and 1,3,5,7-tetrakis(4-benzaldehyde)adamantane (35 mg, 0.064 mmol) were successively added to a 50 mL three-necked flask containing 15 mL of 1,4-dioxane and 5 mL of water at room temperature, replaced by nitrogen three times and reacted at 100° C. overnight. After the completion of the reaction monitored by TLC, the reaction solution was filtered, concentrated and separated by column chromatography (petroleum ether/ethyl acetate (v:v)=2/1) to obtain intermediate 140 (170 mg, yield: 53%) as a white solid.

LCMS: m/z 503.2 (M+H).

Step 8: 4-(methoxy(phenyl)methyl)-6-methyl-2-(1-methyl-1H-pyrazol-4-yl)-1,6-dihydro-7H-pyrrolo[2,3-c]pyridin-7-one (Example A43)

4-(methoxy(phenyl)methyl)-6-methyl-2-(1-methyl-1H-pyrazol-4-yl)-1-tosyl-1,6-dihydro-7H-pyrrolo [2,3-c]pyridin-7-one (40 mg, 0.08 mmol) and sodium hydroxide (16 mg, 0.4 mmol) were successively added to a 25 mL single-necked flask containing 5 mL of methanol and 3 mL of water at room temperature and reacted at 50° C. for one hour. After the completion of the reaction monitored by LC/MS (HHC16015-097R1), the reaction solution was concentrated and separated by Prep-TLC (dichloromethane/methanol=20/1) to obtain Example A43 (18 mg, yield: 64%) as a white solid.

LCMS: m/z 349.2 (M+H). $^1$H-NMR (DMSO, 400 Hz): 12.08 (br, 1H), 8.16 (s, 1H), 7.92 (s, 1H), 7.47-7.45 (m, 2H), 7.34-7.30 (m, 2H), 7.25-7.23 (m, 2H), 6.36 (s, 1H), 5.30 (s, 1H), 3.84 (s, 3H), 3.52 (s, 3H), 3.30 (s, 3H).

Example A44

A44

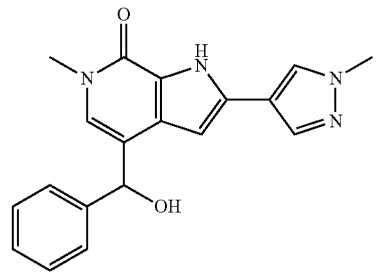

Example A44 was synthesized using a method similar to that of A43 (yield: 93%).

The data for A44 are as follows: LCMS: m/z 335.2 (M+H); $^1$H-NMR (DMSO, 400 Hz): 12.02 (br, 1H), 8.15 (s, 1H), 7.91 (s, 1H), 7.48-7.46 (m, 2H), 7.32-7.28 (m, 2H), 7.22-7.18 (m, 2H), 6.35 (s, 1H), 5.81 (s, 1H), 5.70 (s, 1H), 3.84 (s, 3H), 3.52 (s, 3H).

Synthesis of Example A45

A45

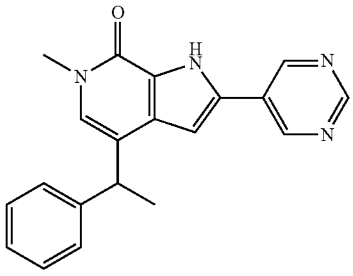

Compound A45 was synthesized according to the synthetic method of Example A15, wherein

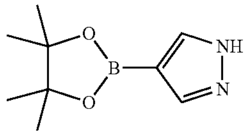

was replaced by

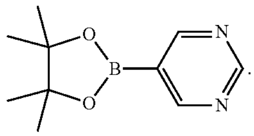
.

The data for compound A45 are as follows: LCMS: m/z 331.1 (M+H).

$^1$H-NMR (DMSO, 400 MHz): 9.29 (s, 2H), 9.08 (s, 1H), 7.41-7.13 (m, 6H), 6.97 (s, 1H), 4.23-4.18 (m, 1H), 3.56 (s, 3H), 1.62 (d, J=7.2 Hz, 3H).

Example A46

A46

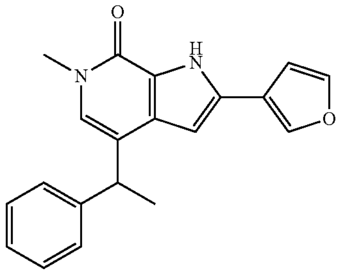

Compound A46 was synthesized according to the synthetic method of Example A15, wherein

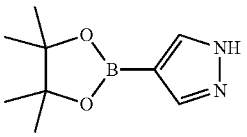

was replaced by

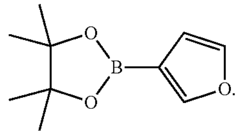

The data for compound A46 are as follows: LCMS: m/z 319.1 (M+H).

$^1$H-NMR (DMSO, 400 MHz): 12.10 (s, 1H), 8.23 (s, 1H), 7.69 (s, 1H), 7.35-7.11 (m, 6H), 6.97 (s, 1H), 6.41 (s, 1H), 4.19-4.14 (m, 1H), 3.54 (s, 3H), 1.59 (d, J=7.2 Hz, 3H).

A46 was subjected SFC resolution to obtain A46-P1 and A46-P2. The data are as follows:

A46-P1: LCMS: m/z 319.4 (M+H). $^1$H-NMR (DMSO, 400 MHz): 12.10 (s, 1H), 8.23 (s, 1H), 7.70-7.69 (m, 1H), 7.35-7.11 (m, 6H), 6.97 (d, J=1.2 Hz, 1H), 6.41 (d, J=2.0 Hz, 1H), 4.19-4.14 (m, 1H), 3.53 (s, 3H), 1.59 (d, J=7.2 Hz, 3H).

A46-P2: LCMS: m/z 319.4 (M+H). $^1$H-NMR (DMSO, 400 MHz): 12.11 (s, 1H), 8.23 (s, 1H), 7.70-7.69 (m, 1H), 7.35-7.11 (m, 6H), 6.97 (d, J=1.2 Hz, 1H), 6.41 (s, 1H), 4.19-4.14 (m, 1H), 3.54 (s, 3H), 1.59 (d, J=7.2 Hz, 3H).

Example A47

A47

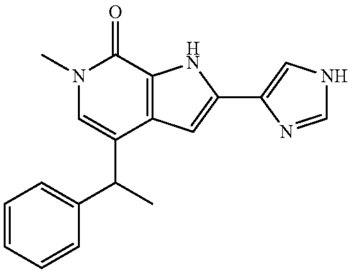

Compound A47 was synthesized according to the synthetic method of Example A15, wherein

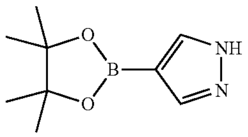

was replaced by

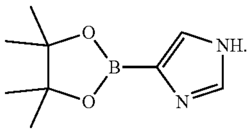

The data for compound A47 are as follows: $^1$H-NMR (d-DMSO, 400 Hz): 12.5-11.5 (m, 2H), 7.69 (s, 1H), 7.64 (s, 1H), 7.33-7.24 (m, 4H), 7.17-7.12 (m, 2H), 6.31 (s, 1H), 4.19-4.16 (m, 1H), 3.63 (s, 3H), 1.57 (d, J=6.8 Hz, 3H).

Synthesis Route of Intermediate 143

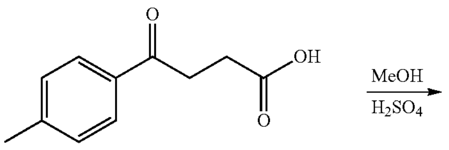

141

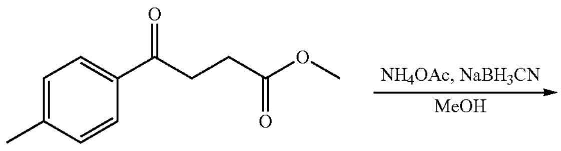

142

-continued

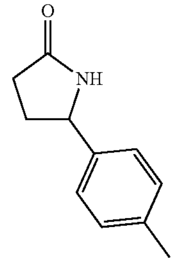

143

Step 1: Synthesis o methyl 4-oxo-4-(p-tolyl)butyrate (Intermediate 142)

4-oxo-4-(p-tolyl)butyric acid (4.5 g, 23.4 mmol), methanol (50 mL) and sulfuric acid (1 mL) were successively added to a dry 100 mL round-bottomed flask at room temperature, stirred at 70° C. and reacted for 5 hours. The solvent was removed by rotary evaporation and the residue was added with water (50 mL) and extracted with dichloromethane (50×3). The organic phases were combined, washed with saturated sodium chloride, dried over anhydrous sodium sulfate, filtered, and the filtrate was concentrated to give methyl 4-oxo-4-(p-tolyl)butyrate (intermediate 142) (4.8 g, yellow oil), yield: 100%.

LCMS: m/z 207.2 (M+H).

Step 2: Synthesis of 5-(p-tolyl)pyrrolidin-2-one (Intermediate 143)

Intermediate 142 (8.2 g, 40.0 mmol), ammonium acetate (30.8 g, 400.0 mmol), sodium cyanoborohydride (5.04 g, 80.0 mmol) and methanol (200 mL) were successively added to a dry 250 mL round-bottomed flask and stirred at 70° C. for 24 hours. After the completion of the reaction monitored by TLC, the solvent was removed by rotary evaporation and the residue was added with water (50 mL) was added, and the pH value was adjusted to about 11 with saturated sodium carbonate. The mixture was extracted with ethyl acetate (100×3). The organic phases were combined, washed with saturated sodium chloride, dried over anhydrous sodium sulfate, filtered, and the filtrate was concentrated and subjected to column chromatography (dichloromethane/methanol=20/1) to give 5-(p-tolyl)pyrrolidin-2-one (intermediate 143) (1.5 g, white solid).

LCMS: m/z 176.2 (M+H).

The Synthesis Route of Example A48

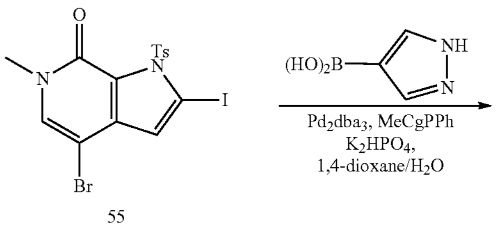

55

-continued

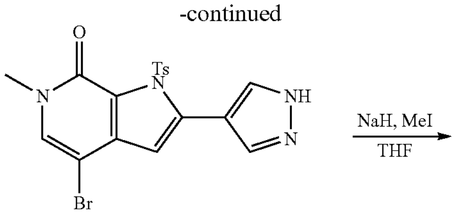

144

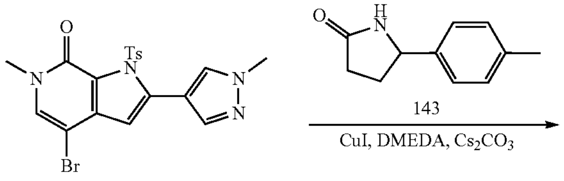

145

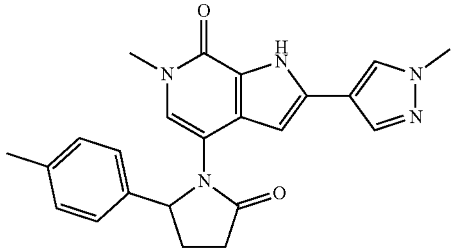

A48

Step 1: Synthesis of 4-bromo-6-methyl-2-(1H-pyrazol-4-yl)-1-tosyl-1,6-dihydro-7H-pyrrolo[2,3-c]pyridin-7-one (Intermediate 144)

Compound 55 (1572 mg, 3.1 mmol), (1H-pyrazol-4-yl) boronic acid (521 mg, 4.65 mmol), tris(dibenzylideneacetone)dipalladium (284 mg, 0.31 mmol), 1,3,5,7-tetramethyl-6-phenyl-2,4,8-trioxa-6-phosphaadamantane (88 mg, 0.31 mmol), sodium carbonate (822 mg, 7.75 mmol), 1,4-dioxane (100 mL) and water (25 mL) were successively added to a dry 100 mL single-necked flask at room temperature and stirred at 50° C. overnight. After the reaction was completed, the reaction mixture was filtered, concentrated under reduced pressure, and the concentrate was subjected to column chromatography (dichloromethane/methanol=20/1) to obtain 4-bromo-6-methyl-2-(1H-pyrazol-4-yl)-1-tosyl-1,6-dihydro-7H-pyrrolo[2,3-c]pyridin-7-one (Intermediate 144) (700 mg, brown solid), yield: 53%.

LCMS: n/z 449.1 (M+H).

Step 2: Synthesis of 4-bromo-6-methyl-2-(1-methyl-1H-pyrazol-4-yl)-1-tosyl-1,6-dihydro-7H-pyrrolo[2,3-c]pyridin-7-one (Intermediate 145)

Sodium hydrogen (65 mg, 1.61 mmol) was added to a 50 mL three-necked flask containing anhydrous tetrahydrofuran, and a solution of intermediate 144 (600 mg, 1.34 mmol) in tetrahydrofuran was slowly added dropwise at 0° C. under nitrogen protection and reacted for 30 minutes. Then methyl iodide (0.1 mL) was added dropwise to the system and reacted at room temperature for 1 hour. After the completion of the reaction monitored by TLC, the reaction mixture was quenched with saturated ammonium chloride solution, diluted with water, and extracted with ethyl acetate. The organic phase was washed successively with water and saturated sodium chloride solution, dried over anhydrous sodium sulfate, filtered and concentrated to obtain a crude product which was purified by column (petroleum ether/ethyl acetate=1/1) to obtain intermediate 145 (300 mg, yield: 49%) as a white solid.

LCMS: m/z 461.1 (M+H).

Step 3: Synthesis of 6-methyl-2-(1-methyl-1H-pyrazol-4-yl)-4-(2-oxo-5-(p-tolyl)pyrrolidin-1-yl)-1,6-dihydro-7H-pyrrolo[2,3-c]pyridin-7-one (Compound A48)

Intermediate 145 (270 mg, 0.59 mmol), cesium carbonate (290 mg, 0.885 mmol), 5-(p-tolyl)pyrrolidin-2-one (123 mg, 0.703 mmol), cuprous iodide (50 mg) and N,N'-dimethylethylenediamine (50 mg) were successively added to a 50 mL three-necked flask containing dry toluene and reacted at 130° C. for 4 hours under nitrogen protection. After the completion of the reaction monitored by TLC, the reaction system was cooled to room temperature, filtered, concentrated and purified by prep-TLC (ethyl acetate) to obtain the final product A48 (10 mg, yield: 4%) as a white solid.

The data for compound A48 are as follows: $^{1}H$-NMR (d-DMSO, 400 Hz): 12.10 (s, 1H), 8.20 (s, 1H), 7.97 (s, 1H), 7.20-7.17 (m, 2H), 7.09-7.04 (m, 3H), 6.52 (s, 1H), 5.21-5.19 (m, 1H), 3.87 (s, 3H), 3.38 (s, 3H), 2.62-2.59 (m, 3H), 2.20 (s, 3H), 1.92-1.84 (m, 1H).

Synthesis Route of Example A49

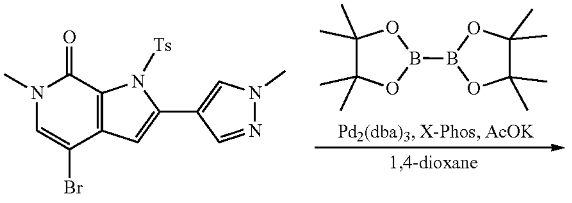

145

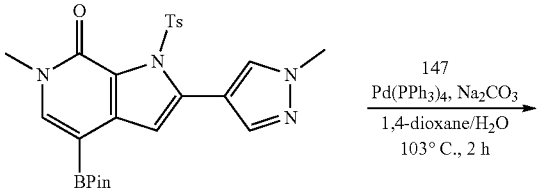

146

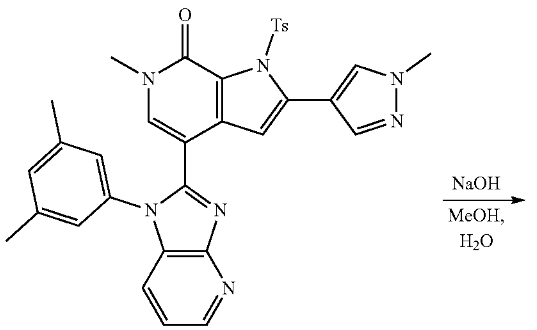

148

-continued

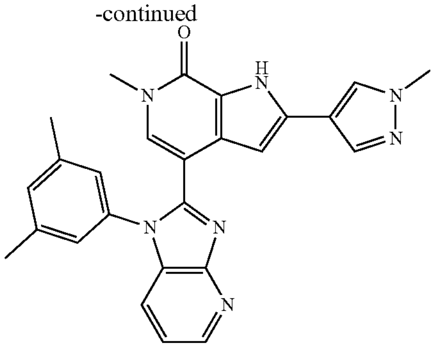

A49

Step 1: Synthesis of 6-methyl-2-(1-methyl-1H-pyrazol-4-yl)-4-(4,4,5,5-tetramethyl-1,3,2-dioxaborolan-2-yl)-1-tosyl-1,6-dihydro-7H-pyrrolo[2,3-c]pyridin-7-one (146)

Intermediate 145 (800 mg, 1.74 mmol), 1,4-dioxane (20 mL), 4,4,4',4',5,5,5',5'-octamethyl-2,2'-bis(1,3,2-dioxaborolane) (663 mg, 2.61 mmol), 2-dicyclohexylphosphino-2,4,6-triisopropylbiphenyl (83 mg, 0.17 mmol), tris(dibenzylideneacetone)dipalladium (159 mg, 0.17 mmol) and potassium acetate (341 mg, 3.48 mmol) were successively added to a dry 25 mL single-necked flask at room temperature, replaced by nitrogen 3 times, heated to 100° C., and reacted for 16 hours. After the completion of the reaction monitored by TLC, the reaction mixture was concentrated under reduced pressure. The residue was purified by silica gel column (petroleum ether:ethyl acetate=10:1) to obtain 6-methyl-2-(1-methyl-1H-pyrazol-4-yl)-4-(4,4,5,5-tetramethyl-1,3,2-dioxaborolan-2-yl)-1-tosyl-1,6-dihydro-7H-pyrrolo[2,3-c]pyridin-7-one (Intermediate 146, 440 mg, yellow solid), yield: 49.94%.

LCMS: m/z 508.9 (M+H).

Intermediate 147: Intermediate 147 was synthesized according to the synthesis method of intermediate 84 by substituting 3,5-dimethylaniline for 3,5-dimethyl-4-fluoroaniline.

147

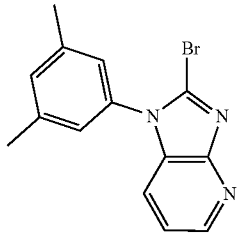

Step 2: Intermediate 148: Synthesis of 4-(1-(3,5-dimethylphenyl)-1H-imidazo[4,5-b]pyridin-2-yl)-6-methyl-2-(1-methyl-1H-pyrazol-4-yl)-1-tosyl-1,6-dihydro-7H-pyrrolo[2,3-c]pyridin-7-one (Intermediate 148)

Intermediate 146 (120 mg, 0.24 mmol), intermediate 147 (71 mg, 0.24 mmol), 1,4-dioxane (3 ml), water (1 mL), palladium tetrakistriphenylphosphine (27 mg, 0.02 mmol) and sodium carbonate (63 mg, 0.59 mmol) were successively added to a dry 25 mL single-necked flask at room temperature, heated to 103° C. and reacted for 2 hours. After the completion of the reaction monitored by TLC, the reaction mixture was concentrated under reduced pressure, and the residue was purified by preparative plate (dichloromethane:methanol=20:1) to obtain 4-(1-(3,5-dimethylphenyl)-1H-imidazo[4,5-b]pyridin-2-yl)-6-methyl-2-(1-methyl-1H-pyrazol-4-yl)-1-tosyl-1,6-dihydro-7H-pyrrolo[2,3-c]pyridin-7-one (intermediate 148, 125 mg, yellow solid), yield: 87.72%.

LCMS: m/z 604.5 (M+H).

Step 3: Synthesis of 4-(1-(3,5-dimethylphenyl)-1H-imidazo[4,5-b]pyridin-2-yl)-6-methyl-2-(1-methyl-1H-pyrazol-4-yl)-1,6-di hydro-7H-pyrrolo[2,3-c]pyridin-7-one (A49)

Compound 148 (60 mg, 0.10 mmol), methanol (4 mL), water (1 mL) and sodium hydroxide (12 mg, 0.30 mmol) were successively added to a dry 25 mL single-necked flask at room temperature, heated to 60° C. and reacted for 16 hours. After the completion of the reaction monitored by TLC, the reaction mixture was concentrated under reduced pressure. The residue was washed with pure ethyl acetate, filtered and the solid was collected to give 4-(1-(3,5-dimethylphenyl)-1H-imidazo[4,5-b]pyridin-2-yl)-6-methyl-2-(1-methyl-1H-pyrazol-4-yl)-1,6-di hydro-7H-pyrrolo[2,3-c]pyridin-7-one (Compound A49, 13 mg, yellow solid), yield: 29.10%.

The data for Example A49 are as follows:

LCMS: m/z 450.2 (M+H).

$^1$H-NMR (DMSO, 400 MHz): 12.25 (s, 1H), 8.50 (s, 1H), 8.20 (s, 1H), 7.93 (s, 1H), 7.65 (d, J=7.2 Hz, 1H), 7.29 (d, J=9.2 Hz, 2H), 7.14 (s, 3H), 6.66 (s, 1H), 3.86 (s, 3H), 3.40 (s, 3H), 2.29 (s, 6H).

Example A50

A50

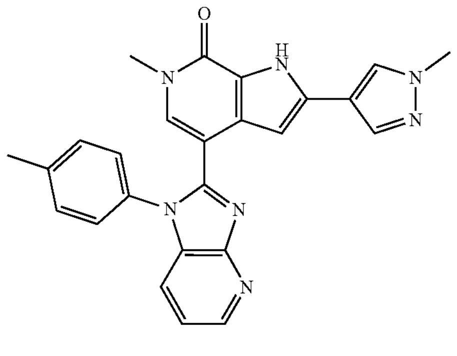

Compound A50 was synthesized according to the synthetic method of compound A49 by substituting

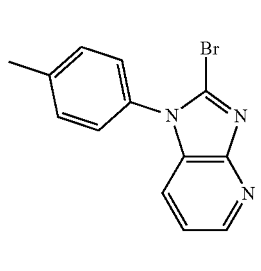

for

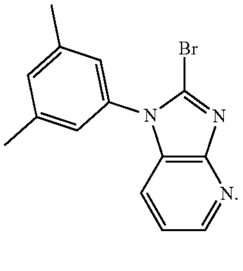

The data for compound A50 are as follows:

LCMS: m/z 436.3 (M+H).

$^1$H-NMR (DMSO, 400 MHz): 12.24 (s, 1H), 8.51-8.49 (m, 1H), 8.16 (d, J=3.2 Hz, 1H), 7.90 (d, J=3.2 Hz, 1H), 7.68-7.65 (m, 1H), 7.41-7.28 (m, 6H), 6.52-6.51 (m, 1H), 3.85 (s, 3H), 3.42 (s, 3H), 2.34 (s, 3H).

Example A51

A51

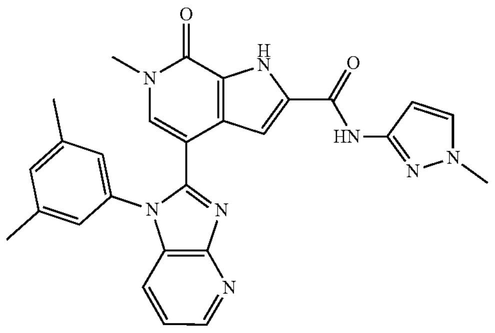

Compound A51 was synthesized according to the synthetic method of compound A49 by substituting

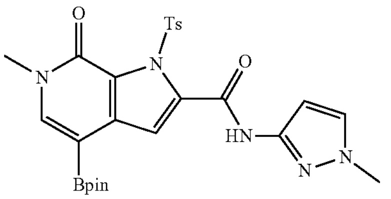

for

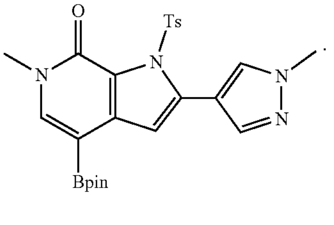

The data for compound A51 are as follows:

LCMS: m/z 493.2 (M+H). $^1$H-NMR (DMSO, 400 MHz): 12.61 (s, 1H), 10.87 (s, 1H), 8.51 (d, J=3.2 Hz, 1H), 7.66 (d, J=3.2 Hz, 1H), 7.61 (d, J=1.2 Hz, 1H), 7.49 (s, 1H), 7.32-7.29 (m, 1H), 7.26 (s, 1H), 7.16 (d, J=8.4 Hz, 3H), 6.58 (s, 1H), 3.78 (s, 3H), 3.38 (s, 3H), 2.30 (s, 6H).

Example A52

A52

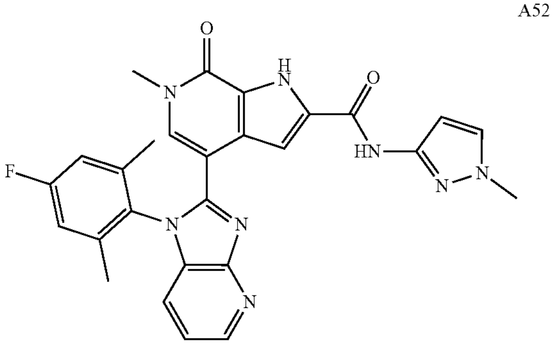 [SMILES: Cc1cc(F)cc(C)c1-n1c(-c2cn(C)c(=O)c3[nH]c(C(=O)Nc4ccn(C)n4)cc23)nc2ncccc21]

Compound A52 was synthesized according to the synthetic method of compound A51 by substituting

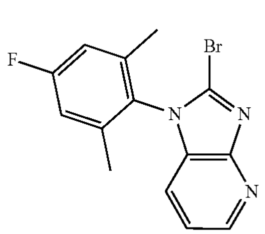

for

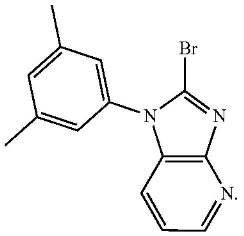

The data for compound A52 are as follows:

LCMS: m/z 511.0 (M+H). 1H NMR (400 MHz, DMSO) δ 12.47 (s, 1H), 10.86 (s, 1H), 8.51 (dd, J=4.7, 1.4 Hz, 1H), 7.66 (dd, J=8.0, 1.4 Hz, 1H), 7.61 (d, J=2.2 Hz, 1H), 7.49 (s, 1H), 7.40-7.20 (m, 4H), 6.58 (d, J=2.2 Hz, 1H), 3.78 (s, 3H), 3.41 (s, 3H), 2.24 (d, J=1.1 Hz, 6H).

Example A53

A53

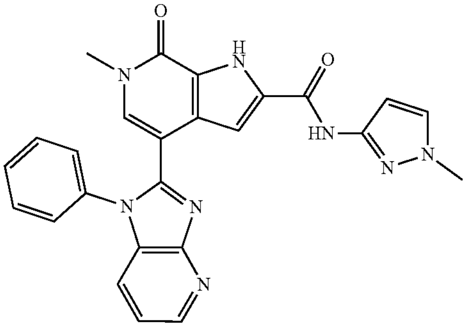

Compound A53 was synthesized according to the synthetic method of compound A51 by substituting

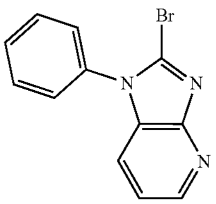

for

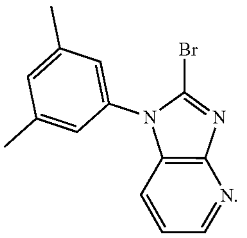

The data for compound A53 are as follows:

LCMS: m/z 465.4 (M+H). $^1$H-NMR (DMSO, 400 Hz): 12.62 (br, 1H), 10.84 (s, 1H), 8.53 (d, J=4.4 Hz, 1H), 7.73 (d, J=8.0 Hz, 1H), 7.61 (s, 1H), 7.56-7.50 (m, 5H), 7.35-7.31 (m, 3H), 6.57 (s, 1H), 3.78 (s, 3H), 3.41 (s, 3H).

Example A54

A54

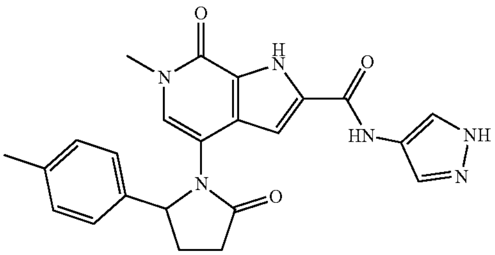

Compound A54 was synthesized according to the synthetic method of compound A51 by substituting

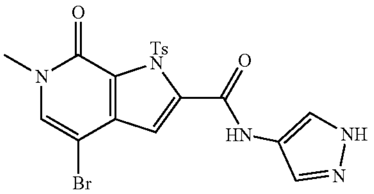

for

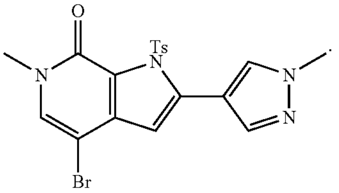

Compound A54-P1 and compound A54-P2 were obtained by chiral resolution using the synthetic method of SFC. The data are as follows:

A54-P1: $^1$H-NMR (d-DMSO, 400 Hz): 12.70 (s, 1H), 12.37 (s, 1H), 10.36 (s, 1H), 8.00-7.96 (m, 1H), 7.66-7.63 (m, 1H), 7.20 (d, J=7.6 Hz, 3H), 7.05 (d, J=7.6 Hz, 3H), 5.23-5.19 (m, 1H), 3.39 (s, 3H), 2.67-2.57 (m, 3H), 2.21 (s, 3H), 1.98-1.92 (m, 1H).

A54-P2: $^1$H-NMR (d-DMSO, 400 Hz): 12.70 (s, 1H), 12.37 (s, 1H), 10.36 (s, 1H), 7.96-7.94 (m, 1H), 7.71-7.67

(m, 1H), 7.20 (d, J=12.0 Hz, 3H), 7.05 (d, J=7.6 Hz, 3H), 5.23-5.19 (m, 1H), 3.39 (s, 3H), 2.67-2.57 (m, 3H), 2.19 (s, 3H), 2.01-1.92 (m, 1H).

Intermediate 151

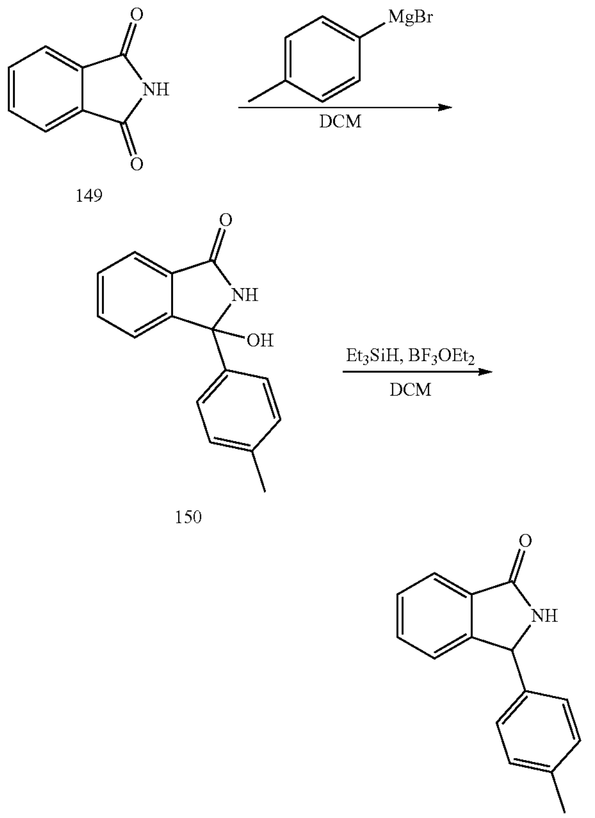

149

150

151

Step 1: Synthesis of 3-hydroxy-3-(p-tolyl)isoindolin-1-one (Intermediate 150)

The compound isoindolin-1,3-dione (2.0 g, 13.6 mmol) was added to a 50 mL three-necked round-bottomed flask containing 20 mL of dichloromethane, the system was cooled to 0° C., and p-phenylmagnesium bromide (1 mol/L, 41 mL, 40.8 mmol) was added dropwise under nitrogen protection and then reacted overnight at room temperature after addition. After the completion of the reaction monitored by TLC, the reaction solution was quenched with saturated aqueous ammonium chloride solution, extracted with dichloromethane, and the organic phase was washed with saturated brine, dried over anhydrous sodium sulfate, filtered, concentrated and separated by column chromatography (ethyl acetate/petroleum ether=1:2) to obtain intermediate 150 (1.5 g, yield: 46%) as a white solid.

LCMS: m/z 222.2 (M-OH).

Step 2: Synthesis of 3-(p-tolyl)isoindolin-1-one (Intermediate 151)

3-hydroxy-3-(p-tolyl)isoindolin-1-one (1.5 g, 6.3 mmol) was added to a 50 mL three-necked flask containing 30 mL of dichloromethane at room temperature and the reaction system was cooled to −15° C. Triethylsilane (7.3 g, 63 mmol) and 40% boron (tri) fluoride etherate (5.7 g, 18.9 mmol) were added dropwise under nitrogen protection and then reacted at room temperature overnight after addition. After the completion of the reaction monitored by TLC, the reaction solution was washed with saturated aqueous sodium bicarbonate solution and saturated brine successively, dried over anhydrous sodium sulfate, filtered, concentrated and then subjected to column chromatography (petroleum ether/ethyl acetate=1/1) to give intermediate 151 (1.2 g, yield: 86%) as a white solid.

The data for intermediate 151 are as follows:

LCMS: m/z 224.2 (M+H). $^1$H-NMR (DMSO, 400 Hz): 9.04 (br, 1H), 7.71 (d, J=7.2 Hz, 1H), 7.55-7.45 (m, 2H), 7.27 (d, J=7.6 Hz, 1H), 7.16 (s, 4H), 5.69 (s, 1H), 2.28 (s, 3H).

Example A55

A55

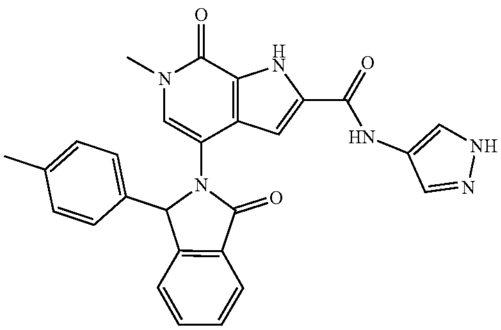

Example A55 was synthesized according to the synthesis conditions of compound A54 by substituting intermediate 151 for intermediate 143. The data are as follows: $^1$H-NMR (d-DMSO, 400 Hz): 12.66 (d, J=10.0 Hz, 1H), 12.32-12.29 (m, 1H), 10.33 (s, 1H), 7.99-7.96 (m, 1H), 7.88 (d, J=7.2 Hz, 1H), 7.66-7.52 (m, 3H), 7.45 (s, 1H), 7.33-7.28 (m, 1H), 7.18-7.05 (m, 5H), 6.30 (s, 1H), 3.56 (s, 3H), 2.15 (s, 3H).

Synthesis Route of Example A56

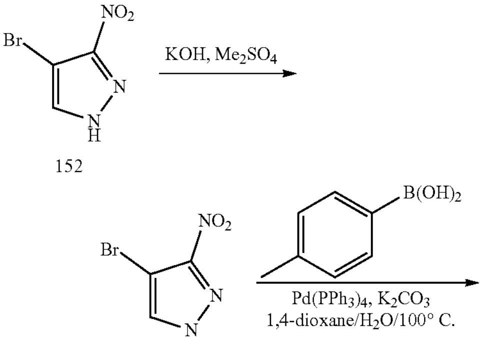

152

153

-continued

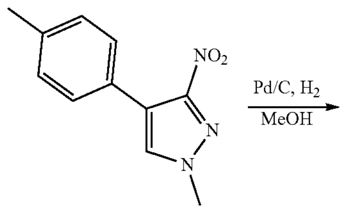

154

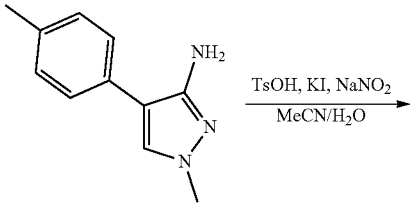

155

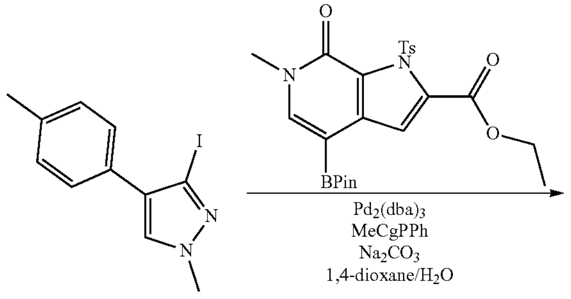

156

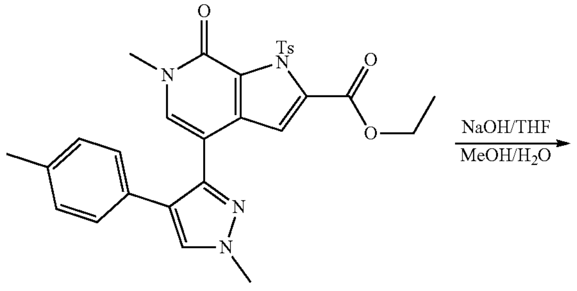

157

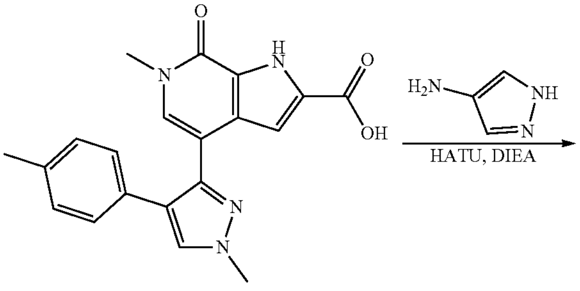

158

-continued

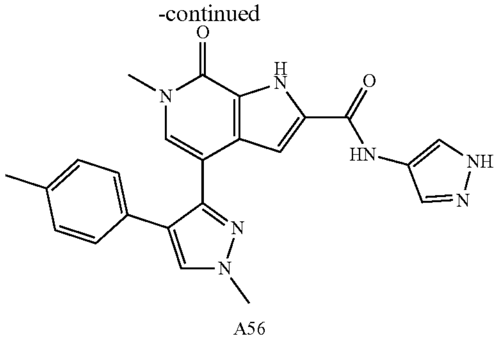

A56

Step 1: Synthesis of 4-bromo-1-methyl-3-nitro-1H-pyrazole (Intermediate 153)

4-bromo-3-nitro-1H-pyrazole (6.0 g, 31.25 mmol), potassium hydroxide (3.6 g, 89.25 mmol), water (60 mL) and dimethyl sulfate (3938 mg, 31.25 mmol) were successively added to a dry 250 mL round-bottomed flask at room temperature, stirred and reacted at room temperature for 16 hours. The reaction mixture was filtered and the filter cake was washed with ethanol/water (50 mL/50 mL) and dried to give 4-bromo-1-methyl-3-nitro-1H-pyrazole 153 (4.2 g, brown powder), yield: 65.0%, LCMS: m/z 206.1 (M+H).

Step 2: Synthesis of 1-methyl-3-nitro-4-(p-tolyl)-1H-pyrazole (Intermediate 154)

Intermediate 153 (4120 mg, 20.0 mmol), 4-methylphenylboronic acid (4080 mg, 30.0 mmol), tetrakistriphenylphosphine palladium (2312 mg, 2.0 mmol), potassium carbonate (5520 mg, 40.0 mmol), 1,4-dioxane (100 mL) and water (25 mL) were successively added to a dry 250 mL round-bottomed flask and stirred at 100° C. for 5 hours under nitrogen protection. After the completion of the reaction monitored by TLC, the reaction mixture was filtered and the filtrate was dried by rotary evaporation and subjected to column chromatography (petroleum ether/ethyl acetate=2/1) to obtain 1-methyl-3-nitro-4-(p-tolyl)-1H-pyrazole (intermediate 154, 2.5 g, yellow solid), yield: 57%.

LCMS: m/z 218.2 (M+H).

Step 3: Synthesis of 1-methyl-4-(p-tolyl)-1H-pyrazol-3-amine (Intermediate 155)

Compound 154 (1.5 g, 6.9 mmol), palladium on carbon (750 mg) and methanol (300 mL) were successively added to a dry 500 mL single-necked flask at room temperature, stirred and reacted at room temperature under hydrogen for 3 hours. The reaction mixture was filtered and the filtrate was concentrated under reduced pressure to obtain 1-methyl-4-(p-tolyl)-1H-pyrazol-3-amine (intermediate 155, 1.25 g, brown solid), yield: 97%, LCMS: m/z 188.2 (M+H).

Step 4: Synthesis of 3-iodo-1-methyl-4-(p-tolyl)-1H-pyrazole (Intermediate 156)

Intermediate 155 (374 mg, 2 mmol), acetonitrile (15 mL), and p-toluenesulfonic acid monohydrate (1140 mg, 6 mmol) were successively added to a dry 100 mL single-necked flask at room temperature in an ice bath. The mixture was stirred in an ice bath for 10 minutes, and then an aqueous solution of potassium iodide (830 mg, 5 mmol) and sodium nitrite (276 mg, 4 mmol) was slowly added dropwise to the above solution. The reaction mixture was stirred and reacted at room temperature for 1 hour. After the reaction was completed, the mixture was added with water (50 mL) and extracted with ethyl acetate (50 mL×3). The organic phase was collected, dried over anhydrous sodium sulfate and filtered. The filtrate was concentrated under reduced pressure, and the concentrate was subjected to column chromatography (petroleum ether/ethyl acetate=10/1) to obtain 3-iodo-1-methyl-4-(p-tolyl)-1H-pyrazole (Intermediate 156, 300 mg, brown solid), yield: 50%.

LCMS: m/z 299.1 (M+H).

Step 5: Synthesis of ethyl 6-methyl-4-(1-methyl-4-(p-tolyl)-1H-pyrazol-3-yl)-7-oxo-1-tosyl-6,7-dihydro-1H-pyrrolidino[2,3-c]pyridin-2-carboxylate (Intermediate 157)

The compound ethyl 6-methyl-7-oxo-4-(4,4,5,5-tetramethyl-1,3,2-dioxaborolan-2-yl)-1-tosyl-6,7-dihydro-1H-pyrrolidino[2,3-c]pyridin-2-carboxylate (460 mg, 0.92 mmol), intermediate 156 (250 mg, 0.84 mmol), tris(dibenzylideneacetone)dipalladium (77 mg, 0.084 mmol), 1,3,5,7-tetramethyl-6-phenyl-2,4,8-trioxa-6-phosphaadamantane (73 mg, 0.25 mmol), sodium carbonate (265 mg, 2.5 mmol), 1,4-dioxane (20 mL) and water (5 mL) were successively added to a dry 100 mL single-necked flask at room temperature, stirred at 50° C. and reacted for 3 hours. After the reaction was completed, the reaction mixture was filtered, concentrated under reduced pressure, and the concentrate was subjected to column chromatography (petroleum ether/ethyl acetate=2/1) to obtain ethyl 6-methyl-4-(1-methyl-4-(p-tolyl)-1H-pyrazol-3-yl)-7-oxo-1-tosyl-6,7-dihydro-1H-pyrrolidino[2,3-c]pyridin-2-carboxylate 157 (280 mg, yellow solid), yield: 51.0%.

LCMS: m/z 545.2 (M+H).

Step 6: Synthesis of 6-methyl-4-(1-methyl-4-(p-tolyl)-1H-pyrazol-3-yl)-7-oxo-6,7-dihydro-1H-pyrrolo[2,3-c]pyridin-2-carboxylic acid (Intermediate 158)

Compound 157 (100 mg, 0.18 mmol), sodium hydroxide (36 mg, 0.9 mmol), methanol (6 mL), tetrahydrofuran (3 mL) and water (2 mL) were successively added to a dry 25 mL single-necked flask at room temperature, stirred at 60° C. and reacted for 3 hours. The reaction mixture was concentrated under reduced pressure, adjusted pH to 3-4, extracted with ethyl acetate, dried, filtered, and concentrated under reduced pressure to give 6-methyl-4-(1-methyl-4-(p-tolyl)-1H-pyrazol-3-yl)-7-oxo-6,7-dihydro-1H-pyrrolo[2,3-c]pyridin-2-carboxylic acid (intermediate 158, 60 mg, yellow solid), yield: 92%.

LCMS: n/z 363.2 (M+H).

Step 7: Synthesis of 6-methyl-4-(1-methyl-4-(p-tolyl)-1H-pyrazol-3-yl)-7-oxo-N-(1H-pyrazol-4-yl)-6,7-dihydro-1H-pyrrolo[2,3-c]pyridin-2-carboxamide (A56)

Intermediate 158 (60 mg, 0.16 mmol), 1H-pyrazol-4-amine (21 mg, 0.25 mmol), 2-(7-azobenzotriazole)-N,N,N',N'-tetramethylurea hexafluorophosphate (95 mg, 0.25 mmol), N,N-diisopropylethylamine (62 mg, 0.48 mmol) and N,N-dimethylformamide (2 mL) were successively added to a dry 25 mL single-necked flask at room temperature, stirred at room temperature and reacted for 2 hours. After the reaction was completed, the mixture was purified by high-performance liquid phase reverse preparative column to obtain 6-methyl-4-(1-methyl-4-(p-tolyl)-1H-pyrazol-3-yl)-7-oxo-N-(1H-pyrazol-4-yl)-6,7-dihydro-1H-pyrrolo[2,3-c]pyridin-2-carboxamide (A56) (5 mg, white solid), yield: 7%.

LCMS: m/z 428.2 (M+H). 1H NMR (400 MHz, DMSO) δ 12.64 (s, 1H), 12.35 (s, 1H), 10.28 (s, 1H), 8.04 (s, 1H), 7.93 (s, 1H), 7.62 (s, 1H), 7.18 (d, J=9.2 Hz, 3H), 7.05 (d, J=7.9 Hz, 2H), 6.74 (s, 1H), 3.93 (s, 3H), 3.49 (s, 3H), 2.22 (s, 3H).

Synthesis Route of Example A57

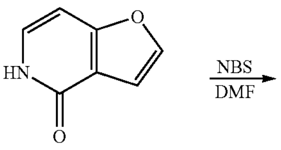

159

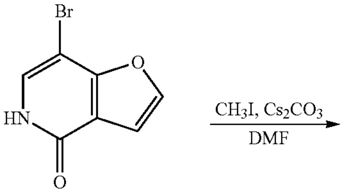

160

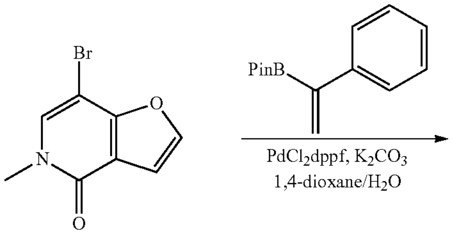

161

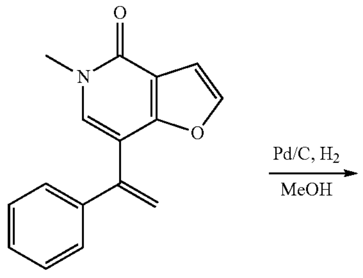

162

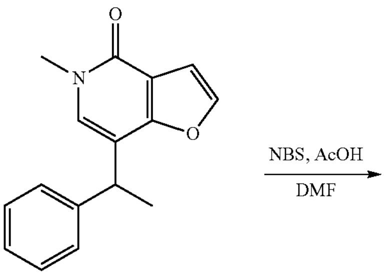

163

-continued

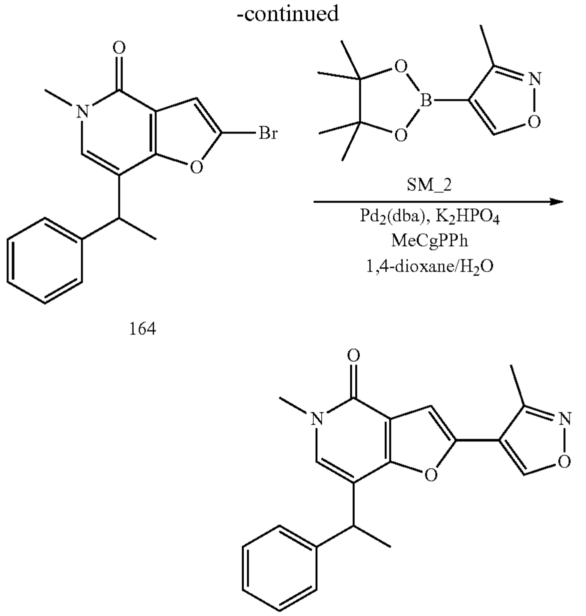

164

A57

Step 1: Synthesis of 7-bromo-5H-furo[3,2-C]pyridin-4-one (Intermediate 160)

Intermediate 159 (2.0 g, 14.8 mmol) was added to a 100 mL single-necked flask containing 25 mL of N,N-dimethylformamide at 0° C. in an ice bath, followed by the slow addition of N-bromosuccinimide (2.9 g, 16.3 mmol). The ice bath was removed and the mixture was reacted at room temperature for 2 hours. After the completion of the reaction monitored by TLC, the reaction system was diluted with water, extracted with ethyl acetate three times, and the organic phase was washed successively with water and saturated sodium chloride solution, dried over anhydrous sodium sulfate, filtered, and concentrated to obtain intermediate 160 (1.5 g, yellow solid), yield: 47%.

LCMS: m/z 216.0 (M+H).

Step 2: Synthesis of 7-bromo-5-methylfuro[3,2-c]pyridin-4(5H)-one (Intermediate 161)

Compound 160 (1.5 g, 7.0 mmol) and cesium carbonate (3.4 g, 10.5 mmol) were successively added to a 100 mL single-necked flask containing 20 mL of dry N,N-dimethylformamide at 0° C. in an ice bath, then methyl iodide (2.0 g, 14.0 mmol) was added dropwise, and the reaction was carried out at room temperature for 4 hours. After the completion of the reaction monitored by LCMS, the reaction system was diluted with water, and the aqueous phase was extracted three times with ethyl acetate, dried, concentrated, and purified by column (petroleum ether/ethyl acetate (v:v) =1/1) to obtain intermediate 161 (1.0 g, white solid), yield: 63%.

LCMS: m/z 230.1 (M+H).

Step 3: Synthesis of 5-methyl-7-(1-phenylvinyl)furo[3,2-c]pyridin-4(5H)-one (Intermediate 162)

Intermediate 161 (1.0 g, 4.39 mmol), styryl borate (1.21 g, 5.26 mmol), anhydrous potassium carbonate (1.51 g, 11.00 mmol), 1,1'-bisdiphenylphosphinoferrocene palladium dichloride (161 mg) and dioxane:water (18 mL, 5/1) were successively added to a dry 100 mL three-necked round-bottomed flask at room temperature, heated to 100° C. under nitrogen protection and reacted for 5 hours. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered, concentrated and purified by column (petroleum ether/ethyl acetate) (v:v)=1/1) to give intermediate 162 (0.74 g, white solid), yield: 67%.

LCMS: m/z 252.1 (M+H).

Step 4: Synthesis of 5-methyl-7-(1-phenylethyl)furo[3,2-c]pyridin-4(5H)-one (Intermediate 163)

Compound 4 (0.74 g, 2.94 mmol) and palladium on carbon (37 mg) were added successively to a 100 mL single-necked flask containing methanol (60 mL) at room temperature and stirred at room temperature for 3 hours under hydrogen protection. After the completion of the reaction monitored by LCMS, the reaction mixture was filtered and concentrated to obtain intermediate 163 (0.61 g, yellow solid), which was used directly in the next step, yield: 82%.

LCMS: m/z 254.3 (M+H).

Step 5: Synthesis of 2-bromo-5-methyl-7-(1-phenylethyl)furo[3,2-c]pyridin-4(5H)-one (Intermediate 164)

Compound 5 (560 mg, 2.21 mmol) and 6 drops of acetic acid were successively added to a 100 mL single-necked flask containing N,N-dimethylformamide at room temperature, and then N-bromosuccinimide (590 mg, 3.32 mmol) was added slowly, stirred at 60° C. and reacted for 2 hours. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered and concentrated. The residue was purified by column (petroleum ether/ethyl acetate=2/1) to obtain intermediate 164 (420 mg, pale yellow solid), yield: 57%.

LCMS: m/z 332.1 (M+H).

1H-NMR ($CDCl_3$, 400 MHz): 7.36-7.23 (m, 5H), 6.89 (s, 1H), 6.80 (s, 1H), 4.29 (q, J=7.2 Hz 1H), 3.55 (s, 3H), 1.67 (d, J=7.2 Hz, 3H).

Step 6: Synthesis of 5-methyl-2-(1-methyl-3-nitro-1H-pyrazol-4-yl)-7-(1-phenylethyl)thieno[3,2-c]pyridin-4(5H)-one (A57)

Intermediate 164 (50 mg, 0.15 mmol), 3-methyl-4-(4,4,5,5-tetramethyl-1,3,2-dioxaborolan-2-yl)isoxazole (35 mg, 0.17 mmol), dipotassium hydrogen phosphate (78 mg, 0.45 mmol), 1,3,5,7-tetramethyl-6-phenyl-2,4,8-trioxa-6-phosphaadamantane (9 mg) and tris(dibenzylideneacetone)dipalladium (14 mg) were successively added to a 50 mL three-necked flask containing mixed solvent of dioxane/water (5/1, 12 mL) and reacted for 4 hours at 60° C. under nitrogen protection. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered and concentrated, and the residue was purified by prep-HPLC to obtain compound A57 (7 mg, white solid), yield: 14%.

LCMS: m/z 335.1 (M+H).

$^1$H-NMR (d-DMSO, 400 MHz): 9.30 (s, 1H), 7.67 (s, 1H), 7.39 (d, J=7.2 Hz, 2H), 7.31-7.28 (m, 2H), 7.20-7.16 (m, 1H), 7.12 (s, 1H), 4.30 (q, J=7.6 Hz, 1H), 3.55 (s, 3H), 2.37 (s, 3H), 1.65 (d, J=7.6 Hz, 3H).

Example A58 Synthesis Route

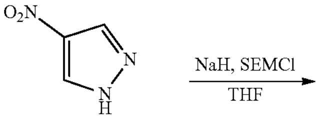

165

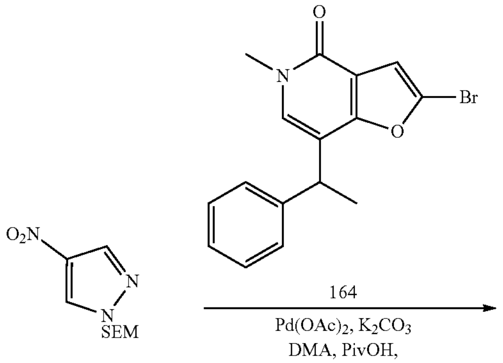

166

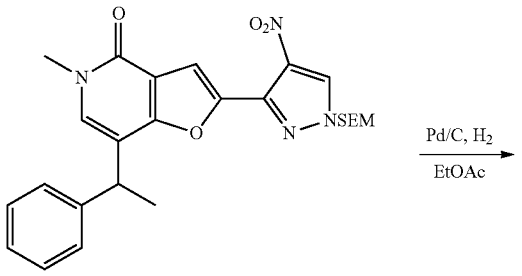

167

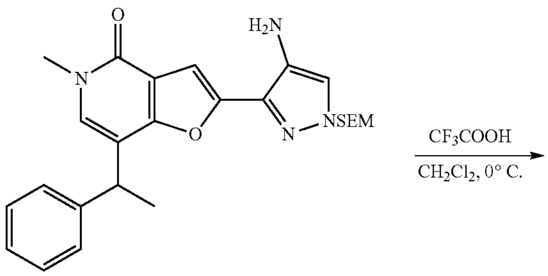

168

-continued

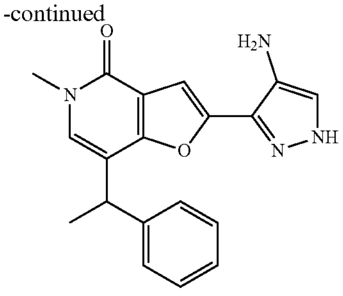

A58

Step 1: Synthesis of 4-nitro-1-(((2-(trimethylsilyl)ethoxy)methyl)-1H-pyrazole (Intermediate 166)

Intermediate 165 (6.6 g, 58.4 mmol) was added to a 100 mL single-necked flask containing 50 mL of tetrahydrofuran at 0° C. in an ice bath, and sodium hydride (4.8 g, 120.8 mmol, 60%) was slowly added in an ice bath and reacted at room temperature for 10 minutes. Then (2-(chloromethoxy)ethyl)trimethylsilane (12.0 mL, 67.8 mmol) was slowly added dropwise, and the mixture was reacted at room temperature for 1.5 hours after removing the ice bath. After the completion of the reaction monitored by TLC, the reaction system was quenched with saturated ammonium chloride, extracted three times with ethyl acetate, and the organic phase was washed successively with water and saturated sodium chloride solution, dried over anhydrous sodium sulfate, filtered, concentrated and purified by a column (petroleum ether/ethyl acetate=10/1) to give intermediate 166 (12 g, yellow liquid), yield: 84%.

1H-NMR ($CDCl_3$, 400 MHz): 8.33 (s, 1H), 8.11 (s, 1H), 5.47 (s, 2H), 3.63 (t, J=8.4 Hz 2H), 0.95 (t, J=8.0 Hz 2H), 0.02 (s, 9H).

Step 2: Synthesis of 5-methyl-2-(4-nitro-1-((2-(trimethylsilyl)ethoxy)methyl)-1H-pyrazol-3-yl)-7-(1-phenethyl)furo[3,2-c]pyridin-4(5H)-one (Intermediate 167)

Intermediate 166 (228 mg, 0.94 mmol), intermediate 164 (280 mg, 0.84 mmol), potassium carbonate (348 mg, 2.52 mmol), palladium acetate (18 mg, 0.08 mmol), pivalic acid (17 mg, 0.17 mmol) and n-butylbis(1-adamantyl)phosphine (29 mg, 0.08 mmol) were successively added to a 100 mL three-necked flask containing 20 mL of dry N,N-dimethylacetamide, reacted at 120° C. for 6 hours under nitrogen protection. After the completion of the reaction monitored by LCMS, the reaction system was diluted with water, and the aqueous phase was extracted three times with ethyl acetate, dried, concentrated, and purified by column (petroleum ether/ethyl acetate=1/2) to obtain intermediate 167 (140 mg, yellow liquid), yield: 30%.

LCMS: m/z 495.2 (M+H).

$^1$H-NMR ($CDCl_3$, 400 MHz): 8.26 (s, 1H), 7.85 (s, 1H), 7.38-7.30 (m, 51H), 7.07 (s, 1H), 5.49-5.38 (m, 2H), 4.36-4.34 (m, 1H), 3.67 (s, 3H), 3.60-3.56 (m, 2H), 1.75 (d, J=7.2 Hz, 3H), 0.93-0.88 (m, 2H), 0.01 (s, 9H).

Step 3: Synthesis of 2-(4-amino-1-((2-(trimethylsilyl)ethoxy)methyl)-1H-pyrazol-3-yl)-5-methyl-7-(1-phenethyl)furo[3,2-c]pyridin-4(5H)-one (Intermediate 168)

Intermediate 167 (140 mg, 0.28 mmol) and palladium on carbon (20 mg, 10%) were successively added to a 100 mL three-necked round-bottomed flask containing 20 mL of anhydrous ethyl acetate at room temperature. The reaction was carried out at room temperature for 2 hours under a hydrogen atmosphere. After the completion of the reaction monitored by LCMS, the reaction system was filtered and concentrated to obtain intermediate 168 (100 mg, colorless liquid), yield: 76%.

LCMS: m/z 465.2 (M+H).

Step 4: Synthesis of 2-(4-amino-1H-pyrazol-3-yl)-5-methyl-7-(1-phenethyl)furo[3,2-c]pyridin-4(5H)-one (A58)

Intermediate 168 (30 mg, 0.06 mmol) and trifluoroacetic acid (2 mL) were added successively to a 25 mL single-necked flask containing dichloromethane (4 mL) at 0° C. and stirred for 6 hours under nitrogen protection. After the completion of the reaction monitored by LCMS, the mixture was filtered and the filtrate was concentrated and purified by prep-HPLC (basic) to obtain compound A58 (5 mg, white solid), yield: 23%.

LCMS: m/z 335.1 (M+H).

$^1$H-NMR (d-DMSO, 400 MHz): 7.59 (s, 1H), 7.40 (d, J=7.2 Hz, 2H), 7.30-7.26 (m, 2H), 7.19-7.17 (m, 1H), 7.12 (s, 1H), 6.98 (s, 1H), 4.36-4.34 (m, 1H), 4.19 (s, 2H), 3.61 (s, 3H), 1.64 (d, J=7.2 Hz, 3H).

Example A59 Synthesis Route

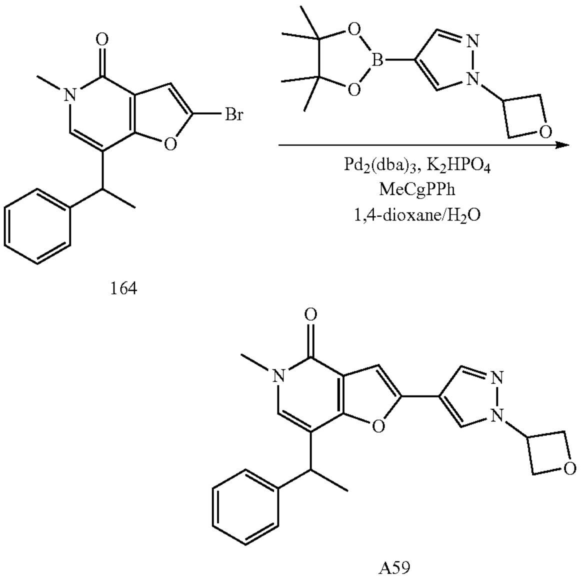

164

A59

Synthesis of 5-methyl-2-(1-(oxetan-3-yl)-1H-pyrazol-4-yl)-7-(1-phenethyl)furo[3,2-c]pyridin-4(5H)-one (A59)

Intermediate 164 (50 mg, 0.15 mmol), 1-(oxetan-3-yl)-4-(4,4,5,5-tetramethyl-1,3,2-dioxaborolan-2-yl)-1H-pyrazole (41 mg, 0.17 mmol), dipotassium hydrogen phosphate (78 mg, 0.45 mmol), 1,3,5,7-tetramethyl-6-phenyl-2,4,8-trioxa-6-phosphaadamantane (9 mg) and tris(dibenzylideneacetone)dipalladium (14 mg) were added successively to a dry 50 mL three-necked flask containing a mixed solvent of dioxane/water (5/1, 12 mL) at room temperature and reacted at 60° C. for 4 hours under nitrogen protection. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered and concentrated, and the residue was purified by prep-HPLC to obtain compound A59 (30 mg, white solid), yield: 53%.

LCMS: m/z 376.2 (M+H).

$^1$H-NMR (d-DMSO, 400 MHz): 8.31 (s, 1H), 7.98 (s, 1H), 7.57 (s, 1H), 7.42 (d, J=7.6 Hz, 2H), 7.32-7.28 (m, 2H), 7.19-7.16 (m, 1H), 6.99 (s, 1H), 5.64 (q, J=6.8 Hz, 1H), 4.96-4.88 (m, 4H), 4.30-4.38 (m, 1H), 3.52 (s, 1H), 1.66 (d, J=7.2 Hz, 3H).

Example A60 Synthesis Route

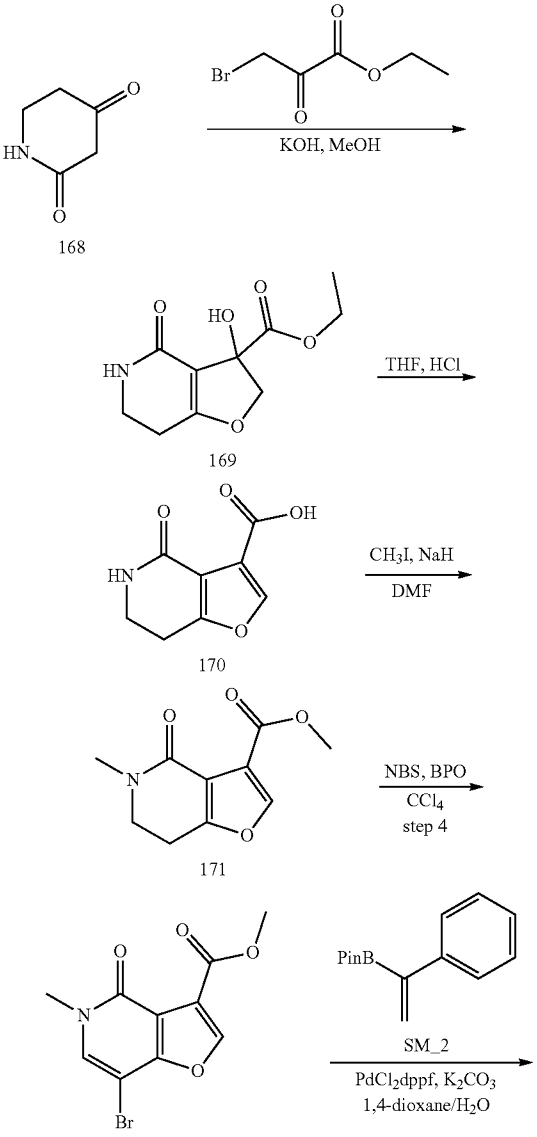

168

169

170

171

172

-continued

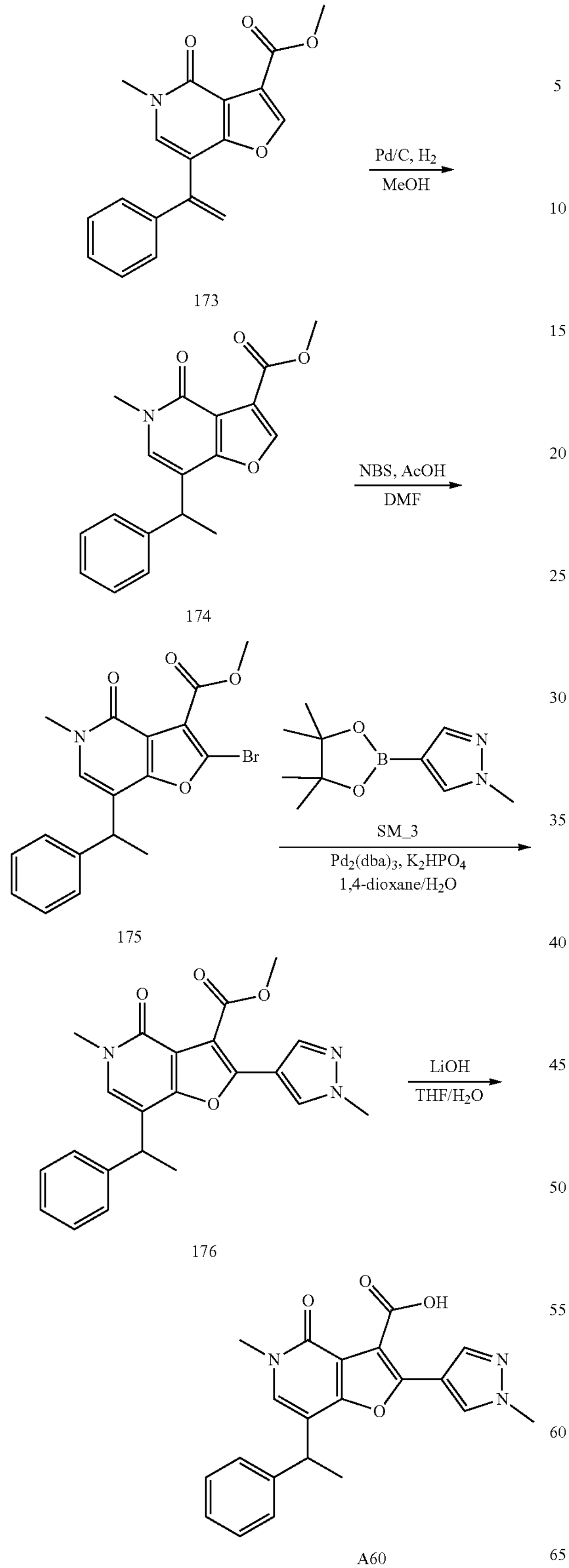

A60

Step 1: Synthesis of ethyl 3-hydroxy-4-oxo-2,3,4,5,6,7-hexahydrofuro[3,2-c]pyridin-3-carboxylate (Intermediate 169)

Potassium hydroxide (9.9 g, 176.8 mmol) was added to a 500 mL single-necked flask containing 250 mL of anhydrous methanol at 0° C. in an ice bath, and intermediate 168 (20 g, 176.8 mmol) was slowly added. The ice bath was removed and the mixture was reacted at room temperature for 1 hour. Then, ethyl 3-bromo-2-oxopropanoate (36.2 g, 185.7 mmol) was slowly added dropwise, and the reaction was carried out at room temperature for 2.5 hours after the ice bath was removed. After the completion of the reaction monitored by LCMS, the reaction system was concentrated and purified by a column (dichloromethane/methanol=10/1) to obtain intermediate 169 (19 g, yellow liquid), yield: 46.6%.

LCMS: m/z 228.1 (M+H).

Step 2: Synthesis of 4-oxo-4,5,6,7-tetrahydrofuro[3,2-c]pyridin-3-carboxylic acid (Intermediate 170)

Intermediate 169 (19 g, 83.6 mmol) was added to a 500 mL three-necked flask containing 300 mL of dry tetrahydrofuran, and an aqueous hydrochloric acid solution (40 mL, 4M) was slowly added, and the reaction was carried out at 80° C. for 3 hours. After the completion of the reaction monitored by LCMS, the mixture was concentrated to remove part of the solvent and then filtered to obtain intermediate 170 (10 g, yellow solid), yield: 65.5%.

LCMS: m/z 182.1 (M+H).

Step 3: Synthesis of methyl 5-methyl-4-oxo-4,5,6,7-tetrahydrofuro[3,2-c]pyridin-3-carboxylate (Intermediate 171)

Intermediate 170 (9 g, 49.7 mmol) and sodium hydride (5.6 g, 60%) were successively added to a 1000 mL three-necked round-bottomed flask containing 500 mL of anhydrous N,N-dimethylformamide at 0° C. The reaction was carried out at 0° C. for 1 hour under nitrogen atmosphere. Then methyl iodide (35.3 g, 248.5 mmol) was slowly added dropwise, and the reaction was carried out at room temperature for 16 hours after the ice bath was removed. After the completion of the reaction monitored by LCMS, the reaction system was quenched with saturated ammonium chloride, diluted with water and extracted with ethyl acetate. The organic phase was washed successively with water and saturated sodium chloride solution, dried over anhydrous sodium sulfate, filtered, concentrated and purified by column (petroleum ether/ethyl acetate=0/1) was to give intermediate 171 (4.7 g, white solid), yield: 45.2%.

LCMS: m/z 210.1 (M+H).

Step 4: Synthesis of methyl 7-bromo-5-methyl-4-oxo-4,5-dihydrofuro[3,2-c]pyridin-3-carboxylate (Intermediate 172)

Intermediate 171 (2.5 g, 12.0 mmol), N-bromosuccinimide (4.3 g, 24.0 mmol) and benzoyl peroxide (581 mg, 2.4 mmol) were successively added to a 1000 mL three-necked round-bottomed flask containing 500 mL of anhydrous carbon tetrachloride at room temperature. The reaction was carried out at 90° C. for 1 hour under nitrogen atmosphere. After the completion of the reaction monitored by LCMS, the reaction system was diluted with water and extracted with ethyl acetate. The organic phase was washed successively with water and saturated sodium chloride solution, dried over anhydrous sodium sulfate, filtered, concentrated and purified by column (petroleum ether/ethyl acetate=1/1) to obtain intermediate 172 (1.15 g, yellow solid), yield: 33.6%.

LCMS: m/z 288.0 (M+H).

Step 5: Synthesis of methyl 5-methyl-4-oxo-7-(1-phenylvinyl)-4,5-dihydrofuro[3,2-c]pyridin-3-carboxylate (Intermediate 173)

Intermediate 172 (1.15 g, 4.02 mmol), styryl boronic acid pinacol ester (1.11 g, 4.86 mmol), anhydrous potassium carbonate (1.66 g, 12.06 mmol), 1,1'-bisdiphenylphosphino-ferrocene palladium dichloride (292 mg) and dioxane:water (18 mL, 5/1) were successively added to a dry 100 mL three-necked round-bottomed flask at room temperature, heated to 70° C. under nitrogen protection and reacted for 4 hours. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered, concentrated and purified by column (petroleum ether/ethyl acetate=1/1) to give intermediate 173 (0.9 g, white solid), yield: 72.4%.

LCMS: m/z 310.1 (M+H).

1H-NMR ($CDCl_3$, 400 MHz): 8.28 (s, 5H), 7.64 (s, 1H), 7.41-7.39 (m, 5H), 5.71 (d, J=14.8 Hz 2H), 3.93 (s, 3H), 3.68 (s, 3H).

Step 6: Synthesis of methyl 5-methyl-4-oxo-7-(1-phenethyl)-4,5-dihydrofuro[3,2-c]pyridin-3-carboxylate (Intermediate 174)

Intermediate 173 (0.9 g, 2.91 mmol) and palladium on carbon (90 mg) were successively added to a 100 mL single-necked flask containing methanol (60 mL) at room temperature and stirred for 3 hours under hydrogen protection at room temperature. After the completion of the reaction monitored by LCMS, the mixture was filtered and the filtrate was concentrated to obtain intermediate 174 (0.8 g, yellow solid), which was directly used in the next step, yield: 88.3%.

LCMS: m/z 312.1 (M+H).

Step 7: Synthesis of methyl 2-bromo-5-methyl-4-oxo-7-(1-phenethyl)-4,5-dihydrofuro[3,2-c]pyridin-3-carboxylate (175)

Intermediate 174 (0.8 mg, 2.57 mmol) and 6 drops of acetic acid were successively added to a 100 mL single-necked flask containing N,N-dimethylformamide at room temperature, then N-bromosuccinimide (686 mg, 3.86 mmol) was slowly added, stirred and reacted at 60° C. for 3 hours. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered and concentrated. The residue was purified by column (petroleum ether/ethyl acetate=2/1) to obtain intermediate 175 (520 mg, pale yellow solid), yield: 51.9%.

LCMS: m/z 390.1 (M+H).

$^1$H-NMR (DMSO, 400 MHz): 7.73 (s, 1H), 7.31-7.29 (m, 4H), 7.22-7.19 (m, 1H), 4.26-4.24 (m, 1H), 3.82 (s, 3H), 3.52 (s, 3H), 1.58 (d, J=7.2 Hz, 3H).

Step 8: Synthesis of methyl 5-methyl-2-(1-methyl-1H-pyrazol-4-yl)-4-oxo-7-(1-phenethyl)-4,5-dihydrofuro[3,2-c]pyridin-3-carboxylate (Intermediate 176)

Intermediate 175 (520 mg, 1.33 mmol), (1-methyl-1H-pyrazol-4-yl)boronic acid (201 mg, 1.60 mmol), dipotassium hydrogen phosphate (694 mg, 3.99 mmol), 1,3,5,7-tetramethyl-6-phenyl-2,4,8-trioxa-6-phosphaadamantane (30 mg) and tris(dibenzylideneacetone)dipalladium (60 mg) were successively added to a 50 mL three-necked flask containing a mixed solvent of dioxane/water (5/1, 30 mL) at room temperature and reacted at 60° C. for 4 hours under nitrogen protection. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered, and the residue was purified by column (petroleum ether/ethyl acetate=1/1) to give intermediate 176 (315 mg, pale yellow solid), yield: 60.4%.

LCMS: m/z 392.2 (M+H).

Step 9: Synthesis of 5-methyl-2-(1-methyl-1H-pyrazol-4-yl)-4-oxo-7-(1-phenethyl)-4,5-dihydrofuro[3,2-c]pyridin-3-carboxylic acid (A60)

Compound 9 (315 mg, 0.8 mmol) and lithium hydroxide monohydrate (168 mg, 4 mmol) were successively added to a 100 mL single-necked flask containing tetrahydrofuran/water (3/1, 20 mL) at room temperature and stirred at room temperature for 16 hours under nitrogen protection. After the completion of the reaction monitored by LCMS, the mixture was adjusted to pH 5-6 with dilute aqueous hydrochloric acid and filtered. The filter cake was washed with pure water and dried to obtain compound A60 (0.2 g, white solid), yield: 65.9%.

LCMS: m/z 378.1 (M+H).

$^1$H-NMR (DMSO, 400 MHz): 8.68 (s, 1H), 8.09 (s, 1H), 7.96 (s, 1H), 7.44-7.42 (m, 2H), 7.34-7.30 (m, 2H), 7.21-7.18 (m, 1H), 4.42-4.40 (m, 1H), 3.94 (s, 3H), 3.71 (s, 3H), 1.67 (d, J=7.2 Hz, 3H).

Example A61 Synthesis Route

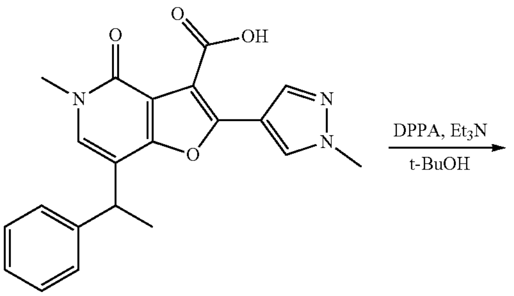

A60

-continued

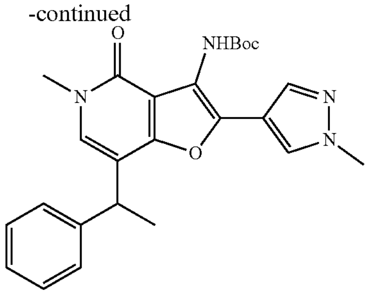

A61

Synthesis of tert-butyl (5-methyl-2-(1-methyl-1H-pyrazol-4-yl)-4-oxo-7-(1-phenethyl)-4,5-dihydrofuro[3,2-c]pyridin-3-yl carbamate (A61)

Example A60 (50 mg, 0.13 mmol), diphenyl azidophosphate (54 mg, 0.20 mmol), and triethyl amine (20 mg, 0.20 mmol) were successively added to a 50 mL three-necked flask containing dry tert-butanol (15 mL) at room temperature, heated to 90° C. under nitrogen protection and reacted for 18 hours. After the completion of the reaction monitored by LCMS, the reaction system was cooled to room temperature, diluted with water and extracted with ethyl acetate. The organic phase was washed successively with water and saturated sodium chloride solution, dried over anhydrous sodium sulfate, filtered, concentrated, and purified by column chromatography (dichloromethane/methanol=20/1) to give Example A61 (20 mg, white solid), yield: 33.7%.

LCMS: m/z 449.5 (M+H).

$^1$H-NMR (MeOD, 400 MHz): 7.84 (s, 1H), 7.68 (s, 1H), 7.39-7.37 (m, 2H), 7.35 (s, 1H), 7.31-7.25 (m, 2H), 7.21-7.16 (m, 1H), 4.35-4.33 (m, 1H), 3.93 (s, 3H), 3.60 (s, 3H), 1.70 (d, J=7.6 Hz, 3H), 1.51 (s, 9H).

Example A62 Synthesis Route

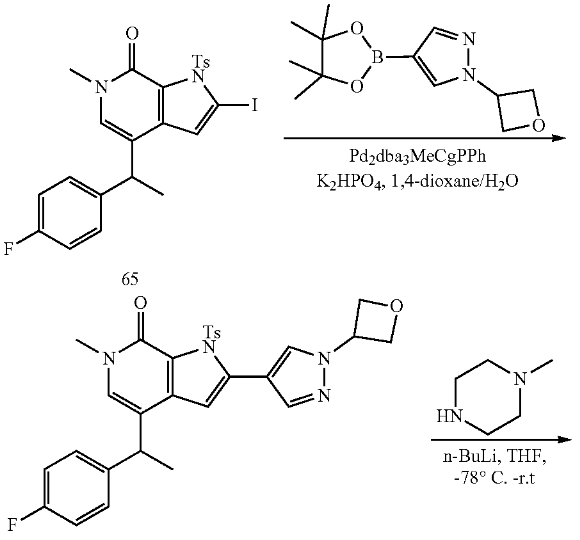

65

177

-continued

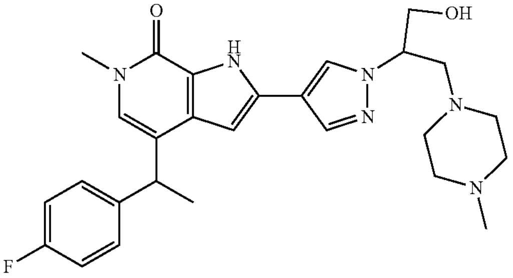

A62

Step 1: 4-(1-(4-fluorophenyl)ethyl)-6-methyl-2-(1-(oxetan-3-yl)-1H-pyrazol-4-yl)-1-tolyl-1,6-dihydro-7H-pyrrolo[2,3-c]pyridin-7-one (Intermediate 177)

Intermediate 65 (200 mg, 0.36 mmol), 1-(oxetan-3-yl)-4-(4,4,5,5-tetramethyl-1,3,2-dioxaborolan-2-yl)-1H-pyrazole (109 mg, 0.44 mmol), dipotassium phosphate (124 mg, 0.55 mmol), tridibenzylideneacetone dipalladium (50 mg) and 1,3,5,7-tetramethyl-6-phenyl-2,4,8-trioxa-6-phosphaadamantane (60 mg) were successively added to a 50 mL three-necked flask containing 12 mL of 1,4-dioxane and 3 mL of water and reacted at 50° C. under nitrogen protection for three hours. After the completion of the reaction monitored by TLC, the reaction solution was diluted with water, extracted twice with ethyl acetate, and the organic phase was collected, washed with saturated brine, dried over anhydrous sodium sulfate, and filtered. The filtrate was concentrated under reduced pressure and subjected to preparative chromatography to obtain intermediate 177 (130 mg, white solid), yield: 65.3%.

LCMS: m/z 546.9 (M+H).

Step 2: 4-(1-(4-fluorophenyl)ethyl)-2-(1-(1-hydroxy-3-(4-methylpiperazin-1-yl)propan-2-yl)-1H-pyrazol-4-yl)-6-methyl-1,6-dihydro-7H-pyrrolo[2,3-c]pyridin-7-one (A62)

N-methylpiperazine (6 mg, 0.06 mmol), tetrahydrofuran (5 mL) and n-butyllithium (0.1 mL, 0.08 mmol) were successively added to a dry 25 mL three-necked flask at −78° C. and stirred at −78° C. for 0.5 h. Then a solution of intermediate 177 (20 mg, 0.04 mmol) in tetrahydrofuran was slowly added and the mixture was warmed to room temperature and stirred for another 1 hour. After the completion of the reaction monitored by LC-MS, methanol was added to quench the reaction. The solution was concentrated to dryness and dimethyl sulfoxide was added. The mixture was filtered and subjected to prep-HPLC (basic) to obtain Example A62 (4 mg, white solid), yield: 22.2%.

LCMS: m/z 493.1 (M+H).

$^1$H-NMR (MeOD, 400 MHz): 8.07 (s, 1H), 7.85 (s, 1H), 7.33-7.30 (m, 2H), 7.03-6.97 (m, 3H), 6.25 (s, 1H), 4.49-4.46 (m, 1H), 4.28-4.23 (m, 1H), 3.86 (d, J=6.0 Hz, 2H), 3.65 (s, 3H), 2.92-2.79 (m, 2H), 2.57-2.38 (m, 8H), 2.23 (s, 3H), 1.65 (d, J=7.2 Hz, 3H).

Example A63 Synthesis Route

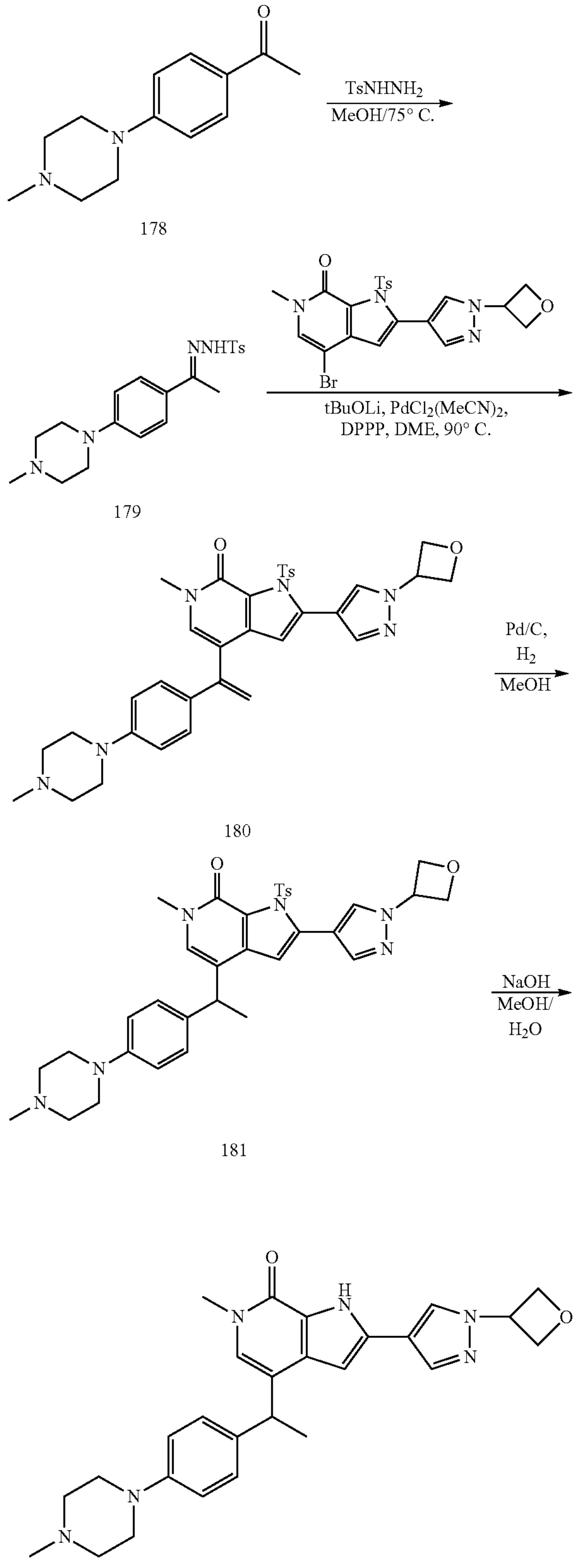

178

179

180

181

A63

Step 1: (Z)-4-methyl-N'-(1-(4-(4-methylpiperazin-1-yl)phenyl)ethylidene)benzenesulfonylhydrazide (179)

Intermediate 178 (2.0 g, 9.2 mmol) and p-toluenesulfonyl hydrazide (5.2 g, 27.5 mmol) were successively added to a 100 mL single-necked flask containing 40 mL of methanol at room temperature and reacted at 75° C. for two hours. After the completion of the reaction monitored by TLC, the reaction solution was concentrated to dryness, and the sample was mixed and passed through the column. The crude product was purified by column chromatography (dichloromethane:methanol=40:1) to obtain intermediate 179 (2.7 g, white solid), yield: 75.8%.

LCMS: m/z 387.5 (M+H).

Step 2: 6-methyl-4-(1-(4-(4-methylpiperazin-1-yl)phenyl)vinyl)-2-(1-(oxetan-3-yl)-1H-pyrazol-4-yl)-1-tolyl-1,6-dihydro-7H-pyrrolo[2,3-c]pyridin-7-one (Intermediate 180)

Intermediate 179 (46 mg, 0.12 mmol), 4-bromo-6-methyl-2-(1-(oxetan-3-yl)-1H-pyrazol-4-yl)-1-tolyl-1,6-dihydro-7H-pyrrolo[2,3-c]pyridin-7-one (50 mg, 0.100 mmol), lithium tert-butoxide (24 mg, 0.30 mmol) 1,3-bis(diphenylphosphino)propane and bis(acetonitrile)palladium(II) chloride (10 mg) were successively added to a 50 mL three-necked flask containing 15 mL of ethylene glycol dimethyl ether at room temperature and reacted at 90° C. for 4 hours. After the completion of the reaction monitored by TLC, the mixture was extracted twice with ethyl acetate. The organic phase was collected, washed with saturated brine, dried over anhydrous sodium sulfate, filtered, and the filtrate was concentrated under reduced pressure. The crude product was purified by column chromatography (dichloromethane:methanol=20:1) to give intermediate 180 (30 mg, white solid), yield: 48.3%.

LCMS: m/z 625.7 (M+H).

Step 3: 6-methyl-4-(1-(4-(4-methylpiperazin-1-yl)phenyl)ethyl)-2-(1-(oxetan-3-yl)-1H-pyrazol-4-yl)-1-tolyl-1,6-dihydro-7H-pyrrolo[2,3-c]pyridin-7-one (Intermediate 181)

Intermediate 180 (30 mg, 0.05 mmol) and Pd/C (3 mg, wt 10%) were successively added to a 50 mL single-necked flask containing 10 mL of methanol at room temperature and the reaction was carried out at room temperature overnight under a hydrogen atmosphere. After the completion of the reaction monitored by TLC, the system was filtered, and the filtrate was concentrated to obtain intermediate 181 (30 mg, white solid), yield: 99.7%.

LCMS: m/z 627.7 (M+H).

Step 4: 6-methyl-4-(1-(4-(4-methylpiperazin-1-yl)phenyl)ethyl)-2-(1-(oxetan-3-yl)-1H-pyrazol-4-yl)-1,6-dihydro-7H-pyrrolo[2,3-c]pyridin-7-one (A63)

Intermediate 181 (30 mg, 0.05 mmol) and sodium hydroxide (6 mg, 0.15 mmol) were successively added to a dry 25 mL single-necked flask containing 8 mL of methanol at room temperature and reacted at 60° C. for two hours. After the completion of the reaction monitored by TLC, the reaction solution was concentrated to dryness, dissolved in dimethyl sulfoxide, filtered, and subjected to prep-HPLC (basic) to obtain Example A63 (6 mg, white solid), yield: 26.5%.

LCMS: m/z 473.1 (M+H).

$^1$H-NMR (DMSO, 400 MHz): 12.04 (s, 1H), 8.37 (s, 1H), 8.07 (s, 1H), 7.14 (d, J=8.4 Hz, 2H), 7.04 (s, 1H), 6.81 (d, J=8.4 Hz, 2H), 6.33 (s, 1H), 5.56-5.51 (m, 1H), 4.93-4.83 (m, 4H), 4.06-4.01 (m, 1H), 3.51 (s, 3H), 3.04-3.02 (m, 4H), 2.41-2.38 (s, 4H), 2.18 (s, 3H), 1.53 (d, J=7.2 Hz, 3H).

Example A64 Synthesis Route

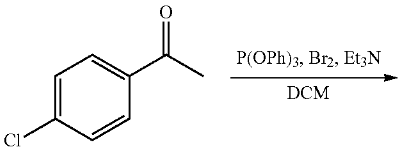

182

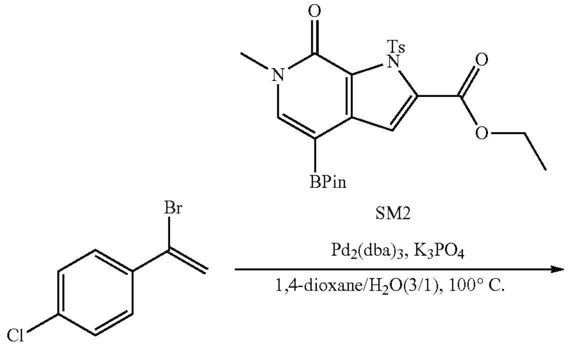

SM2

183

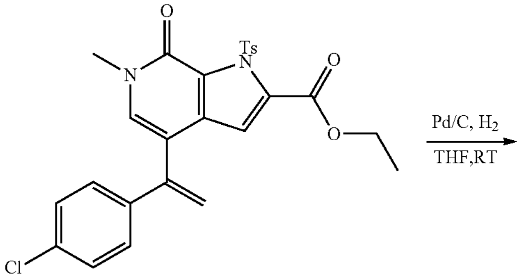

184

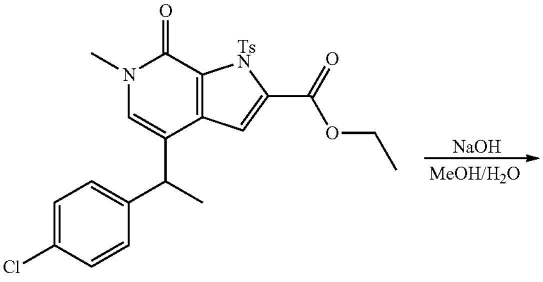

185

-continued

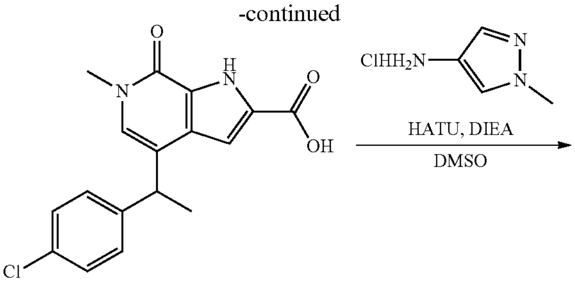

186

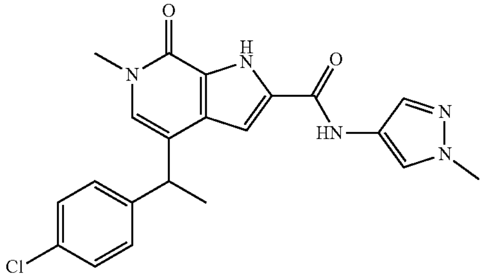

A64

Step 1: Synthesis of 1-(1-bromovinyl)-4-chlorobenzene (Intermediate 183)

Triphenyl phosphite (18.30 g, 58.90 mmol) and dichloromethane (30 mL) were successively added to a dry 250 mL three-necked flask at room temperature and replaced by nitrogen 3 times. The system was cooled to −70° C., and liquid bromine (11.00 g, 68.00 mmol) was slowly added dropwise. The mixture was stirred at −70° C. and reacted for 30 minutes. Triethylamine (9.20 g, 90.60 mmol) and a solution of intermediate 182 (7.00 g, 45.30 mmol) in dichloromethane (30 mL) were successively added. The mixture was stirred at room temperature, reacted for 16 hours, then heated to 50° C. and reacted for another 2 hours. After the completion of the reaction monitored by TLC, the reaction mixture was poured into 100 mL of water, adjusted to pH 8 with 2 mol/L aqueous sodium hydroxide solution, and extracted with dichloromethane (100 mL×2). The organic phase was collected, dried over anhydrous sodium sulfate, filtered, and the filtrate was concentrated under reduced pressure. The residue was purified by silica gel column (pure petroleum ether) to give 1-(1-bromovinyl)-4-chlorobenzene (intermediate 183) (3.00 g, yellow oil), yield: 61.15%.

$^1$H-NMR ($CDCl_3$, 400 MHz): 7.54-7.50 (m, 2H), 7.36-7.25 (m, 2H), 6.10 (d, J=2.0 Hz, 1H), 5.78 (d, J=2.0 Hz, 1H).

Step 2: Synthesis of ethyl 4-(1-(4-chlorophenyl)vinyl)-6-methyl-7-oxo-1-tolyl-6,7-dihydro-1H-pyrrolo[2,3-c]pyridin-2-carboxylate (Intermediate 184)

Intermediate SM2 (1000 mg, 2.00 mmol), intermediate 183 (650 mg, 3.00 mmol), 1,4-dioxane (9 mL), water (3 mL), tris(dibenzylideneacetone)dipalladium (92 mg, 0.10 mmol) and potassium phosphate (1100 mg, 5.00 mmol) were successively added to a dry 25 mL single-necked flask at room temperature, replaced by nitrogen 3 times, heated to 70° C., and reacted for 16 hours. After the completion of the reaction monitored by LCMS, the reaction mixture was concentrated under reduced pressure, and the residue was purified by silica gel column (petroleum ether:ethyl acetate=1:1) to obtain ethyl 4-(1-(4-chlorophenyl)vinyl)-6-methyl-7-oxo-1-tolyl-6,7-dihydro-1H-pyrrolo[2,3-c]pyridin-2-carboxylate (184) (525 mg, yellow solid, purity: 50%), yield: 30.47%.

LCMS: m/z 511.1 (M+H).

Step 3: Synthesis of ethyl 4-(1-(4-chlorophenyl)ethyl)-6-methyl-7-oxo-1-tolyl-6,7-dihydro-1H-pyrrolo[2,3-c]pyridin-2-carboxylate (Intermediate 185)

Compound 3 (525 mg, 0.54 mmol, purity: 50%), tetrahydrofuran (10 mL) and palladium-carbon catalyst (50 mg) were successively added to a dry 50 mL single-necked flask at room temperature, replaced by nitrogen 3 times, stirred at room temperature and reacted for 16 hours. After the completion of the reaction monitored by TLC, the reaction mixture was filtered, and the filtrate was concentrated under reduced pressure to obtain ethyl 4-(1-(4-chlorophenyl)ethyl)-6-methyl-7-oxo-1-tolyl-6,7-dihydro-1H-pyrrolo[2,3-c]pyridin-2-carboxylate 185 (550 mg, yellow solid, purity: 50%), yield: 99.61%.

LCMS: m/z 513.1 (M+H).

Step 4: Synthesis of 4-(1-(4-chlorophenyl)ethyl)-6-methyl-7-oxo-6,7-dihydro-1H-pyrrolo[2,3-c]pyridin-2-carboxylic acid (Intermediate 186)

Intermediate 185 (550 mg, 0.64 mmol; purity: 50%), methanol (6 mL), water (2 mL) and sodium hydroxide (64 mg, 1.61 mmol) were successively added to a dry 25 mL single-necked flask at room temperature, heated to 60° C. and reacted for 3 hours. After the completion of the reaction monitored by TLC, the reaction mixture was concentrated under reduced pressure. The residue was adjusted to pH=6 with 1 mol/L aqueous hydrochloric acid solution and a white solid was precipitated. The mixture was filtered and the solid was collected to obtain 4-(1-(4-chlorophenyl)ethyl)-6-methyl-7-oxo-6,7-dihydro-1H-pyrrolo[2,3-c]pyridin-2-carboxylic acid 186 (80 mg, white solid), yield: 45.12%.

LCMS: m/z 331.1 (M+H).

Step 5: Synthesis of 4-(1-(4-chlorophenyl)ethyl)-6-methyl-N-(1-methyl-1H-pyrazol-4-yl)-7-oxo-6,7-dihydro-1H-pyrrolo[2,3-c]pyridin-2-carboxamide (A64)

Intermediate 186 (80 mg, 0.24 mmol), dimethyl sulfoxide (3 mL), 2-(7-azobenzotriazole)-N, N,N',N'-tetramethylurea hexafluorophosphate (138 mg, 0.36 mmol) and N,N-diisopropylethylamine (0.24 mL, 1.45 mmol) were successively added to a dry 25 mL single-necked flask at room temperature and stirred at room temperature for 30 minutes. 1-methyl-1H-pyrazol-4-amine hydrochloride (65 mg, 0.48 mmol) was added. The mixture was stirred at room temperature and reacted for 20 hours. The reaction solution was purified by reversed-phase column of high performance liquid chromatography to obtain 4-(1-(4-chlorophenyl)ethyl)-6-methyl-N-(1-methyl-1H-pyrazol-4-yl)-7-oxo-6,7-dihydro-1H-pyrrolo[2,3-c]pyridin-2-carboxamide A64 (42 mg, near-white solid), yield: 42.37%.

LCMS: m/z 451.1 (M+H+MeCN).

$^1$H-NMR (DMSO, 400 MHz): 12.22 (s, 1H), 10.28 (s, 1H), 7.97 (s, 1H), 7.51 (s, 1H), 7.34 (s, 4H), 7.21 (s, 1H), 6.79 (s, 1H), 4.24-4.19 (m, 1H), 3.82 (s, 3H), 3.56 (s, 3H), 1.56 (d, J=8.0 Hz, 3H).

Example A65 Synthesis Route

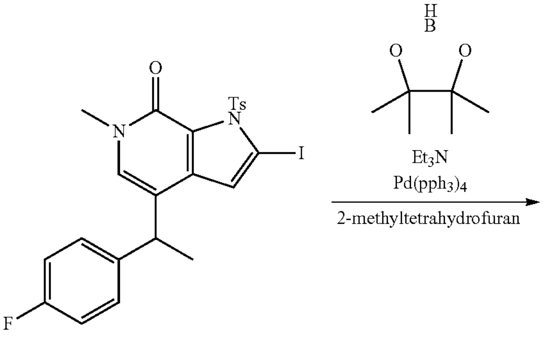

65

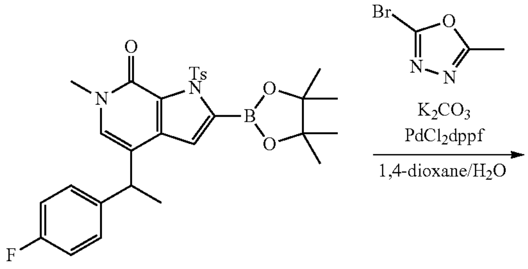

187

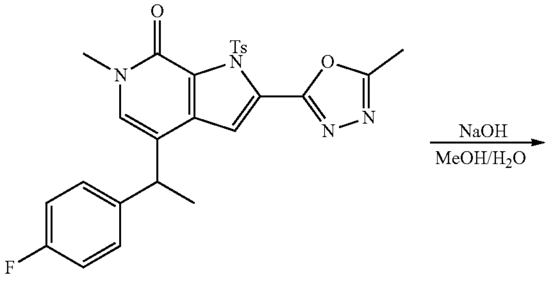

188

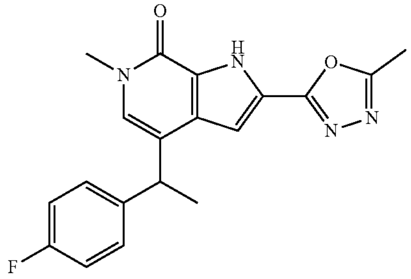

A65

Step 1: 4-(1-(4-fluorophenyl)vinyl)-6-methyl-1-tolyl-1,6-dihydro-7H-pyrrolo[2,3-c]pyridin-7-one (Intermediate 187)

Compound 5 (300 mg, 0.55 mmol), bis(pinacolato)diboron (104 mg, 0.82 mmol), triethylamine (137 mg, 1.36 mmol) and tetrakis-(triphenylphosphine)palladium (50 mg) were successively added to a 50 mL three-necked flask containing 10 mL of 2-methyltetrahydrofuran at room temperature. The reaction was carried out at 85° C. for 5 hours under nitrogen protection. After the completion of the reaction monitored by LC-MS, the mixture was extracted twice with ethyl acetate. The organic phase was collected, washed with saturated brine, dried over anhydrous sodium sulfate, filtered, and the filtrate was concentrated under reduced pressure. The crude product was purified by column chromatography (petroleum ether:ethyl acetate=2:1) to give a crude product 187 (400 mg, yellow oil) as a crude mixture.

LCMS: m/z 551.0 (M+H).

Step 2: 4-(1-(4-fluorophenyl)ethyl)-6-methyl-2-(5-methyl-1,3,4-oxadiazol-2-yl)-1-tolyl-1,6-dihydro-7H-pyrrolo[2,3-c]pyridin-7-one (Intermediate 188)

Intermediate 187 (200 mg, 0.36 mmol), 2-bromo-5-methyl-1,3,4-oxadiazole (77 mg, 0.47 mmol), potassium carbonate (151 mg, 1.1 mmol), 1,1'-bisdiphenylphosphino-ferrocene palladium dichloride (catalytic amount) were successively added to a 50 mL three-necked flask containing 10 mL of 1,4 dioxane and 3 mL of water at room temperature and reacted at 110° C. under nitrogen protection for 5 hours. After the completion of the reaction monitored by TLC, the reaction solution was diluted with water, extracted twice with ethyl acetate, and the organic phase was collected, washed with saturated brine, dried over anhydrous sodium sulfate, and filtered. The filtrate was concentrated under reduced pressure and subjected to preparative chromatography to obtain intermediate 188 (25 mg, white solid), yield: 13.6%.

LCMS: m/z 507.1 (M+H).

Step 3: 4-(1-(4-fluorophenyl)ethyl)-6-methyl-2-(5-methyl-1,3,4-oxadiazol-2-yl)-1,6-dihydro-7H-pyrrolo[2,3-c]pyridin-7-one (A65)

Intermediate 188 (25 mg, 0.05 mmol) and sodium hydroxide (6 mg, 0.15 mmol) were successively added to a dry 25 mL single-necked flask containing 8 mL of methanol at room temperature and reacted at 60° C. for two hours. After the completion of the reaction monitored by TLC, the reaction solution was added with water and a white solid was precipitated, filtered, and subjected to prep-TLC (dichloromethane/methanol=20/1) to obtain Example A65 (10 mg, colorless transparent oil), yield: 57.8%.

LCMS: m/z 353.1 (M+H).

$^1$H-NMR (MeOD, 400 MHz): 7.33-7.30 (m, 2H), 7.15 (s, 1H), 7.92-6.98 (m, 2H), 6.77 (s, 1H), 4.30-4.25 (m, 1H), 3.67 (s, 3H), 2.59 (s, 3H), 1.65 (d, J=7.2 Hz, 3H).

Example A66 Synthesis Route

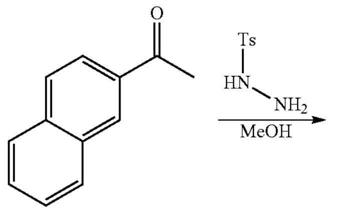

189

-continued

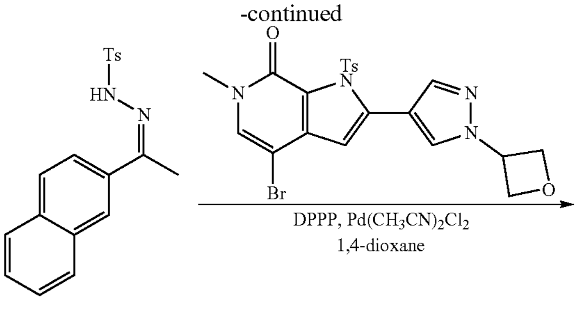

190

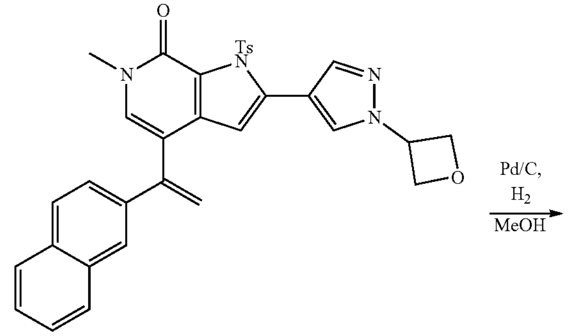

191

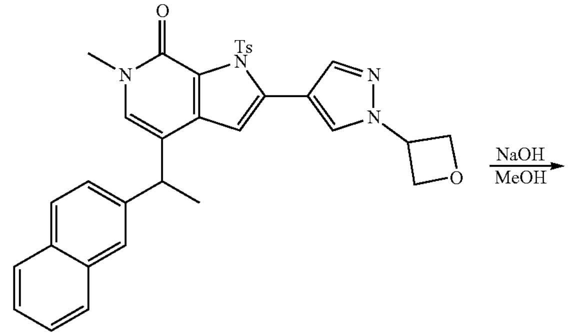

192

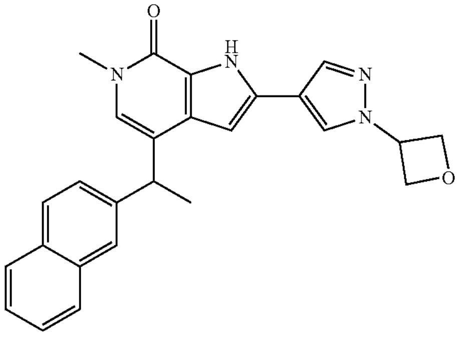

A66

Step 1: (Z)-4-methyl-N'-(1-(naphthalen-2-yl)ethylidene)benzenesulfonylhydrazide (Intermediate 190)

Intermediate 189 (200 mg, 1.18 mmol) and p-toluenesulfonyl hydrazide (284 mg, 1.53 mmol) were successively added to a 50 mL single-necked flask containing 10 mL of methanol at room temperature and reacted at room temperature for two hours. After the completion of the reaction monitored by TLC, the reaction solution was concentrated to dryness, and the sample was mixed and passed through the column. The crude product was purified by column chromatography (petroleum ether:ethyl acetate=2:1) to obtain intermediate 190 (350 mg, white solid), yield: 88%.

LCMS: m/z 339.2 (M+H).

Step 2: 6-methyl-4-(1-(naphthalen-2-yl)vinyl)-2-(1-(oxetan-3-yl)-1H-pyrazol-4-yl)-1-tolyl-1,6-dihydro-7H-pyrrolo[2,3-c]pyridin-7-one (Intermediate 191)

Intermediate 190 (52 mg, 0.15 mmol), 4-bromo-6-methyl-2-(1-(oxetan-3-yl)-1H-pyrazol-4-yl)-1-tolyl-1,6-dihydro-7H-pyrrolo[2,3-c]pyridin-7-one (50 mg, 0.12 mmol), cesium carbonate (96 mg, 0.29 mmol), 1,3-bis(diphenylphosphino)propane and bis(acetonitrile)palladium(II) chloride (catalytic amount) were successively added to a 50 mL three-necked flask containing 10 mL of 1,4 dioxane at room temperature and reacted at 90° C. overnight. After the completion of the reaction monitored by TLC, the reaction mixture was extracted twice with ethyl acetate. The organic phase was collected, washed with saturated brine, dried over anhydrous sodium sulfate, filtered, and the filtrate was concentrated under reduced pressure. The crude product was purified by column chromatography (dichloromethane methanol=20:1) to obtain intermediate 191 (45 mg, white solid), yield: 64%.

LCMS: m/z 577.1 (M+H).

Step 3: 6-methyl-4-(1-(naphthalen-2-yl)ethyl)-2-(1-(oxetan-3-yl)-1H-pyrazol-4-yl)-1-tolyl-1,6-dihydro-7H-pyrrolo[2,3-c]pyridin-7-one (Intermediate 192)

Intermediate 191 (45 mg, 0.15 mmol) and Pd/C (10 mg, Wt 10%) were added successively to a 50 mL single-necked flask containing 10 mL of methanol at room temperature, and the reaction was carried out at room temperature overnight under a hydrogen atmosphere. After the completion of the reaction monitored by TLC, the system was filtered, and the filtrate was concentrated to obtain intermediate 192 (40 mg, white solid), yield: 89%.

LCMS: m/z 579.0 (M+H).

Step 4: 6-methyl-4-(1-(naphthalen-2-yl)ethyl)-2-(1-(oxetan-3-yl)-1H-pyrazol-4-yl)-1,6-dihydro-7H-pyrrolo[2,3-c]pyridin-7-one (A66)

Intermediate 192 (40 mg, 0.07 mmol) and sodium hydroxide (14 mg, 0.35 mmol) were successively added to a dry 50 mL single-necked flask containing 8 mL of methanol at room temperature and reacted at 60° C. for 2.5 hours. After the completion of the reaction monitored by TLC, the reaction solution was concentrated, dried and separated by basic preparative chromatography to obtain Example A66 (9 mg, white solid), yield: 31%.

LCMS: m/z 425.1 (M+H).

$^1$H-NMR (DMSO, 400 MHz): 8.33 (s, 1H), 8.06 (s, 1H), 7.87-7.80 (m, 4H), 7.50-7.43 (m, 3H), 7.17 (s, 1H), 6.36 (s, 1H), 5.53 (q, J=6.8 Hz, 1H), 4.92-4.82 (m, 4H), 4.34-4.32 (m, 1H), 3.55 (s, 3H), 1.68 (d, J=6.8 Hz, 3H).

Example A67 Synthesis Route

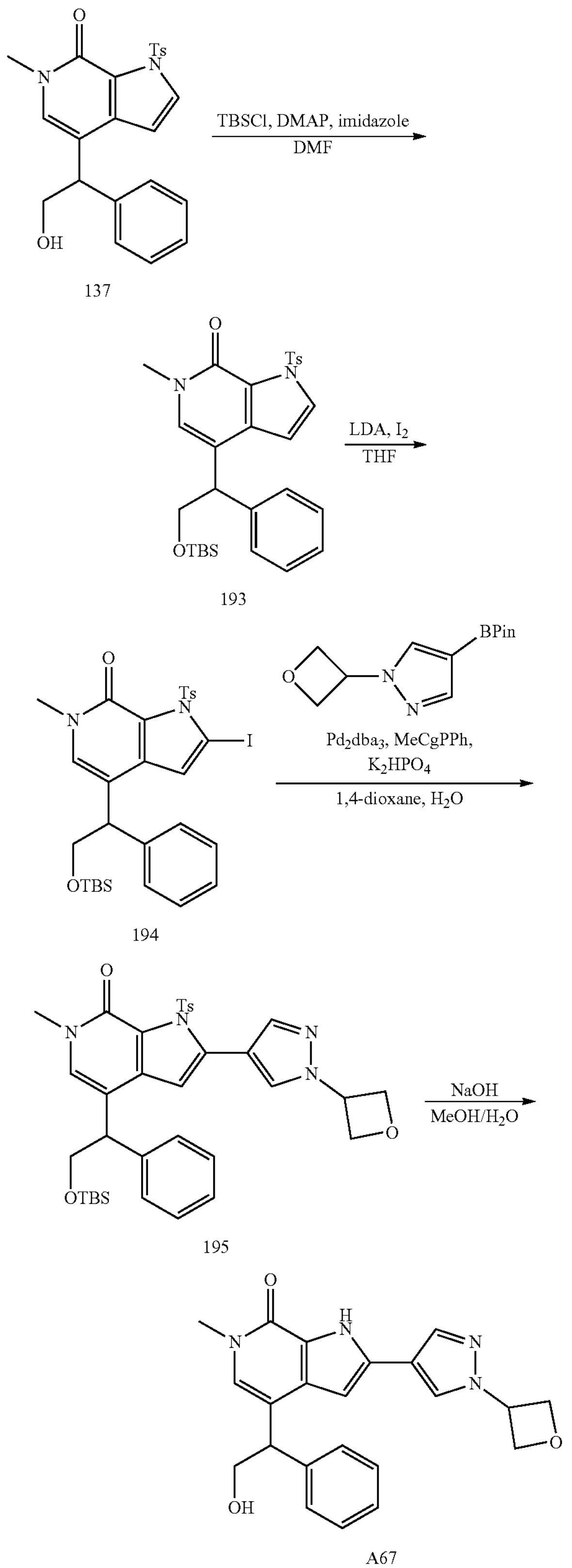

137

193

194

195

A67

Step 1: Synthesis of 4-(2-((tert-butyldimethylsilyl) oxy)-1-phenethyl)-6-methyl-1-tolyl-1,6-dihydro-7H-pyrrolo[2,3-c]pyridin-7-one (Intermediate 193)

Intermediate 137 (1.4 g, 3.32 mmol), imidazole (316 mg, 4.64 mmol), tert-butyl dimethylchlorosilane (750 mg, 4.98 mmol) and 4-dimethylaminopyridine (catalytic amount) were successively added to a 100 mL single-necked flask containing 20 mL of N,N-dimethylformamide at room temperature. The reaction was carried out overnight at room temperature. After the completion of the reaction monitored by TLC, the mixture was poured into 100 mL of water and extracted twice with ethyl acetate. The organic phase was collected, washed with saturated brine, dried over anhydrous sodium sulfate, filtered, and the filtrate was concentrated under reduced pressure. The crude product was purified by column chromatography (petroleum ether:ethyl acetate=2:1) to obtain intermediate 193 (960 mg, white solid), yield: 54.0%.

LCMS: m/z 537.1 (M+H).

Step 2: Synthesis of 4-(2-((tert-butyldimethylsilyl) oxy)-1-phenethyl)-2-iodo-6-methyl-1-tolyl-1,6-dihydro-7H-pyrrolo[2,3-c]pyridin-7-one (Intermediate 194)

Intermediate 193 (400 mg, 0.74 mmol) and lithium diisopropylamide (0.58 mL, 1.10 mmol) were successively added to a dry 100 mL three-necked flask containing 10 mL of tetrahydrofuran at −78° C. and stirred at −78° C. for 1 hour. A solution of N-iodosuccinimide (218 mg, 0.96 mmol) in tetrahydrofuran was slowly added dropwise and then stirred for another 1 hour at −78° C. After the completion of the reaction monitored by LC-MS, saturated ammonium chloride was added to quench the reaction. The reaction mixture was extracted twice with ethyl acetate, and the organic phase was collected, washed with saturated brine, dried over anhydrous sodium sulfate and filtered. The filtrate was concentrated under reduced pressure, and the crude product was purified by column chromatography (petroleum ether/ethyl acetate=3/1) to give intermediate 194 (310 mg, yellow oil), yield: 62.8%.

LCMS: m/z 663.0 (M+H).

Step 3: Synthesis of 4-(2-((tert-butyldimethylsilyl) oxy)-1-phenethyl)-6-methyl-2-(1-(oxetan-3-yl)-1H-pyrazol-4-yl)-1-tolyl-1,6-dihydro-7H-pyrrolo[2,3-c] pyridin-7-one (Intermediate 195)

Intermediate 194 (310 mg, 0.47 mmol), 1-(oxetan-3-yl))-4-(4,4,5,5-tetramethyl-1,3,2-dioxaborolan-2-yl)-1H-pyrazole (140 mg, 0.56 mmol), dipotassium phosphate (160 mg, 0.70 mmol), tris(dibenzylideneacetone)dipalladium (catalytic amount) and 1,3,5,7-tetramethyl-6-phenyl-2,4,8-trioxa-6-phosphaadamantane (catalytic amount) were successively added to a 100 mL three-necked flask containing 8 mL of 1,4-dioxane and 2 mL of water at room temperature and reacted at 50° C. for three hours. After the completion of the reaction monitored by TLC, the reaction solution was diluted with water, extracted twice with ethyl acetate, and the organic phase was collected, washed with saturated brine, dried over anhydrous sodium sulfate, and filtered The filtrate was concentrated under reduced pressure. The crude product was purified by column chromatography (petroleum ether/ethyl acetate=1/2) to obtain intermediate 195 (260 mg, yellow solid), yield: 84.4%.

LCMS: m/z 659.1 (M+H).

Step 4: 4-(2-hydroxy-1-phenethyl)-6-methyl-2-(1-(oxetan-3-yl)-1H-pyrazol-4-yl)-1,6-dihydro-7H-pyrrolo[2,3-c]pyridin-7-one (A67)

Intermediate 195 (50 mg, 0.08 mmol) and sodium hydroxide (46 mg, 1.20 mmol) were successively added to a dry 25 mL single-necked flask containing 1.5 mL of methanol and 0.5 mL of water at room temperature and reacted at 70° C. for 6 hours. After the completion of the reaction monitored by TLC, the reaction solution was purified by reversed phase column of high performance liquid chromatography to obtain Example A67 (16 mg, white solid), yield: 54.1%.

LCMS: m/z 391.2 (M+H).

$^1$H-NMR (DMSO, 400 MHz): 12.07 (s, 1H), 8.40 (s, 1H), 8.11 (s, 1H), 7.38-7.14 (m, 6H), 6.43 (s, 1H), 5.60-5.53 (m, 1H), 4.96-4.81 (m, 4H), 4.12-3.92 (m, 3H), 3.53 (s, 3H).

Example A68 Synthesis Route

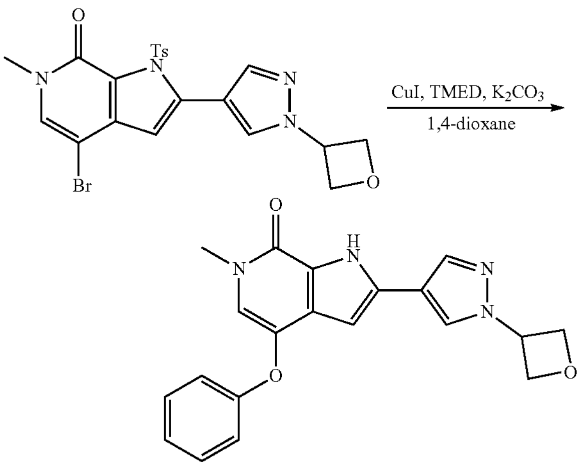

A68

Step 1: Synthesis of 6-methyl-2-(1-(oxetan-3-yl)-1H-pyrazol-4-yl)-4-phenoxy-1,6-dihydro-7H-pyrrolo [2,3-c]pyridin-7-one (A68)

Compound 2 (80 mg, 0.16 mmol), phenol (75 mg, 0.8 mmol), cuprous iodide (15 mg, 0.08 mmol), tetramethylethylenediamine (19 mg, 0.16 mmol) and cesium carbonate (261 mg, 0.8 mmol) were successively added to a 30 mL microwave tube containing dioxane (10 mL) and subjected to microwave reaction under nitrogen protection for 2.5 hours. After the completion of the reaction monitored by LCMS, the reaction mixture was filtered and the filtrate was concentrated and purified by prep-HPLC to give Example A68 (2 mg, white solid), yield: 3.5%.

LCMS: m/z 363.1 (M+H). $^1$H-NMR (MeOD, 400 MHz): 8.16 (s, 1H), 7.96 (s, 1H), 7.30 (t, J=8.0 Hz, 2H), 7.09 (s, 1H), 7.06-6.98 (m, 3H), 6.21 (s, 1H), 5.58-5.55 (m, 1H), 5.06-5.01 (m, 4H), 3.63 (s, 31H).

Example A69 Synthesis Route

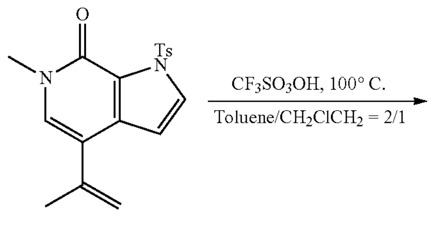

196

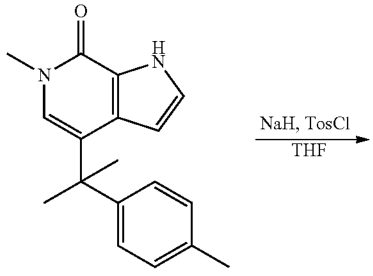

197

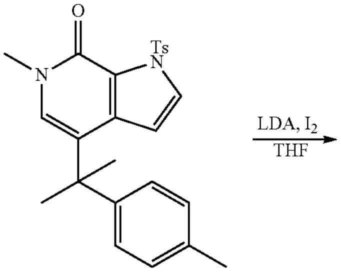

198

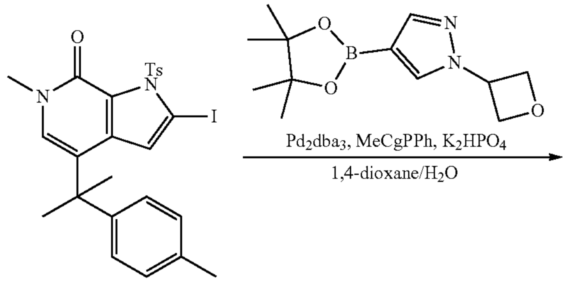

199

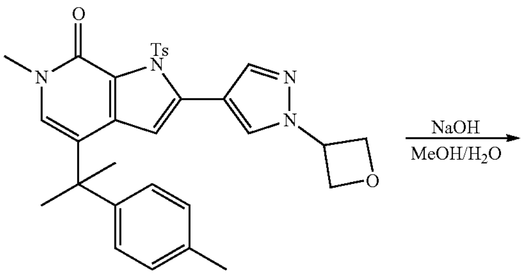

200

-continued

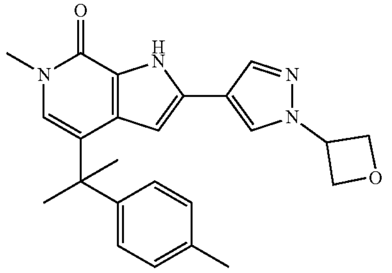

A69

Step 1: Synthesis of 6-methyl-4-(2-(p-tolyl)propan-2-yl)-1,6-dihydro-7H-pyrrolo[2,3-c]pyridin-7-one (Intermediate 197)

The compound 6-methyl-4-(prop-1-en-2-yl)-1-tosyl-1,6-dihydro-7H-pyrrolo[2,3-c]pyridin-7-one (380 mg, 1.11 mmol) and trifluoromethanesulfonic acid (921 mg, 5.55 mmol) were successively added to a 50 mL round-bottomed flask containing 4 mL of toluene and 2 mL of 1,2-dichloroethane, heated to 100° C. under nitrogen protection and reacted overnight. After the completion of the reaction monitored by LCMS, the reaction solution was quenched with an aqueous solution, extracted with ethyl acetate, and the organic phase was washed with saturated brine, dried over anhydrous sodium sulfate, filtered, concentrated, and purified by column chromatography (dichloromethane/methanol=15/1) to give intermediate 197 (300 mg, yield: 96.4%) as a white solid.

LCMS: m/z 281.2 (M+H).

$^1$H-NMR (CD3OD, 400 Hz): 7.17-7.14 (m, 3H), 7.05-7.03 (m, 3H), 5.65 (d, J=2.8 Hz, 1H), 3.69 (s, 3H), 2.27 (s, 3H), 1.67 (s, 6H).

Step 2: Synthesis of 6-methyl-4-(2-(p-tolyl)propan-2-yl)-1-tosyl-1,6-dihydro-7H-pyrrolo[2,3-c]pyridin-7-one (Intermediate 198)

Sodium hydride (128 mg, 3.21 mmol, 60% wt) was added to a solution of 6-methyl-4-(2-(p-tolyl)propan-2-yl)-1,6-dihydro-7H-pyrrolo[2,3-c]pyridin-7-one (300 mg, 1.07 mmol) in tetrahydrofuran (10 mL) under nitrogen at 0° C. and then reacted for 1 hour at 0° C. Then p-toluenesulfonyl chloride (306 mg, 1.61 mmol) was added and reacted at 0° C. for 3 hours. After the completion of the reaction monitored by LCMS, the reaction solution was quenched with an aqueous solution, extracted with ethyl acetate, and the organic phase was washed with saturated brine, dried over anhydrous sodium sulfate, filtered, concentrated and purified by column chromatography (petroleum ether/ethyl acetate=2/1) to give intermediate 198 (220 mg, yield: 47.3%) as a white solid.

LCMS: m/z 435.3 (M+H).

Step 3: Synthesis of 2-iodo-6-methyl-4-(2-(p-tolyl)propan-2-yl)-1-tosyl-1,6-dihydro-7H-pyrrolo[2,3-c]pyridin-7-one (Intermediate 199)

6-methyl-4-(2-(p-tolyl)propan-2-yl)-1-tosyl-1,6-dihydro-7H-pyrrolo[2,3-c]pyridin-7-one (220 mg, 0.51 mmol) was added to a 50 mL three-necked flask containing 10 mL of THF at room temperature, the reaction system was cooled to −78° C., and lithium diisopropylamide (2 mol/L, 0.38 mL, 0.76 mmol) was added dropwise under nitrogen protection and then reacted for half an hour at −78° C. A solution of iodine (193 mg, 0.76 mmol) in tetrahydrofuran (2 mL) was added dropwise to the above reaction system under the protection of nitrogen at −78° C. and then reacted at −78° C. for 1 hour. After the completion of the reaction monitored by LC/MS, the reaction solution was quenched with saturated aqueous ammonium chloride solution, extracted with ethyl acetate, and the organic phase was washed with saturated aqueous sodium sulfite solution and saturated brine, dried over anhydrous sodium sulfate, filtered and concentrated to obtain intermediate 199 (250 mg, yield: 88%) as a white solid.

LCMS: m/z 561.1 (M+H).

Step 4: Synthesis of 6-methyl-2-(1-(oxetan-3-yl)-1H-pyrazol-4-yl)-4-(2-(p-tolyl)propan-2-yl)-1-tolyl-1,6-dihydro-7H-pyrrolo[2,3-c]pyridin-7-one (Intermediate 200)

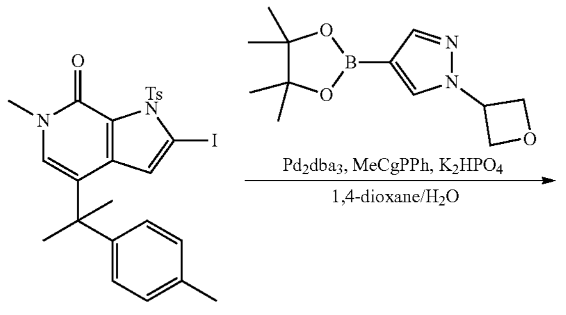

199

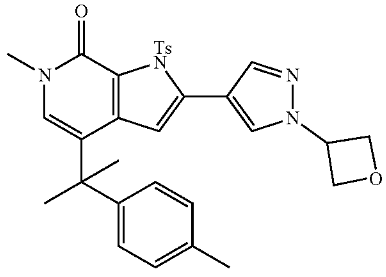

200

2-iodo-6-methyl-4-(2-(p-tolyl)propan-2-yl)-1-tosyl-1,6-dihydro-7H-pyrrolo[2,3-c]pyridin-7-one (100 mg, 0.18 mmol), 1-(oxetan-3-yl)-4-(4,4,5,5-tetramethyl-1,3,2-dioxaborolan-2-yl)-1H-pyrazole (54 mg, 0.22 mmol), tris(dibenzylideneacetone)dipalladium (18 mg, 0.02 mmol), dipotassium hydrogen phosphate trihydrate (93 mg, 0.54 mmol) and 1,3,5,7-tetramethyl-6-phenyl-2,4,8-trioxa-6-phosphaadamantane (12 mg, 0.04 mmol) were successively added to a 25 mL three-necked flask containing 5 mL of 1,4-dioxane and 1 mL of water at room temperature, replaced by nitrogen three times and reacted at 60° C. for 3 hours. After the completion of the reaction monitored by LCMS, the reaction solution was filtered, concentrated, and purified by preparative plate (petroleum ether/ethyl acetate=1/2) to obtain intermediate 200 (68 mg, yield: 68.5%) as a white solid.

LCMS: m/z 557.3 (M+H).

Step 5: Synthesis of 6-methyl-2-(1-(oxetan-3-yl)-1H-pyrazol-4-yl)-4-(2-(p-tolyl)propan-2-yl)-1,6-dihydro-7H-pyrrolo[2,3-c]pyridin-7-one (A69)

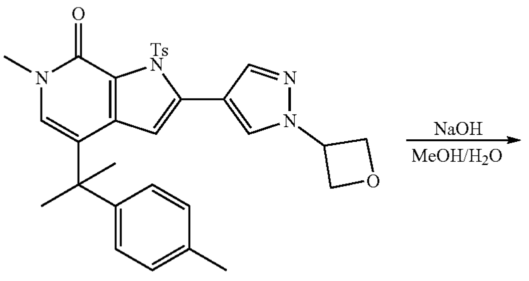

200

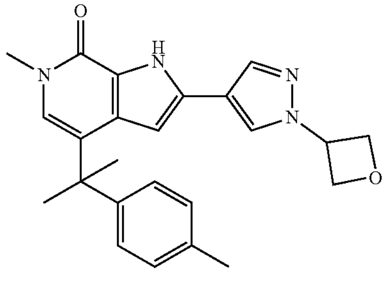

A69

6-methyl-2-(1-(oxetan-3-yl)-1H-pyrazol-4-yl)-4-(2-(p-tolyl)propan-2-yl)-1-tolyl-1,6-dihydro-7H-pyrrolo[2,3-c]pyridin-7-one (68 mg, 0.12 mmol) and sodium hydroxide (24 mg, 0.6 mmol) were successively added to a 25 mL single-necked flask containing 6 mL of methanol and 2 mL of water at room temperature, heated to 70° C. and reacted for 2 hours. After the completion of the reaction monitored by LCMS, the reaction solution was diluted with water, filtered, and the filter cake was collected and dried to obtain compound HHX-M136-1 (20 mg, yield: 40.7%) as a white solid.

LCMS: m/z 403.2 (M+H).

$^1$H-NMR (DMSO, 400 Hz): 12.01 (s, 1H), 8.27 (s, 1H), 7.99 (s, 1H), 7.20-7.05 (m, 5H), 5.79 (s, 11H), 5.54 (m, 1H), 4.93-4.83 (m, 4H), 3.59 (s, 3H), 2.24 (s, 3H), 1.64 (s, 6H).

Example A70 Synthesis Route

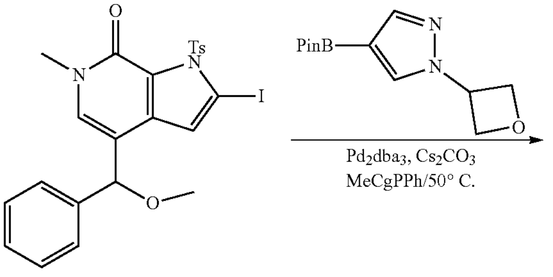

139

-continued

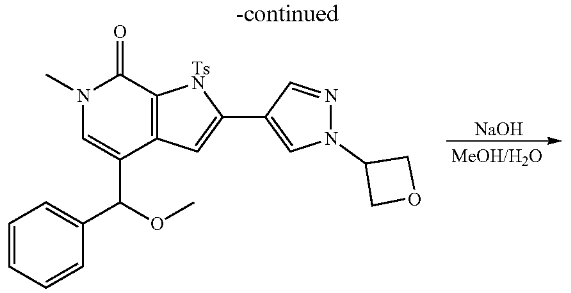

201

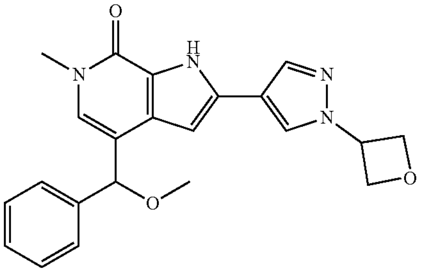

A70

Step 1: Synthesis of 4-(methoxy(phenyl)methyl)-6-methyl-2-(1-(oxetan-3-yl)-1H-pyrazol-4-yl)-1-tolyl-1,6-dihydro-7H-pyrrolo[2,3-c]pyridin-7-one (Intermediate 201)

2-iodo-4-(methoxy(phenyl)methyl)-6-methyl-1-p-tosyl-1,6-dihydro-7H-pyrrolo[2,3-c]pyridin-7-one (135 mg, 0.246 mmol), 1-(oxetan-3-yl)-4-(4,4,5,5-tetramethyl-1,3,2-dioxaborolan-2-yl)-1H-pyrazole (68 mg, 0.271 mmol), tris(dibenzylideneacetone)dipalladium (23 mg, 0.025 mmol), dipotassium hydrogen phosphate trihydrate (10 mg, 0.492 mmol) and 1,3,5,7-tetrakis(4-benzaldehyde)adamantane (7 mg, 0.025 mmol) were successively added to a 25 mL three-necked flask containing 10 mL of 1,4-dioxane and 2 mL of water at room temperature, replaced by nitrogen three times, and the reaction was carried out at 50° C. for two hours. After completion of the reaction monitored by TLC, the reaction solution was filtered, concentrated, and separated by Prep-TLC (petroleum ether/ethyl acetate=1/1) to obtain compound 8 (90 mg, yield: 67%) as a white solid.

LCMS: m/z 545.2 (M+H).

Step 2: Synthesis of 4-(methoxy(phenyl)methyl)-6-methyl-2-(1-(oxetan-3-yl)-1H-pyrazol-4-yl)-1-tolyl-1,6-dihydro-7H-pyrrolo[2,3-c]pyridin-7-one (A70)

4-(methoxy(phenyl)methyl)-6-methyl-2-(1-(oxetan-3-yl)-1H-pyrazol-4-yl)-1-tolyl-1,6-dihydro-7H-pyrrolo[2,3-c] pyridin-7-one (90 mg, 0.165 mmol) and sodium hydroxide (33 mg, 0.825 mmol) were successively added to a 25 mL single-necked flask containing 5 mL of methanol and 2 mL of water at room temperature and reacted at 70° C. for two hours. After the completion of the reaction monitored by TLC, the reaction solution was concentrated and separated by Prep-TLC (dichloromethane/methanol=10/1) to obtain Example A70 (17 mg, yield: 64%) was a white solid.

LCMS: m/z 391.1 (M+H).

$^1$H-NMR (DMSO, 400 Hz): 8.41 (s, 1H), 8.11 (s, 1H), 7.47 (d, J=7.6 Hz, 2H), 7.34-7.30 (m, 2H), 7.25-7.23 (m, 2H), 6.43 (s, 1H), 5.58-5.55 (m, 1H), 5.30 (s, 1H), 4.95-4.91 (m, 2H), 4.89-4.85 (m, 2H), 3.52 (s, 3H), 3.31 (s, 3H).

Example A71 Synthesis Route

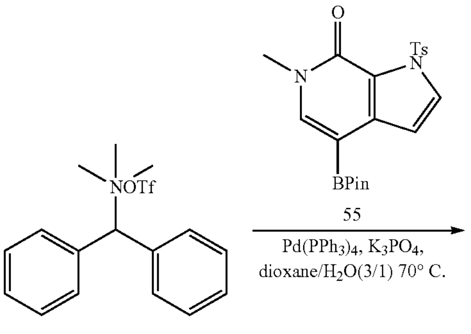

78

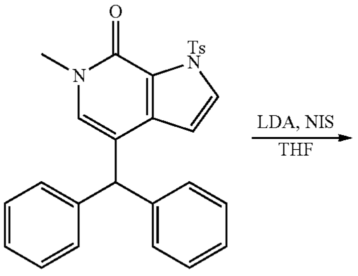

202

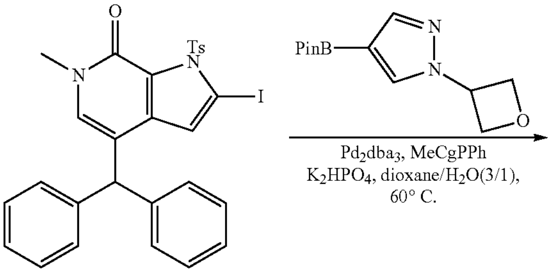

203

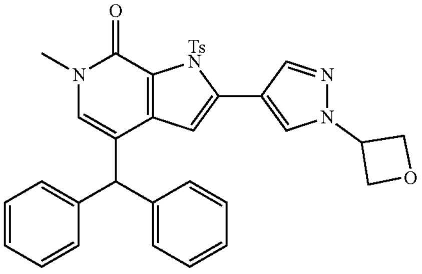

204

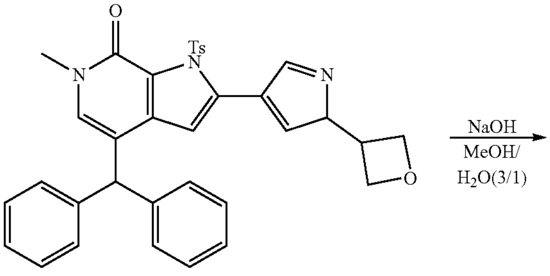

204

-continued

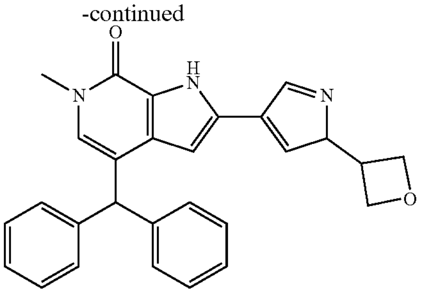

A71

Step 1: 4-diphenylmethyl-6-methyl-1-tosyl-1,6-dihydro-7H-pyrrolo[2,3-c]pyridin-7-one (Intermediate 202)

Intermediate 78 (500 mg, 1.33 mmol), 6-methyl-4-(4,4,5,5-tetramethyl-1,3,2-dioxaborolan-2-yl)-1-tosyl-1,6-dihydro-7H-pyrrolo[2,3-c]pyridin-7-one (855 mg, 1.99 mmol), potassium phosphate (561 mg, 2.66 mmol) and tetrakis-(triphenylphosphine)palladium (100 mg) were successively added to a 50 mL three-necked flask containing 10 mL of mixed solvent dioxane:water (3:1) at room temperature and reacted at 70° C. for three hours under nitrogen protection. After the completion of the reaction monitored by TLC, the reaction solution was diluted with water and extracted with ethyl acetate. The organic phase was washed with water and saturated sodium chloride solution successively, dried over anhydrous sodium sulfate, filtered and concentrated. The crude product was purified by column chromatography (petroleum ether:ethyl acetate=1: 1) to obtain intermediate 202 (600 g, white solid), yield: 96%.

$^1$H-NMR ($CDCl_3$,400 Hz): 8.02 (d, J=8.4 Hz, 2H), 7.74 (s, 1H), 7.31-7.24 (m, 8H), 7.13-7.10 (m, 4H), 6.28 (s, 1H), 6.07 (s, 1H), 5.45 (s, 1H), 3.38 (s, 3H), 2.40 (s, 3H).

Step 2: 4-benzyl-2-iodo-6-methyl-1-tolyl-1,6-dihydro-7H-pyrrolo[2,3-c]pyridin-7-one (203)

Intermediate 202 (100 mg, 0.21 mmol) was added to a 50 mL three-necked flask containing 8 mL of anhydrous tetrahydrofuran at room temperature and cooled to −78° C. under nitrogen protection, and then lithium diisopropylamide (0.14 mL, 0.28 mmol, 2N) was added dropwise and reacted at this temperature for 45 minutes. A solution of N-iodosuccinimide (58 mg, 0.25 mmol) in tetrahydrofuran was slowly dropwise at −78° C. and reacted for 1 hour. After the completion of the reaction monitored by TLC, the reaction mixture was quenched with saturated ammonium chloride solution, diluted with water and extracted twice with ethyl acetate. The organic phase was collected, washed with saturated brine, dried over anhydrous sodium sulfate and filtered, and the filtrate was concentrated under reduced pressure. The crude product was purified by prep-TLC (petroleum ether:ethyl acetate=1:1) to give intermediate 203 (63 mg, white solid), yield: 51%.

$^1$H-NMR ($CDCl_3$,400 Hz): 8.28 (d, J=8.8 Hz, 2H), 7.37-7.25 (m, 8H), 7.10-7.18 (m, 4H), 6.46 (s, 1H), 6.30 (s, 1H), 5.38 (s, 1H), 3.40 (s, 3H), 2.43 (s, 3H).

Step 3: 4-benzoyl-6-methyl-2-(1-(oxetan-3-yl)-1H-pyrazol-4-yl)-1-tolyl-1,6-dihydro-7H-pyrrolo[2,3-c]pyridin-7-one (Intermediate 204)

203 (63 mg, 0.105 mmol), 1-(oxetan-3-yl)-4-(4,4,5,5-tetramethyl-1,3,2-dioxaborolan-2-yl)-1H-pyrazole (32 mg, 0.127 mmol), tris(bisbenzylideneacetone) dipalladium (23 mg, 0.025 mmol), dipotassium hydrogen phosphate trihydrate (28 mg, 0.158 mmol) and 1,3,5,7-tetramethyl-6-phenyl-2,4,8-trioxa-6-phosphaadamantane (7 mg, 0.025 mmol) were successively added to a 50 mL three-necked flask containing 10 mL of 1,4-dioxane and 2 mL of water at room temperature, replaced by nitrogen three times, and reacted at 60° C. overnight. After the completion of the reaction monitored by TLC, the reaction solution was filtered, concentrated and separated by Prep-TLC (petroleum ether/ethyl acetate=1/1) to obtain intermediate 204 (40 mg, yield: 66%) as a white solid.

$^1$H-NMR ($CDCl_3$,400 Hz): 7.96 (d, J=8.4 Hz, 2H), 7.66 (s, 1H), 7.52 (s, 1H), 7.31-7.24 (m, 8H), 7.10 (d, J=7.2 Hz, 4H), 6.36 (s, 1 H), 6.00 (s, 1H), 5.44 (s, 2H), 5.08-5.03 (s, 2H), 5.08-5.03 (m, 4H), 3.43 (s, 3H), 2.42 (s, 3H).

Step 4: 4-benzoyl-6-methyl-2-(1-(oxetan-3-yl)-1H-pyrazol-4-yl)-1,6-dihydro-7H-pyrrolo[2,3-c]pyridin-7-one (A71)

204 (40 mg, 0.067 mmol) and sodium hydroxide (5 mg, 0.135 mmol) were successively added to a 25 mL single-necked flask containing 5 mL of methanol and 2 mL of water at room temperature and reacted at 60° C. for two hours. After the completion of the reaction monitored by TLC, the reaction solution was concentrated and separated by Prep-HPLC (basic) to obtain Example A71 (20 mg, yield: 69%) as a white solid.

$^1$H-NMR (DMSO-d, 400 Hz): 8.32 (s, 1H), 8.03 (s, 1H), 7.32-7.28 (m, 4H), 7.23-7.20 (m, 6H), 6.44 (s, 1H), 6.13 (s, 1H), 5.56-5.50 (m, 2H), 4.92-4.88 (m, 2H), 4.85-4.82 (m, 2H), 3.40 (s, 3H).

Example A72 Synthesis Route

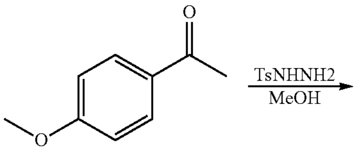

205

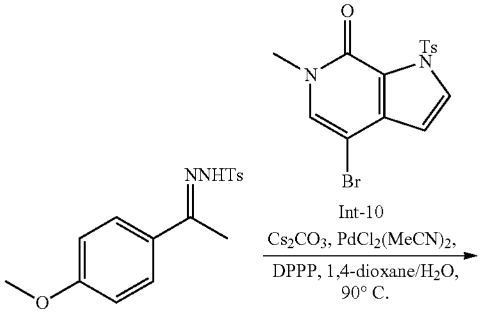

Int-10

206

-continued

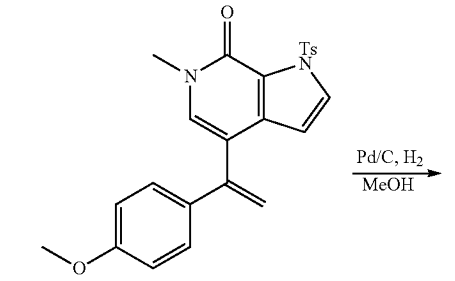

207

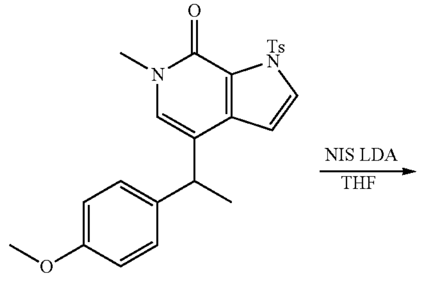

208

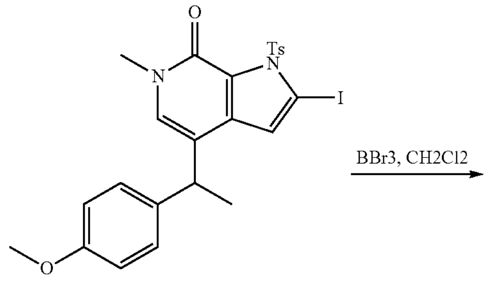

209

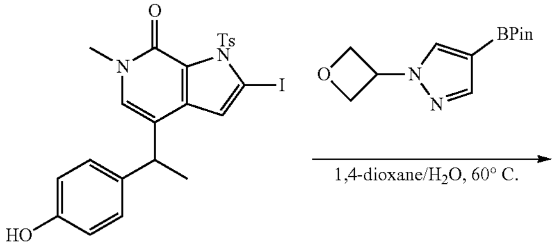

210

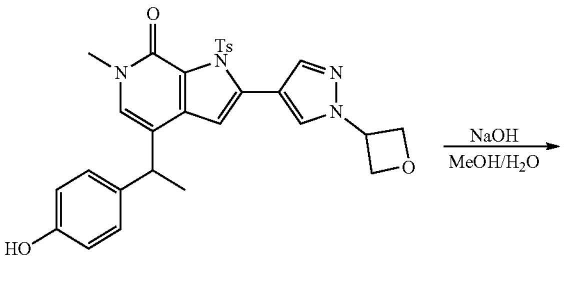

211

-continued

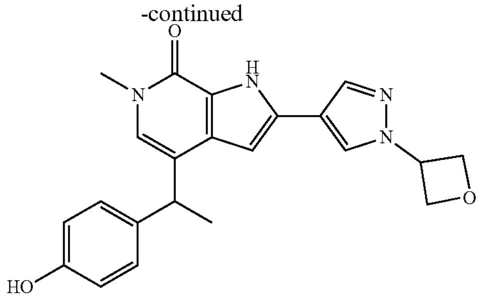

A72

Step 1: Synthesis of (Z)—N'-(1-(4-((ethoxyphenyl) ethylidene)-4-methylbenzenesulfonylhydrazide (Intermediate 206)

Intermediate 205 (1.0 g, 6.7 mmol) and p-toluenesulfonyl hydrazide (1.86 g, 10.0 mmol) were successively added to a 50 mL single-necked flask containing 10 mL of methanol at room temperature, and reacted at room temperature for 6 hours. After the completion of the reaction monitored by TLC, the reaction solution was concentrated. The residue was purified by column chromatography (petroleum ether: ethyl acetate=2:1) to obtain intermediate 206 (1.5 g, white solid), yield: 70.8%.

LCMS: m/z 319.1 (M+H).

Step 2: Synthesis of 4-(1-(4-methoxyphenyl)vinyl)-6-methyl-1-p-tosyl-1,6-dihydro-7H-pyrrolo[2,3-c] pyridin-7-one (Intermediate 207)

Intermediate 206 (1 g, 3.14 mmol), 4-bromo-6-methyl-1-tolyl-1,6-dihydro-7H-pyrrolo[2,3-c]pyridin-7-one (1.2 g, 3.14 mmol), cesium carbonate (3.1 g, 9.42 mmol), 1,3-bis (diphenylphosphino) propane (catalytic amount) and bis (acetonitrile)palladium(II) chloride (catalytic amount) were successively added to a 50 mL three-necked flask containing 20 mL of 1,4-dioxane at room temperature and reacted at 90° C. overnight. After the completion of the reaction monitored by TLC, the mixture was extracted twice with ethyl acetate. The organic phase was collected, washed with saturated brine, dried over anhydrous sodium sulfate, filtered, and the filtrate was concentrated under reduced pressure. The residue was purified by column chromatography (petroleum ether:ethyl acetate=1:1) to obtain intermediate 207 (1 g, white solid), yield: 73.3%.

LCMS: m/z 435.1 (M+H).

Step 3: Synthesis of 4-(1-(4-methoxyphenyl)ethyl)-6-methyl-1-p-tosyl-1,6-dihydro-7H-pyrrolo[2,3-c] pyridin-7-one (Intermediate 208)

Compound 3 (1.0 g, 2.30 mmol) and palladium-carbon catalyst (100 mg, 10% wt) were added successively to a 250 mL single-necked flask containing 100 mL of methanol at room temperature, and the reaction was carried out at room temperature for 15 hours under a hydrogen atmosphere. After the completion of the reaction monitored by TLC, the system was filtered, and the filtrate was concentrated to obtain product 4 (900 mg, white solid), yield: 89.7%.

LCMS: m/z 437.1 (M+H).

Step 4: Synthesis of 2-iodo-4-(1-(4-methoxyphenyl)ethyl)-6-methyl-1-p-tosyl-1,6-dihydro-7H-pyrrolo[2,3-c]pyridin-7-one (Intermediate 209)

Intermediate 207 (900 mg, 2.06 mmol), tetrahydrofuran (15 mL) and lithium diisopropylamide (1.55 mL, 3.10 mmol) were successively added to a dry 100 mL three-necked flask at −78° C. and stirred at −78° C. for 1 hour. A solution of N-iodosuccinimide (695 mg, 3.1 mmol) in tetrahydrofuran was slowly added dropwise and stirred at −78° C. for another 2 hours. After the completion of the reaction monitored by LCMS, saturated ammonium chloride was added to quench the reaction. The mixture was extracted twice with ethyl acetate, and the organic phase was collected, washed with saturated brine, dried over anhydrous sodium sulfate, and filtered. The filtrate was concentrated under reduced pressure. The residue was purified by column chromatography (petroleum ether/ethyl acetate=2/1) to obtain intermediate 208 (580 mg, white solid), yield: 50.0%.

LCMS: m/z 563.1 (M+H).

Step 5: Synthesis of 4-(1-(4-hydroxyphenyl)ethyl)-2-iodo-6-methyl-1-p-tosyl-1,6-dihydro-7H-pyrrolo[2,3-c]pyridin-7-one (Intermediate 210)

Intermediate 208 (100 mg, 0.18 mmol) and boron tribromide (0.27 mL, 0.54 mmol) were successively added to a 50 mL single-necked flask containing 15 mL of dichloromethane at 0° C. and reacted at 0° C. for 5 hours. After the completion of the reaction monitored by TLC, methanol was added to quench the reaction, and the reaction solution was concentrated. The residue was purified by preparative plate (petroleum ether:ethyl acetate=0:1) to give intermediate 209 (60 mg, white solid), yield: 61.5%.

LCMS: m/z 549.0 (M+H).

Step 6: 4-(1-(4-hydroxyphenyl)ethyl)-6-methyl-2-(1-(oxetan-3-yl)-1H-pyrazol-4-yl)-1-tosyl-1,6-dihydro-7H-pyrrolo[2,3-c]pyridin-7-one (Intermediate 211)

Intermediate 209 (60 mg, 0.11 mmol), 1-(oxetan-3-yl)-4-(4,4,5,5-tetramethyl-1,3,2-dioxaborolan-2-yl)-1H-pyrazole (36 mg, 0.14 mmol), dipotassium phosphate (75 mg, 0.33 mmol), tris(dibenzylideneacetone)dipalladium (catalytic amount) and 1,3,5,7-tetramethyl-6-phenyl-2,4,8-trioxa-6-phosphaadamantane (catalytic amount) were successively added to a 50 mL three-necked flask containing 15 mL of 1,4-dioxane and 3 mL of water at room temperature and reacted at 60° C. for 4 hours. After the completion of the reaction monitored by LCMS, the reaction solution was diluted with water, extracted twice with ethyl acetate, and the organic phase was collected, washed with saturated brine, dried over anhydrous sodium sulfate, and filtered. The filtrate was concentrated under reduced pressure. The residue was purified by preparative plate (dichloromethane/methanol=10/1) to give intermediate 211 (50 mg, white solid), yield: 83.9%.

LCMS: m/z 545.2 (M+H).

Step 7: Synthesis of 4-(1-(4-hydroxyphenyl)ethyl)-6-methyl-2-(1-(oxetan-3-yl)-1H-pyrazol-4-yl)-1,6-dihydro-7H-pyrrolo[2,3-c]pyridin-7-one (A72)

Intermediate 211 (50 mg, 0.092 mmol) and sodium hydroxide (18 mg, 0.46 mmol) were successively added to a dry 25 mL single-necked flask containing 3 mL of methanol and 1 mL of water at room temperature and reacted at 60° C. for 4 hours. After the completion of the reaction monitored by TLC, the reaction mixture was filtered, and the filtrate was separated by preparative chromatography to obtain Example A72 (12 mg, white solid), yield: 33.5%.

LCMS: m/z 391.2 (M+H).

$^1$H-NMR (DMSO, 400 MHz): 12.07 (s, 1H), 8.38 (s, 1H), 8.10 (s, 1H), 7.11 (d, J=8.4 Hz, 2H), 7.03 (s, 1H), 6.65 (d, J=8.4 Hz, 2H), 6.34 (s, 1H), 5.58-5.55 (m, 1H), 4.95-4.85 (m, 4H), 4.05-4.03 (m, 1H), 3.52 (s, 3H), 1.54 (d, J=7.2 Hz, 3H).

Example A73 Synthesis Route

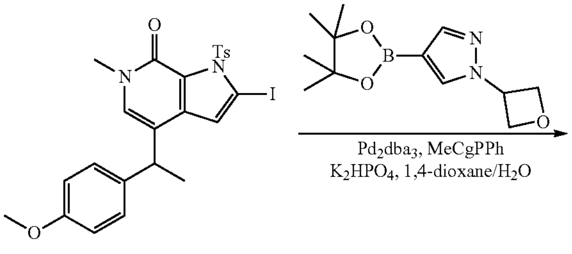

209

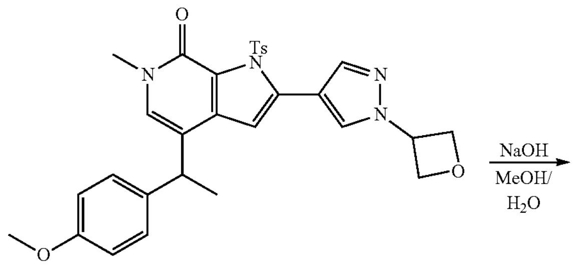

212

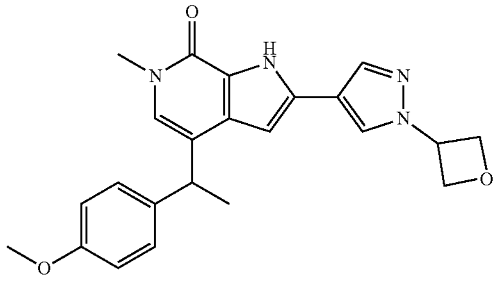

A73

Step 1: 4-(1-(4-methoxyphenyl)ethyl)-6-methyl-2-(1-(oxetan-3-yl)-1H-pyrazol-4-yl)-1-tolyl-1,6-dihydro-7H-pyrrolo[2,3-c]pyridin-7-one (Intermediate 206)

Compound 1 (100 mg, 0.18 mmol), 1-(oxetan-3-yl)-4-(4,4,5,5-tetramethyl-1,3,2-dioxaborolan-2-yl)-1H-pyrazole (53 mg, 0.21 mmol), dipotassium phosphate (61 mg, 0.27 mmol), tris(dibenzylideneacetone)dipalladium (catalytic amount) and 1,3,5,7-tetramethyl-6-phenyl-2,4,8-trioxa-6-phosphaadamantane (catalytic amount) were successively added to a 100 mL three-necked flask containing 8 mL of 1,4-dioxane and 2 mL of water at room temperature and reacted at 50° C. for three hours. After the completion of the reaction monitored by TLC, the reaction solution was diluted with water and extracted twice with ethyl acetate. The organic phase was collected, washed with saturated brine, dried over anhydrous sodium sulfate, filtered, and the filtrate was concentrated under reduced pressure. The residue was purified by column chromatography (petroleum ether/ethyl acetate=1/2) to obtain product 206 (70 mg, white solid), yield: 71.8%. LCMS: m/z 559.1 (M+H).

Step 2: 4-(1-(4-methoxyphenyl)ethyl)-6-methyl-2-(1-(oxetan-3-yl)-1H-pyrazol-4-yl)-1,6-dihydro-7H-pyrrolo[2,3-c]pyridin-7-one (A73)

Intermediate 206 (70 mg, 0.13 mmol) and sodium hydroxide (15 mg, 0.38 mmol) were successively added to a dry 50 mL single-neck flask containing 9 mL of methanol and 3 mL of water at room temperature and reacted at 70° C. for 2 hours. After the completion of the reaction monitored by TLC, the reaction solution was added with 30 mL of water and a white solid was precipitated, filtered, and the filter cake was collected and dried to obtain product A73 (37 mg, white solid), yield: 73.0%, LCMS: m/z 405.2 (M+H).

1H-NMR (DMSO, 400 MHz): 12.07 (s, 1H), 8.38 (s, 1H), 8.09 (s, 1H), 7.24 (d, J=8.4 Hz, 2H), 7.07 (s, 1H), 6.83 (d, J=8.8 Hz, 2H), 6.34 (d, J=2.4 Hz, 1H), 5.60-5.53 (m, 1H), 4.95-4.85 (m, 4H), 4.13-4.07 (m, 1H), 3.70 (s, 3H), 3.53 (s, 3H), 1.56 (d, J=7.2 Hz, 3H).

Example A74 Synthesis Route

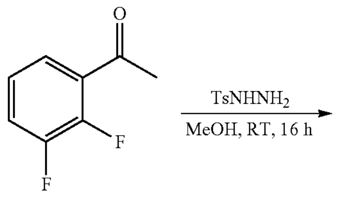

213

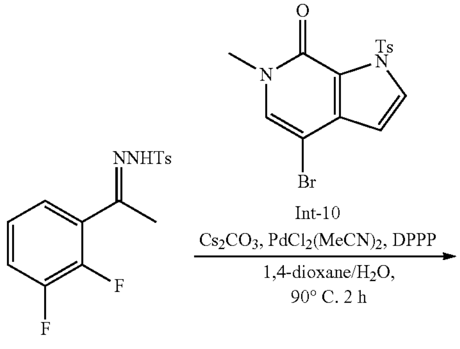

214

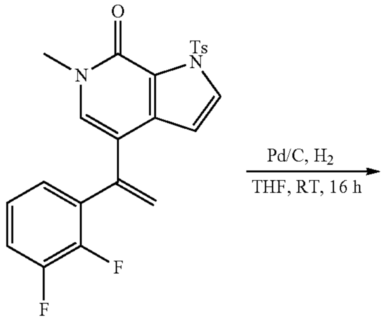

215

-continued

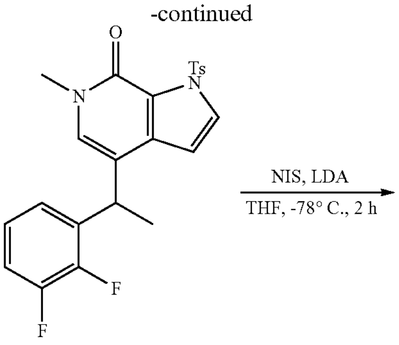

216

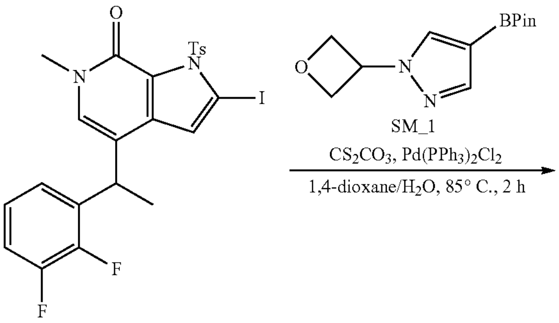

217

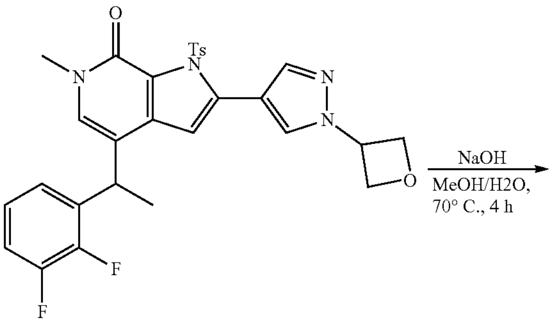

218

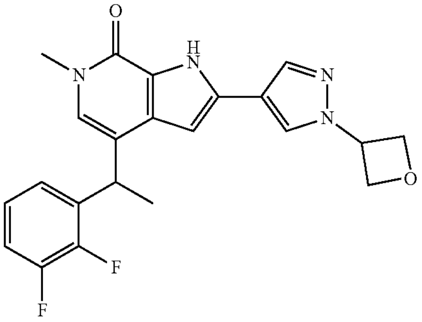

A74

Step 1: Synthesis of ((Z)—N'-(1-(2-(2,3-difluorophenyl)ethylidene)-4-methylbenzenesulfonylhydrazide (Intermediate 214)

Intermediate 213 (1.0 g, 6.40 mmol), methanol (40 mL) and p-toluenesulfonyl hydrazide (1.79 g, 9.61 mmol) were successively added to a dry 100 mL single-necked flask at room temperature. The mixture was stirred at room temperature and reacted for 16 hours. After the completion of the reaction monitored by TLC, the reaction solution was concentrated under reduced pressure. The residue was purified by column chromatography (petroleum ether:ethyl acetate=5:1) to give (Z)—N'-(1-(2-(2,3-difluorophenyl)ethylidene)-4-methylbenzenesulfonylhydrazide (intermediate 214) (2.00 g, white solid), yield: 96.27%. LCMS: m/z 325.2 (M+H).

Step 2: Synthesis of 4-(1-(2,3-difluorophenyl)vinyl)-6-methyl-1-tosyl-1,6-dihydro-7H-pyrrolo[2,3-c]pyridin-7-one (Intermediate 215)

Compound Int-10 (1.00 g, 2.62 mmol), intermediate 214 (1.28 g, 3.93 mmol), 1,4-dioxane (20 mL), cesium carbonate (1.71 g, 5.25 mmol), 1,3-bis(diphenylphosphine)propane (101 mg, 0.26 mmol) and bis(acetonitrile)palladium(II) chloride (68 mg, 0.26 mmol) were successively added to a dry 100 mL single-necked flask at room temperature, replaced by nitrogen 3 times, heated to 90° C. and reacted for 2 hours. After the completion of the reaction monitored by TLC, the mixture was poured into 50 mL of water and extracted with ethyl acetate (30 mL×2). The organic phase was collected, washed with saturated brine, dried over anhydrous sodium sulfate, filtered, and the filtrate was concentrated under reduced pressure. The residue was purified by column chromatography (petroleum ether:ethyl acetate=4:1) to obtain 4-(1-(2,3-difluorophenyl)vinyl)-6-methyl-1-tosyl-1,6-dihydro-7H-pyrrolo[2,3-c]pyridin-7-one (intermediate 215) (0.80 g, white solid) as a crude product, yield: 69.24%. LCMS: m/z 441.1 (M+H).

Step 3: Synthesis of 4-(1-(2,3-difluorophenyl)ethyl)-6-methyl-1-tosyl-1,6-dihydro-7H-pyrrolo[2,3-c]pyridin-7-one (Intermediate 216)

Intermediate 215 (800 mg, 1.82 mmol), tetrahydrofuran (30 mL) and palladium-carbon catalyst (80 mg, 10% Wt) were successively added to a dry 100 mL single-necked flask at room temperature, replaced by hydrogen three times, and the mixture was stirred at room temperature for 16 hours. After the completion of the reaction monitored by TLC, the reaction solution was filtered, and the filtrate was collected and concentrated under reduced pressure to obtain 4-(1-(2,3-difluorophenyl)ethyl)-6-methyl-1-tosyl-1,6-dihydro-7H-pyrrolo[2,3-c]pyridin-7-one (intermediate 216) (800 mg, white solid), yield: 99.54%.

$^1$H-NMR ($CDCl_3$, 400 MHz): 8.01 (d, J=8.4 Hz, 2H), 7.80 (d, J=3.6 Hz, 1H), 7.30 (d, J=8.4 Hz, 2H), 7.03-6.94 (m, 2H), 6.87 (s, 1H), 6.83-6.80 (m, 1H), 6.25 (d, J=3.6 Hz, 1H), 4.50-4.45 (m, 1H), 3.53 (s, 3H), 2.40 (s, 3H), 1.58 (d, J=6.8 Hz, 3H).

Step 4: Synthesis of 4-(1-(2,3-difluorophenyl)ethyl)-2-iodo-6-methyl-1-tolyl-1,6-dihydro-7H-pyrrolo[2,3-c]pyridin-7-one (Intermediate 217)

Intermediate 216 (400 mg, 0.90 mmol) and tetrahydrofuran (20 mL) were successively added to a dry 100 mL three-necked flask at room temperature. The system was replaced by nitrogen three times, cooled to −78° C., and lithium diisopropylamide (2M, 0.59 mL, 1.18 mmol) was slowly added dropwise and then stirred at −78° C. for 1 hour. A solution of N-iodosuccinimide (244 mg, 1.08 mmol) in tetrahydrofuran (5 mL) was slowly added dropwise, stirred at −78° C. and reacted for 1 hour. After the completion of the reaction monitored by LCMS, the reaction mixture was quenched by adding saturated aqueous ammonium chloride solution (30 mL) and extracted with ethyl acetate (25 mL×2). The organic phase was collected, washed with saturated brine, dried over anhydrous sodium sulfate, filtered, and the filtrate was concentrated under reduced pressure. The residue was purified by column chromatography (petroleum ether/ethyl acetate=3/1) to give 4-(1-(2,3-difluorophenyl)ethyl)-2-iodo-6-methyl-1-tolyl-1,6-dihydro-7H-pyrrolo[2,3-c]pyridin-7-one (intermediate 217) (270 mg, white solid), yield: 52.55%.

$^1$H-NMR (DMSO, 400 MHz): 8.09 (d, J=8.4 Hz, 2H), 7.48 (d, J=8.4 Hz, 2H), 7.39 (s, 1H), 7.31-7.25 (m, 1H), 7.16-7.06 (m, 2H), 6.83 (s, 1H), 4.46-4.41 (m, 1H), 3.44 (s, 3H), 2.40 (s, 3H), 1.53 (d, J=7.2 Hz, 3H).

Step 5: Synthesis of 4-(1-(2,3-difluorophenyl)ethyl)-6-methyl-2-(1-(oxetan-3-yl)-1H-pyrazol-4-yl)-1-tosyl-1,6-dihydro-7H-pyrrolo[2,3-c]pyridin-7-one (Intermediate 218)

Intermediate 217 (100 mg, 0.185 mmol), 1,4-dioxane (6 mL), water (2 mL), 1-(oxetan-3-yl)-4-(4,4,5,5-tetramethyl-1,3,2-dioxaborolan-2-yl)-1H-pyrazole (57 mg, 0.23 mmol), cesium carbonate (115 mg, 0.35 mmol) and bistriphenylphosphonium palladium dichloride (12 mg, 0.02 mmol) were successively added to a dry 100 mL three-necked flask at room temperature, replaced by nitrogen 3 times, heated to 85° C. and reacted for 2 hours. After the completion of the reaction monitored by TLC, the reaction mixture was poured into 20 mL of water, and extracted with ethyl acetate (20 mL×2). The organic phase was collected, washed with saturated brine, dried over anhydrous sodium sulfate, filtered, and the filtrate was concentrated under reduced pressure. The residue was purified by column chromatography (petroleum ether:ethyl acetate=1:2) to give 4-(1-(2,3-difluorophenyl)ethyl)-6-methyl-2-(1-(oxetan-3-yl)-1H-pyrazol-4-yl)-1-tosyl-1,6-dihydro-7H-pyrrolo[2,3-c]pyridin-7-one (intermediate 218) (80 mg, yellow solid), yield: 80.53%.

LCMS: m/z 565.1 (M+H).

Step 6: Synthesis of 4-(1-(2,3-difluorophenyl)ethyl)-6-methyl-2-(1-(oxetan-3-yl)-1H-pyrazol-4-yl)-1,6-dihydro-7H-pyrrolo[2,3-c]pyridin-7-one (A74)

Intermediate 218 (80 mg, 0.14 mmol), methanol (3 mL), water (1 mL) and sodium hydroxide (17 mg, 0.43 mmol) were successively added to a dry 50 mL single-necked flask at room temperature, heated to 70° C. and reacted for 4 hours. After the completion of the reaction monitored by TLC, the reaction mixture was poured into 9 mL of water, a white solid was precipitated, filtered, and the filter cake was collected and dried to obtain 4-(1-(2,3-difluorophenyl)ethyl)-6-methyl-2-(1-(oxetan-3-yl)-1H-pyrazol-4-yl)-1,6-dihydro-7H-pyrrolo[2,3-c]pyridin-7-one A74 (13 mg, white solid), yield: 22.35%.

LCMS: m/z 411.1 (M+H). 1H-NMR (DMSO, 400 MHz): 12.15 (s, 1H), 8.40 (s, 1H), 8.11 (s, 1H), 7.26 d, J=6.0 Hz, 1H), 7.12-7.07 (m, 3H), 6.31 (s, 1H), 5.60-5.53 (m, 1H), 4.93-4.87 (m, 4H), 4.50-4.45 (m, 1H), 3.54 (s, 3H), 1.60 (d, J=6.0 Hz, 3H).

Example A75 Synthesis Route

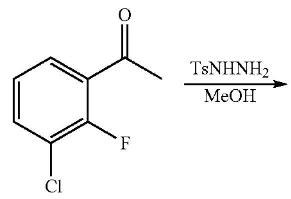

219

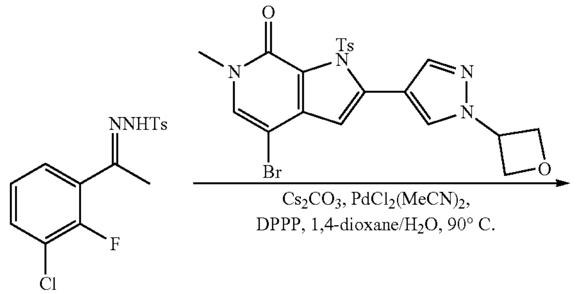

220

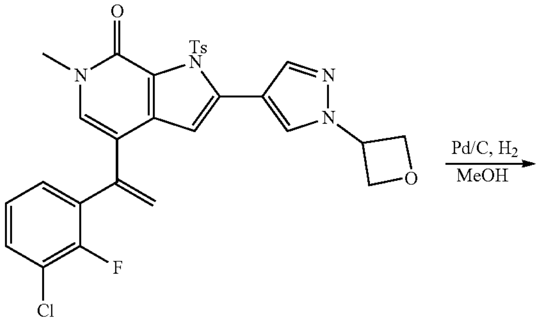

221

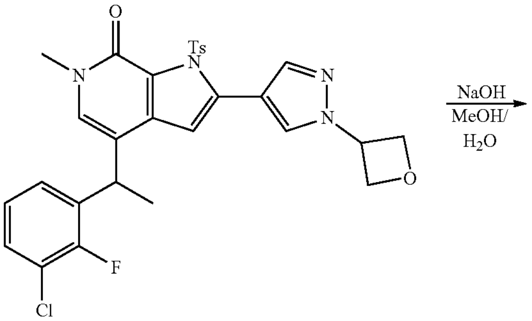

222

-continued

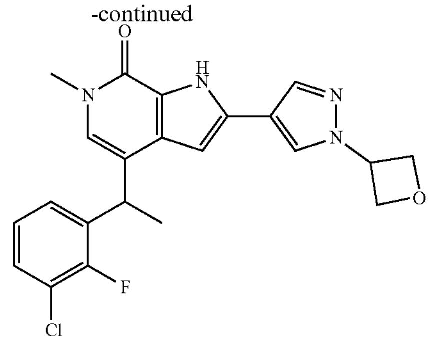

A75

Step 1: Synthesis of (Z)—N'-(1-(3-chloro-2-fluorophenyl)ethylidene)-4-methylbenzenesulfonylhydrazide (Intermediate 220)

Compound 1 (500 mg, 2.9 mmol) and p-toluenesulfonyl hydrazide (809 mg, 4.35 mmol) were successively added to a 50 mL single-necked flask containing 5 mL of methanol at room temperature and reacted for 16 hours at room temperature. After the completion of the reaction monitored by TLC, the reaction solution was concentrated to dryness. The crude product was purified by column chromatography (petroleum ether:ethyl acetate=2:1) to obtain intermediate 220 (900 mg, white solid), yield: 91.2%.

LCMS: m/z 341.0 (M+H).

Step 2: Synthesis of 4-(1-(3-chloro-2-fluorophenyl) vinyl)-6-methyl-2-(1-(oxetan-3-yl)-1H-pyrazol-4-yl)-1-tosyl-1,6-dihydro-7H-pyrrolo[2,3-c]pyridin-7-one (Intermediate 221)

Compound 2 (44 mg, 0.13 mmol), 4-bromo-6-methyl-2-(1-(oxetan-3-yl)-1H-pyrazol-4-yl)-1-tolyl-1,6-dihydro-7H-pyrrolo[2,3-c]pyridin-7-one (50 mg, 0.10 mmol), cesium carbonate (98 mg, 0.30 mmol), bis(acetonitrile)palladium (II) chloride (catalytic amount) and 1,3-bis(diphenylphosphino)propane (catalytic amount) were successively added to a 50 mL three-necked flask containing 10 mL of 1,4-dioxane at room temperature and reacted 90° C. overnight. After the completion of the reaction monitored by TLC, the reaction mixture was extracted twice with ethyl acetate. The organic phase was collected, washed with saturated brine, dried over anhydrous sodium sulfate, filtered, and the filtrate was concentrated under reduced pressure. The crude product was purified by column chromatography (petroleum ether: ethyl acetate=1:1.5) to give intermediate 221 (50 mg, white solid), yield: 86.9%, LCMS: m/z 579.6 (M+H).

Step 3: Synthesis of 4-(1-(3-chloro-2-fluorophenyl) ethyl)-6-methyl-2-(1-(oxetan-3-yl)-1H-pyrazol-4-yl)-1-tosyl-1,6-dihydro-7H-pyrrolo[2,3-c]pyridin-7-one (Intermediate 222)

Compound 3 (50 mg, 0.09 mmol) and Pd/C (5 mg, 10% Wt) were successively added to a 50 mL single-necked flask containing 10 mL of methanol at room temperature, and the reaction was carried out overnight at room temperature under a hydrogen atmosphere. After the completion of the reaction monitored by TLC, the system was filtered, and the filtrate was concentrated to obtain intermediate 222 (50 mg, colorless liquid), yield: 99.7%.

LCMS: m/z 581.0 (M+H).

Step 4: Synthesis of 4-(1-(3-chloro-2-fluorophenyl)ethyl)-6-methyl-2-(1-(oxetan-3-yl)-1H-pyrazol-4-yl)-1,6-dihydro-7H-pyrrolo[2,3-c]pyridin-7-one (A75)

Intermediate 222 (50 mg, 0.086 mmol), and sodium hydroxide (34 mg, 0.86 mmol) were added successively to a dry 25 mL single-necked flask containing 3 mL of methanol and 1 mL of water at room temperature and reacted at 70° C. for 2 hours. After the completion of the reaction monitored by TLC, the reaction solution was concentrated under reduced pressure, and the residue was purified by reversed phase column of high performance liquid chromatography to obtain product A75 (7 mg, white solid), yield: 19.1%.

LCMS: m/z 468.1 ($M+H+CH_3CN$).

$^1$H-NMR (DMSO, 400 MHz): 12.15 (s, 1H), 8.40 (s, 1H), 8.11 (s, 1H), 7.44-7.39 (m, 1H), 7.28-7.25 (m, 1H), 7.15-7.12 (m, 2H), 6.30 (s, 1H), 5.58-5.55 (m, 1H), 4.95-4.91 (m, 2H), 4.88-4.85 (m, 2H), 4.47-4.45 (m, I H), 3.54 (s, 3H), 1.60 (d, J=7.2 Hz, 3H).

Effect Example: In Vitro Enzyme Activity Assay

In this example, the half inhibitory activity ($IC_{50}$) of the compounds of the present invention against the bromodomain protein BRD4 BD1 was determined.

1. Test Methods

The inhibitory activity of the compound against BRD4 BD1 was determined by using Homogeneous Time-Resolved Fluorescence (HTRF).

2. Reagents, Consumables and Instruments

The proteins BRD4 BD1/BD2 used in the experiment were purchased from Active Motif Company (Cat. No. 31380/31446); Streptavidin XL-665 (#610SAXLA) and EPIgeneous Binding Domain Kit A (#62BDAPEG) were purchased from Cisbio Bioassays Company, [Lys(5,8,12,16)Ac]H4(1-21)-biotin (#64989), and [Lys(5,8,12,16)Ac]H4(1-25) were products of AnaSpec company; OTX015 and ABBV-075 were purchased from SelleckChem. 384 Well ProxiPlate (#6008280) was purchased from PerkinElmer. The multifunctional microplate reader used for the experimental was a product of PerkinElmer, model: Envision 2104. The experimental water was Millipore-Q pure water.

3. Compound Formulation 10 mM of stock solution of compound in DMSO was diluted to 1 mM with DMSO and stored, and then diluted 10 times with Binding Domain dilution buffer (purchased from Cisbio Bioassays) for use (the concentration of DMSO in the final system was 0.1%), 1:5 gradient dilution, a total of 5 concentrations.

4. Test Method: 1 Batch, 2 Duplicate Wells 1) 5 μL of test compound was transferred to 45 μL of Binding Domain dilution buffer.
2) 2 μL of 10× compound (4 μL Binding Domain dilution buffer: positive control; 6 μL enzyme buffer (purchased from Cisbio Bioassays): negative control) was transferred to the reaction plate.
3) 4 μL of 5×BRD4(1) or BRD4(2) (30 nM in final system) was added to the reaction plate.
4) 4 μL of 5×[Lys(5,8,12,16)Ac]H4(1-21)-biotin was added to the reaction plate, and the plate was covered with a film, and incubated at 37° C. for 30 min.
5) A detection mixture of SA-XL665 (2×) and anti-H3K9me0-Eu(K) (2×) was prepared in detection buffer (purchased from Cisbio Bioassays).
6) 10 μL of detection mixture (2×) was added to each well, and incubated for 3 h at room temperature, and the mp value was read using a multi-plate reader Envision. The parameters were set as follows.

| | |
|---|---|
| Top mirror | LANCE/DELFIA Dual/Bias(446) |
| Exc. Filter | UV2 (TRF) 320 |
| Ems. Filter | APC 665 |
| 2$^{nd}$ Ems. Filter | Europium 615 |

5. Experimental Results

The inhibitory activity data ($IC_{50}$) of the compounds of the examples of the present invention against bromodomain proteins BRD4 BD1 and BRD4 BD2 are all less than or equal to 1 M, preferably the inhibitory activity data ($IC_{50}$) of the compounds of the examples of the present invention against bromodomain proteins BRD4 BD1 are less than or equal to 100 nM. For example, the inhibitory activity data ($IC_{50}$) of some compounds of the present invention against the bromodomain proteins BRD4 BD1 and BRD4 BD2 are shown in Table 1 below, wherein:

A represents the $IC_{50}$ of the compound is less than or equal to 10 nM;

B represents the $IC_{50}$ of the compound is greater than 10 nM but less than or equal to 100 nM;

C represents the $IC_{50}$ of the compound is greater than 100 nM but less than or equal to 1 μM.

TABLE 1

$IC_{50}$ values (nM) of the compounds of the present invention against BRD4 BD1 binding

| Compound No. | BRD4(BD1) $IC_{50}$ | BRD4(BD2) $IC_{50}$ | Compound No. | BRD4(BD1) $IC_{50}$ | BRD4(BD2) $IC_{50}$ |
|---|---|---|---|---|---|
| A1 | C | B | A2 | C | B |
| A3 | C | B | A4 | C | B |
| A5 | C | A | A6 | C | A |
| A7 | C | A | A8 | C | A |
| A9 | C | B | A10 | C | B |
| A11 | C | A | A12 | C | A |
| A13 | C | A | A14 | C | A |
| A15 | C | A | A16 | C | B |
| A17 | C | A | A18 | C | A |
| A19 | C | A | A20 | C | B |
| A21 | C | B | A22 | C | B |

TABLE 1-continued

IC$_{50}$ values (nM) of the compounds of the present invention against BRD4 BD1 binding

| Compound No. | BRD4(BD1) IC$_{50}$ | BRD4(BD2) IC$_{50}$ | Compound No. | BRD4(BD1) IC$_{50}$ | BRD4(BD2) IC$_{50}$ |
|---|---|---|---|---|---|
| A23 | C | B | A24 | C | B |
| A25 | C | B | A26 | C | B |
| A27 | C | B | A28 | C | B |
| A29 | C | B | A30 | B | A |
| A31 | B | A | A32 | B | A |
| A33 | C | B | A34 | C | B |
| A35 | C | B | A36 | C | B |
| A37 | C | B | A38 | C | B |
| A39 | C | B | A40 | B | A |
| A41 | C | C | A42 | C | B |
| A43 | C | B | A44 | C | B |
| A45 | B | A | A46 | B | A |
| A47 | B | A | A48 | C | B |
| A49 | B | A | A50 | B | B |
| A51 | B | A | A52 | B | A |
| A53 | C | B | A54 | C | B |
| A55 | C | B | A56 | C | B |
| A57 | C | A | A58 | C | A |
| A59 | C | B | A60 | C | B |
| A61 | C | A | A62 | C | A |
| A63 | C | B | A64 | C | B |
| A67 | C | B | A68 | C | B |
| A69 | C | B | A70 | C | B |
| A71 | C | B | A72 | C | B |
| A73 | C | A | A74 | C | A |
| A75 | C | A | | | |

It can be seen that the compounds of the present application have very good inhibitory activities against BRD4-BD2, while the activity against BD1 is relatively low, so the compounds of the present invention are selective inhibitors of BRD4-BD2, thus providing a new and effective treatment options.

All documents mentioned herein are incorporated by reference in the present application as if each document is individually incorporated by reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A compound of formula (I), deuterated compound, stereoisomer, racemate, geometric isomer, tautomer, prodrug, hydrate, solvate or pharmaceutically acceptable salt thereof:

(I)

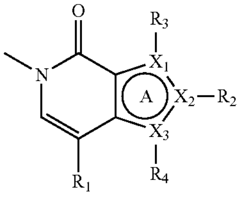

wherein, ring A is a five-membered aromatic heterocycle, and $X_1$ is N, and $X_2$ and $X_3$ are each C $R_4$ is hydrogen, and $R^1$ is selected from the group consisting of

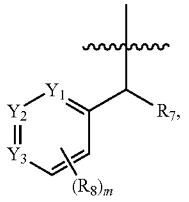

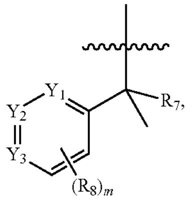

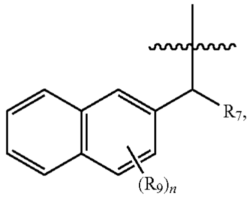

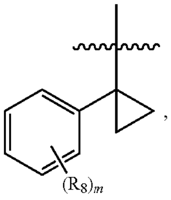

, and

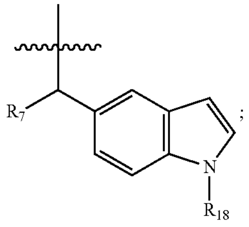

;

$Y_1$, $Y_2$ and $Y_3$ are each independently C or N, provided that not all of $Y_1$, $Y_2$, and $Y_3$ are nitrogen;

$R_7$ is selected from the group consisting of hydrogen, unsubstituted or halogenated C1-C5 alkyl, unsubstituted or halogenated C3-C8 cycloalkyl, hydroxy, C1-C4 alkyl substituted with hydroxy, methoxy, halogen, phenyl, benzyl, phenoxy, phenoxy substituted with trifluoromethyl, trifluoromethoxy, phenoxy substituted with trifluoromethoxy, 5-8 membered heteroaryl and 3-8 membered heterocycloalkyl;

each $R_8$ is a substituent on the phenyl or the six-membered heteroaryl, m is an integer from 0 to 4; when m≥2, each $R_8$ is the same or different; the substituents represented by $R_8$ are each independently selected from the group consisting of hydrogen, C1-C6 alkyl, nitro, cyano, halogen, trifluoromethoxy, hydroxy, hydroxymethyl, amino, C1-C6 alkoxy, C3-C6 cycloalkyloxy, and unsubstituted 3-8 membered heterocycloalkyl and 3-8 membered heterocycloalkyl substituted with C1-C6 alkyl;

each $R_9$ is a substituent on the naphthyl, n is an integer from 0 to 4; when n≥2, each $R_9$ is the same or different; the substituents represented by $R_9$ are each independently selected from the group consisting of C1-C6 alkyl, nitro, cyano, halogen, trifluoromethoxy, hydroxy, hydroxymethyl, amino, C1-C6 alkoxy, C3-C6 cycloalkyloxy, and unsubstituted 4-8 membered heterocycloalkyl and 4-8 membered heterocycloalkyl substituted with C1-C6 alkyl;

$R_{18}$ is hydrogen, C1-C6 alkyl or hydroxyl;

$R_2$ is selected from the group consisting of —CO—NH—$R_6$, unsubstituted or substituted 5-8-membered heteroaryl, and C1-C6 alkyl; wherein, the "substituted" refers to substitution with one or more substituents selected from the group consisting of unsubstituted C1-C6 alkyl and C1-C6 alkyl substituted with one or more substituents selected from the group consisting of group C, halogen, hydroxy, 3-12 membered heterocycloalkyl, C1-C6 alkoxy, C3-C6 cycloalkyl, C3-C6 cycloalkyloxy, C1-C6 alkyl-C(O)O—, C1-C6 alkoxycarbonyl, nitro, cyano, C1-C6 alkylamido, and amino; the group C consists of halogen, hydroxyl, C3-C6 cycloalkyl, 3-12-membered heterocycloalkyl, and 3-12-membered heterocycloalkyl substituted with C1-C6 alkyl;

$R_6$ is unsubstituted or halogenated C1-C6 alkyl, unsubstituted or halogenated C3-C6 cycloalkyl, unsubstituted 5-8 membered heteroaryl or 5-8 membered heteroaryl substituted with C1-C6 alkyl, or unsubstituted 5-8 membered heterocycloalkyl or 5-8 membered heterocycloalkyl substituted with C1-C6 alkyl; and $R_3$ is C1-C6 alkyl, halogen, amino or hydrogen.

2. The compound, deuterated compound, stereoisomer, racemate, geometric isomer, tautomer, prodrug, hydrate, solvate or pharmaceutically acceptable salt thereof of claim 1, wherein:

$R_2$ is selected from the group consisting of —CO—NH—$R_6$, and unsubstituted or substituted 5-8-membered heteroaryl; wherein, the "substituted" refers to substitution with one or more substituents selected from the group consisting of C1-C6 alkyl, halogenated C1-C6 alkyl, halogen, hydroxyl, 3-12 membered heterocycloalkyl, C1-C6 alkoxy, C3-C6 cycloalkyl, C3-C6 cycloalkyloxy, C1-C6 alkyl-C(O)O—, $R_6$ is unsubstituted or halogenated C1-C6 alkyl, unsubstituted or halogenated C3-C6 cycloalkyl, unsubstituted 5-8 membered heteroaryl or 5-8 membered heteroaryl substituted with C1-C6 alkyl, or unsubstituted 5-8 membered heterocycloalkyl or 5-8 membered heterocycloalkyl substituted with C1-C6 alkyl; and $R_3$ is C1-C6 alkyl, halogen, amino, or hydrogen.

3. The compound, deuterated compound, stereoisomer, racemate, geometric isomer, tautomer, prodrug, hydrate, solvate or pharmaceutically acceptable salt thereof of claim 1, wherein the compound is:

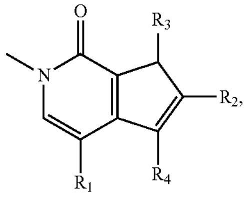

wherein, $R_1$, $R_2$, and $R_4$ are defined as in claim 1, and $R_3$ is hydrogen.

4. The compound, deuterated compound, stereoisomer, racemate, geometric isomer, tautomer, prodrug, hydrate, solvate or pharmaceutically acceptable salt thereof of claim 1, wherein the compound is:

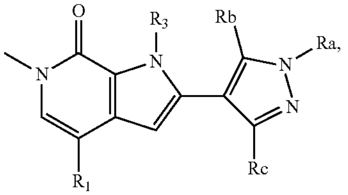

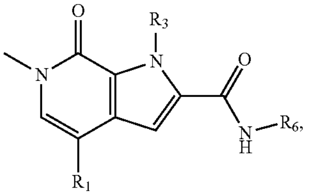

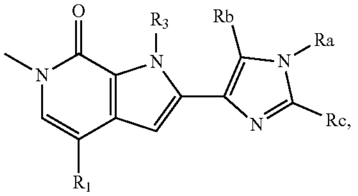

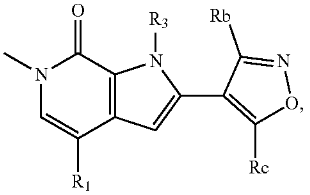

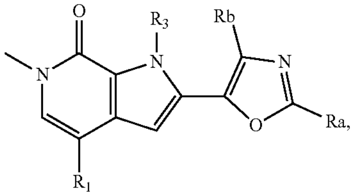

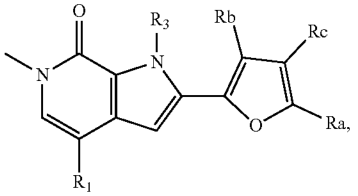

-continued

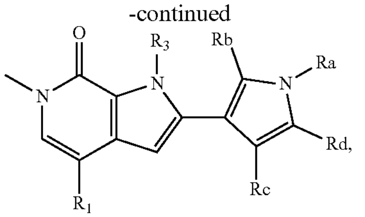

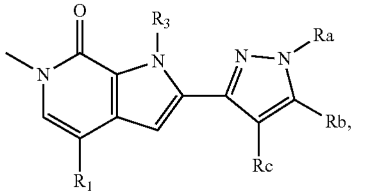

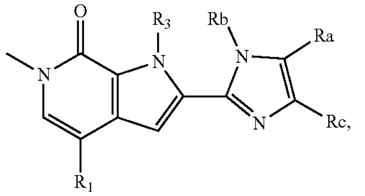

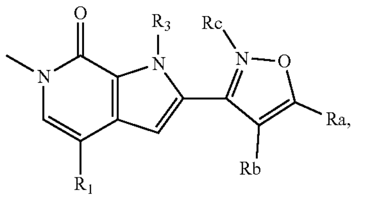

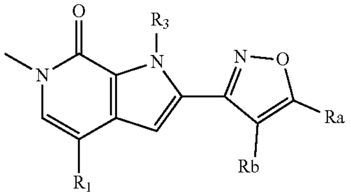

or

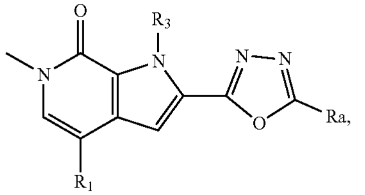

wherein, $R_1$, $R_3$ and $R_6$ are defined as in claim 1;

Ra, Rb, Rc and Rd are each independently hydrogen, halogen, unsubstituted or halogenated C1-C6 alkyl, or 3-12-membered heterocycloalkyl.

5. The compound, deuterated compound, stereoisomer, racemate, geometric isomer, tautomer, prodrug, hydrate, solvate or pharmaceutically acceptable salt thereof of claim 1, wherein $R_4$ is hydrogen, and $R_1$ is

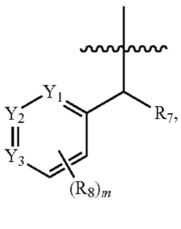

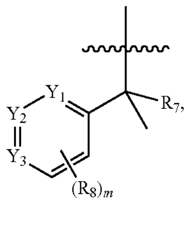

-continued

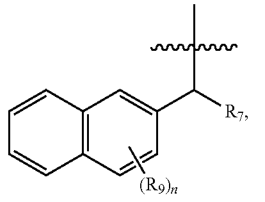

or

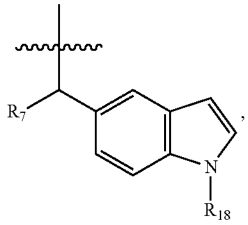

wherein, $Y_1$, $Y_2$ and $Y_3$ are each independently C or N, provided that not all of $Y_1$, $Y_2$, and $Y_3$ are nitrogen;

$R_7$ is selected from hydrogen, unsubstituted or halogenated C1-C5 alkyl, unsubstituted or halogenated C3-C8 cycloalkyl, hydroxy, C1-C4 alkyl substituted with hydroxy, methoxy, halogen, phenyl, benzyl, phenoxy, phenoxy substituted with trifluoromethyl, trifluoromethoxy, phenoxy substituted with trifluoromethoxy, 5-8 membered heteroaryl or 3-8 membered heterocycloalkyl;

$R_8$ is a substituent on the phenyl or the six-membered heteroaryl, m is 0, 1, or 2; when m is 2, each $R_8$ is the same or different; the substituents represented by $R_8$ are each independently selected from the group consisting of hydrogen, C1-C6 alkyl, halogen, trifluoromethoxy, hydroxy, hydroxymethyl, C1-C6 alkoxy, C3-C6 cycloalkyloxy, and unsubstituted 3-8 membered heterocycloalkyl and 3-8 membered heterocycloalkyl substituted with C1-C6 alkyl;

$R_9$ is a substituent on the naphthyl, n is 0, 1, or 2; when n is 2, each $R_9$ is the same or different; the substituents represented by $R_9$ are each independently selected from the group consisting of C1-C6 alkyl, nitro, cyano, halogen, trifluoromethoxy, hydroxy, hydroxymethyl, and C1-C6 alkoxy; and $R_{18}$ is hydrogen, C1-C6 alkyl or hydroxyl.

6. The compound, deuterated compound, stereoisomer, racemate, geometric isomer, tautomer, prodrug, hydrate, solvate or pharmaceutically acceptable salt thereof of claim 1, wherein $R_2$ is selected from the group consisting of —CO—NH—$R_6$, and unsubstituted or substituted 5-8-membered heteroaryl; wherein, the "substituted" refers to substitution with one or more substituents selected from the group consisting of unsubstituted C1-C4 alkyl or C1-C4 alkyl substituted by one or more substituents selected from the group consisting of group C and 5-8 membered heterocycloalkyl $R_6$ is selected from the group consisting of unsubstituted or halogenated C1-C4 alkyl, unsubstituted or halogenated C3-C6 cycloalkyl, unsubstituted 5-6 membered heteroaryl or 5-6 membered heteroaryl substituted with C1-C6 alkyl, or unsubstituted 5-6 membered heterocycloalkyl and 5-6 membered heterocycloalkyl substituted with C1-C6 alkyl; and the group C consists of halogen, hydroxyl, 4-6-membered heterocycloalkyl, and 4-6-membered heterocycloalkyl substituted with C1-C4 alkyl.

7. The compound, deuterated compound, stereoisomer, racemate, geometric isomer, tautomer, prodrug, hydrate, solvate or pharmaceutically acceptable salt thereof of claim 1, wherein the compound of formula (I) is selected from the following specific compounds:

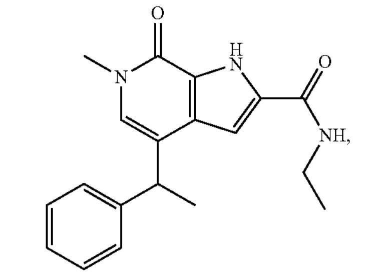
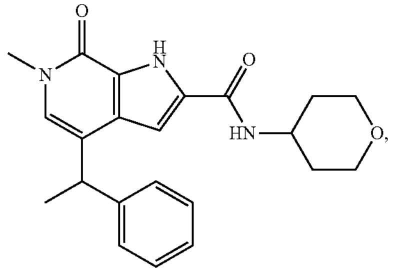
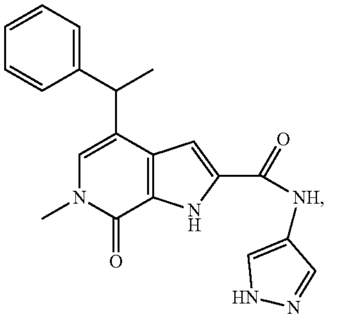
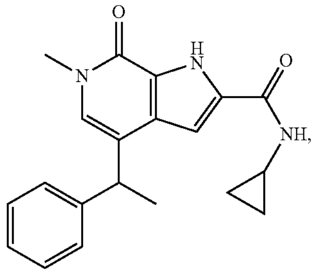
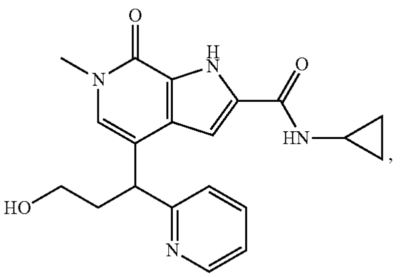
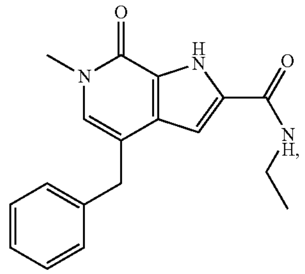
-continued
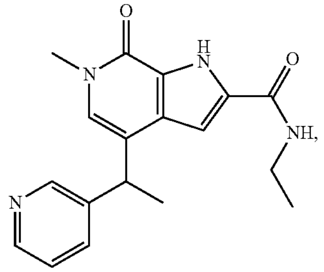
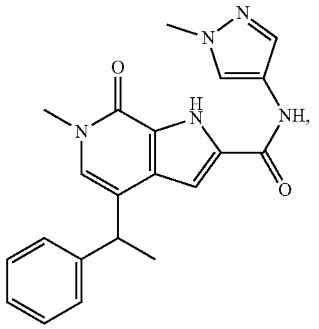
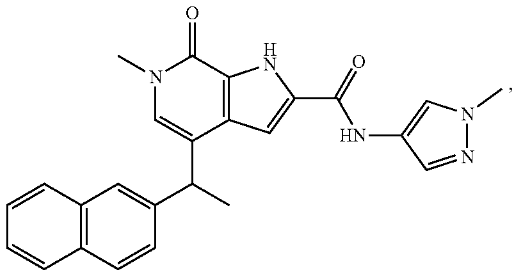
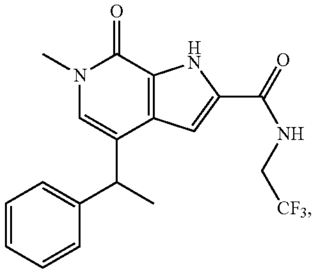
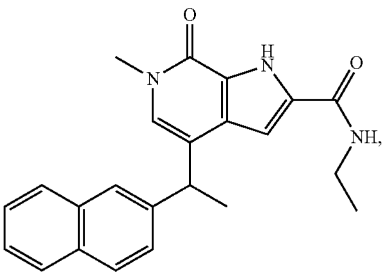
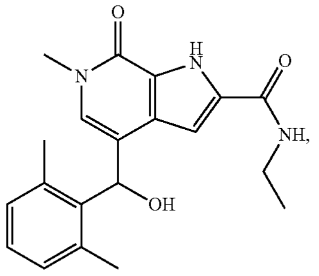

-continued
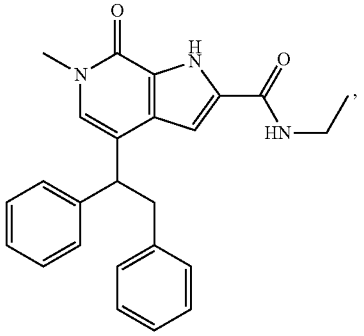
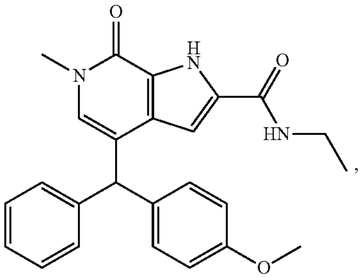
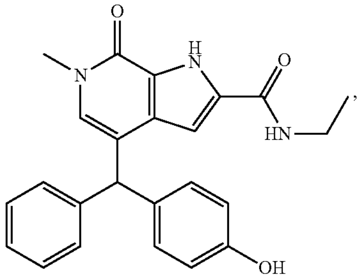
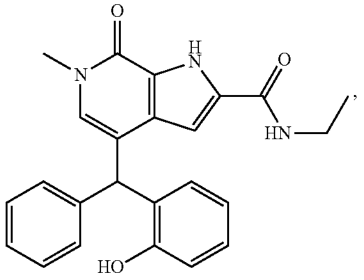
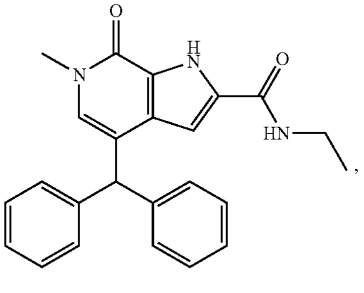
-continued
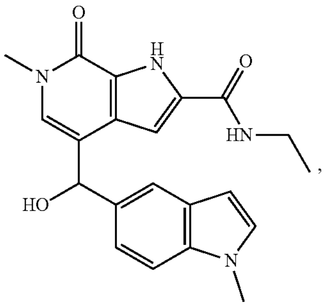
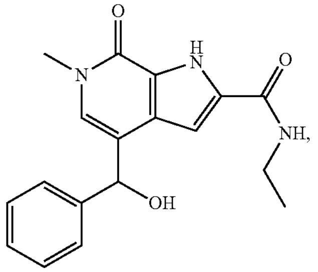
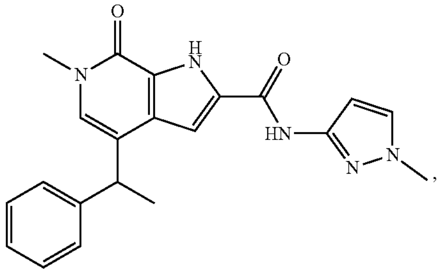
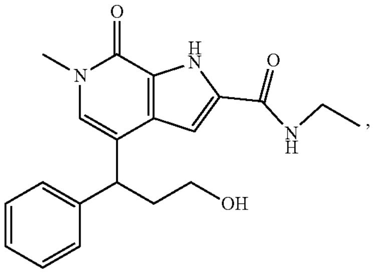
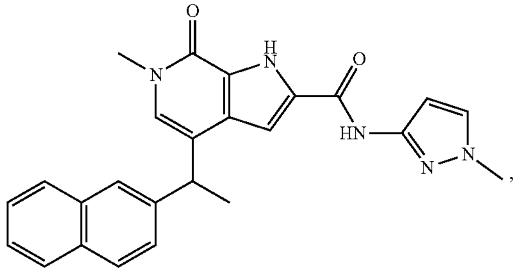
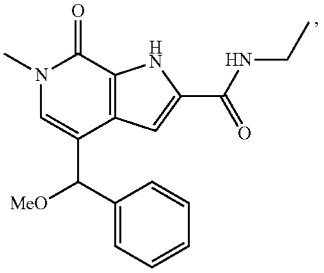

-continued
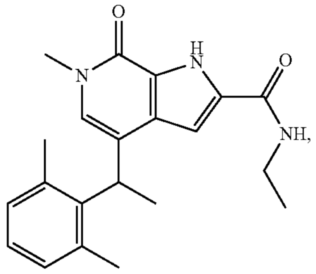
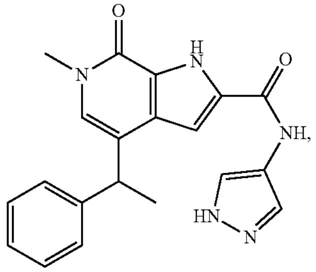
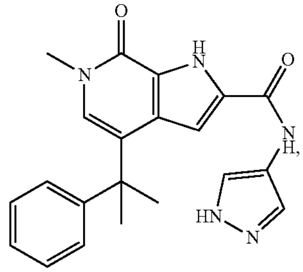
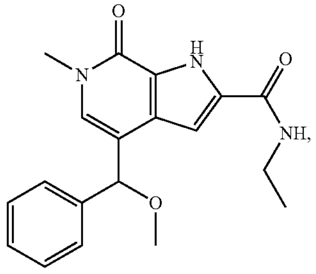
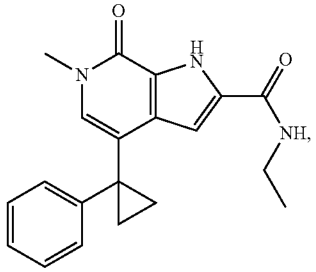
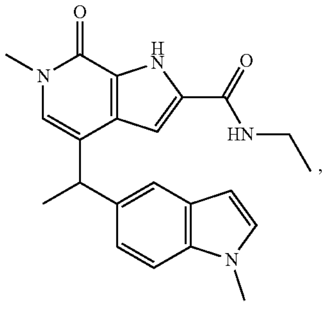
-continued
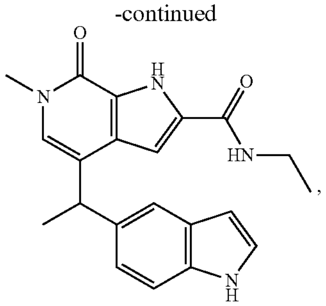
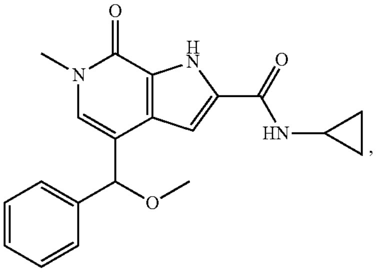
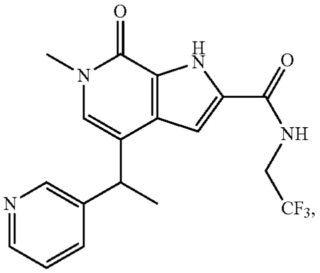
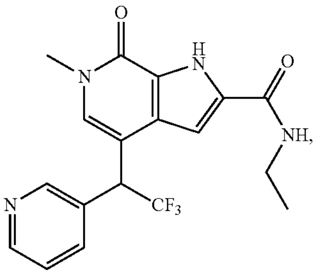
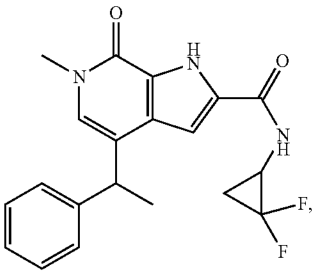
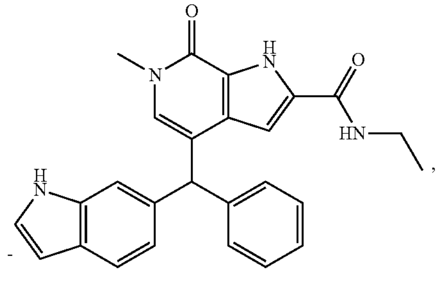

-continued
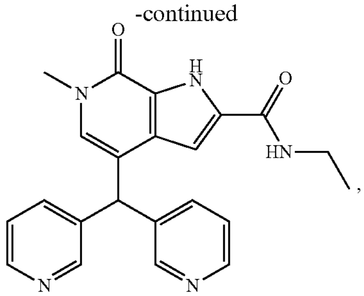
,
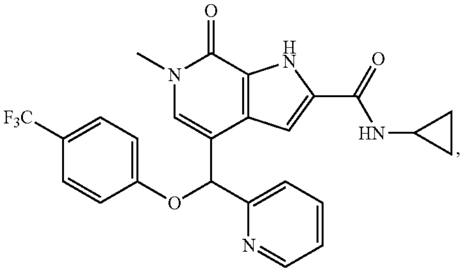
,
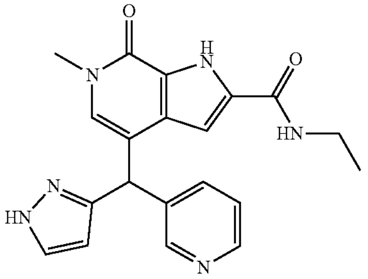
,
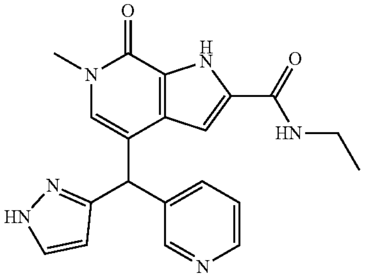
,
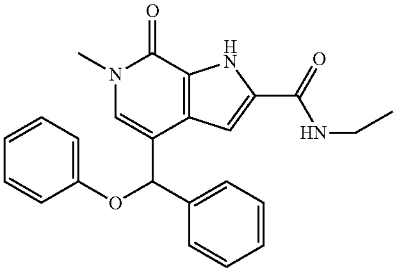
,
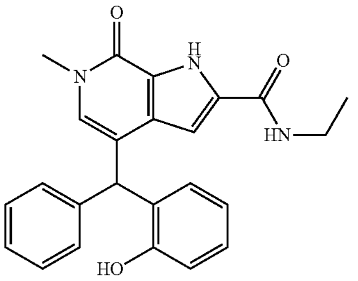
,
-continued
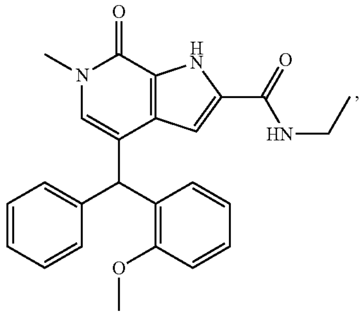
,
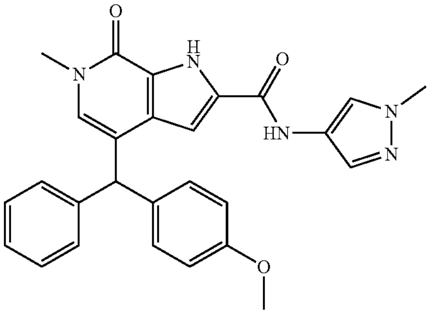
,
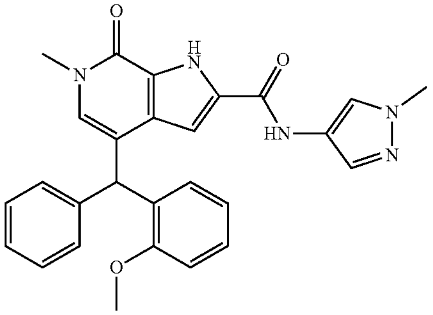
,
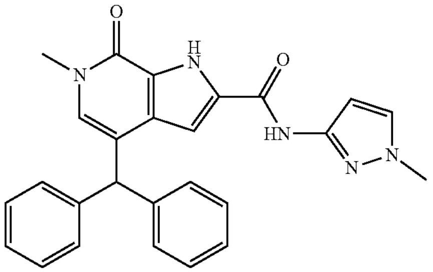
,
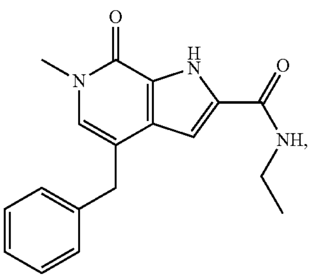
,

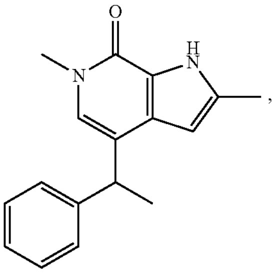
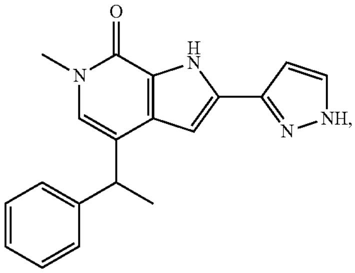
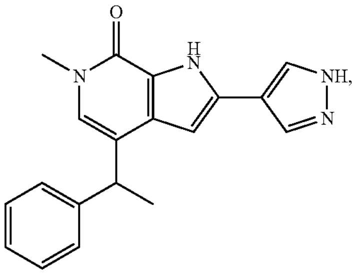
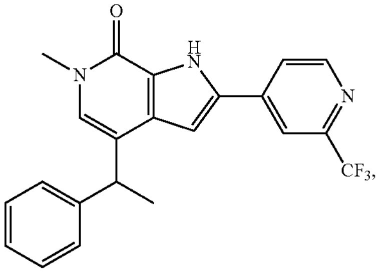
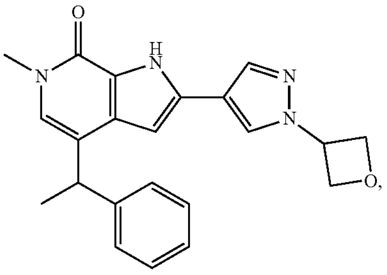
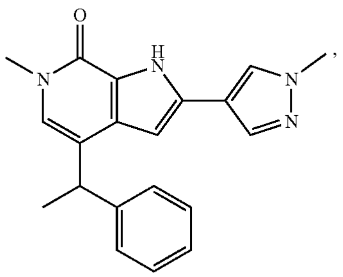
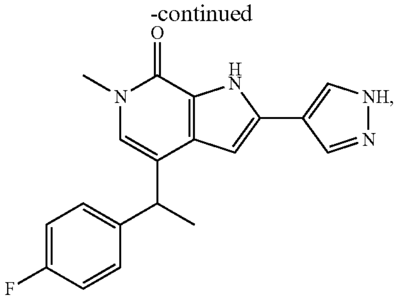
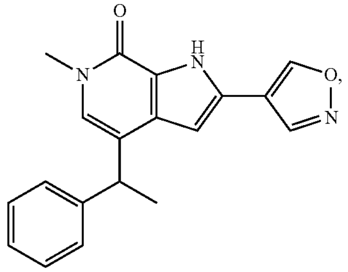
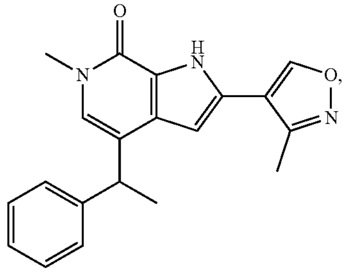
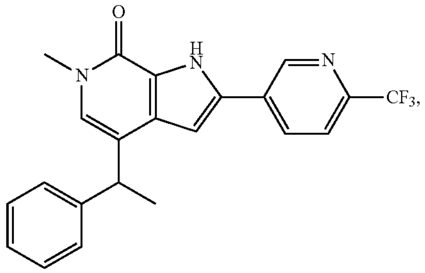
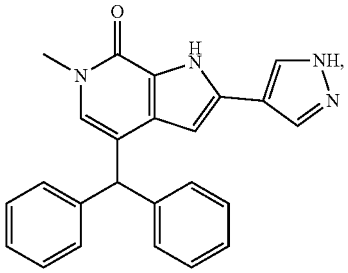
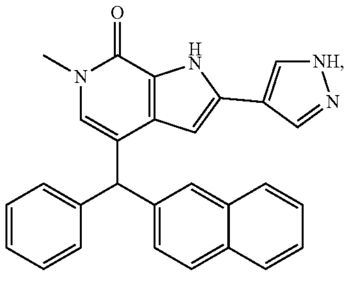

-continued
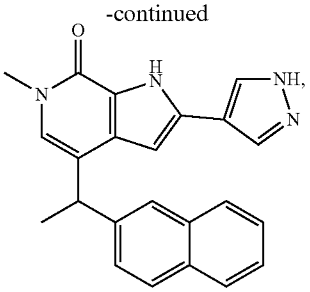
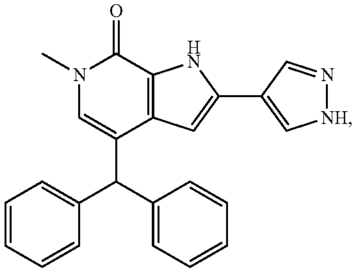
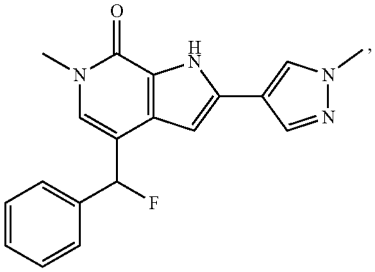
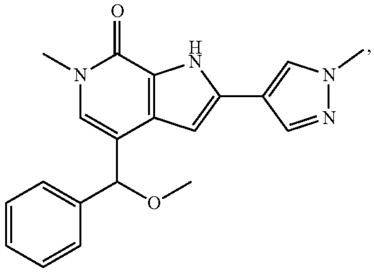
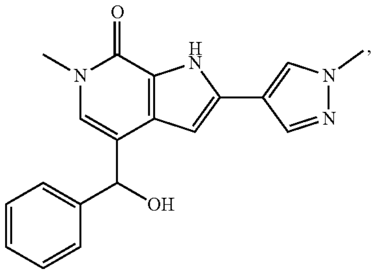
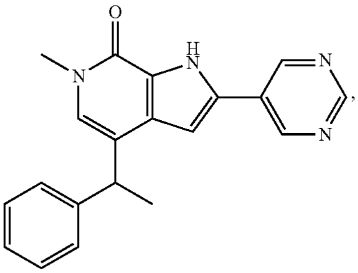
-continued
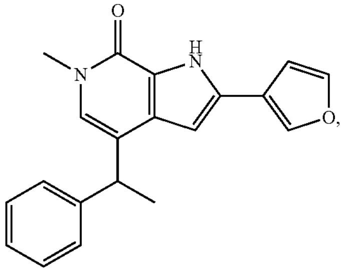
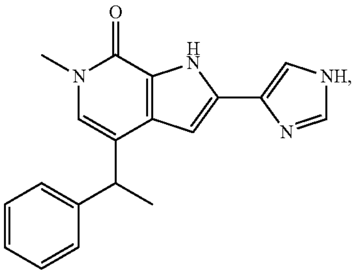
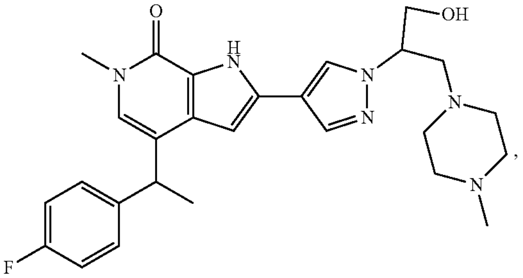
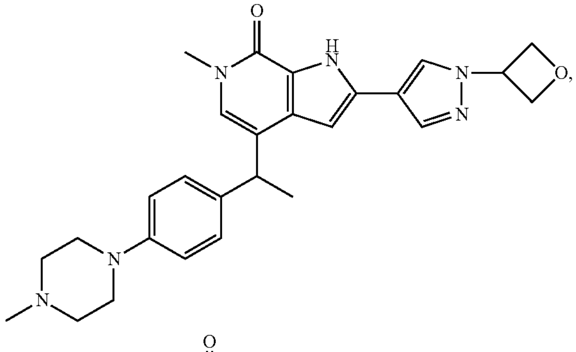
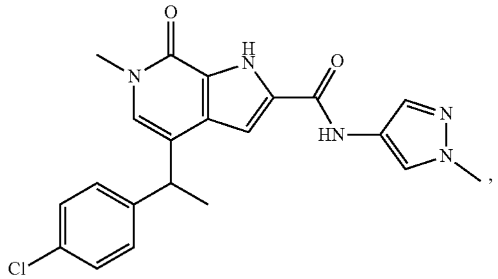
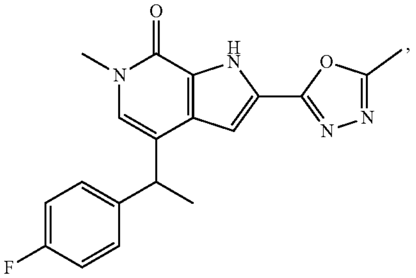

-continued

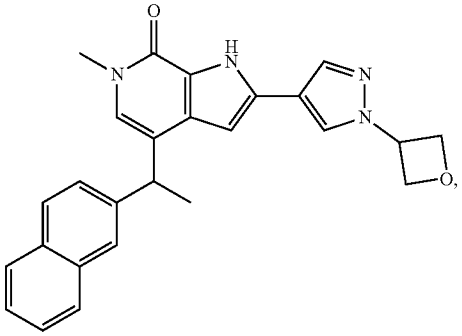

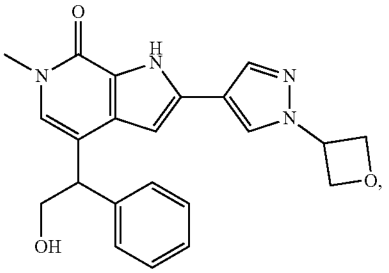

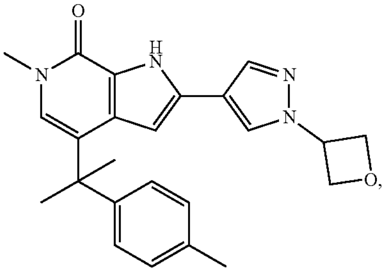

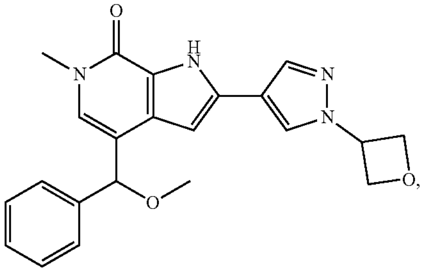

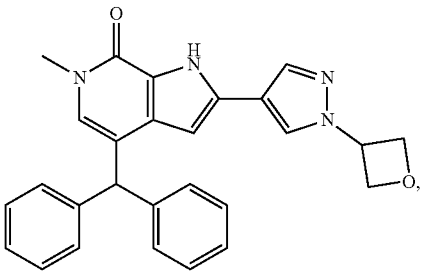

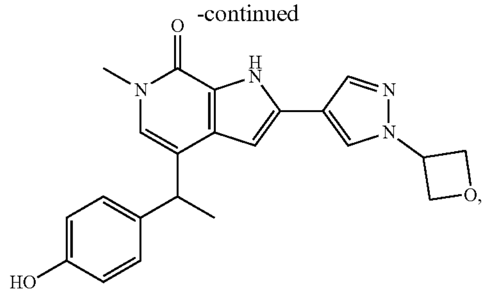

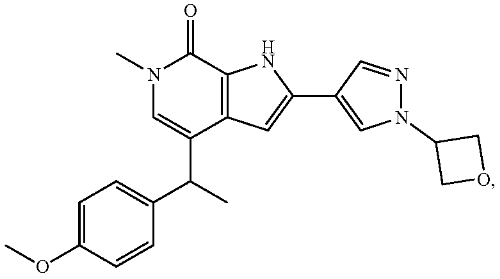

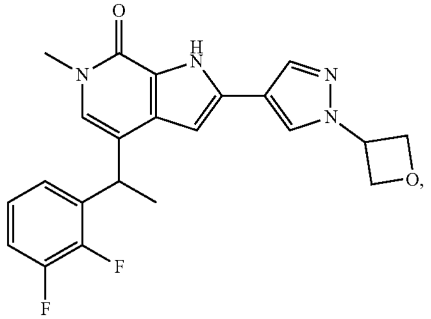

or

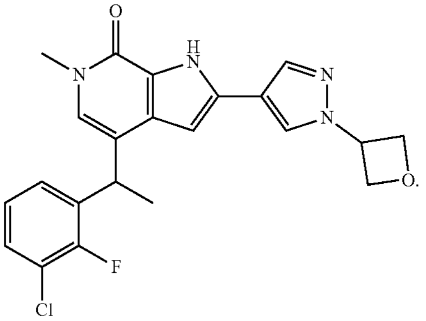

8. A pharmaceutical composition comprising the compound of formula (I), deuterated compound, stereoisomer, racemate, geometric isomer, tautomer, prodrug, hydrate, solvate or pharmaceutically acceptable salt thereof of claim 1; and a pharmaceutically acceptable carrier.

9. A method for treating a disease mediated by a bromodomain protein comprising administering to a subject in need thereof the compound, deuterated compound, stereoisomer, racemate, geometric isomer, tautomer, prodrug, hydrate, solvate or pharmaceutically acceptable salt thereof of claim 1.

10. The method of claim 9, wherein the disease mediated by a bromodomain protein is selected from the group consisting of cancer, inflammatory disease, cardiovascular disease, viral infection, fibrotic disease, metabolic disease, acute rejection of transplanted organs, multiple organ dysfunction syndrome and Alzheimer's disease.

* * * * *